United States Patent
Arayama et al.

(10) Patent No.: US 9,116,426 B2
(45) Date of Patent: Aug. 25, 2015

(54) DYE COMPOUND, METHOD OF PRODUCING DIPYRROMETHENE METAL COMPLEX COMPOUND, METHOD OF PRODUCING DYE MULTIMER, SUBSTITUTED PYRROLE COMPOUND, COLORED CURABLE COMPOSITION, COLOR FILTER, METHOD OF PRODUCING COLOR FILTER, SOLID-STATE IMAGE SENSOR AND LIQUID CRYSTAL DISPLAY DEVICE

(71) Applicant: FUJIFILM Corporation, Minato-ku, Tokyo (JP)

(72) Inventors: Kyohei Arayama, Shizuoka (JP); Hiroaki Idei, Shizuoka (JP); Shinichi Kanna, Shizuoka (JP); Kenta Ushijima, Shizuoka (JP); Akiyoshi Goto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/746,698

(22) Filed: Jan. 22, 2013

(65) Prior Publication Data

US 2013/0137018 A1 May 30, 2013

Related U.S. Application Data

(63) Continuation of application No. PCT/JP2011/065527, filed on Jun. 30, 2011.

(30) Foreign Application Priority Data

| Jul. 23, 2010 | (JP) | 2010-166556 |
| Sep. 14, 2010 | (JP) | 2010-205970 |
| Sep. 14, 2010 | (JP) | 2010-205971 |
| Jan. 12, 2011 | (JP) | 2011-004275 |
| Jan. 13, 2011 | (JP) | 2011-005197 |

(51) Int. Cl.

| G02B 5/00 | (2006.01) |
| G03F 7/004 | (2006.01) |
| G03F 7/00 | (2006.01) |
| C07D 207/34 | (2006.01) |
| C07F 1/00 | (2006.01) |
| C07F 3/00 | (2006.01) |
| C07F 9/00 | (2006.01) |
| C07F 15/06 | (2006.01) |
| C09B 57/10 | (2006.01) |
| G02B 5/22 | (2006.01) |

(52) U.S. Cl.
CPC ............ *G03F 7/0007* (2013.01); *C07D 207/34* (2013.01); *C07F 1/005* (2013.01); *C07F 3/003* (2013.01); *C07F 9/005* (2013.01); *C07F 15/065* (2013.01); *C09B 57/10* (2013.01); *G02B 5/223* (2013.01)

(58) Field of Classification Search
CPC .... G03F 7/0007; G02B 5/223; C07D 207/34; C07F 1/005; C07F 15/065; C07F 9/005; C07F 3/003; C09B 57/10
USPC ............................ 430/7, 270.1; 548/402, 403
See application file for complete search history.

(56) References Cited

U.S. PATENT DOCUMENTS

| 4,521,591 A | 6/1985 | Jan et al. |
| 5,578,419 A | 11/1996 | Itoh et al. |
| 5,610,003 A * | 3/1997 | Lussier ........................ 430/555 |
| 5,789,137 A | 8/1998 | Itoh et al. |
| 5,948,597 A | 9/1999 | Itoh et al. |
| 6,306,550 B1 | 10/2001 | Itoh et al. |
| 2007/0117031 A1 | 5/2007 | Mizukawa et al. |
| 2008/0076044 A1 | 3/2008 | Mizukawa et al. |
| 2010/0055582 A1 | 3/2010 | Mizukawa et al. |

FOREIGN PATENT DOCUMENTS

| JP | 57-155258 A | 9/1982 |
| JP | 4-119891 A | 4/1992 |
| JP | 05271567 A | 10/1993 |
| JP | 6-75375 A | 3/1994 |
| JP | 11-352685 A | 12/1999 |
| JP | 11-352686 A | 12/1999 |

(Continued)

OTHER PUBLICATIONS

Office Action issued in corresponding Taiwan Patent Application 100123075, with an English language translation (Nov. 2014).*

(Continued)

*Primary Examiner* — John A McPherson
(74) *Attorney, Agent, or Firm* — Sughrue Mion, PLLC

(57) ABSTRACT

The invention provides a dye compound having a partial structure represented by the following formula (5):

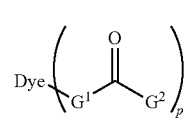

(5)

wherein in formula (5), Dye represents a dye structure; $G^1$ represents NR or an oxygen atom; $G^2$ represents a monovalent substituent group having an $-Es'$ value as a steric parameter of 1.5 or more; p represents an integer from 1 to 8; when p is 2 or greater, the two or more structures represented by p may be the same or different from each other; and R represents a hydrogen atom or a monovalent substituent group.

17 Claims, No Drawings

(56) References Cited

FOREIGN PATENT DOCUMENTS

| | | | |
|---|---|---|---|
| JP | 2000-19729 A | 1/2000 |
| JP | 2000-19738 A | 1/2000 |
| JP | 2001-207092 A | 7/2001 |
| JP | 3279035 B2 | 4/2002 |
| JP | 2002-236360 A | 8/2002 |
| JP | 3324279 B2 | 9/2002 |
| JP | 2005-313632 A | 11/2005 |
| JP | 2007-138051 A | 6/2007 |
| JP | 2009-227639 A | 10/2009 |
| JP | 2009-234969 A | 10/2009 |
| JP | 2010-85454 A | 4/2010 |

OTHER PUBLICATIONS

International Search Report issued in International Application No. PCT/JP2011/065527 on Oct. 4, 2011, 7 pages.

Written Opinion of the ISA issued in International Application No. PCT/JP2011/065527 on Oct. 4, 2011, 6 pages.

First Notice of Examination Opinions, dated Mar. 14, 2014, issued in corresponding CN Application No. 201180035943.2, 8 pages in English and Chinese.

Notice of Reasons for Rejection, dated Feb. 4, 2014, issued in related JP Application No. 2011-162388, 4 pages in English and Japanese.

* cited by examiner

DYE COMPOUND, METHOD OF PRODUCING DIPYRROMETHENE METAL COMPLEX COMPOUND, METHOD OF PRODUCING DYE MULTIMER, SUBSTITUTED PYRROLE COMPOUND, COLORED CURABLE COMPOSITION, COLOR FILTER, METHOD OF PRODUCING COLOR FILTER, SOLID-STATE IMAGE SENSOR AND LIQUID CRYSTAL DISPLAY DEVICE

CROSS-REFERENCE TO RELATED APPLICATIONS

This application is a continuation application of International Application No. PCT/JP2011/065527, filed Jun. 30, 2011, which is incorporated herein by reference. Further, this application claims priority from Japanese Patent Application No. 2010-166556, filed Jul. 23, 2010, Japanese Patent Application No. 2010-205970, filed Sep. 14, 2010, Japanese Patent Application No. 2010-205971, filed Sep. 14, 2010, Japanese Patent Application No. 2011-004275, filed Jan. 12, 2011, and Japanese Patent Application No. 2011-005197, filed Jan. 13, 2011, which are incorporated herein by reference.

BACKGROUND OF THE INVENTION

1. Technical Field

The present invention provides a dye compound, a method of producing a dipyrromethene metal complex compound, a method of producing a dye multimer, a substituted pyrrole compound, a colored curable composition, a color filter, a method of producing a color filter, a solid-state image sensor, and a liquid crystal display device.

2. Related Art

A pigment dispersion method is one of the methods of producing a color filter used in liquid crystal display devices or solid-state imaging sensors, and one of such pigment dispersion methods is a method of producing a color filter by photolithography using a colored curable composition prepared by dispersing a pigment in a curable composition of various kinds. Specifically, a film is formed on a support by applying a colored curable composition thereon with a spin coater, roll coater or the like, and drying the applied composition. Then, the film is exposed to light in a patterned manner and developed, whereby colored pixels are formed. A color filter is produced by repeating the process for a number of times corresponding to the number of colors to be used in the color filter.

The above method has been widely appreciated as a suitable method of producing color filters for color displays, because the composition is stable with respect to light or heat due to the use of a pigment, and sufficient positional accuracy is secured by performing patterning by photolithography.

In the field of color filters used for solid-state image sensors such as CCDs, use of a dye instead of a pigment has been studied with the aim of achieving a high resolution (see, for example, Japanese Patent Application Laid-Open (JP-A) No. 6-75375). However, dye-containing colored curable compositions are accompanied by new problems as set forth below.

(1) dyes, being in a state in which molecules thereof are dispersed, exhibit inferior light fastness or heat fastness compared with pigments, which are typically an aggregation of molecules.

(2) dyes, being in a state in which molecules thereof are dispersed, exhibit inferior solvent resistance compared with pigments, which are typically an aggregation of molecules.

(3) dyes tend to exhibit interaction with other components in the composition, which makes it difficult to adjust the solubility (developability) of a cured portion (exposed portion) and an uncured portion (unexposed portion).

(4) when a dye has a low molar absorption coefficient ($\varepsilon$), it needs to be used in large amounts, and the amount of other components in the composition, such as a polymerizable compound (monomer), a binder or a photopolymerization initiator need to be reduced. As a result, curability of the colored curable composition, heat resistance after being cured, or developability of the uncured portion, may deteriorate.

As a means for solving the problems caused by the use of a dye, specifically those related to (1) light fastness and heat fastness and (4) molar absorption coefficient ($\varepsilon$), use of a dipyrromethene metal complex as a dye has been considered (see, for example, United States Patent Application Laid-Open No. 2008-0076044).

Dipyrromethene metal complexes are known for their excellent light fastness and heat fastness, high molar absorption coefficient and favorable absorption properties in terms of color reproduction (see, for example, United States Patent Application Laid-Open No. 2008-0076044), and are used to produce color filters for liquid crystal display devices or solid-state image sensors (see, for example, United States Patent Application Laid-Open No. 2008-0076044). Dipyrromethene metal complexes are also used as a sensitizer for a radical polymerization initiator in a polymerizable composition that polymerizes with visible light, or as a functional compound of various kinds (see, for example, Japanese Patent No. 3279035, Japanese Patent No. 3324279, JP-A No. 11-3526685, JP-A No. 11-352686, JP-A No. 2000-19729, JP-A No. 2000-19738 and JP-A No. 2002-236360).

Further, in order to improve the solubility or the like, use of a porphyrin compound having a steric parameter of 0.5 or more has been proposed (see, for example, JP-A No. 2005-313632). However, even though the solubility is improved, other properties such as heat fastness are yet to be satisfied.

Problems to be Solved by the Invention

There has been a demand for a colored curable composition containing a dipyrromethene compound as a dye that exhibits even more improved light fastness, heat fastness and alkali resistance. The alkali resistance refers to an ability of a colored curable composition to resist discoloration of a dye contained therein due to decomposition, dissolution or the like, when the composition is formed into a layer and the layer contacts an alkali solution used as a developer.

Further, as mentioned in problem (2), there has been a need to improve solvent resistance of the composition in order to use a dye as a colorant. The solvent resistance is an ability of the composition to retain a colorant within a cured portion formed in a patterned manner from the composition, while suppressing elution of the colorant from the cured portion. When producing an RGB color filter by photolithography, since patterns of different colors are formed in a sequential manner, a resist solution of one color covers a pattern of a different color. During this step, color mixing may occur when a colorant component in a cured portion leaks into a colored curable composition of a different color. Accordingly, the cured portion needs to exhibit an extremely high solvent resistance during a process of producing a color filter. In this regard, dyes, which are formed of dispersed molecules, are inferior in solvent resistance to pigments, which are formed of molecules aggregating via a strong intermolecular force.

Further, in the production of color filters, since a heat treatment may be carried out after the application, exposure and development, in order to increase the cure degree of a colored pattern, fixability of a dye in a cured portion is also an issue. Dyes, which are formed of dispersed molecules, can move with a smaller thermal energy compared to pigments which are formed of aggregated molecules. Therefore, fixability in a cured portion of dyes, which tend to cause color transfer to an adjacent pattern of a different color, has been an important issue to be addressed.

The present invention has been made in view of the above circumstances, and aims to accomplish the following goals.

Specifically, one aspect of the present invention is to provide a dye compound that exhibits favorable heat fastness, alkali resistance and color purity.

A further aspect of the present invention is to provide a method of producing a dipyrromethene metal complex compound suitable as the dye compound, a method of producing a dye multimer including the dipyrromethene metal complex as a partial structure of the dye, and a novel substituted pyrrole compound suitably used for obtaining the dipyrromethene metal complex compound in the method.

Yet further aspect of the present invention is to provide a colored curable composition that exhibits favorable heat fastness, alkali resistance and color purity, a color filter having a colored pattern that exhibits favorable heat fastness and color purity even when it is formed into a thin film, a method of producing the color filter, and a solid-state image sensor including the color filter.

Means for Solving the Problems

The present inventors have made extensive studies on various kinds of dyes, and have found that a dye compound having a specific structure exhibits a favorable color hue and a high absorption coefficient, excellent solubility in a solvent, and excellent robustness such as solvent resistance and heat fastness.

In particular, the present inventors have found that a colored curable composition exhibits high solvent resistance and heat fastness when it includes a dye compound that functions as a polymerizable component, the dye compound being produced by introducing a polymerizable group into a dye multimer having a dipyrromethene dye compound as a structural unit, a dye compound that forms a dipyrromethene metal complex, or a dipyrromethene dye compound.

Further, the present inventors have found that by using a dye compound into which an alkali-soluble group is optionally introduced, a colored curable composition that forms a cured film that exhibits favorable pattern formability (i.e., small dependency on alkali developer concentration) can be obtained.

The following are specific examples of the embodiments of the present invention. However, the invention is not limited to these examples.

<1> A dye compound having a partial structure represented by the following formula (5):

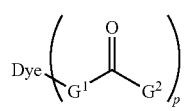

(5)

wherein in formula (5), Dye represents a dye structure; $G^1$ represents NR or an oxygen atom; $G^2$ represents a monovalent substituent group having an $-Es'$ value as a steric parameter of 1.5 or more; p represents an integer from 1 to 8; when p is 2 or greater, the two or more structures represented by p may be the same or different from each other; and R represents a hydrogen atom or a monovalent substituent group.

<2> The dye compound according to <1>, wherein the partial structure represented by formula (5) is a partial structure represented by the following formula (6):

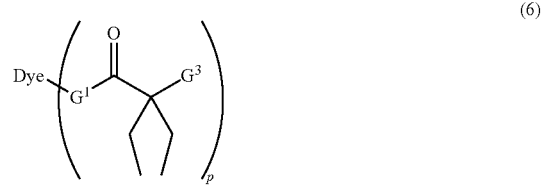

(6)

wherein in formula (6), Dye represents a dye structure; $G^1$ represents a nitrogen atom or an oxygen atom; $G^3$ represents a carbon atom, a sulfur atom, an oxygen atom or a nitrogen atom; p represents 1 or 2; and when p is 2, the two structures represented by p may be the same or different from each other.

<3> The dye compound according to <1> or <2>, wherein Dye in formula (5) is a residual group of a dye compound selected from the group consisting of an azo dye, an azomethine dye, a dipyrromethene dye, a quinone dye, a carbonium dye, a quinoneimine dye, an azine dye, a polymethine dye, a quinophthalone dye, a phthalocyanine dye, a perinone dye, an indigo dye, a thioindigo dye, a quinoline dye, a nitro dye, a nitroso dye and a metal complex compound of these dyes.

<4> The dye compound according to any one of <1> to <3>, wherein Dye in formula (5) is a residual group of a dipyrromethene compound or a residual group of a dipyrromethene metal complex compound obtained from the dipyrromethene compound and a metal or a metal compound.

<5> The dye compound according to <4>, wherein the dipyrromethene metal complex compound is a dipyrromethene metal complex compound obtained from a dipyrromethene compound represented by the following formula (M) and a metal or a metal compound, or a tautomer of the dipyrromethene metal complex compound:

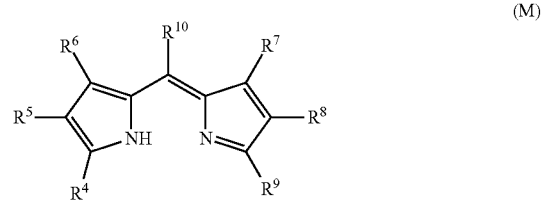

(M)

wherein in formula (M), each of $R^4$ to $R^{10}$ independently represents a hydrogen atom or a monovalent substituent group; at least one substituent group selected from $R^4$ to $R^{10}$ is linked to $G^1$ in formula (5); and $R^4$ and $R^9$ are not bonded to each other to form a ring.

<6> The dye compound according to <4> or <5>, wherein the dipyrromethene metal complex compound obtained from the dipyrromethene compound represented by formula (M) and the metal or the metal compound, or the tautomer of the dipyrromethene compound, is a dipyrromethene metal complex compound represented by the following formula (7) or the following formula (8) or a tautomer thereof:

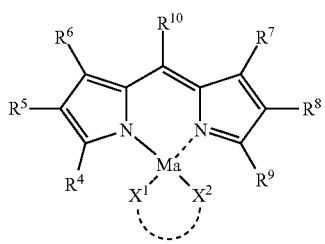

(7)

wherein in formula (7), each of $R^4$ to $R^9$ independently represents a hydrogen atom or a monovalent substituent group; $R^{10}$ represents a hydrogen atom, a halogen atom, an alkyl group, an aryl group, or a heterocyclic group; Ma represents a metal atom or a metal compound; $X^1$ represents a group capable of being bonded to Ma; $X^2$ represents a group that neutralizes a charge of Ma; $X^1$ and $X^2$ may be bonded to each other to form a 5-membered, 6-membered or 7-membered ring together with Ma; and $R^4$ and $R^9$ are not bonded to each other to form a ring;

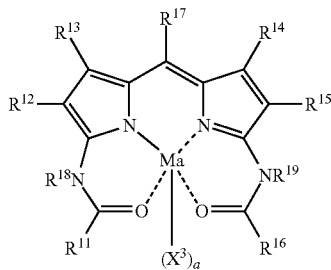

(8)

wherein in formula (8), each of $R^{11}$ and $R^{16}$ independently represent an alkyl group, an alkenyl group, an aryl group, a heterocyclic group, an alkoxy group, an aryloxy group, an alkylamino group, an arylamino group, or a heterocyclic amino group; each of $R^{12}$ to $R^{15}$ independently represents a hydrogen atom or a monovalent substituent group; $R^{17}$ represents a hydrogen atom, a halogen atom, an alkyl group, an aryl group, or a heterocyclic group; Ma represents a metal atom or a metal compound; each of $R^{18}$ and $R^{19}$ independently represents a hydrogen atom, an alkyl group, an alkenyl group, an aryl group, a heterocyclic group, an acyl group, an alkylsulfonyl group, or an arylsulfonyl group; $R^{11}$ and $R^{18}$ may be bonded to each other to form a 5-membered, 6-membered or 7-membered ring; $R^{16}$ and $R^{19}$ may be bonded to each other to form a 5-membered, 6-membered or 7-membered ring; $X^3$ represents a group capable of being bonded to Ma; a represents 0, 1 or 2; and when a is 2, the two of $X^3$ may have the same structure or different structures.

<7> The dye compound according to <6>, wherein each of $R^{11}$ and $R^{16}$ in formula (8) independently represents a monovalent substituent group having an –Es' value as a steric parameter of 1.5 or more.

<8> The dye compound according to any one of <1> to <7>, further comprising a polymerizable group.

<9> The dye compound according to any one of <6> to <8>, wherein Ma in formula (7) or formula (8) is any one of Zn, Co, V=O or Cu.

<10> The dye compound according to any one of <6> to <9>, wherein Ma in formula (7) or formula (8) is Zn.

<11> The dye compound according to any one of <1> to <10>, further comprising an alkali soluble group.

<12> A dye compound, which is a dye multimer, comprising, as a partial structure of a dye moiety, a group obtained by removing 1 to 10 hydrogen atoms from the dye compound according to any one of <1> to <11>.

<13> The dye compound according to <12>, comprising at least one structural unit represented by the following formula (A), formula (B) or formula (C), or having a structure represented by the following formula (D):

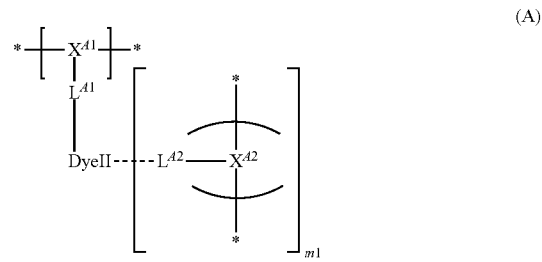

(A)

wherein in formula (A), $X^{A1}$ represents a linking group formed by polymerization; $L^{A1}$ represents a single bond or a divalent linking group; Dye II represents a linking group having a structure formed by removing from one to (m1+1) hydrogen atoms from the partial structure represented by formula (5), wherein Dye in formula (5) is a dye structure formed by removing any one or two hydrogen atoms from a dipyrromethene metal complex compound obtained from a dipyrromethene compound represented by the following formula (M) and a metal or a metal compound; $X^{A2}$ represents a linking group formed by polymerization; $L^{A2}$ represents a single bond or a divalent linking group; m1 represents an integer from 0 to 3; when m1 is 2 or more, the two or more structures in the brackets may be the same or different from each other; and Dye II and $L^{A2}$ are linked to each other via covalent bonding, ionic bonding or coordinate bonding;

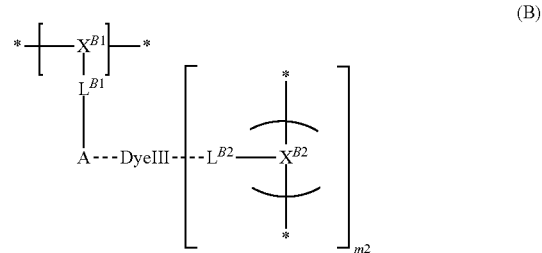

(B)

wherein in formula (B), $X^{B1}$ represents a linking group formed by polymerization; $L^{B1}$ represents a single bond or a divalent linking group; A represents a group capable of being bonded to Dye III via ionic bonding or coordinate bonding; Dye III represents a linking group having a structure formed by removing from one to (m2+1) hydrogen atoms from the partial structure represented by formula (5), wherein Dye in formula (5) is a dye structure formed by removing any one or two hydrogen atoms from a dipyrromethene metal complex compound obtained from a dipyrromethene compound represented by the following formula (M) and a metal or a metal compound; $X^{B2}$ represents a linking group formed by polymerization; $L^{B2}$ represents a single bond or a divalent linking group; m2 represents an integer from 0 to 3; when m2 is 2 or greater, the two or more structures in the brackets may be the same or different from each other; and Dye III and $L^{B2}$ may be linked to each other via covalent bonding, ionic bonding or coordinate bonding;

  (C)

wherein in formula (C), $L^{C1}$ represents a single bond or a divalent linking group; Dye IV represents a linking group having a structure formed by removing two hydrogen atoms from the partial structure represented by formula (5), wherein Dye in formula (5) is a dye structure formed by removing any one or two hydrogen atoms from a dipyrromethene metal complex compound obtained from a dipyrromethene compound represented by the following formula (M) and a metal or a metal compound; m3 represents an integer from 1 to 4; and when m3 is 2 or more, the two or more of $L^{C1}$ may be the same or different from each other;

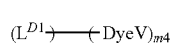  (D)

wherein in formula (D), $L^{D1}$ represents a linking group having a valency of m4; m4 represents an integer from 2 to 100; when m4 is 2 or more, the two or more structures of Dye V may be the same or different from each other; Dye V represents a linking group having a structure formed by removing one hydrogen atom from the partial structure represented by formula (5), wherein Dye in formula (5) is a dye structure formed by removing any one or two hydrogen atoms from a dipyrromethene metal complex compound obtained from a dipyrromethene compound represented by the following formula (M) and a metal or a metal compound;

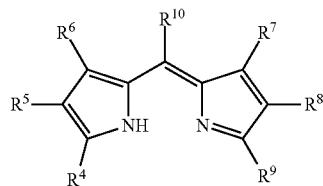  (M)

wherein in formula (M), each of $R^4$ to $R^{10}$ independently represents a hydrogen atom or a monovalent substituent group; a hydrogen atom is removed from at least one substituent group selected from $R^4$ to $R^{10}$; and $R^4$ and $R^9$ are not bonded to each other to form a ring.

<14> The dye compound according to <13>, wherein the structural unit represented by formula (A) is a structural unit derived from a dye monomer represented by the following formula (1):

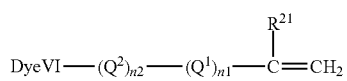  (1)

wherein in formula (1), $R^{21}$ represents a hydrogen atom, a halogen atom, an alkyl group, or an aryl group; $Q^1$ represents —N($R^2$)C(=O)—, —OC(=O)—, —C(=O)N($R^2$)—, —C(=O)O—, a group represented by the following formula (2), a group represented by the following formula (3), or a group represented by the following formula (4); $Q^2$ represents a divalent linking group; each of n1 and n2 independently represents 0 or 1; Dye VI represents a linking group having a structure formed by removing two hydrogen atoms from the partial structure represented by formula (5), wherein Dye in formula (5) is a dye structure formed by removing any one or two hydrogen atoms from a dipyrromethene metal complex compound obtained from a dipyrromethene compound represented by the following formula (7) or (8) and a metal or a metal compound; and $R^2$ represents a hydrogen atom, an alkyl group, an aryl group, or a heterocyclic group;

  (2)

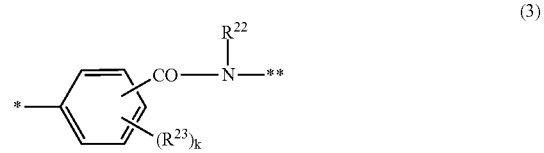  (3)

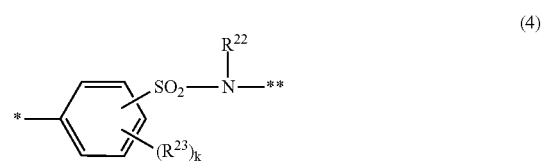  (4)

wherein in formulas (2) to (4), $R^{22}$ represents a hydrogen atom, an alkyl group, an aryl group, or a heterocyclic group; each of $R^{23}$ independently represents a hydrogen atom or a monovalent substituent group; k represents an integer from 0 to 4; when k is 2 or more, the two or more of $R^{23}$ may be the same or different from each other; * indicates a bonding site to the —C($R^{21}$)=CH$_2$ group in formula (1), and ** indicates a bonding site to $Q^2$ or Dye VI (when n2=0) in formula (1);

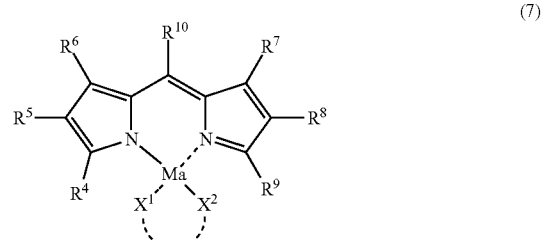  (7)

wherein in formula (7), each of $R^4$ to $R^9$ independently represents a hydrogen atom or a monovalent substituent group; $R^{10}$ represents a hydrogen atom, a halogen atom, an alkyl group, an aryl group, or a heterocyclic group; Ma represents a metal atom or a metal compound; $X^1$ represents a group capable of being bonded to Ma; $X^2$ represents a group that neutralizes a charge of Ma; $X^1$ and $X^2$ may be bonded to each other to form a 5-membered, 6-membered or 7-membered ring together with Ma; but $R^4$ and $R^9$ are not bonded to each other to form a ring;

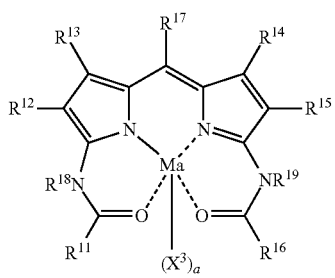

(8)

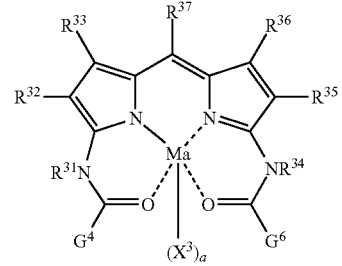

(I)

wherein in formula (8), each of $R^{11}$ and $R^{16}$ independently represents an alkyl group, an alkenyl group, an aryl group, a heterocyclic group, an alkoxy group, an aryloxy group, an alkylamino group, an arylamino group, or a heterocyclic amino group; each of $R^{12}$ to $R^{15}$ independently represents a hydrogen atom or a monovalent substituent group; $R^{17}$ represents a hydrogen atom, a halogen atom, an alkyl group, an aryl group, or a heterocyclic group; Ma represents a metal atom or a metal compound; each of $R^{18}$ and $R^{19}$ independently represents a hydrogen atom, an alkyl group, an alkenyl group, an aryl group, a heterocyclic group, an acyl group, an alkylsulfonyl group, or an arylsulfonyl group; $R^{11}$ and $R^{18}$ may be bonded to each other to form a 5-membered, 6-membered or 7-membered ring; $R^{16}$ and $R^{19}$ may be bonded to each other to form a 5-membered, 6-membered or 7-membered ring; $X^3$ represents a group capable of being bonded to Ma; and a represents 0, 1 or 2.

<15> The dye compound according to <14>, further comprising, as a copolymerization component, a monomer having a different structure from the structure of the dye monomer represented by formula (1) and having a terminal ethylenically unsaturated bond.

<16> The dye compound according to any one of <12> to <15>, further comprising an alkali soluble group.

<17> The dye compound according to <16>, wherein the alkali soluble group exists in at least one selected from the group consisting of the dye multimer comprising at least one structural unit represented by formula (A), formula (B) or formula (C), the dye multimer represented by formula (D), the dye monomer represented by formula (1), and the dye monomer having a different structure from the structure of the dye monomer represented by formula (1) and having a terminal ethylenically unsaturated bond.

<18> The dye compound according to <16> or <17>, wherein the alkali soluble group exists in Dye II in formula (A), Dye III in formula (B), Dye IV in formula (C), Dye V in formula (D), or Dye VI in formula (1).

<19> The dye compound according to any one of <12> to <18>, further comprising a polymerizable group introduced therein by adding, to the dye compound, a compound having a group that can react with a substituent group in the dye compound and a polymerizable group.

<20> A method of producing a dipyrromethene metal complex compound represented by the following formula (1), the method comprising allowing a dipyrromethene compound represented by the following formula (XI) to react with a metal derivative represented by formula (XIII):

wherein in formula (1), each of $G^4$ and $G^6$ independently represents a monovalent substituent group having an –Es' value as a steric parameter of 1.5 or more; each of $R^{32}$, $R^{33}$, $R^{35}$ and $R^{36}$ independently represents a hydrogen atom or a monovalent substituent group; $R^{37}$ represents a hydrogen atom, a halogen atom, an alkyl group, an aryl group, or a heterocyclic group; each of $R^{31}$ and $R^{34}$ independently represents a hydrogen atom, an alkyl group, an alkenyl group, an aryl group, a heterocyclic group, an acyl group, an alkylsulfonyl group, or an arylsulfonyl group; Ma represents a metal atom or a metal compound; $X^3$ represents a group capable of being bonded to Ma; and a represents 0, 1 or 2;

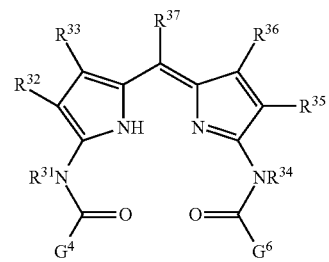

(XI)

wherein in formula (XI), each of $G^4$ and $G^6$ independently represents a monovalent substituent group having an –Es' value as a steric parameter of 1.5 or more; each of $R^{32}$, $R^{33}$, $R^{35}$ and $R^{36}$ independently represents a hydrogen atom or a monovalent substituent group; $R^{37}$ represents a hydrogen atom, a halogen atom, an alkyl group, an aryl group, or a heterocyclic group; and each of $R^{31}$ and $R^{34}$ independently represents a hydrogen atom, an alkyl group, an alkenyl group, an aryl group, a heterocyclic group, an acyl group, an alkylsulfonyl group, or an arylsulfonyl group;

$$Ma(X^1)_b \quad (XIII)$$

wherein in formula (XIII), Ma represents a metal or a metal compound; $X^1$ represents a group capable of being bonded to Ma; and b represents an integer from 1 to 4.

<21> The method of producing a dipyrromethene metal complex compound according to <20>, wherein the dipyrromethene compound represented by formula (XI) is obtained by allowing a compound represented by the following formula (V) to react with a compound represented by the following formula (X):

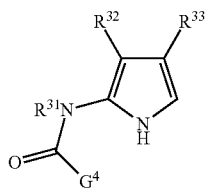

(V)

wherein in formula (V), $R^{31}$ represents a hydrogen atom, an alkyl group, an alkenyl group, an aryl group, a heterocyclic group, an acyl group, an alkylsulfonyl group, or an arylsulfonyl group; each of $R^{32}$ and $R^{33}$ independently represents a hydrogen atom or a monovalent substituent group; and $G^4$ represents a monovalent substituent group having an −Es' value as a steric parameter of 1.5 or more;

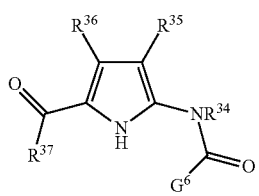

(X)

wherein in formula (X), $R^{34}$ represents a hydrogen atom, an alkyl group, an alkenyl group, an aryl group, a heterocyclic group, an acyl group, an alkylsulfonyl group, or an arylsulfonyl group; each of $R^{35}$ and $R^{36}$ independently represents a hydrogen atom or a monovalent substituent group; $R^{37}$ represents a hydrogen atom, a halogen atom, an alkyl group, an aryl group, or a heterocyclic group; and $G^6$ represents a monovalent substituent group having an −Es' value as a steric parameter of 1.5 or more.

<22> The method of producing a dipyrromethene metal complex compound according to <21>, wherein the compound represented by formula (X) is obtained by allowing a compound represented by the following formula (IX) to react with an acylation agent:

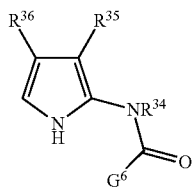

(IX)

wherein in formula (IX), $R^{34}$ represents a hydrogen atom, an alkyl group, an alkenyl group, an aryl group, a heterocyclic group, an acyl group, an alkylsulfonyl group, or an arylsulfonyl group; each of $R^{35}$ and $R^{36}$ independently represents a hydrogen atom or a monovalent substituent group; and $G^6$ represents a monovalent substituent group having an −Es' value as a steric parameter of 1.5 or more.

<23> The method of producing a dipyrromethene metal complex compound according to <22>, wherein the dipyrromethene compound represented by formula (XI) is obtained by allowing a compound represented by the following formula (V), a compound represented by the following formula (IX) and a compound represented by the following formula (XII) to react with each other:

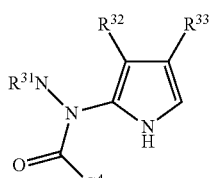

(V)

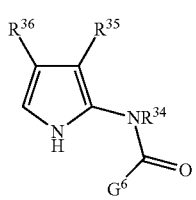

(IX)

$R^{37}C(OR^{38})_3$ (XII)

wherein in formulas (V), (IX) and (XII), each of $G^4$ and $G^6$ independently represents a monovalent substituent group having an −Es' value as a steric parameter of 1.5 or more; each of $R^{32}$, $R^{33}$, $R^{35}$ and $R^{36}$ independently represents a hydrogen atom or a monovalent substituent group; $R^{37}$ represents a hydrogen atom, a halogen atom, an alkyl group, an aryl group, or a heterocyclic group; each of $R^{31}$ and $R^{34}$ independently represents a hydrogen atom, an alkyl group, an alkenyl group, an aryl group, a heterocyclic group, an acyl group, an alkylsulfonyl group, or an arylsulfonyl group; and $R^{38}$ represents an alkyl group or an aryl group.

<24> The method of producing a dipyrromethene metal complex compound according to any one of <21> to <23>, wherein the compound represented by formula (V) is obtained by forming the substituent group represented by $G^4$ by chemically converting a leaving group represented by $X^{11}$ in a compound represented by the following formula (IV):

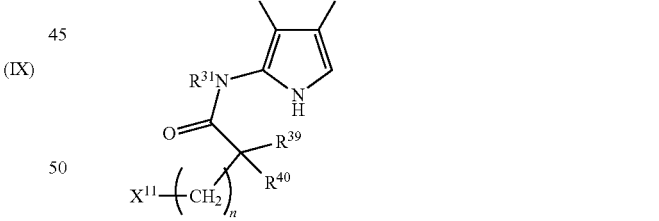

(IV)

wherein in formula (IV), $R^{31}$ represents a hydrogen atom, an alkyl group, an alkenyl group, an aryl group, a heterocyclic group, an acyl group, an alkylsulfonyl group, or an arylsulfonyl group; each of $R^{32}$ and $R^{33}$ independently represents a hydrogen atom or a monovalent substituent group; each of $R^{39}$ and $R^{40}$ independently represents an alkyl group having two or more carbon atoms, an alkenyl group, an aryl group or a heterocyclic group; $X^{11}$ represents a monovalent leaving group; and n represents an integer from 0 to 10.

<25> The method of producing a dipyrromethene metal complex compound according to <24>, wherein the compound represented by formula (IV) is obtained by allowing a compound represented by the following formula (II) to react with a compound represented by the following formula (III):

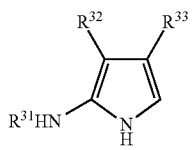
(II)

wherein in formula (II), $R^{31}$ represents a hydrogen atom, an alkyl group, an alkenyl group, an aryl group, a heterocyclic group, an acyl group, an alkylsulfonyl group, or an arylsulfonyl group; and each of $R^{32}$ and $R^{33}$ independently represents a hydrogen atom or a monovalent substituent group;

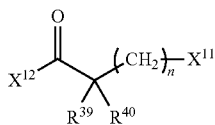
(III)

wherein in formula (III), each of $R^{39}$ and $R^{40}$ independently represents an alkyl group having two or more carbon atoms, an alkenyl group, an aryl group or a heterocyclic group; $X^{11}$ represents a monovalent leaving group; $X^{12}$ represents a monovalent leaving group; and n represents an integer from 0 to 10.

<26> A method of producing a dye multimer having a structural unit derived from a dye monomer represented by the following formula (1) by radical polymerization:

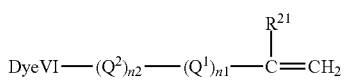
(1)

wherein in formula (1), $R^{21}$ represents a hydrogen atom, a halogen atom, an alkyl group, or an aryl group; $Q^1$ represents —N($R^2$)C(=O)—, —OC(=O)—, —C(=O)N($R^2$)—, —C(=O)O—, a group represented by the following formula (2), a group represented by the following formula (3), or a group represented by the following formula (4); $Q^2$ represents a divalent linking group; each of n1 and n2 independently represents 0 or 1; Dye VI represents a linking group having a structure formed by removing two hydrogen atoms from a partial structure represented by the following formula (5), wherein Dye in formula (5) is a dye structure formed by removing any one or two hydrogen atoms from a dipyrromethene metal complex compound obtained from a dipyrromethene compound represented by the following formula (7) or (8) and a metal or a metal compound; and $R^2$ represents a hydrogen atom, an alkyl group, an aryl group, or a heterocyclic group;

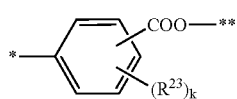
(2)

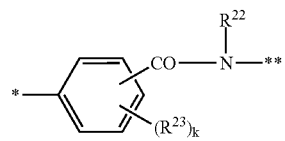
(3)

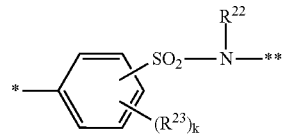
(4)

wherein in formulas (2) to (4), $R^{22}$ represents a hydrogen atom, an alkyl group, an aryl group, or a heterocyclic group; each of $R^{23}$ independently represents a hydrogen atom or a monovalent substituent group; k represents an integer from 0 to 4; when k is 2 or more, the two or more of $R^{23}$ may be the same or different from each other; * indicates a bonding site to the —C($R^{21}$)=$CH_2$ group in formula (1), and ** indicates a bonding site to $Q^2$ or Dye VI (when n2=0) in formula (1);

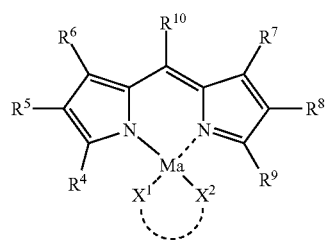
(7)

wherein in formula (7), each of $R^4$ to $R^9$ independently represents a hydrogen atom or a monovalent substituent group; $R^{10}$ represents a hydrogen atom, a halogen atom, an alkyl group, an aryl group, or a heterocyclic group; Ma represents a metal atom or a metal compound; $X^1$ represents a group capable of being bonded to Ma; $X^2$ represents a group that neutralizes a charge of Ma; $X^1$ and $X^2$ may be bonded to each other to form a 5-membered, 6-membered or 7-membered ring together with Ma; and $R^4$ and $R^9$ are not bonded to each other to form a ring;

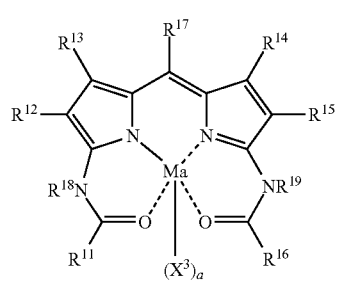
(8)

wherein in formula (8), each of $R^{11}$ and $R^{16}$ independently represents an alkyl group, an alkenyl group, an aryl group, a heterocyclic group, an alkoxy group, an aryloxy group, an alkylamino group, an arylamino group, or a heterocyclic amino group; each of $R^{12}$ to $R^{15}$ independently represents a hydrogen atom or a monovalent substituent group; $R^{17}$ represents a hydrogen atom, a halogen atom, an alkyl group, an aryl group, or a heterocyclic group; Ma represents a metal atom or a metal compound; each of $R^{18}$ and $R^{19}$ independently represents a hydrogen atom, an alkyl group, an alkenyl group, an aryl group, a heterocyclic group, an acyl group, an alkylsulfonyl group, or an arylsulfonyl group; $R^{11}$ and $R^{18}$ may be bonded to each other to form a 5-membered, 6-membered or 7-membered ring; $R^{16}$ and $R^{19}$ may be bonded to each other to form a 5-membered, 6-membered or 7-membered ring; $X^3$ represents a group capable of being bonded to Ma; and a represents 0, 1 or 2;

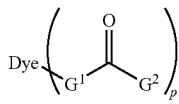

(5)

wherein in formula (5), Dye represents a dye structure; $G^1$ represents NR or an oxygen atom; $G^2$ represents a monovalent substituent group having an –Es' value as a steric parameter of 1.5 or more; p represents an integer from 1 to 8; when p is 2 or greater, the two or more structures represented by p may be the same or different from each other; and R represents a hydrogen atom or a monovalent substituent group.

<27> A method of producing a polymerizable group-containing dye multimer, the method comprising:

obtaining a multimer by homopolymerization of a dye monomer represented by the following formula (1) or by copolymerization of a dye monomer represented by formula (1) and a monomer having a structure different from the structure of the dye monomer represented by (1) and having a terminal ethylenically unsaturated bond; and introducing a polymerizable group into the multimer by adding, to the multimer, a compound having a group that can react with the multimer and the polymerizable group:

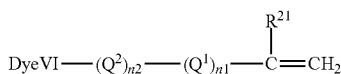

(1)

wherein in formula (1), $R^{21}$ represents a hydrogen atom, a halogen atom, an alkyl group, or an aryl group; $Q^1$ represents —N($R^2$)C(=O)—, —OC(=O)—, —C(=O)N($R^2$)—, —C(=O)O—, a group represented by the following formula (2), a group represented by the following formula (3), or a group represented by the following formula (4); $Q^2$ represents a divalent linking group; each of n1 and n2 independently represents 0 or 1; DyeVI represents a linking group having a structure formed by removing two hydrogen atoms from a partial structure represented by the following formula (5), wherein Dye in formula (5) is a dye structure formed by removing any one or two hydrogen atoms from a dipyrromethene metal complex compound obtained from a dipyrromethene compound represented by the following formula (7) or (8) and a metal or a metal compound; and $R^2$ represents a hydrogen atom, an alkyl group, an aryl group, or a heterocyclic group;

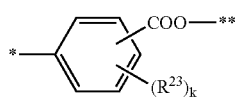

(2)

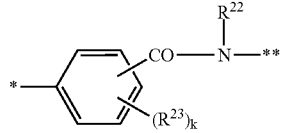

(3)

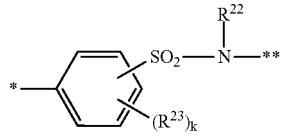

(4)

wherein in formulas (2) to (4), $R^{22}$ represents a hydrogen atom, an alkyl group, an aryl group, or a heterocyclic group; each of $R^{23}$ independently represents a hydrogen atom or a monovalent substituent group; k represents an integer from 0 to 4; when k is 2 or more, the two or more of $R^{23}$ may be the same or different from each other; * indicates a bonding site to the —C($R^{21}$)=CH$_2$ group in formula (1), and ** indicates a bonding site to $Q^2$ or Dye VI (when n2=0) in formula (1);

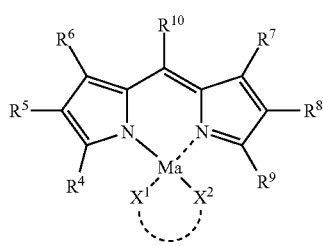

(7)

wherein in formula (7), each of $R^4$ to $R^9$ independently represents a hydrogen atom or a monovalent substituent group; $R^{10}$ represents a hydrogen atom, a halogen atom, an alkyl group, an aryl group, or a heterocyclic group; Ma represents a metal atom or a metal compound; $X^1$ represents a group capable of being bonded to Ma; $X^2$ represents a group that neutralizes a charge of Ma; $X^1$ and $X^2$ may be bonded to each other to form a 5-membered, 6-membered or 7-membered ring together with Ma; and $R^4$ and $R^9$ are not bonded to each other to form a ring;

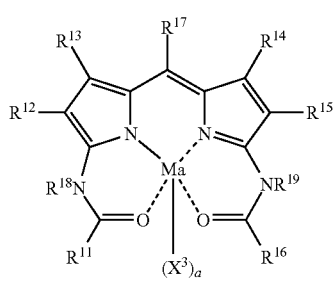

(8)

wherein in formula (8), each of $R^{11}$ and $R^{16}$ independently represents an alkyl group, an alkenyl group, an aryl group, a heterocyclic group, an alkoxy group, an aryloxy group, an alkylamino group, an arylamino group, or a heterocyclic amino group; each of $R^{12}$ to $R^{15}$ independently represents a hydrogen atom or a monovalent substituent group; $R^{17}$ represents a hydrogen atom, a halogen atom, an alkyl group, an aryl group, or a heterocyclic group; Ma represents a metal atom or a metal compound; each of $R^{18}$ and $R^{19}$ independently represents a hydrogen atom, an alkyl group, an alkenyl group, an aryl group, a heterocyclic group, an acyl group, an alkylsulfonyl group, or an arylsulfonyl group; $R^{11}$ and $R^{18}$ may be bonded to each other to form a 5-membered, 6-membered or 7-membered ring; $R^{16}$ and $R^{19}$ may be bonded to each other to form a 5-membered, 6-membered or 7-membered ring; $X^3$ represents a group capable of being bonded to Ma; and a represents 0, 1 or 2;

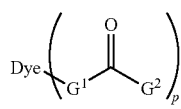

(5)

wherein in formula (5), Dye represents a dye structure; $G^1$ represents NR or an oxygen atom; $G^2$ represents a monovalent substituent group having an –Es' value as a steric parameter of 1.5 or more; p represents an integer from 1 to 8; when p is 2 or greater, the two or more structures represented by p may be the same or different from each other; and R represents a hydrogen atom or a monovalent substituent group.

<28> A substituted pyrrole compound represented by the following formula (V):

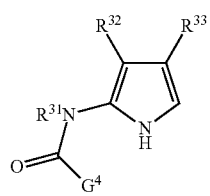

(V)

wherein in formula (V), $R^{31}$ represents a hydrogen atom, an alkyl group, an alkenyl group, an aryl group, a heterocyclic group, an acyl group, an alkylsulfonyl group, or an arylsulfonyl group; each of $R^{32}$ and $R^{33}$ independently represents a hydrogen atom or a monovalent substituent group; and $G^4$ represents a monovalent substituent group having an –Es' value as a steric parameter of 1.5 or more.

<29> A substituted pyrrole compound represented by the following formula (X):

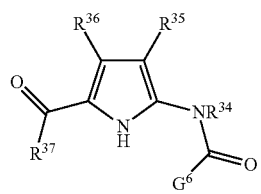

(X)

wherein in formula (X), $R^{34}$ represents a hydrogen atom, an alkyl group, an alkenyl group, an aryl group, a heterocyclic group, an acyl group, an alkylsulfonyl group, or an arylsulfonyl group; each of $R^{35}$ and $R^{36}$ independently represents a hydrogen atom or a monovalent substituent group; $R^{37}$ represents a hydrogen atom, a halogen atom, an alkyl group, an aryl group, or a heterocyclic group; and $G^6$ represents a monovalent substituent group having an –Es' value as a steric parameter of 1.5 or more.

<30> A colored curable composition comprising the dye compound according to any one of <1> to <19> and a polymerizable compound.

<31> A color filter formed from the colored curable composition according to <30>.

<32> A method of producing a color filter, the method comprising:
applying the colored curable composition according to <30> to a substrate;
exposing the colored curable composition to light via a mask; and
developing the exposed colored curable composition to form a pattern image.

<33> A solid-state image sensor comprising the color filter according to <31>.

<34> A liquid crystal display device comprising the color filter according to <31>.

Effect of the Invention

Since the dye compound according to the invention exhibits favorable heat fastness and color purity, the compound is effectively used as a colorant used for inkjet inks or as a colorant used in a sublimation thermal sensitive transfer method. Further, since the dye compound is superior in alkali resistance, a pixel pattern can be formed into a thin film (for example, 1 μm or less). Therefore, the dye compound is particularly effectively used as a dye for a colored composition for producing a color filter for a color separation filter of a solid-state image sensor that requires a high precision (for example, 0.5 to 2.0 μm) and a rectangular profile of a cross section.

According to the invention, it is possible to provide a dye compound that exhibits favorable heat fastness, alkali resistance and color purity.

Further, according to the invention, it is possible to provide a method of producing a dipyrromethene metal complex compound suitable as the dye compound, a method of producing a dye multimer including the dipyrromethene metal complex as a partial structure of the dye, and a novel substituted pyrrole compound suitably used for obtaining the dipyrromethene metal complex compound in the method.

Yet further, according to the invention, it is possible to provide a colored curable composition that exhibits favorable heat fastness, alkali resistance and color purity, a color filter having a colored pattern that exhibits favorable heat fastness and color purity even when it is formed into a thin film, a method of producing the color filter, and a solid-state image sensor including the color filter.

DETAILED DESCRIPTION OF THE INVENTION

In the following, the dye compound, the method of producing a dipyrromethene metal complex compound, the method of producing a dye multimer, the substituted pyrrole compound, the colored curable composition, the color filter, the method of producing a color filter, the solid-state image sensor, and the liquid crystal display device according to the invention are described in detail.

It should be noted that the description is based on the representative embodiments of the invention, but the invention is not limited to these embodiments.

In the present specification, the numerical range represented by "A to B" refers to a value that includes A and B as the upper and lower limits. Further, the term "alkyl group"

refers to an alkyl group having any structure of linear, branched or cyclic, and the alkyl group may be substituted or unsubstituted.

<Dye Compound>

The dye compound of the invention is a dye compound having a partial structure represented by formula (5) and at least one substituent group having a steric parameter (–Es' value) of 1.5 or more. In the invention, the steric parameter refers to a parameter that indicates the size of a substituent group, and the –Es' values described in the present specification are based on J. A. Macphee et al., Tetrahedron, Vol. 34, pp. 3553-3562, and Structural Activity Correlation and Drug Design, Chemistry extra edition, 107, Fujita Toshio Ed., published on Feb. 20, 1986 by Kagaku-Dojin Publishing Company, INC.

The dye compound of the invention is a dye compound which has a partial structure of formula (5) and at least one substituent group with a steric parameter (–Es' value) of 1.5 or more, preferably 2.0 or more, more preferably 3.0 or more, still more preferably 4.0 or more, and particularly preferably 5.0 or more.

The reason why heat fastness is improved is believed to be that dissociation of an amide bond or an ester bond in the dye compound is inhibited by a substituent group having a steric parameter (–Es' value) of 1.5 or more that is present in the vicinity of the amide bond or the ester bond.

The substituent group may be specified based on other steric parameters than the –Es' value, but the invention is not impaired thereby.

The following are specific examples of the substituent group having a steric parameter (–Es' value) of 1.5 or more, but the invention is not limited thereto.

TABLE 1

| Class | Substituent Structure | –Es' |
|---|---|---|
| Primary | (structure) | 1.63 |
| Secondary | (structure) | 1.81 |
|  | (structure) | 2.00 |
|  | (structure) | 2.00 |
|  | (structure) | 2.03 |
|  | (structure) | 2.03 |
|  | (structure) | 2.08 |
|  | (structure) | 2.38 |
|  | (structure) | 3.06 |
| Secondary | (structure) | 3.21 |
|  | (structure) | 3.23 |
|  | (structure) | 5.01 |
|  | (structure) | 6.53 |
|  | (structure) | 6.97 |
| Tertiary | (structure) | 2.28 |

TABLE 1-continued
| Class | Substituent Structure | —Es' |
|---|---|---|
| Tertiary | 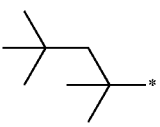 [SMILES: *C(C)(C)CC(C)(C)C] | 2.48 |
| | 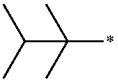 [SMILES: *C(C)(C)C(C)C] | 3.54 |
| | 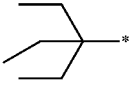 | 5.29 |
| | 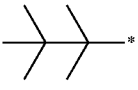 [SMILES: *C(C)(C)C(C)(C)C] | 5.40 |
| | 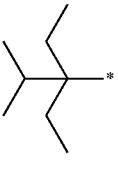 | 6.20 |
| | 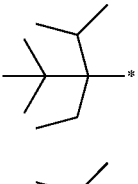 | 6.62 |
| | 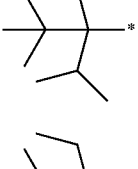 | 6.73 |
| | 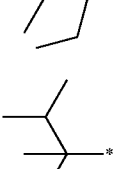 | 7.21 |
| | 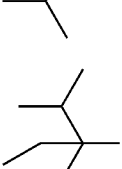 | 7.38 |
| | 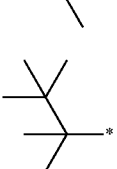 | 7.38 |
| | 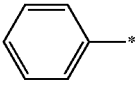 [SMILES: *c1ccccc1] | 7.56 |
TABLE 2
| Substituent Structure | —Es' |
|---|---|
| 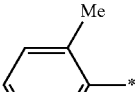 | 2.31 |
| 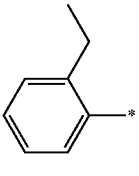 [SMILES: *c1ccccc1CC] | 2.82 |
| 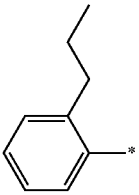 [SMILES: *c1ccccc1CCC] | 2.97 |
| 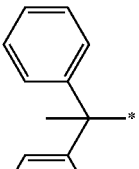 | 3.04 |
| 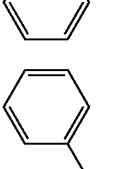 | 3.73 |
| 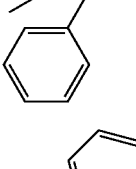 | 4.55 |
| 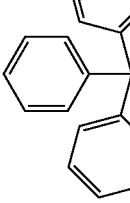 | 4.91 |

TABLE 2-continued

| Substituent Structure | —Es' |
|---|---|
| 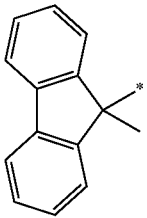 [SMILES: *C1(C)c2ccccc2-c2ccccc21] | 1.81 |
| 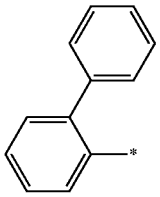 [SMILES: *c1ccccc1-c1ccccc1] | 3.01 |
| 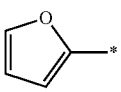 | 2.63 |
| 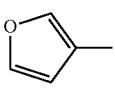 | 2.33 |
| 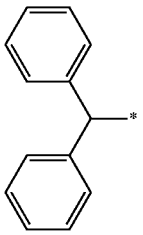 [SMILES: *C(c1ccccc1)c1ccccc1] | 1.50 |
| 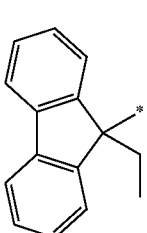 | 2.07 |
| 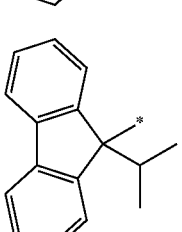 | 3.46 |
| 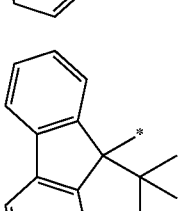 | 4.32 |
| 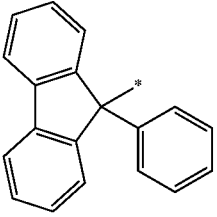 [SMILES: *C1(c2ccccc2)c2ccccc2-c2ccccc21] | 3.23 |

TABLE 3

| Substituent Structure | —Es' |
|---|---|
| 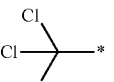 | 1.75 |
| 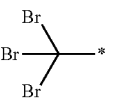 | 2.14 |
| 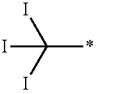 [SMILES: *C(I)(I)I] | 2.62 |
| 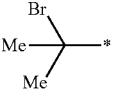 | 1.77 |
| 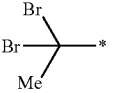 | 1.92 |
| 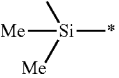 | 1.79 |
|  | 2.07 |
| 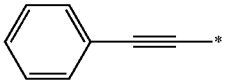 | 1.97 |

With regard to the substituent group $G^2$ in formula (5) of the dye compound of the invention, any hydrogen atom on the aforementioned substituent group having a –Es' value of 1.5 or more may be further substituted by a substituent group that may be arbitrarily selected.

The dye compound of the invention is a dye compound having a partial structure of formula (5).

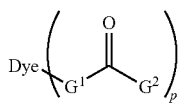

(5)

(In formula (5), Dye represents a dye structure, $G^1$ represents NR or an oxygen atom, and $G^2$ represents a monovalent substituent group having a steric parameter (−Es' value) of 1.5 or more. p represents 1 to 8, preferably 1 to 6, more preferably 1 to 4, and particularly preferably 1 to 2. When p is 2 or more, the two or more structures in the parenthesis (represented by p) may be the same or different from each other. R represents a hydrogen atom or a monovalent substituent group).

The dye compound is preferably a compound having, as a partial structure represented by formula (5), a partial structure represented by the following formula (11).

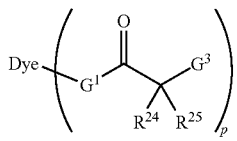

(11)

(In formula (11), Dye represents a dye structure, $G^1$ represents a nitrogen atom or an oxygen atom, $G^3$ represents a carbon atom, a sulfur atom, an oxygen atom, or a nitrogen atom, $R^{24}$ and $R^{25}$ each independently represent an alkyl group, an alkenyl group, an aryl group, or a heterocyclic group having two or more carbon atoms. p represents an integer from 1 to 8, and when p is 2 or more, the two or more structures in the parenthesis may be the same or different from each other).

The dye compound is more preferably a compound having, as a partial structure represented by formula (5), a partial structure of the following formula (6).

Formulas (5), (6) and (11) each represent a partial structure of the dye structure of the invention, and include a dye compound in which any hydrogen atom is substituted by an arbitrarily selected substituent group.

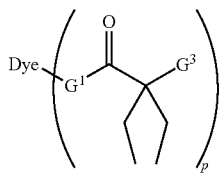

(6)

(In formula (6), Dye represents a dye structure, $G^1$ represents a nitrogen atom or an oxygen atom, $G^3$ represents a carbon atom, a sulfur atom, an oxygen atom, or a nitrogen atom. p represents 1 or 2, and when p is 2, the two or more structures in the parenthesis represented by p may be the same or different from each other).

The dye structure, represented by Dye, in the invention is not specifically limited, and various structures including known dye structures may be used. Examples of the known dye structures include an azo dye, an azomethine dye (for example, an indoaniline dye and an indophenol dye), a dipyrromethene dye, a quinone dye (for example, a benzoquinone dye, a naphthoquinone dye, an anthraquinone dye, and an anthrapyridone dye), a carbonium dye (for example, a diphenyl methane dye, a triphenyl methane dye, a xanthene dye, and an acridine dye), a quinonimine dye (for example, an oxazine dye and a thiazine dye), an azine dye, a polymethine dye (for example, an oxonol dye, a mellocyanine dye, an arylidene dye, a styryl dye and a cyanine dye, and among cyanine dyes, a squarylium dye and a croconium dye), a quinophthalone dye, a phthalocyanine dye, a perinone dye, an indigo dye, a thio indigo dye, a quinoline dye, a nitro dye, a nitroso dye and metal complex dyes thereof. Among these dyes, an azo dye, an azomethine dye, a dipyrromethene dye, a quinone dye (in particular, an anthraquinone dye), a carbonium dye (in particular, a xanthene dye), and a polymethine dye (in particular, a cyanine dye and an oxonol dye) are preferable, and an azo dye, a dipyrromethene dye, an azomethine dye and a polymethine dye are more preferable. In particular, a dipyrromethene dye is preferable. Specific compounds are described in, for example, "Dye Handbook—New Edition" (The Society of Synthetic Organic Chemistry, Japan edition; Maruzen Company, Limited, 1970), "Color Index" (The Society of Dyers and colorists), and "Dye Handbook" (Okawara and others; Kodansha Ltd., 1986).

The substitution site of these dyes for introducing a substituent group having a −Es' value of 1.5 or more may be arbitrarily selected. However, from the viewpoint of improving stability of spectral characteristics of the dye, the substituent group is preferably introduced into a site adjacent to a chromophore group or into a conjugation site. In particular, the substituent group is most preferably introduced into an auxochrome group which has a significant effect on a maximum absorption wavelength (λmax) or a molar absorption coefficient. Alternatively, the substituent group is most preferably introduced into a substituent group on an atom having large HOMO and LUMO coefficients calculated by a molecular orbital method, and in particular, on an atom having a large difference between the HOMO coefficient and the LUMO coefficient.

In the following, specific dyes that are suitably applied to the present technique are explained in detail.

<Dipyrromethene Compound>

The dye compound of the invention is preferably a dipyrromethene compound, or a dipyrromethene metal complex compound obtained from a dipyrromethene compound and a metal or a metal compound.

The dipyrromethene metal complex compound is preferably a dipyrromethene metal complex compound or a tautomer thereof, which are obtained from a dipyrromethene compound represented by the following formula (M) and a metal or a metal compound. Among them, a dye compound derived from a dipyrromethene metal complex compound represented by the following formula (7) or a dipyrromethene metal complex compound represented by the following formula (8).

[Dipyrromethene Metal Complex Compound Obtained from a Dipyrromethene Compound Represented by Formula (M) or a Tautomer Thereof and a Metal or a Metal Compound]

One preferred embodiment of the dye compound of the invention is a dye compound including, as a dye moiety, a complex formed from a dye compound represented by the following formula (M) (i.e., dipyrromethene compound) or a tautomer thereof and a metal or a metal compound (hereinbelow, also referred to as a "specific complex").

In the present specification, a compound including a dipyrromethene structure is referred to as a "dipyrromethene compound", and a complex formed from a compound including a dipyrromethene structure and a metal or a metal compound is referred to as a "dipyrromethene metal complex compound".

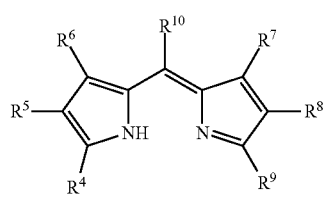
(M)

In formula (M), each of $R^4$ to $R^{10}$ independently represents a hydrogen atom or a monovalent substituent group, and at least one of $R^4$ to $R^{10}$ is linked to $G^1$ in formula (5). However, $R^4$ and $R^9$ are not bonded to each other to form a ring.

Examples of the monovalent substituent group represented by $R^4$ to $R^9$ in formula (M) include a halogen atom (for example, a fluorine atom, a chlorine atom, and a bromine atom), an alkyl group (a linear, branched, or cyclic alkyl group having preferably 1 to 48 carbon atoms, and more preferably 1 to 24 carbon atoms such as methyl, ethyl, propyl, isopropyl, butyl, t-butyl, pentyl, hexyl, heptyl, octyl, 2-ethylhexyl, dodecyl, hexadecyl, cyclopropyl, cyclopentyl, cyclohexyl, 1-norbornyl, or 1-adamantyl), an alkenyl group (an alkenyl group having preferably 2 to 48 carbon atoms, and more preferably 2 to 18 carbon atoms such as vinyl, aryl or 3-buten-1-yl), an aryl group (an aryl group having preferably 6 to 48 carbon atoms and more preferably 6 to 24 carbon atoms, such as phenyl or naphthyl), a heterocyclic group (a heterocyclic group having preferably 1 to 32 carbon atoms and more preferably 1 to 18 carbon atoms, such as 2-thienyl, 4-pyridyl, 2-furyl, 2-pyrimidinyl, 1-pyridyl, 2-benzothiazolyl, 1-imidazolyl, 1-pyrazolyl, benzotriazol-1-yl), a silyl group (a silyl group having preferably 3 to 38 carbon atoms and more preferably 3 to 18 carbon atoms, such as trimethylsilyl, triethylsilyl, tributylsilyl, t-butyldimethylsilyl, or t-hexyldimethylsilyl), a hydroxyl group, a cyano group, a nitro group, an alkoxy group (an alkoxy group having preferably 1 to 48 carbon atoms and more preferably 1 to 24 carbon atoms such as methoxy, ethoxy, 1-butoxy, 2-butoxy, isopropoxy, t-butoxy, dodecyloxy, or a cycloalkyloxy group, such as cyclopentyloxy and cyclohexyloxy), an aryloxy group (an aryloxy group having preferably 6 to 48 carbon atoms and more preferably 6 to 24 carbon atoms, such as phenoxy or 1-naphthoxy), a heterocyclic oxy group (a heterocyclic oxy group having preferably 1 to 32 carbon atoms and more preferably 1 to 18 carbon atoms, such as 1-phenyltetrazol-5-oxy and 2-tetrahydropyranyloxy), a silyloxy group (a silyloxy group having preferably 1 to 32 carbon atoms and more preferably 1 to 18 carbon atoms, such as trimethylsilyloxy, t-butyldimethylsilyloxy or diphenylmethylsilyloxy), an acyloxy group (an acyloxy group having preferably 2 to 48 carbon atoms and more preferably 2 to 24 carbon atoms, such as acetoxy, pivaloyloxy, benzoyloxy, or dodecanoyloxy), an alkoxy carbonyloxy group (an alkoxy carbonyloxy group having preferably 2 to 48 carbon atoms, and more preferably 2 to 24 carbon atoms, such as ethoxycarbonyloxy or t-butoxycarbonyloxy, or a cycloalkyloxycarbonyloxy group such as cyclohexyloxycarbonyloxy), an aryloxycarbonyloxy group (an aryloxycarbonyloxy group having preferably 7 to 32 carbon atoms, and more preferably 7 to 24 carbon atoms, such as phenoxycarbonyloxy), a carbamoyloxy group (a carbamoyloxy group having preferably 1 to 48 carbon atoms, and more preferably 1 to 24 carbon atoms, such as N,N-dimethylcarbamoyloxy, N-butylcarbamoyloxy, N-phenylcarbamoyloxy, or N-ethyl-N-phenylcarbamoyloxy), a sulfamoyloxy group (a sulfamoyloxy group having preferably 1 to 32 carbon atoms, and more preferably 1 to 24 carbon atoms, such as N,N-diethylsulfamoyloxy or N-propylsulfamoyloxy), an alkylsulfonyloxy group (an alkylsulfonyloxy group having preferably 1 to 38 carbon atoms, and more preferably 1 to 24 carbon atoms, such as methylsulfonyloxy, hexadecylsulfonyloxy, or cyclohexylsulfonyloxy), an arylsulfonyloxy group (an arylsulfonyloxy group having preferably 6 to 32 carbon atoms, and more preferably 6 to 24 carbon atoms, such as phenylsulfonyloxy), an acyl group (an acyl group having preferably 1 to 48 carbon atoms, and more preferably 1 to 24 carbon atoms, such as formyl, acetyl, pyvaloyl, benzoyl, tetradecanoyl or cyclohexanoyl), an alkoxycarbonyl group (an alkoxy carbonyl group having preferably 2 to 48 carbon atoms, and more preferably 2 to 24 carbon atoms, such as methoxycarbonyl, ethoxycarbonyl, octadecyloxycarbonyl, cyclohexyloxycarbonyl, or 2,6-di-tert-butyl-4-methylcyclohexyloxycarbonyl), an aryloxycarbonyl group (an aryloxycarbonyl group having preferably 7 to 32 carbon atoms, and more preferably 7 to 24 carbon atoms such as phenoxycarbonyl), a carbamoyl group (a carbamoyl group having preferably 1 to 48 carbon atoms, and more preferably 1 to 24 carbon atoms, such as carbamoyl, N,N-diethylcarbamoyl, N-ethyl-N-octylcarbamoyl, N,N-dibutylcarbamoyl, N-propylcarbamoyl, N-phenylcarbamoyl, N-methyl-N-phenylcarbamoyl, or N,N-dicyclohexylcarbamoyl), an amino group (an amino group having preferably 32 or less carbon atoms, and more preferably 24 or less carbon atoms, such as amino, methylamino, N,N-dibutylamino, tetradecylamino, 2-ethylhexylamino, or cyclohexylamino), an anilino group (an anilino group having preferably 6 to 32 carbon atoms, and more preferably 6 to 24, such as anilino or N-methylanilino), a heterocyclic amino group (a heterocyclic amino group having preferably 1 to 32 carbon atoms, and more preferably 1 to 18 carbon atoms such as 4-pyridylamino), a carbonamido group (a carbonamido group having preferably 2 to 48 carbon atoms, and more preferably 2 to 24 carbon atoms, such as acetamido, benzamide, tetradecaneamido, pivaloylamido, or cyclohexaneamido), a ureido group (a ureido group having preferably 1 to 32 carbon atoms, and more preferably 1 to 24 carbon atoms, such as ureido, N,N-dimethylureido, or N-phenylureido), an imido group (an imido group having preferably 36 or less carbon atoms, and more preferably 24 or less carbon atoms, such as N-succinimido or N-phthalimido), an alkoxy carbonylamino group (an alkoxy carbonylamino group having preferably 2 to 48 carbon atoms, and more preferably 2 to 24 carbon atoms, such as methoxycarbonylamino, ethoxycarbonylamino, t-butoxycarbonylamino, octadecyloxycarbonylamino, or cyclohexyloxycarbonylamino), an aryloxycarbonylamino group (an aryloxycarbonylamino group having preferably 7 to 32 carbon atoms, and more preferably 7 to 24 carbon atoms such as phenoxycarbonylamino), a sulfonamido group (a sulfonamido group having preferably 1 to 48 carbon atoms, and more preferably 1 to 24 carbon atoms, such as methane sulfonamide, butane sulfonamide, benzene sulfonamide, hexadecane sulfonamide, or cyclohexane sulfonamide), a sulfamoylamino group (a sulfamoylamino group having preferably 1 to 48 carbon atoms, and more preferably 1 to 24 carbon atoms, such as N,N-dipropylsulfamoylamino or N-ethyl-N-dodecylsulfamoylamino), an azo group (an azo group having preferably 1 to 32 carbon atoms, and more preferably 1 to 24 carbon atoms, such as phenylazo or 3-pyrazolylazo), an alkylthio group (an alkylthio group having preferably 1 to 48 carbon atoms, and more preferably 1 to 24 carbon atoms, such as methylthio, ethylthio, octylthio, or cyclohexylthio), an arylthio group (an arylthio group having preferably 6 to 48 carbon atoms, and more preferably 6 to 24 carbon atoms such as phenylthio), a heterocyclic thio group (a heterocyclic thio group having preferably 1 to 32 carbon atoms, and more preferably 1 to 18 carbon atoms, such as 2-benzothiazolylthio, 2-pyridylthio, or 1-phenyltetrazolylthio), an alkylsulfinyl group (an alkylsulfinyl group having preferably 1 to 32 carbon atoms, and more preferably 1 to 24 carbon atoms such as dodecane sulfinyl), an arylsulfinyl group (an arylsulfinyl group having preferably 6 to 32 carbon atoms, and more preferably 6 to 24 carbon atoms such as phenylsulfinyl), an alkylsulfonyl group (an alkylsulfonyl group having preferably 1 to 48 carbon atoms, and more preferably 1 to 24 carbon atoms, such as methylsulfonyl, ethylsulfonyl, propylsulfonyl, butylsulfonyl, isopropylsulfonyl, 2-ethylhexylsulfonyl, hexadecylsulfonyl, octylsulfonyl, or cyclohexylsulfonyl), an arylsulfonyl group (an arylsulfonyl group having preferably 6 to 48 carbon atoms, and more preferably 6 to 24 carbon atoms such as phenylsulfonyl or 1-naphthylsulfonyl), a sulfamoyl group (a sulfamoyl group having preferably 32 or less carbon atoms, and more preferably 24 or less carbon atoms, such as sulfamoyl, N,N-dipropylsulfamoyl, N-ethyl-N-dodecylsulfamoyl, N-ethyl-N-phenylsulfamoyl, or N-cyclohexylsulfamoyl), a sulfo group, a phosphonyl group (a phosphonyl group having preferably 1 to 32 carbon atoms, and more preferably 1 to 24 carbon atoms, such as phenoxyphosphonyl, octyloxyphosphonyl, or phenylphosphonyl), a phosphinoylamino group (a phosphinoylamino group having preferably 1 to 32 carbon atoms, and more preferably 1 to 24 carbon atoms such as diethoxyphosphinoylamino or dioctyloxyphosphinoylamino).

When the monovalent substituent group represented by $R^4$ to $R^9$ in formula (M) can be further substituted, the substituent group may have a substituent group such as those explained with regard to $R^4$ to $R^9$, and when there are two or more substituent groups, they may be the same or different from each other.

Each pair of $R^4$ and $R^5$, $R^5$ and $R^6$, $R^7$ and $R^8$, and $R^8$ and $R^9$ in formula (M) may independently be bonded to each other to form a 5-membered, 6-membered, or 7-membered saturated or unsaturated ring. When the 5-membered, 6-membered or 7-membered ring can be further substituted, the ring may have a substituent group such as those explained with regard to $R^4$ to $R^9$, and when there are two or more substituent groups, they may be the same or different from each other.

When $R^4$ and $R^5$, $R^5$ and $R^6$, $R^7$ and $R^8$ or $R^8$ and $R^9$ in formula (M) are bonded to each other to form a 5-membered, 6-membered or 7-membered saturated or unsaturated ring, examples thereof include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring, and a pyridazine ring. Among these, a benzene ring and a pyridine ring are preferred.

$R^{10}$ in formula (M) preferably represents a hydrogen atom, a halogen atom, an alkyl group, an aryl group, or a heterocyclic group, and definitions and preferred ranges of the halogen atom, alkyl group, aryl group and heterocyclic group are the same as that of the substituent groups explained with respect to $R^4$ to $R^9$, respectively.

When $R^{10}$ represents an alkyl group, an aryl group, or a heterocyclic group and these substituent groups can be substituted, the alkyl group, aryl group, heterocyclic group may be substituted by a substituent group explained with respect to the monovalent substituent group represented by $R^4$ to $R^9$. When there are two or more substituent groups, they may be the same or different from each other.

—Metal or Metal Compound—

The specific complex of the invention is a complex formed from a compound represented by formula (M) or a tautomer thereof and a metal or a metal compound.

The metal or the metal compound may be any kind of a metal or a metal compound that can form a complex, and examples thereof include a divalent metal atom, a divalent metal oxide, a divalent metal hydroxide, and a divalent metal chloride. Examples of the metal or the metal compound include Zn, Mg, Si, Sn, Rh, Pt, Pd, Mo, Mn, Pb, Cu, Ni, Co and Fe, metal chlorides such as AlCl, InCl, FeCl, $TiCl_2$, $SnCl_2$, $SiCl_2$ and $GeCl_2$, metal oxides such as TiO and VO, and metal hydroxides such as $Si(OH)_2$.

Among these, from the viewpoint of stability, spectral characteristics, heat fastness, light fastness or production suitability of a complex, Fe, Zn, Mg, Si, Pt, Pd, Mo, Mn, Cu, Ni, Co, TiO and VO are preferable, Zn, Mg, Si, Pt, Pd, Cu, Ni, Co and VO are more preferable, and Zn is most preferable.

Next, more preferred examples of the specific complex of the invention represented by formula (M) are explained.

In the more preferred examples of the specific complex of the invention, in formula (M), $R^4$ and $R^9$ each independently represent a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxy carbonyl group, a carbamoyl group, an amino group, an anilino group, a heterocyclic amino group, a carbonamido group, a ureido group, an imido group, an alkoxycarbonylamino group, an aryloxycarbonylamino group, a sulfonamido group, an azo group, an alkylthio group, an arylthio group, a heterocyclic thio group, an alkylsulfonyl group, an arylsulfonyl group, or a phosphinoylamino group; $R^5$ and $R^8$ each independently represent a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imido group, an alkoxycarbonylamino group, a sulfonamido group, an azo group, an alkylthio group, an arylthio group, a heterocyclic thio group, an alkylsulfonyl group, an arylsulfonyl group, or a sulfamoyl group; $R^6$ and $R^7$ each independently represent a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamido group, a ureido group, an imido group, an alkoxycarbonylamino group, a sulfonamido group, an azo group, an alkylthio group, an arylthio group, a heterocyclic thio group, an alkylsulfonyl group, an arylsulfonyl group, a sulfamoyl group, or a phosphinoylamino group; $R^{10}$ represents a hydrogen atom, a halogen atom, an alkyl group, an aryl group, or a heterocyclic group; and the metal or the metal compound is Zn, Mg, Si, Pt, Pd, Mo, Mn, Cu, Ni, Co, TiO, or V=O.

In the still more preferred examples of the specific complex of the invention, in formula (M), $R^4$ and $R^9$ each independently represent a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamido group, a ureido group, an imido group, an alkoxycarbonylamino group, an aryloxycarbonylamino group, a sulfonamido group, an azo group, an alkylsulfonyl group, an arylsulfonyl group, or a phosphinoylamino group; $R^5$ and $R^8$ each independently represent an alkyl group, an alkenyl group, an aryl group, a heterocyclic group, a cyano group, a nitro group, an acyl group, an alkoxycarbonyl group, an aryloxycarbonyl group, a carbamoyl group, an imido group, an alkylsulfonyl group, an arylsulfonyl group, or a sulfamoyl group; $R^6$ and $R^7$ each independently represent a hydrogen atom, an alkyl group, an alkenyl group, an aryl group, a heterocyclic group, a cyano group, an acyl group, an alkoxycarbonyl group, a carbamoyl group, a carbonamido group, a ureido group, an imido group, an alkoxycarbonylamino group, a sulfonamido group, an alkylthio group, an arylthio group, a heterocyclic thio group, an alkylsulfonyl group, an arylsulfonyl group, or a sulfamoyl group; $R^{10}$ represents a hydrogen atom, a halogen atom, an alkyl group, an aryl group, or a heterocyclic group; and the metal or the metal compound is Zn, Mg, Si, Pt, Pd, Cu, Ni, Co, or V=O.

In the particularly preferred examples of the specific complex of the invention, in formula (M), $R^4$ and $R^9$ each independently represent a hydrogen atom, an alkyl group, an aryl group, a heterocyclic group, an amino group, a heterocyclic amino group, a carbonamido group, a ureido group, an imido group, an alkoxycarbonylamino group, a sulfonamido group, an azo group, an alkylsulfonyl group, an arylsulfonyl group, or a phosphinoylamino group; $R^5$ and $R^8$ each independently represent an alkyl group, an aryl group, a heterocyclic group, a cyano group, an acyl group, an alkoxycarbonyl group, a carbamoyl group, an alkylsulfonyl group, or an arylsulfonyl group; $R^6$ and $R^7$ each independently represent a hydrogen atom, an alkyl group, an aryl group, or a heterocyclic group; $R^{10}$ represents a hydrogen atom, an alkyl group, an aryl group, or a heterocyclic group; and the metal or the metal compound is Zn, Cu, Co, or V=O.

Further, embodiments represented by the following formula (7) or the following formula (8) are also particularly preferred.

[Dipyrromethene Metal Complex Compound Represented by Formula (7)]

One embodiment of the dye compound of the invention is a dipyrromethene metal complex compound represented by the following formula (7).

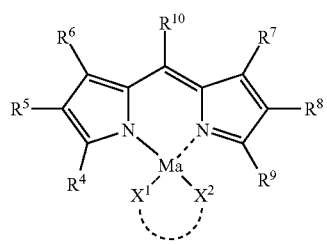

(7)

In formula (7), $R^4$ to $R^9$ each independently represent a hydrogen atom or a substituent group, $R^{10}$ represents a hydrogen atom, a halogen atom, an alkyl group, an aryl group, or a heterocyclic group. Ma represents a metal atom or a metal compound. $X^1$ represents a group capable of being bonded to Ma, $X^2$ represents a group that neutralizes a charge of Ma, $X^1$ and $X^2$ may be bonded to each other to form a 5-membered, 6-membered or 7-membered ring together with Ma, and $R^4$ and $R^9$ are not bonded to each other to form a ring.

The dipyrromethene metal complex compound represented by formula (7) includes a tautomer.

When the dipyrromethene metal complex compound represented by formula (7) is introduced into a structural unit represented by formula (A) to formula (C), which will be explained later, a multimer represented by formula (D), or a monomer represented by formula (1), the site for introduction is not specifically limited. However, from the viewpoint of synthesis suitability, the dipyrromethene metal complex compound is preferably introduced at any one of $R^4$ to $R^9$, more preferably at any one of $R^4$, $R^6$, $R^7$ and $R^9$, still more preferably $R^4$ or $R^9$.

With regard to a method of introducing an alkali soluble group into the dye compound of the invention, an alkali soluble group may be introduced into at least one substituent group of $R^4$ to $R^{10}$, $X^1$ and $X^2$ of the dipyrromethene metal complex compound represented by formula (7). Among these substituent groups, any one of $R^4$ to $R^9$ and $X^1$ is preferable, more preferably any one of $R^4$, $R^6$, $R^7$ and $R^9$, still more preferably $R^4$ or $R^9$.

The dipyrromethene metal complex compound represented by formula (7) may have a functional group other than an alkali soluble group, as long as the effect of the invention is not impaired.

$R^4$ to $R^9$ in formula (7) have the same definitions as $R^4$ to $R^9$ in formula (M), respectively, and preferred embodiments thereof are also the same.

In formula (7), Ma represents a metal atom or a metal compound. The metal atom or the metal compound may be any metal atom or any metal compound as long as it can form a complex, and examples thereof include a divalent metal atom, a divalent metal oxide, a divalent metal hydroxide, and a divalent metal chloride.

Specific examples include Zn, Mg, Si, Sn, Rh, Pt, Pd, Mo, Mn, Pb, Cu, Ni, Co, and Fe, metal chlorides such as AlCl, InCl, FeCl, TiCl$_2$, SnCl$_2$, SiCl$_2$, and GeCl$_2$, metal oxides such as TiO and VO, and metal hydroxides such as Si(OH)$_2$.

Among these, from the viewpoint of stability, spectral characteristics, heat resistance, light resistance or production suitability the complex, the metal or the metal complex is preferably Fe, Zn, Mg, Si, Pt, Pd, Mo, Mn, Cu, Ni, Co, TiO or V=O, more preferably Zn, Mg, Si, Pt, Pd, Cu, Ni, Co or V=O, particularly preferably Zn, Co, V=O or Cu, most preferably Zn.

In formula (7), $R^{10}$ represents a hydrogen atom, a halogen atom, an alkyl group, an aryl group, or a heterocyclic group, preferably a hydrogen atom.

In formula (7), $X^1$ may be any group as long as it can be bonded to Ma. Specific examples thereof include water, alcohols (for example, methanol, ethanol and propanol) and the compounds described in "Metal Chelates" ([1] written by Sakaguchi Takeichi, Ueno Keihei (1995, Nankodo Co., Ltd.), [2] (1996) and [3] (1997), etc.). Among these, from the viewpoint of producibility, water, carboxylic acid compounds and alcohols are preferable, and water and carboxylic compounds are more preferable.

In formula (7), examples of the "group that neutralizes a charge of Ma" represented by $X^2$ include a halogen atom, a hydroxyl group, a carboxylic acid group, a phosphoric acid group, and a sulfonic acid group. Among these, from the viewpoint of producibility, a halogen atom, a hydroxyl group, a carboxylic acid group, and a sulfonic acid group are preferable, and a hydroxyl group and a carboxylic acid group are more preferable.

In formula (7), $X^1$ and $X^2$ may be bonded to each other to form a 5-membered, 6-membered or 7-membered ring together with Ma. The 5-membered, 6-membered or 7-membered ring may be a saturated ring or an unsaturated ring. The 5-membered, 6-membered or 7-membered ring may consist entirely of carbon atoms, or may form a heterocycle including at least one selected from a nitrogen atom, an oxygen atom and/or a sulfur atom.

In a preferred embodiment of the compound represented by formula (7), $R^4$ to $R^9$ each independently are selected from the preferred embodiments as mentioned above, $R^{10}$ is selected from the preferred embodiments as mentioned above, Ma is Zn, Cu, Co, or V=O, $X^1$ is water or a carboxylic acid compound, $X^2$ is a hydroxyl group or a carboxylic acid group, and $X^1$ and $X^2$ may be bonded to each other to form a 5-membered or 6-membered ring.

[Dipyrromethene Metal Complex Compound Represented by Formula (8)]

One embodiment of the dye compound of invention is a dipyrromethene metal complex compound represented by the following formula (8).

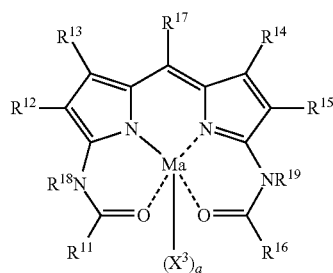

(8)

In formula (8), $R^{11}$ and $R^{16}$ each independently represent an alkyl group, an alkenyl group, an aryl group, a heterocyclic group, an alkoxy group, an aryloxy group, an alkylamino group, an arylamino group, or a heterocyclic amino group. $R^{12}$ to $R^{15}$ each independently represent a hydrogen atom or a monovalent substituent group. $R^{17}$ represents a hydrogen atom, a halogen atom, an alkyl group, an aryl group, or a heterocyclic group. Ma represents a metal atom or a metal compound. $R^{18}$ and $R^{19}$ each independently represent a hydrogen atom, an alkyl group, an alkenyl group, an aryl group, a heterocyclic group, an acyl group, an alkylsulfonyl group, or an arylsulfonyl group. $R^{11}$ and $R^{18}$ may be bonded to each other to form a 5-membered, 6-membered or 7-membered ring, and $R^{16}$ and $R^{19}$ may be bonded to each other to form a 5-membered, 6-membered or 7-membered ring. $X^3$ represents a group capable of being bonded to Ma, and a represents 0, 1 or 2. The dipyrromethene metal complex compound represented by formula (8) includes a tautomer.

The site at which the dipyrromethene metal complex compound represented by formula (8) is introduced into a dye multimer (explained later) is not specifically limited, as long as the effect of the invention is not impaired. However, the site is preferably any one of $R^{11}$ to $R^{16}$, $X^3$ and $R^{18}$ to $R^{19}$. Among these, from the viewpoint of synthesis suitability, the site for introduction is preferably introduced at any one of $R^{11}$ to $R^{16}$ and $X^3$, more preferably at any one of $R^{11}$, $R^{13}$, $R^{14}$ and $R^{16}$, still more preferably at $R^{11}$ or $R^{16}$.

In a method of introducing an alkali soluble group to the dye compound of the invention, when a dye monomer or a structural unit having an alkali soluble group is used, one or more substituent groups selected from $R^{11}$ to $R^{17}$, $X^3$ and $R^{18}$ to $R^{19}$ of the dipyrromethene metal complex compound represented by formula (8) may have an alkali soluble group. Among these substituent groups, any one of $R^{11}$ to $R^{16}$ and $X^3$ is preferable, any one of $R^{11}$, $R^{13}$, $R^{14}$ and $R^{16}$ is more preferable, and any one of $R^{11}$ and $R^{16}$ is still more preferable.

The dipyrromethene metal complex compound represented by formula (8) may have a functional group other than an alkali soluble group, as long as the effect of the invention is not impaired.

Definitions of $R^{12}$ to $R^{15}$ are the same as that of $R^5$ to $R^8$ in formula (M), respectively, and preferred embodiments thereof are also the same. Definitions of $R^{17}$ are the same as that of $R^{10}$ in formula (M), and preferred embodiments thereof are also the same. Definitions of Ma are the same as that of Ma in formula (7), and preferred embodiments thereof are also the same.

More specifically, $R^{12}$ to $R^{15}$ in formula (8) are preferably an alkoxycarbonyl group, an aryloxycarbonyl group, a carbamoyl group, an alkylsulfonyl group, an arylsulfonyl group, a nitrile group, an imido group, or a carbamoylsulfonyl group; more preferably an alkoxycarbonyl group, an aryloxycarbonyl group, a carbamoyl group, an alkylsulfonyl group, a nitrile group, an imido group, or a carbamoylsulfonyl group; still more preferably an alkoxycarbonyl group, an aryloxycarbonyl group, a carbamoyl group, a nitrile group, an imido group, or a carbamoylsulfonyl group; and particularly preferably an alkoxycarbonyl group, an aryloxycarbonyl group, or a carbamoyl group.

$R^{13}$ and $R^{14}$ are preferably a substituted or unsubstituted alkyl group, a substituted or unsubstituted aryl group, or a substituted or unsubstituted heterocyclic group; more preferably a substituted or unsubstituted alkyl group or a substituted or unsubstituted aryl group. Specific examples of the more preferred alkyl group, aryl group and heterocyclic group include the specific examples of $R^6$ and $R^7$ in formula (M).

In formula (8), $R^{11}$ and $R^{16}$ each independently represent an alkyl group (a linear, branched, or cyclic alkyl group having preferably 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl, 1-adamantyl, or triethylmethyl), an alkenyl group (an alkenyl group having preferably 2 to 24 carbon atoms, more preferably 2 to 12 carbon atoms, such as vinyl, aryl, or 3-buten-1-yl), an aryl group (an aryl group having preferably 6 to 36 carbon atoms, more preferably 6 to 18 carbon atoms, such as phenyl, naphthyl, or o-tolyl), a heterocyclic group (a heterocyclic group having preferably 1 to 24 carbon atoms, more preferably 1 to 12 carbon atoms, such as 2-thienyl, 4-pyridyl, 2-furyl, 2-pyrimidinyl, 2-pyridyl, 2-benzothiazolyl, 1-imidazolyl, 1-pyrazolyl, or benzotriazol-1-yl), an alkoxy group (an alkoxy group having preferably 1 to 36 carbon atoms, more preferably 1 to 18 carbon atoms, such as methoxy, ethoxy, propyloxy, butoxy, hexyloxy, 2-ethylhexyloxy, dodecyloxy, or cyclohexyloxy), an aryloxy group (an aryloxy group having preferably 6 to 24 carbon atoms, more preferably 1 to 18 carbon atoms, such as phenoxy or naphthyloxy), an alkylamino group (an alkylamino group having preferably 1 to 36 carbon atoms, more preferably 1 to 18 carbon atoms, such as methylamino, ethylamino, propylamino, butylamino, hexylamino, 2-ethylhexylamino, isopropylamino, t-butylamino, t-octylamino, cyclohexylamino, N,N-diethylamino, N,N-dipropylamino, N,N-dibutylamino, or N-methyl-N-ethylamino), an arylamino group (an arylamino group having preferably 6 to 36 carbon atoms, more preferably 6 to 18 carbon atoms, such as phenylamino, naphthylamino, N,N-diphenylamino, or N-ethyl-N-phenylamino), or a heterocyclic amino group (a heterocyclic amino group having preferably 1 to 24 carbon atoms, more preferably 1 to 12 carbon atoms, such as 2-aminopyrrole, 3-aminopyrazole, 2-aminopyridine, or 3-aminopyridine).

Among these, $R^{11}$ and $R^{16}$ are preferably an alkyl group, an alkenyl group, an aryl group, a heterocyclic group, an alkylamino group, an arylamino group, or a heterocyclic amino group; more preferably an alkyl group, an alkenyl group, an aryl group, or a heterocyclic group; still more preferably an alkyl group, an alkenyl group, or an aryl group; and particularly preferably an alkyl group.

In formula (8), $R^{18}$ and $R^{19}$ each independently represent a hydrogen atom, an alkyl group (a linear, branched, or cyclic alkyl group having preferably 1 to 36 carbon atoms, more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl, or 1-adamantyl), an alkenyl group (an alkenyl group having preferably 2 to 24 carbon atoms, more preferably 2 to 12 carbon atoms, such as vinyl, aryl, or 3-buten-1-yl), an aryl group (an aryl group having preferably 6 to 36 carbon atoms, more preferably 6 to 18 carbon atoms, such as phenyl or naphthyl), a heterocyclic group (a heterocyclic group having preferably 1 to 24 carbon atoms, more preferably 1 to 12 carbon atoms, such as 2-thienyl, 4-pyridyl, 2-furyl, 2-pyrimidinyl, 2-pyridyl, 2-benzothiazolyl, 1-imidazolyl, 1-pyrazolyl, or benzotriazol-1-yl), an acyl group (an acyl group having preferably 1 to 24 carbon atoms, more preferably 2 to 18 carbon atoms, such as acetyl, pivaloyl, 2-ethylhexyl, benzoyl, or cyclohexanoyl), an alkylsulfonyl group (an alkylsulfonyl group having preferably 1 to 24 carbon atoms, more preferably 1 to 18 carbon atoms, such as methylsulfonyl, ethylsulfonyl, isopropylsulfonyl, or cyclohexylsulfonyl), an arylsulfonyl group (an arylsulfonyl group having preferably 6 to 24 carbon atoms, more preferably 6 to 18 carbon atoms, such as phenylsulfonyl or naphthylsulfonyl).

Among these, $R^{18}$ and $R^{19}$ are preferably a hydrogen atom, an alkyl group, an alkenyl group, an aryl group, or a heterocyclic group, more preferably a hydrogen atom or an alkyl group, and particularly preferably a hydrogen atom, respectively.

In formula (8), $R^{11}$ and $R^{18}$ may be bonded to each other to form a 5-membered ring (for example, cyclopentane, pyrrolidine, tetrahydrofuran, dioxolan, tetrahydrothiophene, pyrrole, furan, thiophene, indole, benzofuran, and benzothiophene), a 6-membered ring (for example, cyclohexane, piperidine, piperazine, morpholine, tetrahydropyran, dioxane, pentamethylene sulfide, dithiane, benzene, piperidine, piperazine, pyridazine, quinoline, and quinazoline), or a 7-membered ring (for example, cycloheptane and hexamethylene imine), together with carbon atoms.

In formula (8), $R^{16}$ and $R^{19}$ may be bonded to each other to form a 5-membered ring (for example, cyclopentane, pyrrolidine, tetrahydrofuran, dioxolan, tetrahydrothiophene, pyrrole, furan, thiophene, indole, benzofuran, and benzothiophene), a 6-membered ring (for example, cyclohexane, piperidine, piperazine, morpholine, tetrahydropyran, dioxane, pentamethylene sulfide, dithiane, benzene, piperidine, piperazine, pyridazine, quinoline, and quinazoline), or a 7-membered ring (for example, cycloheptane and hexamethylene imine), together with carbon atoms.

In formula (8), each of $R^{11}$ and $R^{16}$ preferably independently represents a monovalent substituent group having a steric parameter (−Es' value) of 1.5 or more, more preferably 2.0 or more, still more preferably 3.5 or more, and particularly preferably 5.0 or more.

Examples of the group represented by $X^3$ that can be bonded to Ma in formula (8) include a halogen atom, a hydroxyl group, a carboxylic acid group, a phosphoric acid group, a sulfonic acid group, and the compounds described in "Metal Chelates" ([1] written by Sakaguchi Takeichi, Ueno Keihei (1995, Nankodo Co., Ltd.), [2] (1996), and [3] (1997), etc.)

Among these, from the viewpoint of producibility, a halogen atom, a hydroxyl group, a carboxylic acid group, and a sulfonic acid group are preferable, and a halogen atom, a hydroxyl group and a carboxylic acid group are more preferable. a represents 0, 1 or 2, and when a is 2, the two of $X^3$ may have the same structure or different structures from each other.

In the preferred embodiments of the compound represented by formula (8), definitions of $R^{12}$ to $R^{15}$ are each independently the same as that of $R^5$ to $R^8$ in formula (M), definitions of $R^{17}$ are the same as that of $R^{10}$ in formula (M), Ma is Zn, Cu, Co or V=O, $R^{18}$ and $R^{19}$ each independently represent a hydrogen atom or an alkyl group, $R^{11}$ and $R^{16}$ each independently represent an alkyl group, an alkenyl group or an aryl group having an −Es' value of 2.0 or more, $X^3$ is a group bonded to Ma via an oxygen atom, and a is 0 or 1. $R^{11}$ and $R^{18}$ may be bonded to each other to form a 5-membered or 6-membered ring, or $R^{16}$ and $R^{19}$ may be bonded to each other to form a 5-membered or 6-membered ring.

In the more preferred embodiments of the compound represented by formula (8), definitions of $R^{12}$ to $R^{15}$ each independently are the same as the preferred embodiments of $R^5$ to $R^8$ in formula (M), definitions of $R^{17}$ are the same as the preferred embodiments of $R^{10}$ in formula (M), Ma is Zn, $R^{18}$ and $R^{19}$ each independently represent a hydrogen atom or an alkyl group, $R^{11}$ and $R^{16}$ each independently represent an alkyl group, an alkenyl group or an aryl group having an −Es' value of 3.5 or more, $X^1$ is a group bonded to Ma via an oxygen atom, and a is 0 or 1. $R^{11}$ and $R^{18}$ may be bonded to each other to form a 5-membered or 6-membered ring, or $R^{16}$ and $R^{19}$ may be bonded to form a 5-membered or 6-membered ring.

From the viewpoint of the coloring ability, the molar absorption coefficient of the dipyrromethene metal complex compound represented by formula (7) or formula (8) is preferably as high as possible. Further, from the viewpoint of improving the color purity, the maximum absorption wavelength (λmax) is preferably from 520 nm to 580 nm, more preferably from 530 nm to 570 nm. When a dipyrromethene metal complex compound having a maximum absorption wavelength within this range is used in a colored curable composition, a color filter that exhibits favorable color reproducibility may be produced.

Further, the dipyrromethene metal complex compound preferably has a molar absorption coefficient at a maximum absorption wavelength (λmax) of at least 1,000 times as great as a molar absorption coefficient at 450 nm, more preferably at least 10,000 times, further preferably at least 100,000 times. When a dipyrromethene metal complex compound satisfying the relationship of molar absorption coefficient is used in a colored curable composition, a color filter (in particular, a blue color filter) that exhibits even higher transmittance may be produced.

The maximum absorption wavelength and the molar absorption coefficient descried in the present specification are measured with a spectrophotometer (CARY5, trade name, manufactured by Varian Inc.)

From the viewpoint of solubility, the melting point of the dipyrromethene metal complex compound represented by formula (7) or formula (8) is preferably not too high.

The dipyrromethene metal complex compound represented by formula (7) or formula (8) may be synthesized according to the method described in U.S. Pat. Nos. 4,774, 339 and 5,433,896, JP-A Nos. 2001-240761 and 2002-

155052, Japanese Patent No. 3614586, Aust. J. Chem, 1965, 11, 1835-1845, and J. H. Boger et al, Heteroatom Chemistry, Vol. 1, No. 5, 389 (1990). Specifically, for example, the method described in paragraphs [0131] to [0157] of JP-A No. 2008-292970 may be used in the invention.

The following are specific examples of the dipyrromethene metal complex compound of the invention. However, the invention is not limited to these examples.

| Exemplary Compound | R11 | R12 | R13 | R14 | R15 | R16 | X |
|---|---|---|---|---|---|---|---|
| M-1 | C(Et)3 | 4-methyl-2,6-di-t-Bu-phenyl ester | i-Pr | i-Pr | 4-methyl-2,6-di-t-Bu-phenyl ester | C(Et)3 | —OC(O)CH3 |
| M-2 | C(Et)3 | 4-methyl-2,6-di-t-Bu-phenyl ester | i-Pr | i-Pr | 4-methyl-2,6-di-t-Bu-phenyl ester | C(Et)3 | —Cl |
| M-3 | C(Et)3 | 4-methyl-2,6-di-t-Bu-phenyl ester | i-Pr | i-Pr | 4-methyl-2,6-di-t-Bu-phenyl ester | C(Et)3 | —F |
| M-4 | C(Et)3 | 4-methyl-2,6-di-t-Bu-phenyl ester | i-Pr | i-Pr | 4-methyl-2,6-di-t-Bu-phenyl ester | C(Et)3 | —Br |

-continued

| Exemplary Compound | R¹¹ | R¹² | R¹³ | R¹⁴ | R¹⁵ | R¹⁶ | X |
|---|---|---|---|---|---|---|---|
| M-5 | C(Et)₃ | 4-methyl-2,6-di-t-Bu-cyclohexyl ester | i-Pr | i-Pr | 4-methyl-2,6-di-t-Bu-cyclohexyl ester | C(Et)₃ | —BF₄ |
| M-6 | C(Et)₃ | 4-methyl-2,6-di-t-Bu-cyclohexyl ester | i-Pr | i-Pr | 4-methyl-2,6-di-t-Bu-cyclohexyl ester | C(Et)₃ | —PF₆ |
| M-7 | C(Et)₃ | 4-methyl-2,6-di-t-Bu-cyclohexyl ester | i-Pr | i-Pr | 4-methyl-2,6-di-t-Bu-cyclohexyl ester | C(Et)₃ | lactate |
| M-8 | C(Et)₃ | 4-methyl-2,6-di-t-Bu-cyclohexyl ester | i-Pr | i-Pr | 4-methyl-2,6-di-t-Bu-cyclohexyl ester | C(Et)₃ | benzoate |

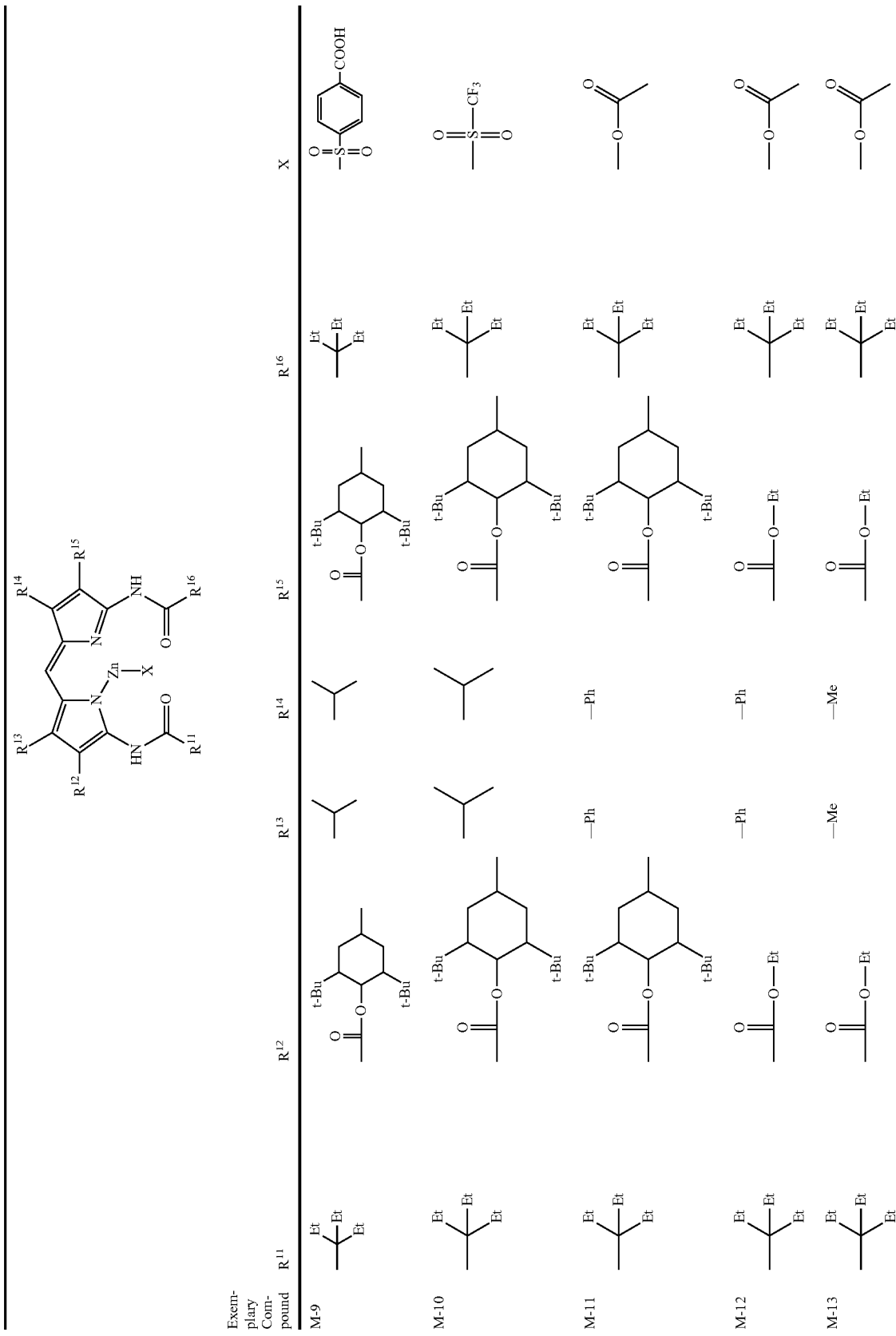

-continued

| Exemplary Compound | R11 | R12 | R13 | R14 | R15 | R16 | X |
|---|---|---|---|---|---|---|---|
| M-14 | C(Et)3 | —CN | —Me | —Me | —CN | C(Et)3 | OAc |
| M-15 | C(Et)3 | C(=O)NHPh | —Me | —Me | C(=O)NHPh | C(Et)3 | OAc |
| M-16 | CH2-t-Bu | 2,6-di-t-Bu-4-methylphenyl ester | i-Pr | i-Pr | 2,6-di-t-Bu-4-methylphenyl ester | CH2-t-Bu | OAc |
| M-17 | CH2-t-Bu | 2,6-di-t-Bu-4-methylphenyl ester | 2,4-dimethylphenyl | 2,4-dimethylphenyl | 2,6-di-t-Bu-4-methylphenyl ester | CH2-t-Bu | OAc |

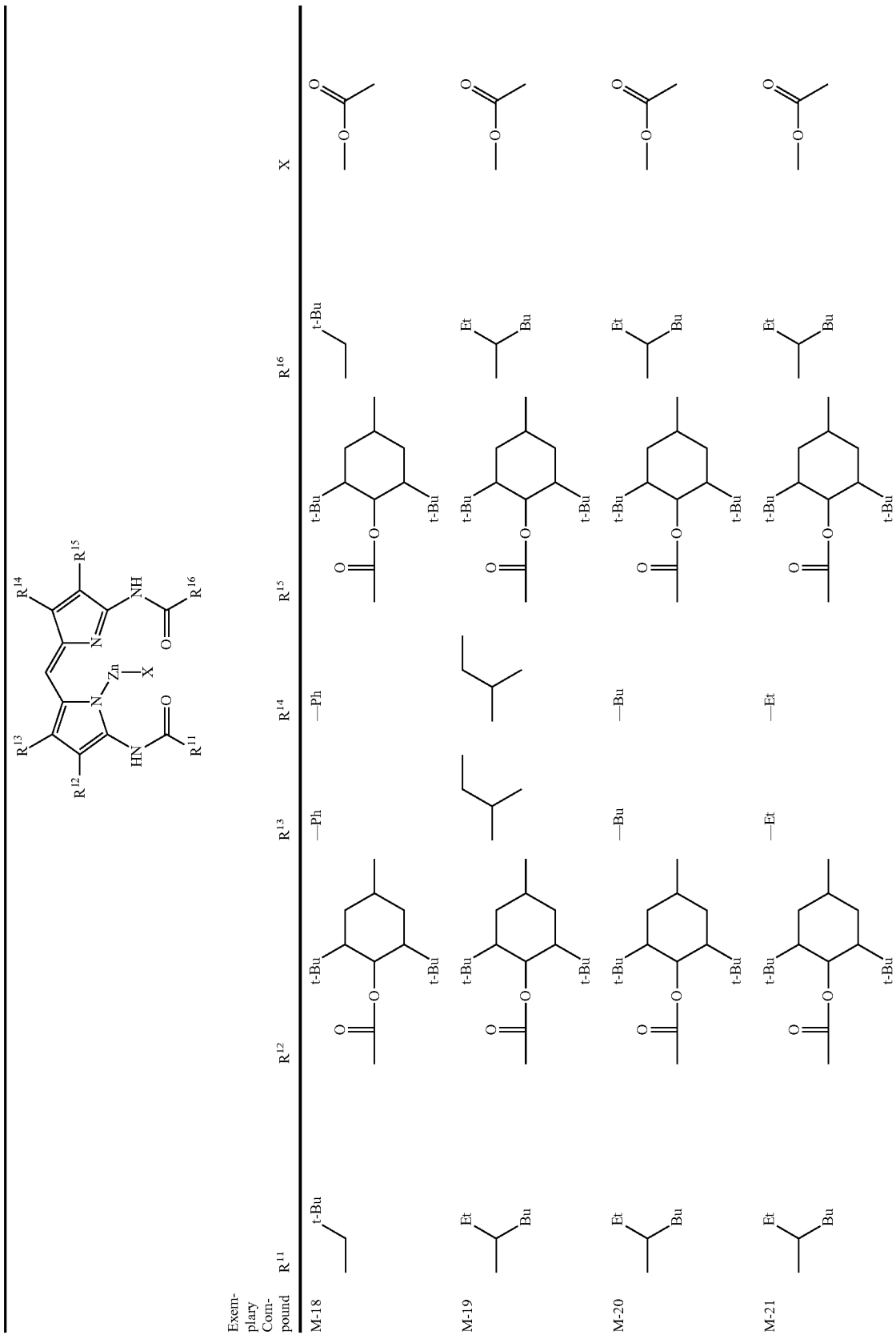

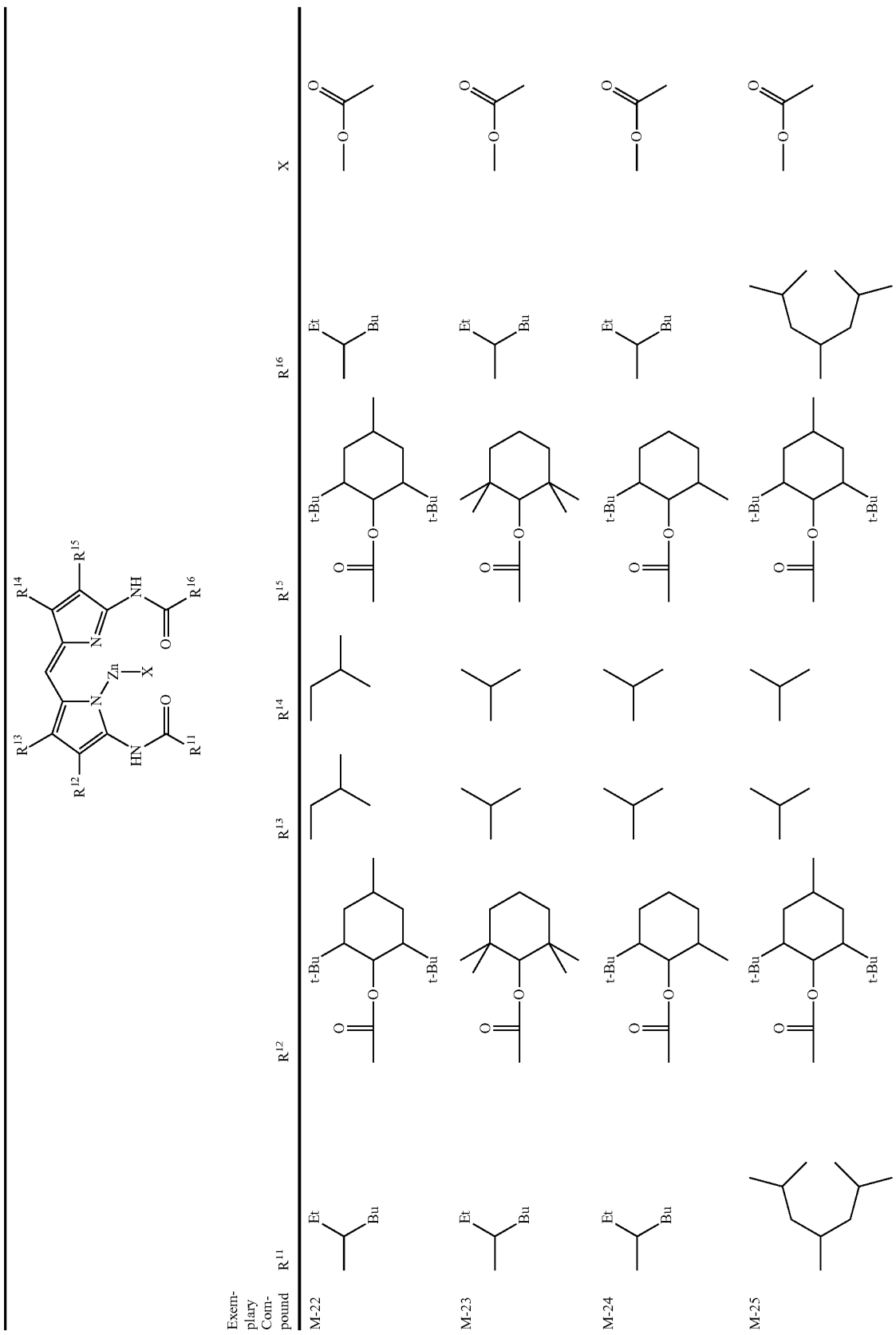

-continued

| Exemplary Compound | $R^{11}$ | $R^{12}$ | $R^{13}$ | $R^{14}$ | $R^{15}$ | $R^{16}$ | X |
|---|---|---|---|---|---|---|---|
| M-26 | 2,4,6-triisopropylcyclohexyl | 3,5-di-t-Bu-4-acetoxyphenyl | —Ph | —Ph | 3,5-di-t-Bu-4-acetoxyphenyl | 2,4,6-triisopropylcyclohexyl | OAc |
| M-27 | 2,4,6-triisopropylcyclohexyl | 4-ethoxycarbonyl | —Ph | —Ph | 4-ethoxycarbonyl | 2,4,6-triisopropylcyclohexyl | OAc |
| M-28 | t-Bu | 3,5-di-t-Bu-4-acetoxyphenyl | i-Pr | i-Pr | 3,5-di-t-Bu-4-acetoxyphenyl | t-Bu | OAc |
| M-29 | t-Bu | —CN | —Me | —Me | —CN | t-Bu | OAc |

-continued

| Exemplary Compound | R¹¹ | R¹² | R¹³ | R¹⁴ | R¹⁵ | R¹⁶ | X |
|---|---|---|---|---|---|---|---|
| M-30 | t-Bu | —C(O)NH₂ | —Me | —Me | —C(O)NH₂ | t-Bu | OAc |
| M-31 | | | | | | | OAc |
| M-32 | | | | | | | OAc |
| M-33 | | | | | | | OAc |

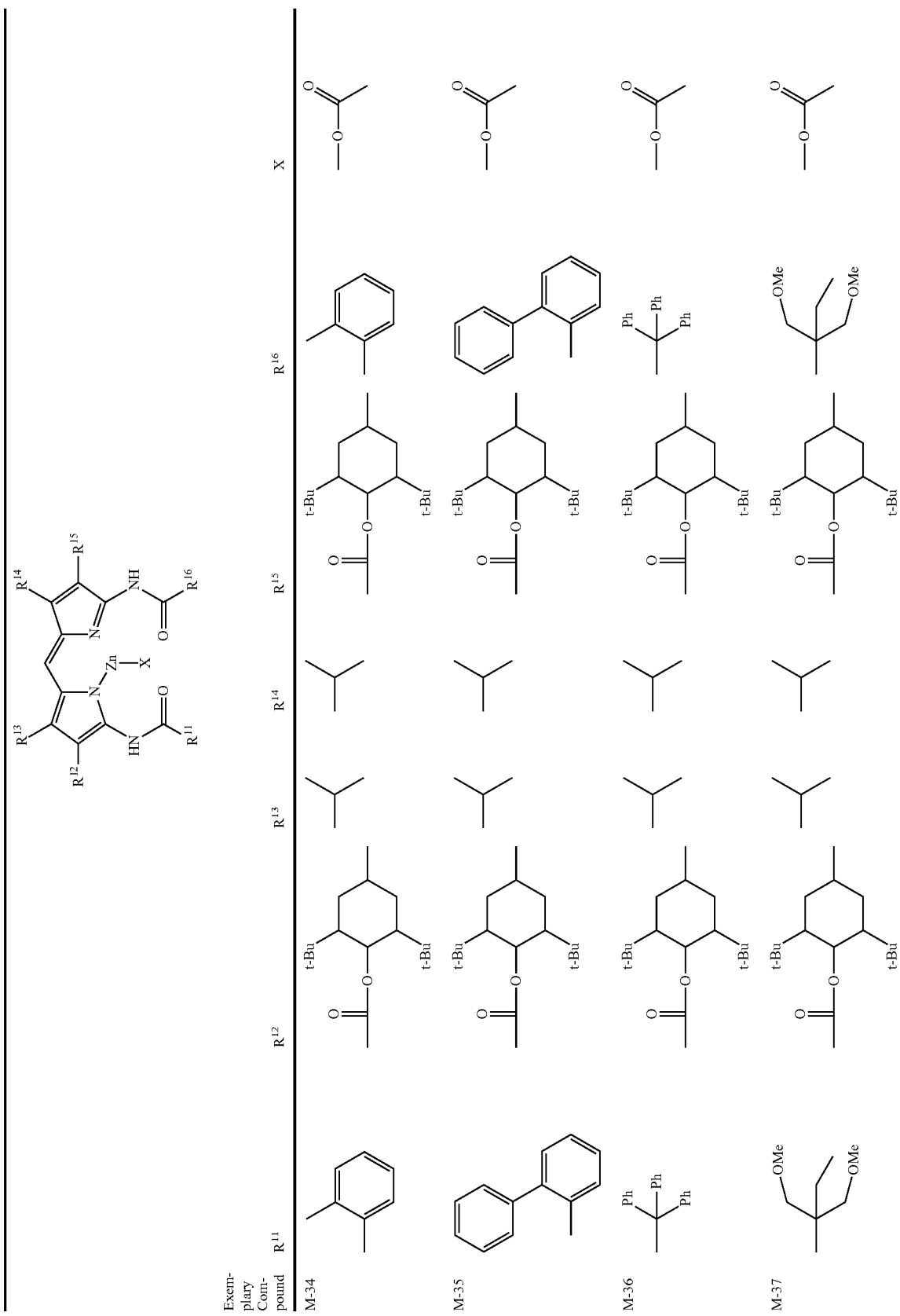

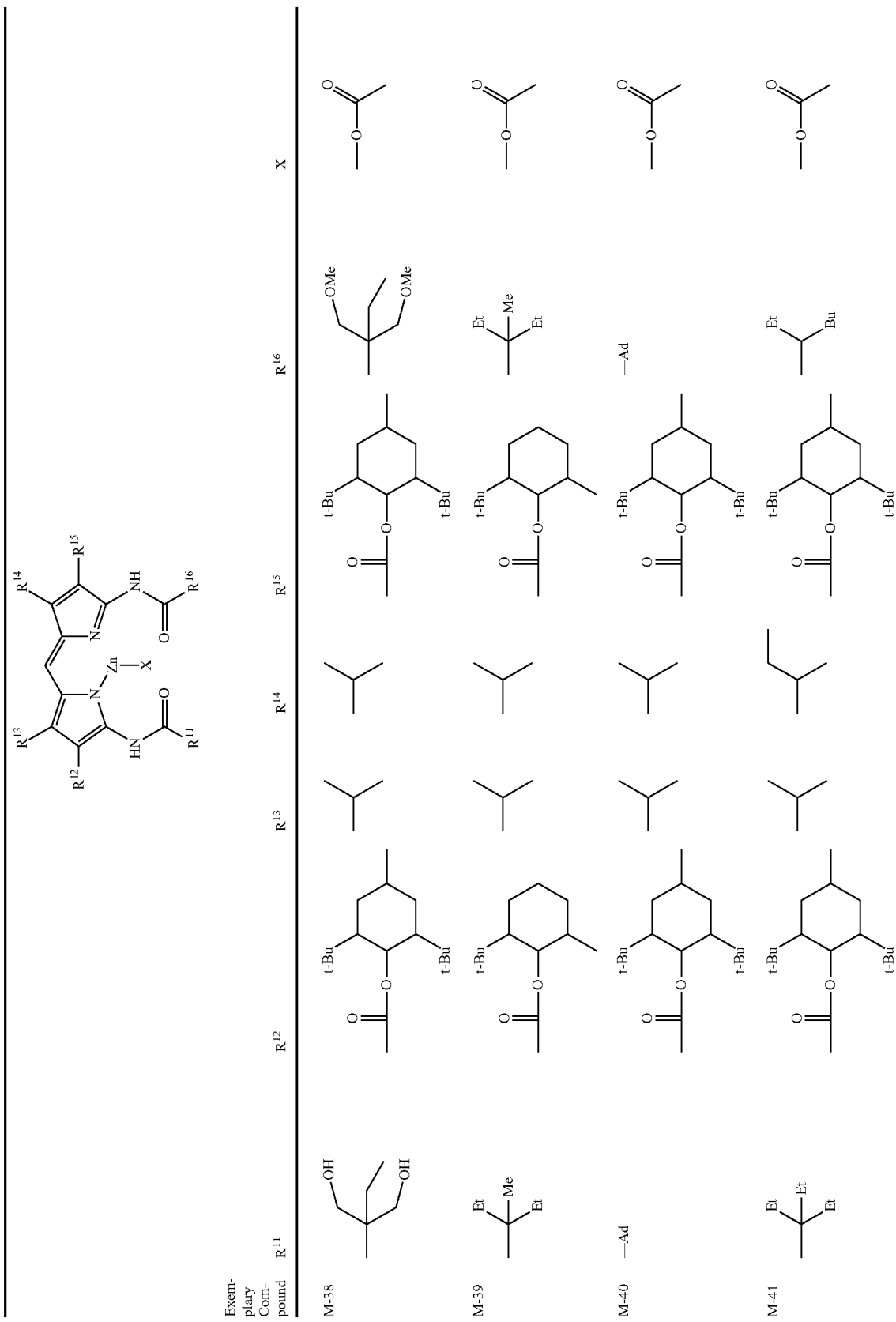

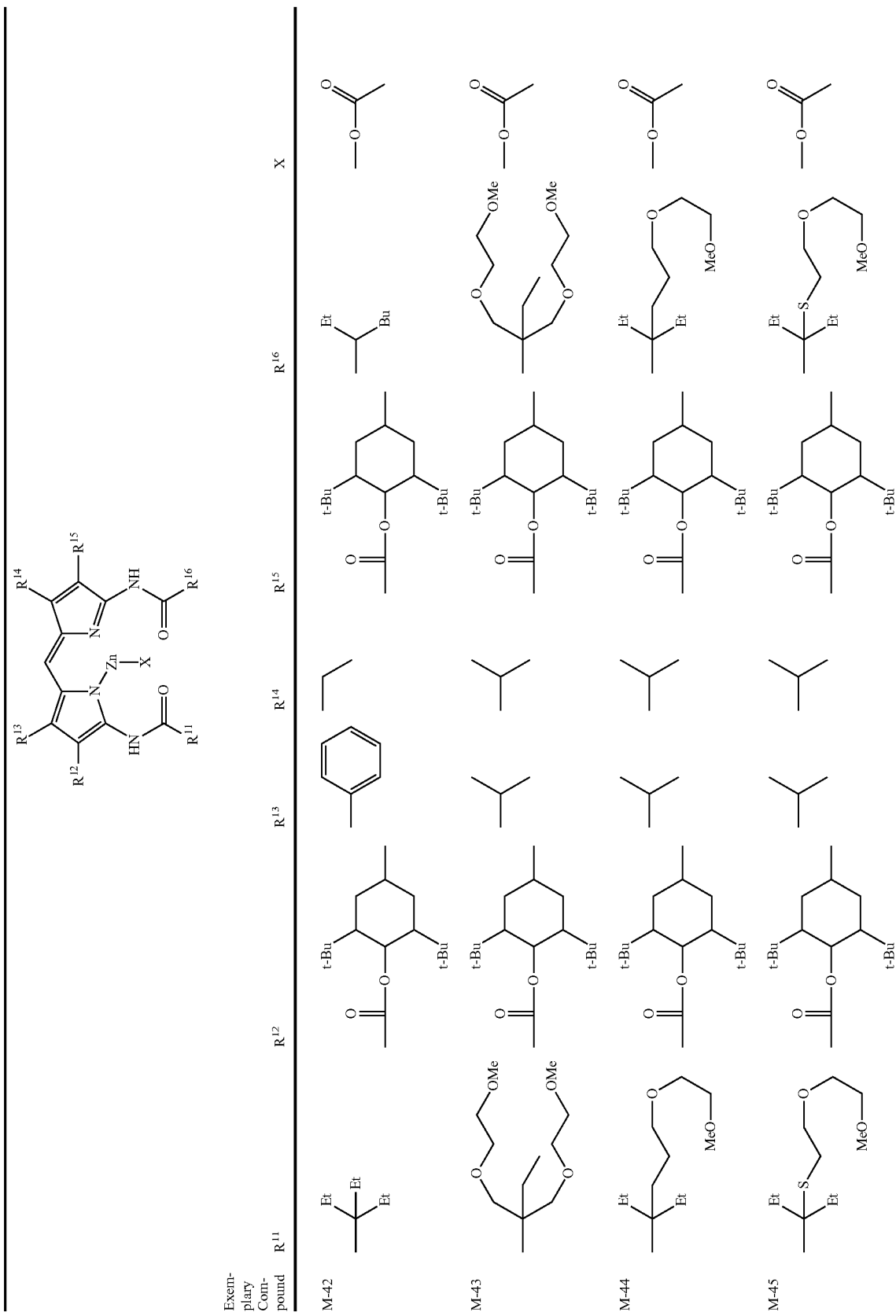

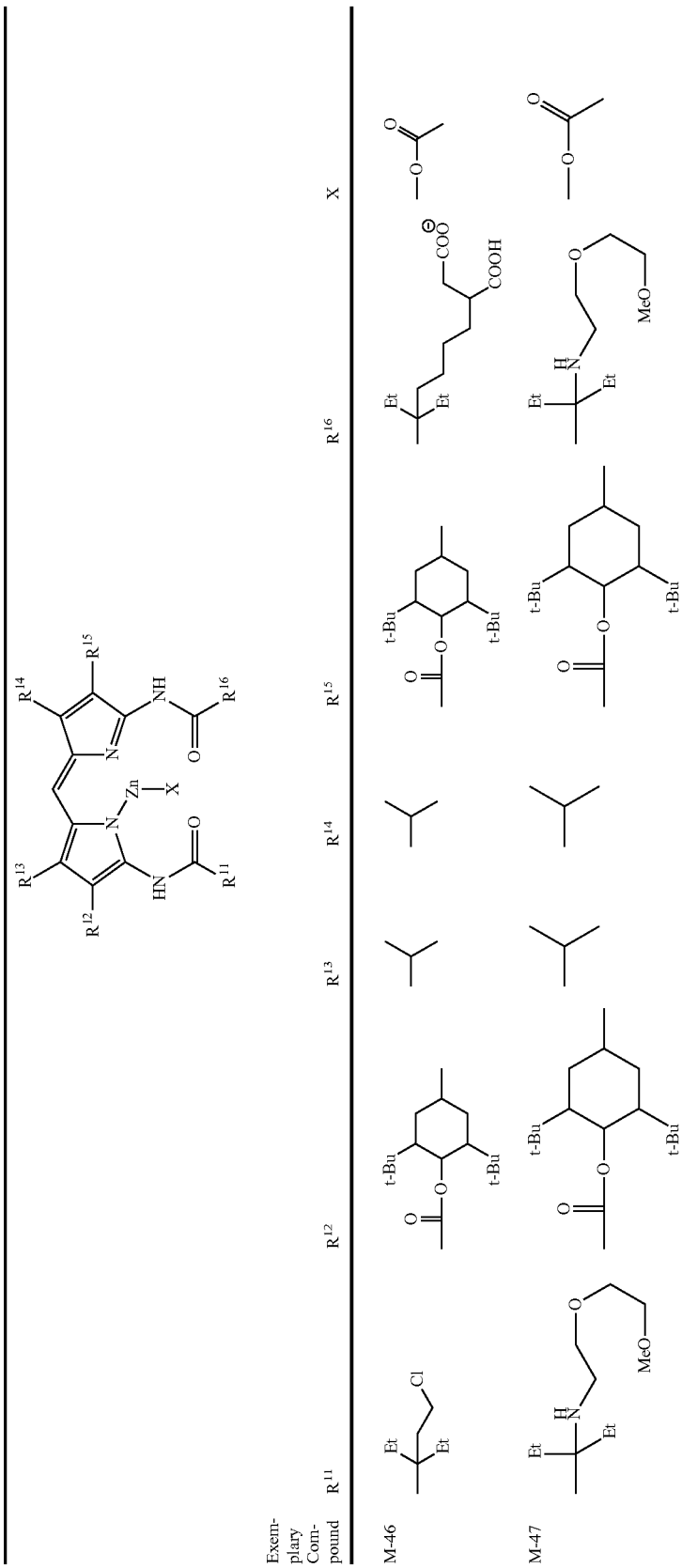

| Exemplary Compound | R²¹ | R²² | R²³ | R²⁴ | R²⁵ | X |
|---|---|---|---|---|---|---|
| M-48 | t-Bu, t-Bu, O-C(=O)CH₃ cyclohexyl | iPr | iPr | t-Bu, t-Bu, O-C(=O)CH₃ cyclohexyl | C(Et)₃ | OC(=O)CH₃ |
| M-49 | t-Bu, t-Bu, O-C(=O)CH₃ cyclohexyl | iPr | iPr | t-Bu, t-Bu, O-C(=O)CH₃ cyclohexyl | C(Et)₃ | —Cl |

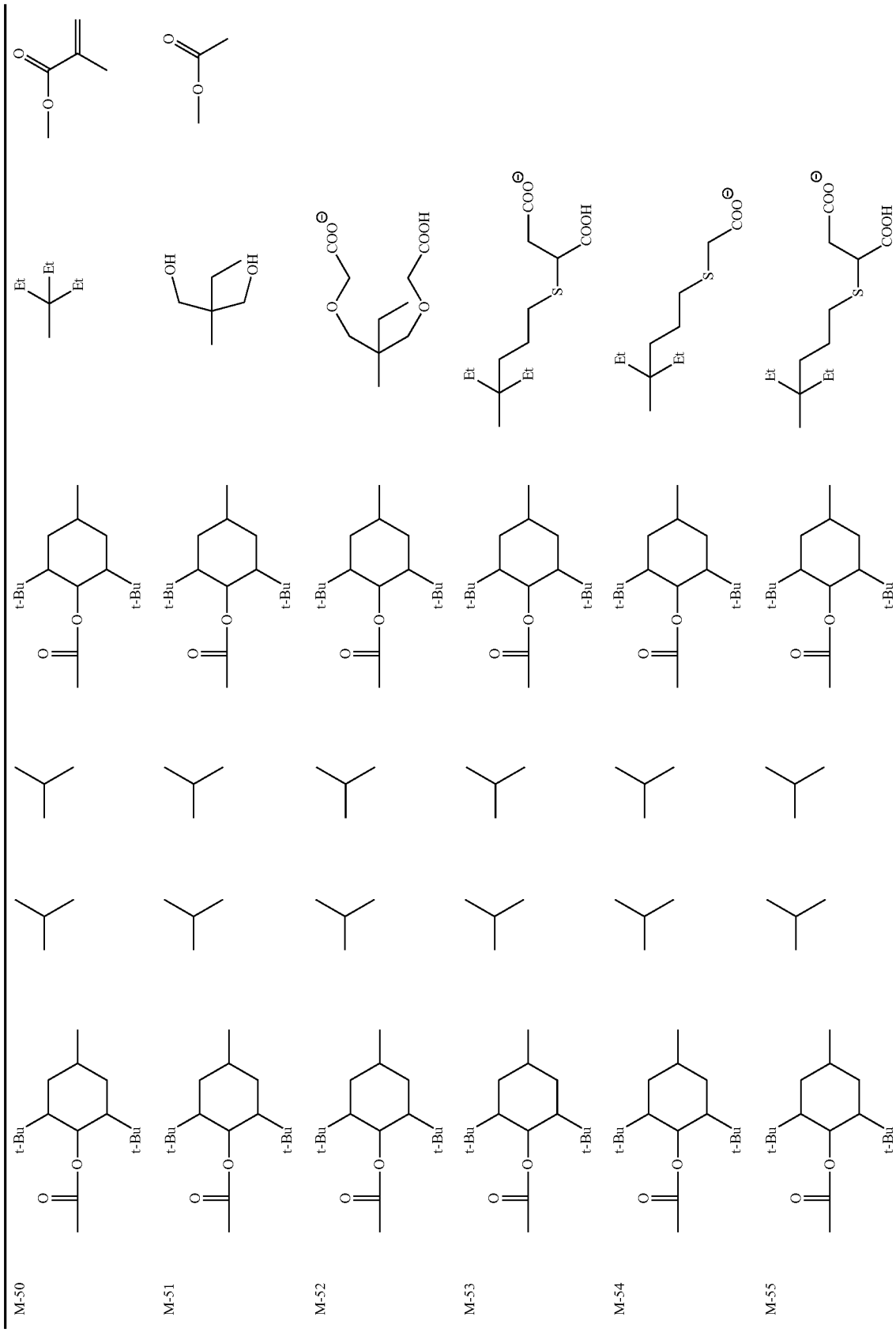

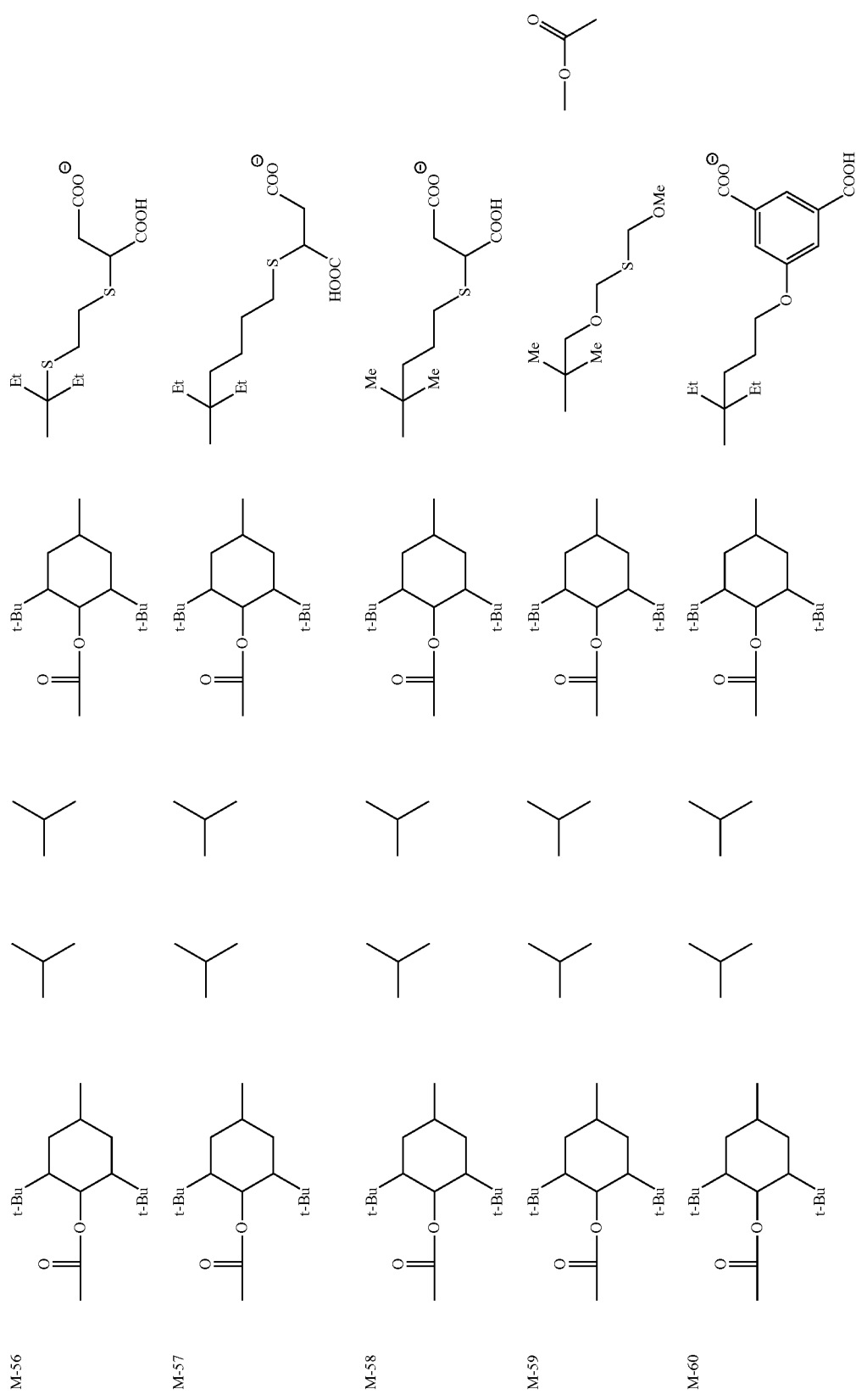

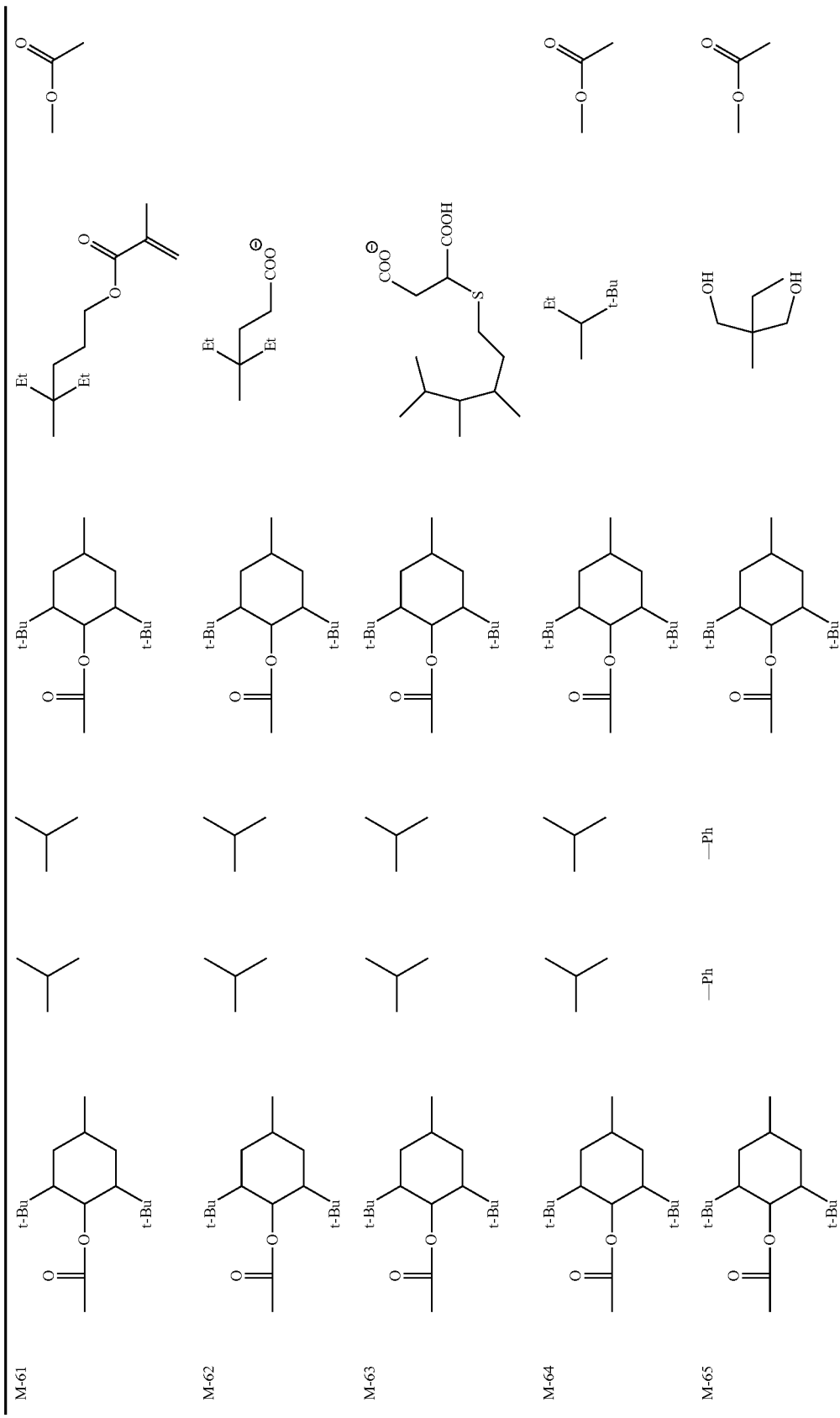

-continued

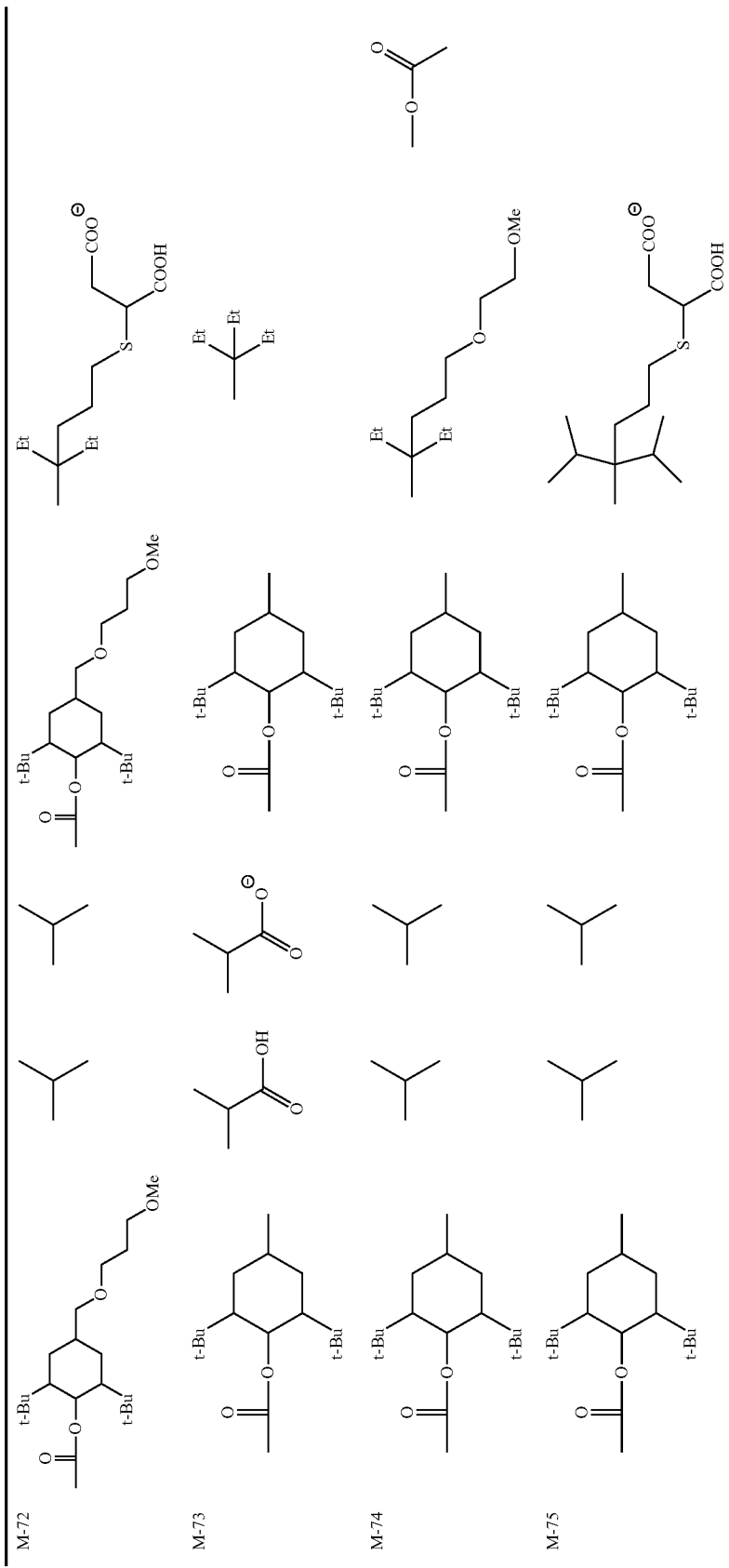

| Exemplary Compound | R³¹ | R³² | R³³ | R³⁴ | R³⁵ | X |
|---|---|---|---|---|---|---|
| M-76 | 4-methyl-2,6-di-t-Bu-cyclohexyl acetate | i-Pr | i-Pr | 4-methyl-2,6-di-t-Bu-cyclohexyl acetate | C(Et)₃ | OC(O)CH₃ |
| M-77 | 4-methyl-2,6-di-t-Bu-cyclohexyl acetate | i-Pr | i-Pr | 4-methyl-2,6-di-t-Bu-cyclohexyl acetate | C(Et)₃ | —Cl |

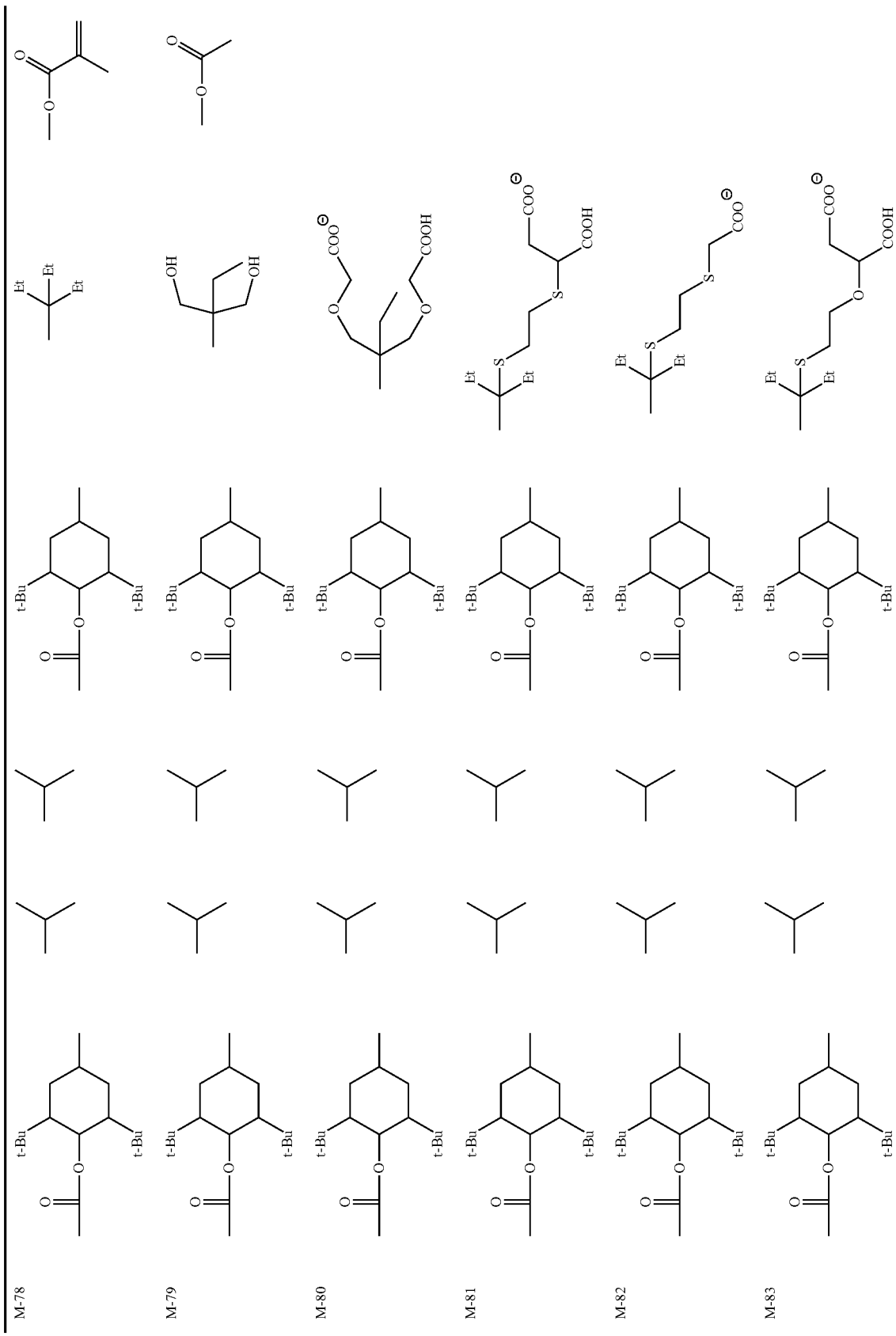

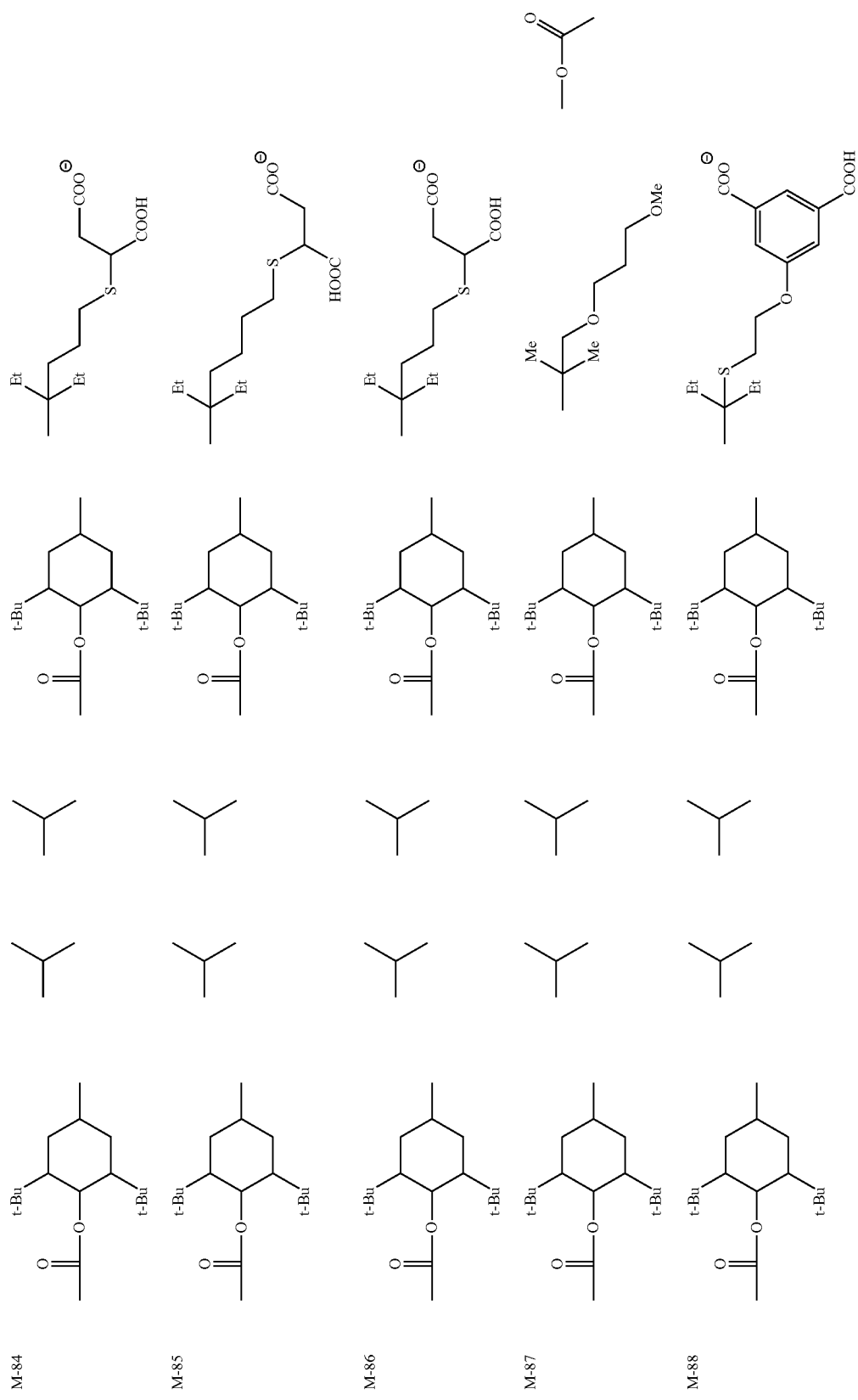

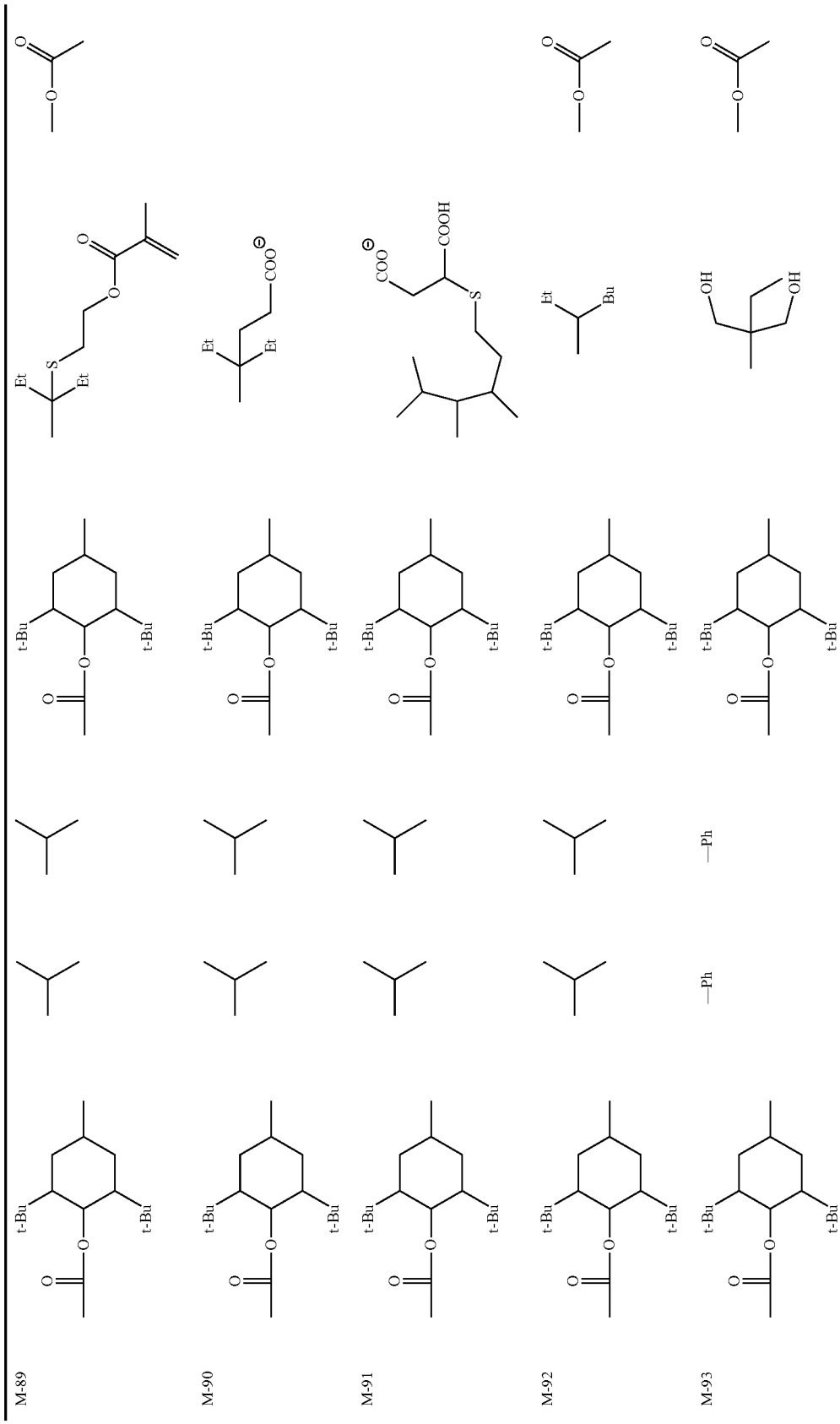

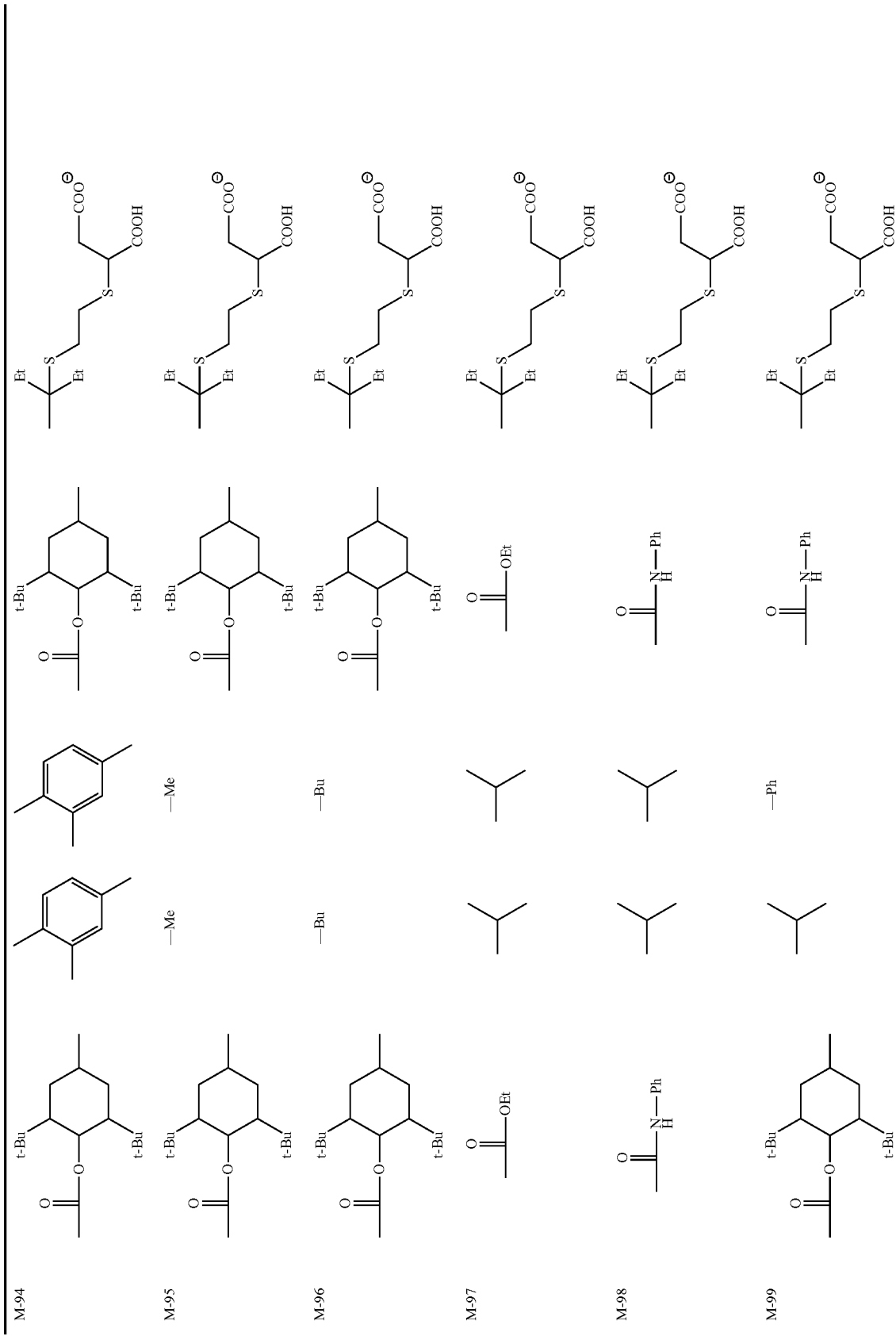

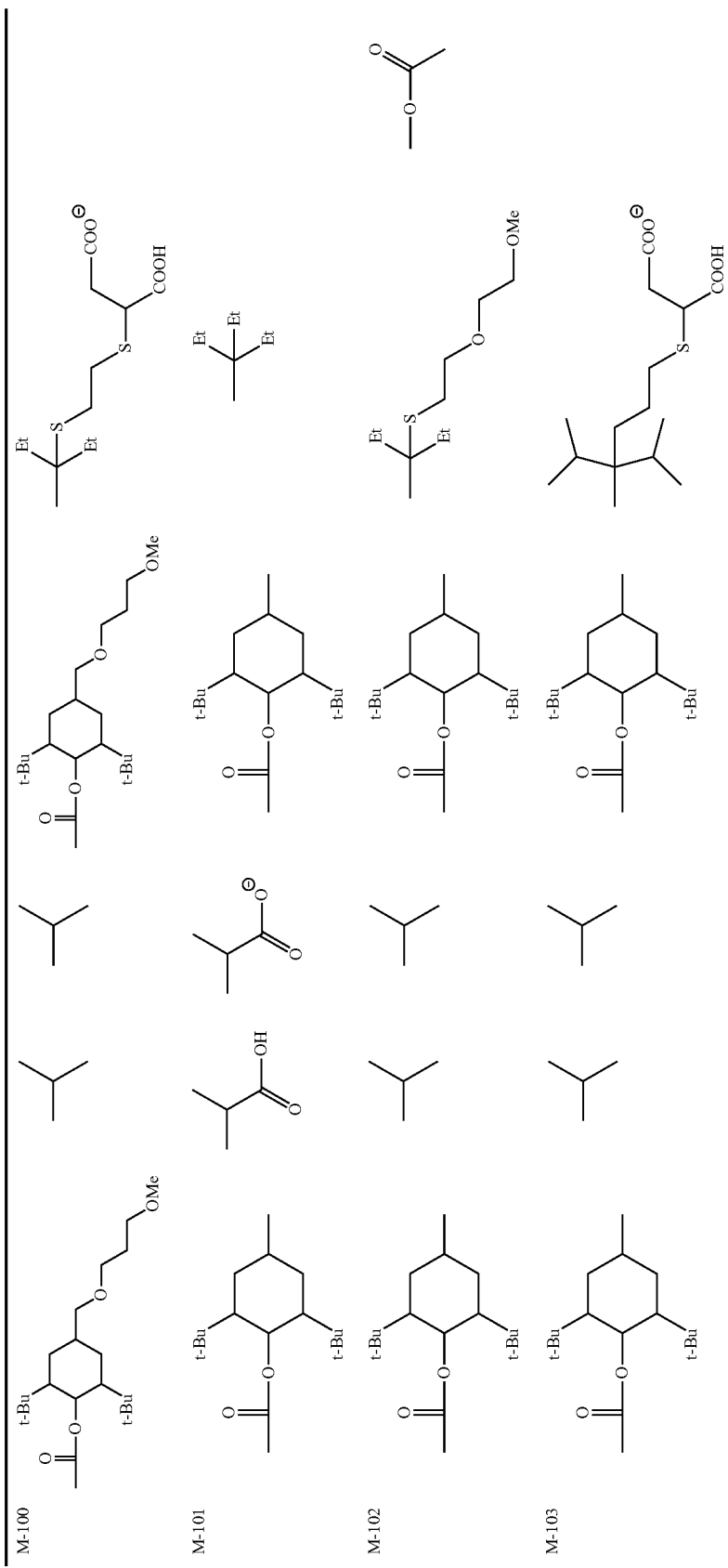

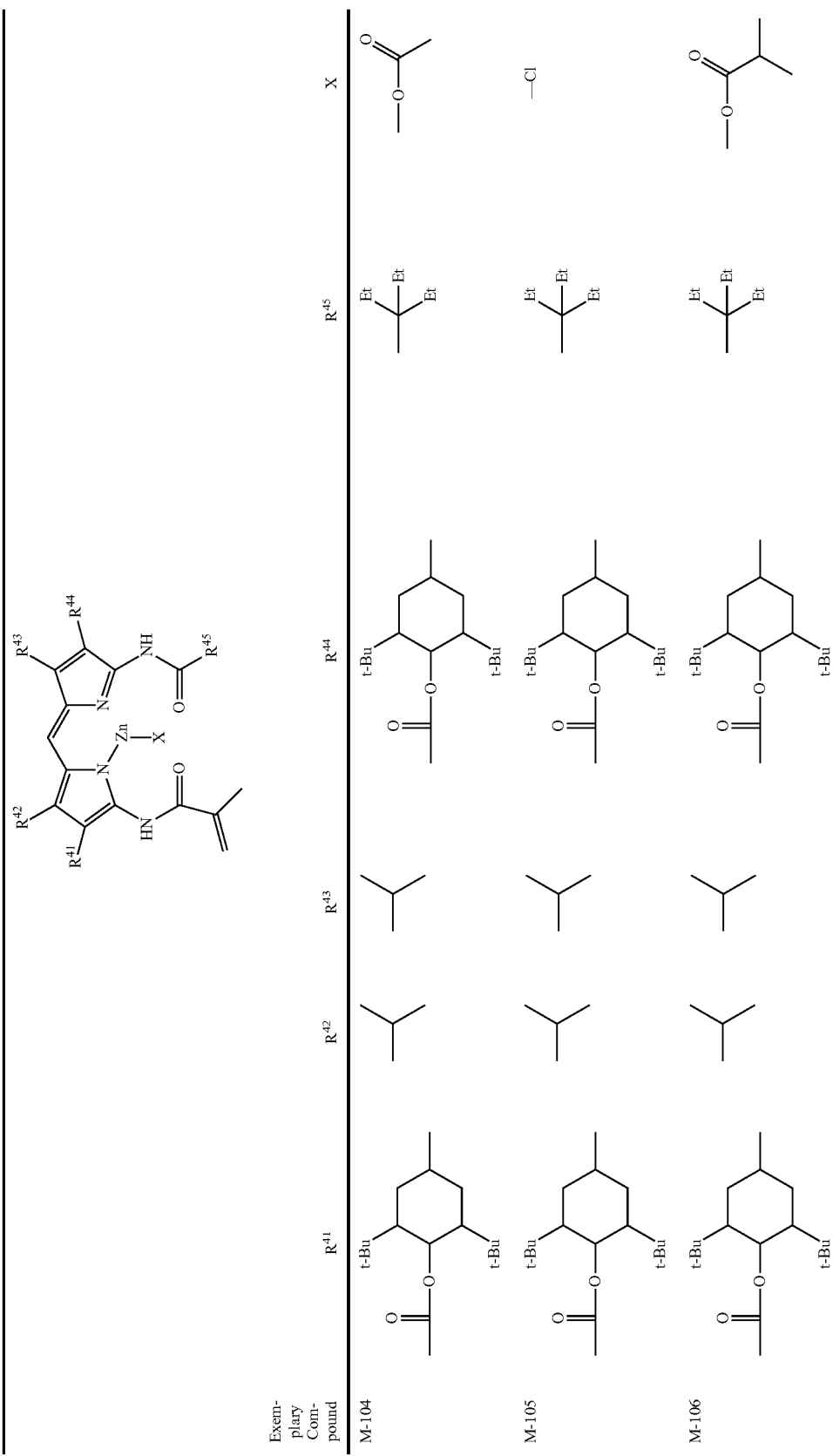
| Exemplary Compound | R⁴¹ | R⁴² | R⁴³ | R⁴⁴ | R⁴⁵ | X |
|---|---|---|---|---|---|---|
| M-104 | t-Bu / t-Bu cyclohexyl acetate | i-Pr | i-Pr | t-Bu / t-Bu cyclohexyl acetate | C(Et)₃ | OC(O)CH₃ |
| M-105 | t-Bu / t-Bu cyclohexyl acetate | i-Pr | i-Pr | t-Bu / t-Bu cyclohexyl acetate | C(Et)₃ | Cl |
| M-106 | t-Bu / t-Bu cyclohexyl acetate | i-Pr | i-Pr | t-Bu / t-Bu cyclohexyl acetate | C(Et)₃ | OC(O)CH(CH₃)₂ |

-continued

| Exemplary Compound | R⁴¹ | R⁴² | R⁴³ | R⁴⁴ | R⁴⁵ | X |
|---|---|---|---|---|---|---|
| M-107 | 4-methyl-2,6-di-t-Bu-cyclohexyl acetate | isopropyl | isopropyl | 4-methyl-2,6-di-t-Bu-cyclohexyl acetate | HOCH₂C(CH₃)(Et)CH₂OH | acetate |
| M-108 | 4-methyl-2,6-di-t-Bu-cyclohexyl acetate | isopropyl | isopropyl | 4-methyl-2,6-di-t-Bu-cyclohexyl acetate | ⁻OOCCH₂O-CH₂C(CH₃)(Et)CH₂-OCH₂COOH | |
| M-109 | 4-methyl-2,6-di-t-Bu-cyclohexyl acetate | isopropyl | isopropyl | 4-methyl-2,6-di-t-Bu-cyclohexyl acetate | ⁻OOCCH(S-CH₂CH₂C(Et)₂CH₃)COOH | |
| M-110 | 4-methyl-2,6-di-t-Bu-cyclohexyl acetate | isopropyl | isopropyl | 4-methyl-2,6-di-t-Bu-cyclohexyl acetate | ⁻OOCCH₂-S-CH₂CH₂C(Et)₂CH₃ | |

-continued

| Exemplary Compound | R⁴¹ | R⁴² | R⁴³ | R⁴⁴ | R⁴⁵ | X |
|---|---|---|---|---|---|---|
| M-111 | 2,6-di-t-Bu-4-methylphenyl acetate | iPr | iPr | 2,6-di-t-Bu-4-methylphenyl acetate | -O-CH₂CH₂-C(Et)₂-CH(COOH)-CH₂-COO⁻ | |
| M-112 | 2,6-di-t-Bu-4-methylphenyl acetate | iPr | iPr | 2,6-di-t-Bu-4-methylphenyl acetate | -S-CH₂CH₂-C(Et)(SEt)-CH(COOH)-CH₂-COO⁻ | |
| M-113 | 2,6-di-t-Bu-4-methylphenyl acetate | iPr | iPr | 2,6-di-t-Bu-4-methylphenyl acetate | -S-CH₂CH₂CH₂-C(Et)₂-CH(COOH)(HOOC)-COO⁻ | |

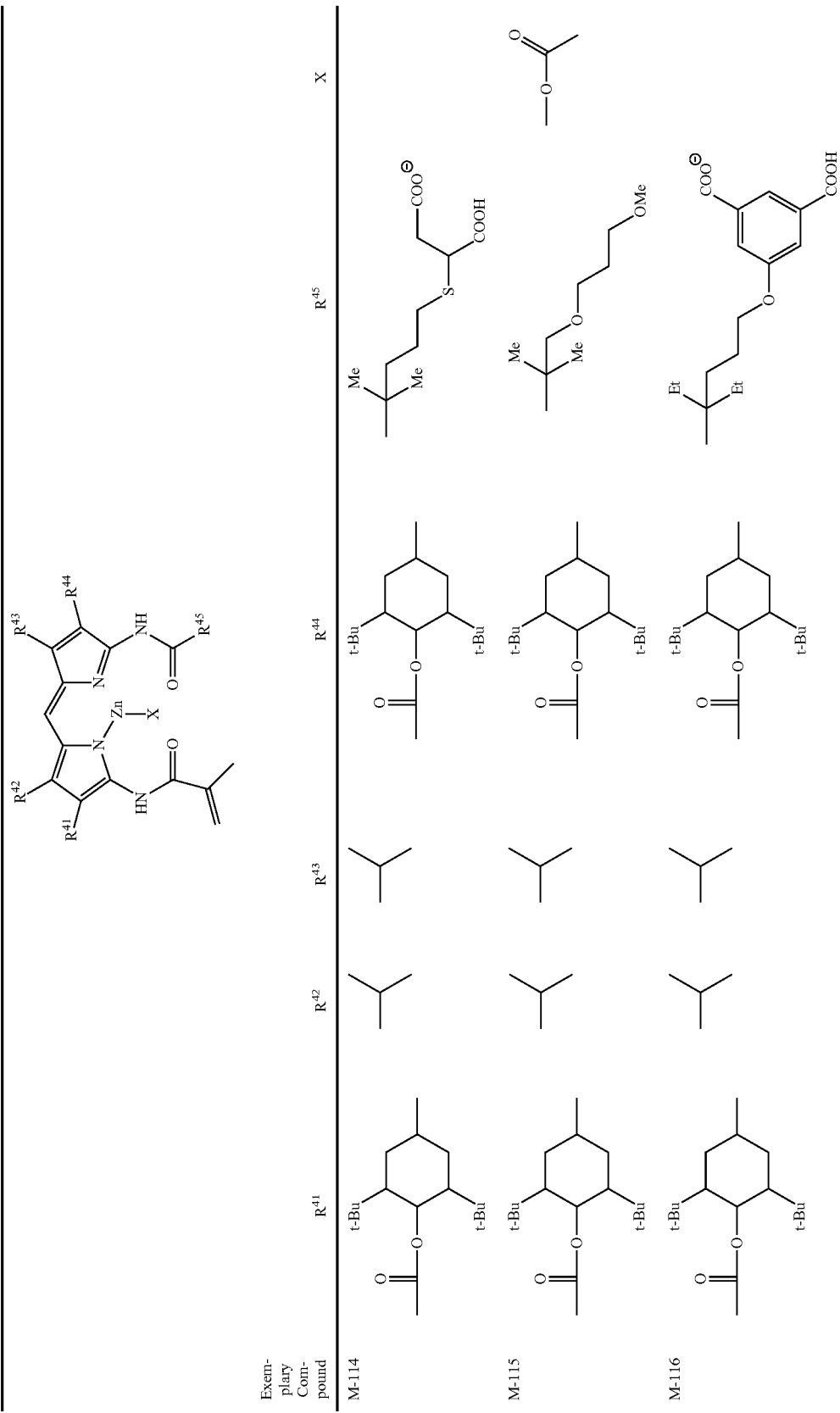

-continued

| Exemplary Compound | R⁴¹ | R⁴² | R⁴³ | R⁴⁴ | R⁴⁵ | X |
|---|---|---|---|---|---|---|
| M-117 | 4-methyl-2,6-di-t-Bu-cyclohexyl acetate | i-Pr | i-Pr | 4-methyl-2,6-di-t-Bu-cyclohexyl acetate | 4,4-diethyl-hexyl methacrylate | acetate |
| M-118 | 4-methyl-2,6-di-t-Bu-cyclohexyl acetate | i-Pr | i-Pr | 4-methyl-2,6-di-t-Bu-cyclohexyl acetate | 3,3-diethyl-butanoate (COO⁻) | |
| M-119 | 4-methyl-2,6-di-t-Bu-cyclohexyl acetate | i-Pr | i-Pr | 4-methyl-2,6-di-t-Bu-cyclohexyl acetate | 2-((3,4-dimethyl-5-methylhexyl)thio)succinate (COO⁻, COOH) | |

-continued

| Exemplary Compound | R⁴¹ | R⁴² | R⁴³ | R⁴⁴ | R⁴⁵ | X |
|---|---|---|---|---|---|---|
| M-120 | 2,6-di-t-Bu-4-Me-cyclohexyl acetate | i-Pr | i-Pr | 2,6-di-t-Bu-4-Me-cyclohexyl acetate | CH(Et)(Bu) | OAc |
| M-121 | 2,6-di-t-Bu-4-Me-cyclohexyl acetate | Ph | Ph | 2,6-di-t-Bu-4-Me-cyclohexyl acetate | C(CH₂OH)₂Et | OAc |
| M-122 | 2,6-di-t-Bu-4-Me-cyclohexyl acetate | 2,4-diMe-Ph | 2,4-diMe-Ph | 2,6-di-t-Bu-4-Me-cyclohexyl acetate | -(CH₂)₃-C(Et)₂-CH₂-S-CH(COOH)CH₂COO⁻ | |
| M-123 | 2,6-di-t-Bu-4-Me-cyclohexyl acetate | Me | Me | 2,6-di-t-Bu-4-Me-cyclohexyl acetate | -(CH₂)₃-C(Et)₂-CH₂-S-CH(COOH)CH₂COO⁻ | |

-continued

[Structure: pyrrole-based Zn complex with substituents R⁴¹, R⁴², R⁴³, R⁴⁴, R⁴⁵ and X, featuring a methacrylamide group]

| Exemplary Compound | R⁴¹ | R⁴² | R⁴³ | R⁴⁴ | R⁴⁵ | X |
|---|---|---|---|---|---|---|
| M-124 | 2,6-di-t-Bu-4-methylcyclohexyl acetate | —Bu | —Bu | 2,6-di-t-Bu-4-methylcyclohexyl acetate | —S—CH₂CH(CH₂CH(Et)(Et))(CH₃) linked to CH(COO⁻)(COOH) | |
| M-125 | —C(O)OEt | isopropyl | isopropyl | —C(O)OEt | —S—CH₂CH₂—S—C(CH₃)(Et)(Et) linked to CH(COO⁻)(COOH) | |
| M-126 | —C(O)NH—Ph | isopropyl | isopropyl | —C(O)NH—Ph | —S—CH₂CH(CH₂CH(Et)(Et))(CH₃) linked to CH(COO⁻)(COOH) | |

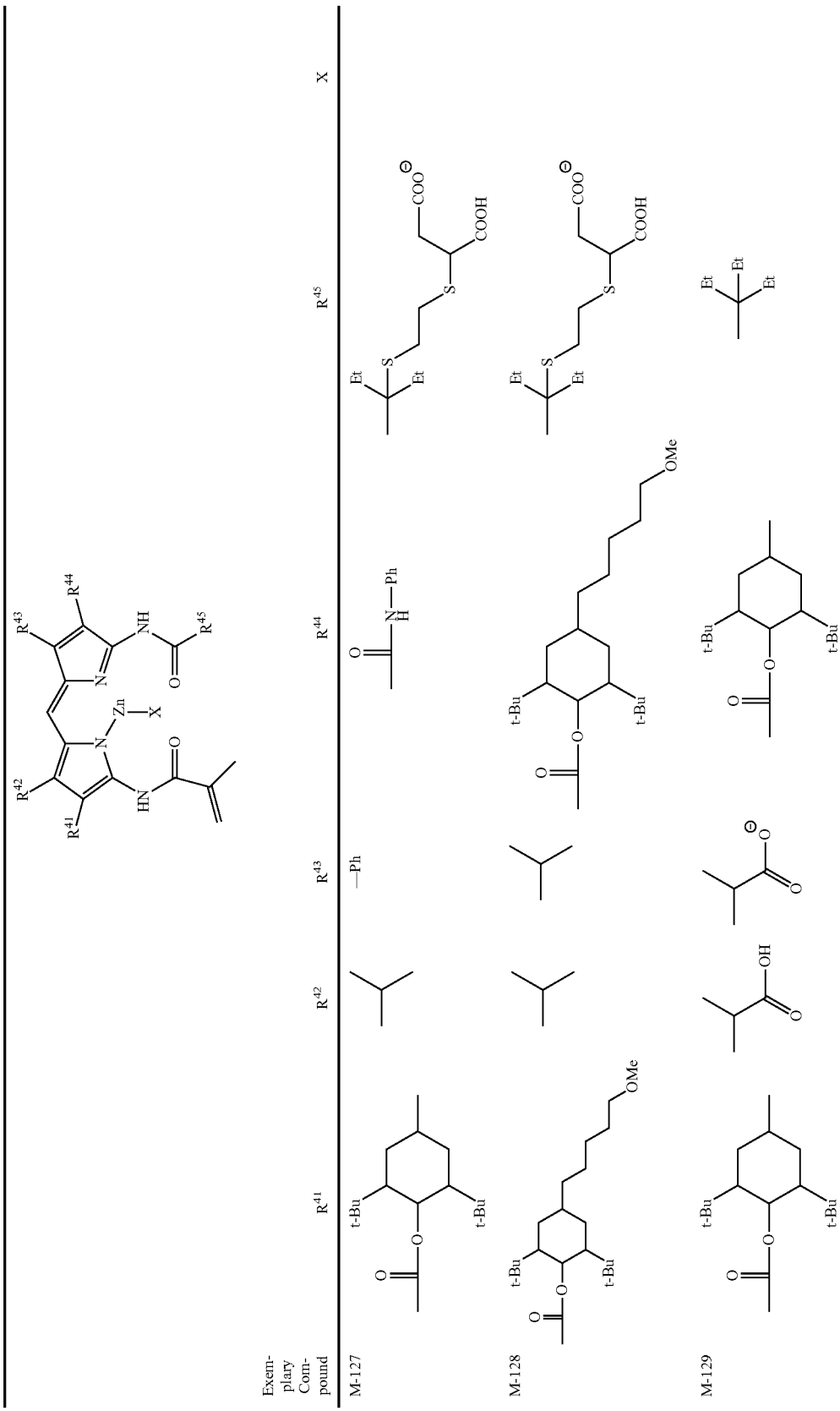

-continued
| Exemplary Compound | R<sup>41</sup> | R<sup>42</sup> | R<sup>43</sup> | R<sup>44</sup> | R<sup>45</sup> | X |
|---|---|---|---|---|---|---|
| M-130 |  | 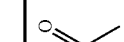 | 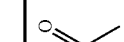 |  | 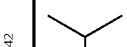 |  |
| M-131 |  |  |  |  |  | |

M-132
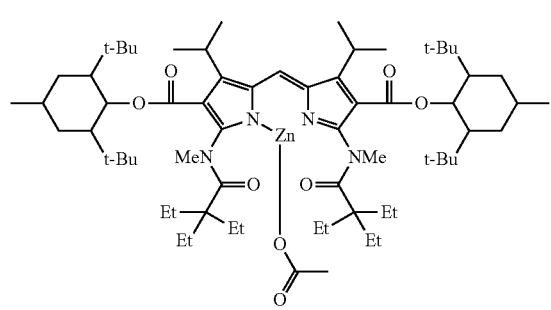
M-133
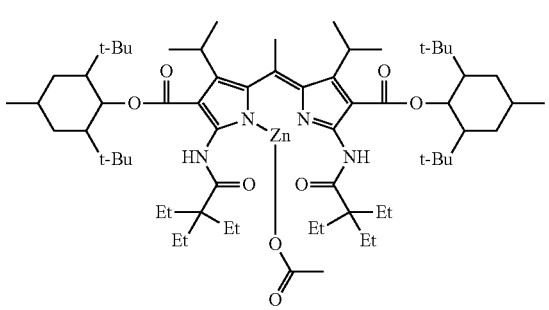
M-134
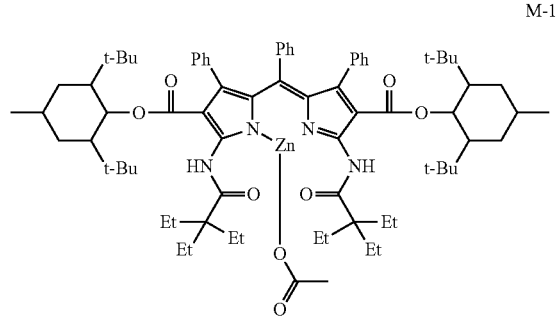
M-135
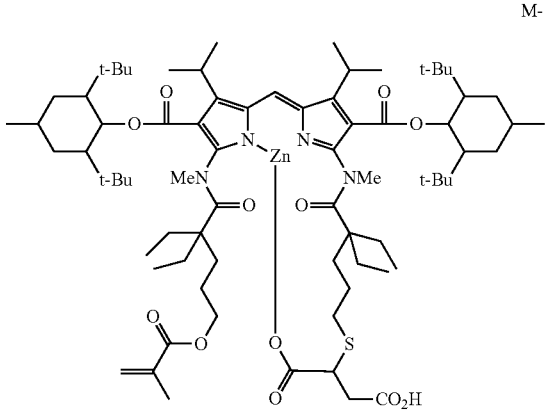
M-136
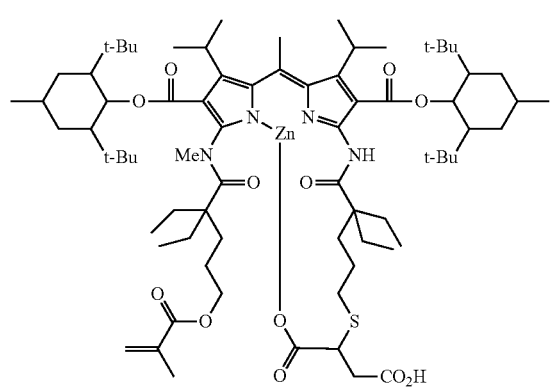
M-137
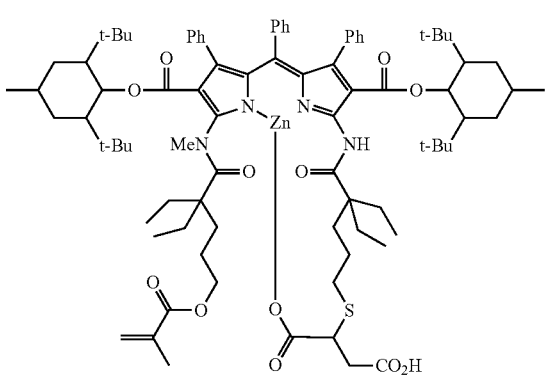
M-138
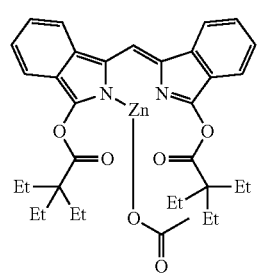
M-139
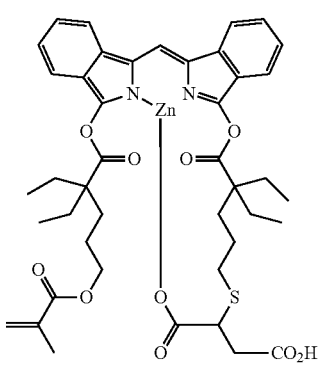

-continued
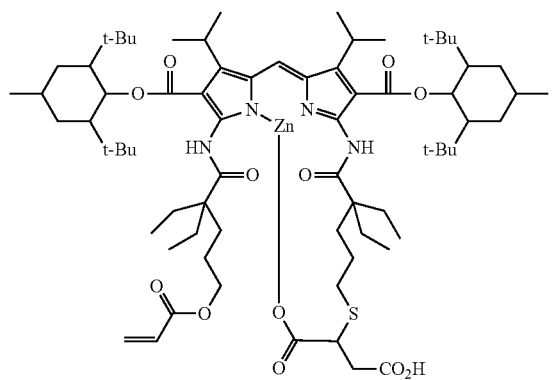
M-140
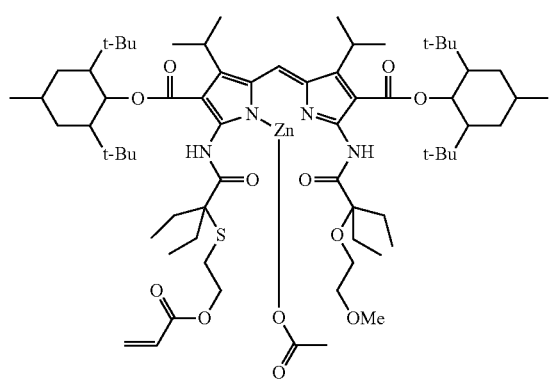
M-141
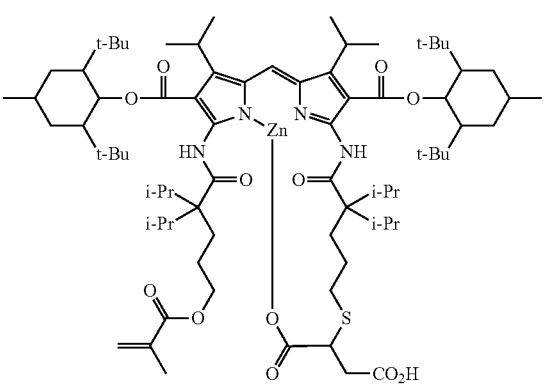
M-142
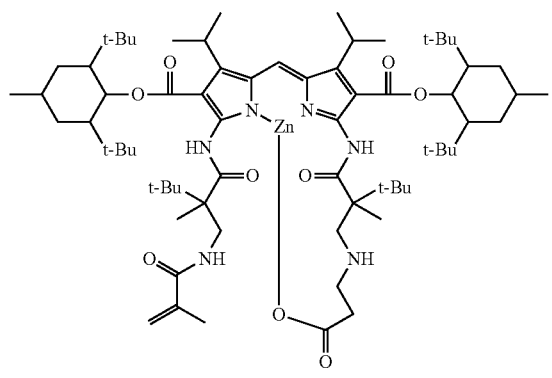
M-143
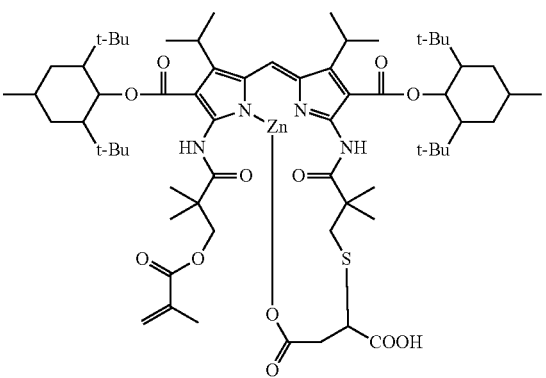
M-144

M-145
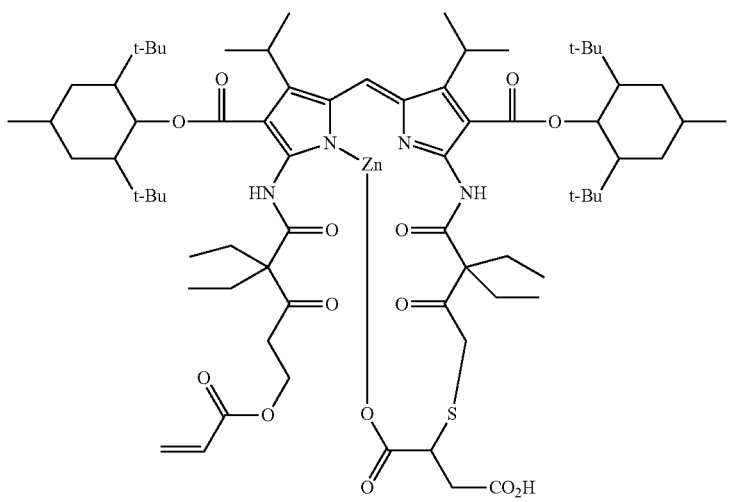
M-146
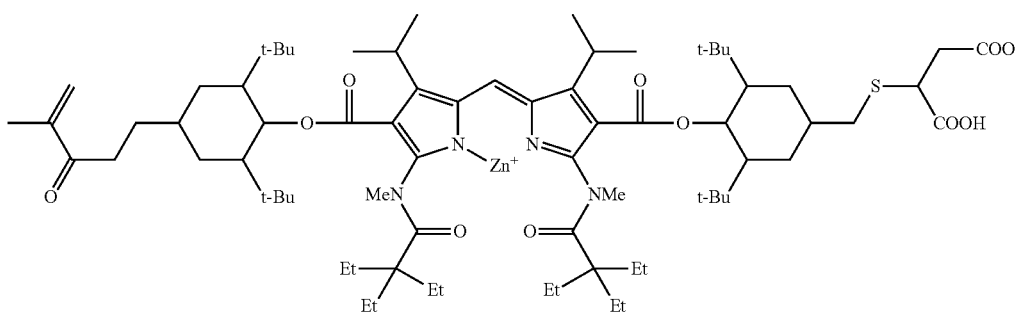
M-147
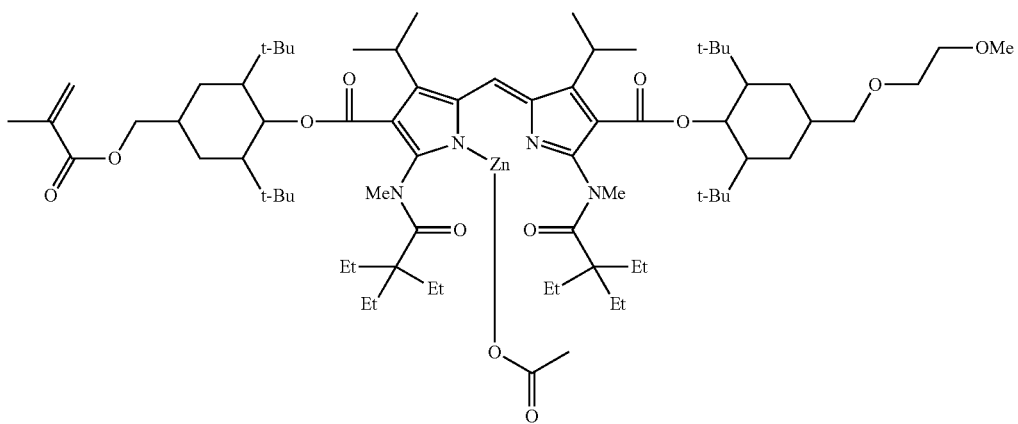
M-148
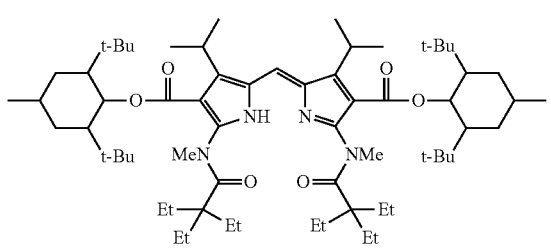
M-149
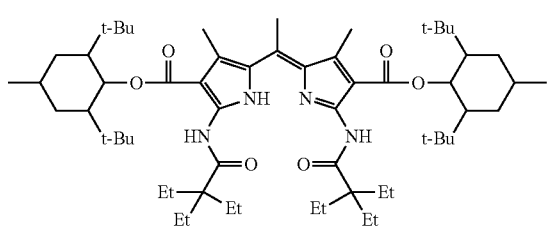

-continued
M-150
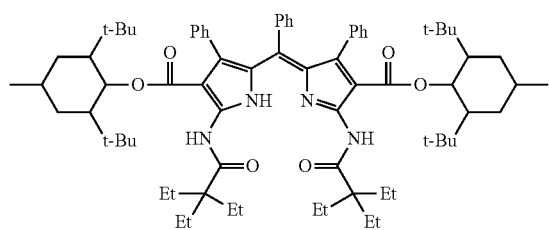
M-151
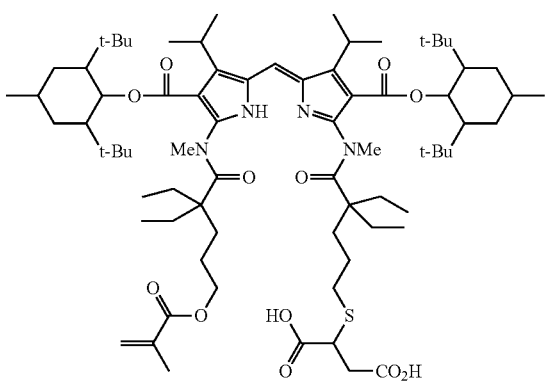
M-152
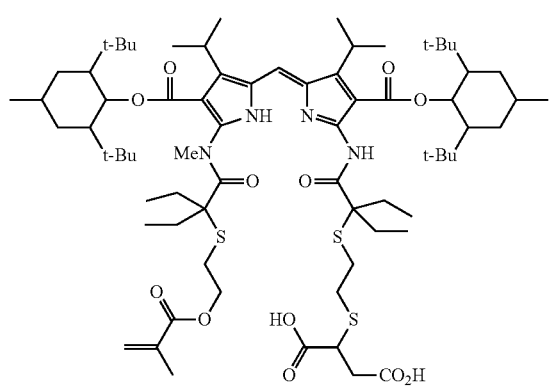
M-153
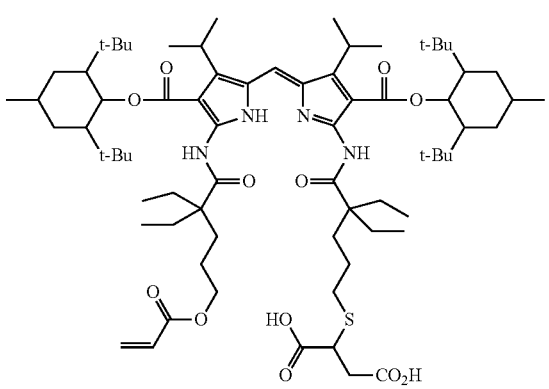
M-154
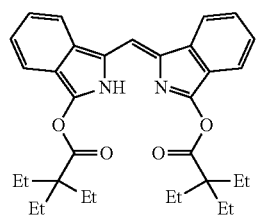
M-155
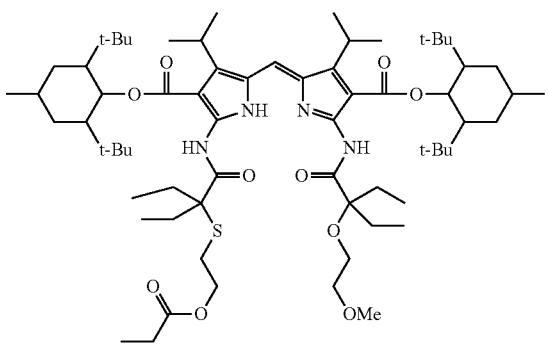
M-156
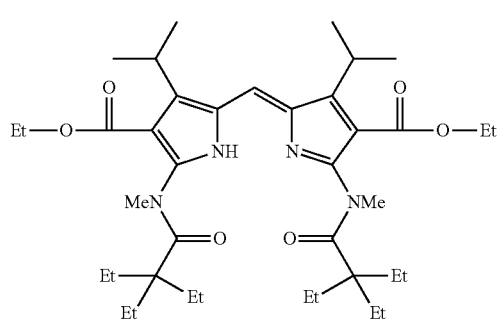

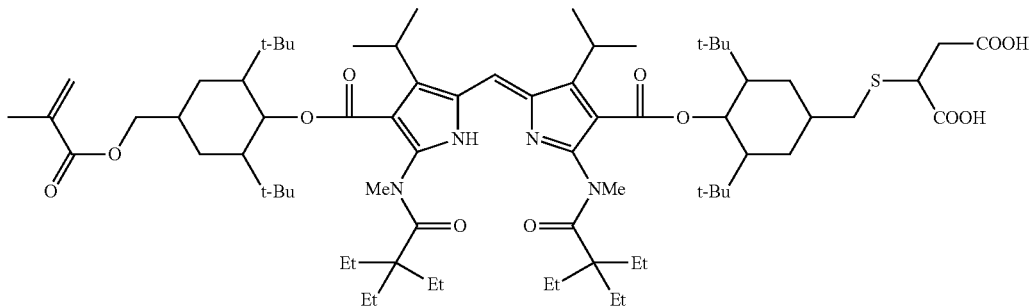

M-157

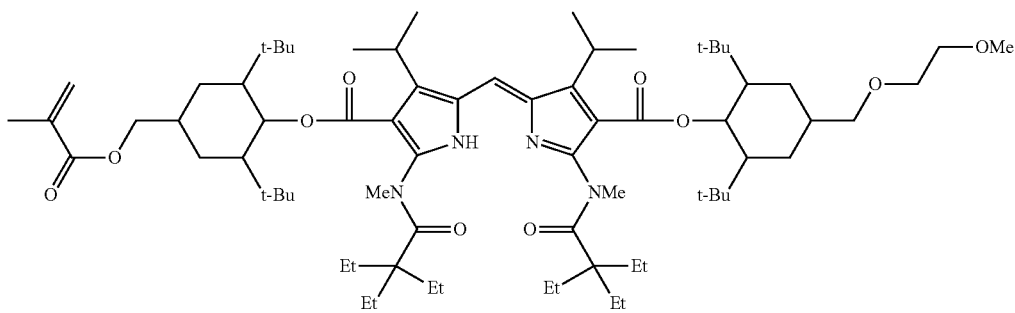

M-158

<Azo Dye>

The azo dye may be a compound having a structure represented by the following formula (9). In the azo dye represented by formula (9), a bulky acyl group of the invention functions effectively when an acylamino group is introduced as an auxochrome group, or an acyloxy group is introduced as a substituent group, into the azo dye.

Cp—N═N-D      formula (9)

In formula (9), Cp represents a coupling component and D represents a diazo component. Examples of the coupling component include aromatic hydrocarbon rings such as phenols, naphthols and anilines, heterocycles such as pyrazolones, aminopyridines and pyridones, and open-chain type active methylene compounds. Examples of the diazo component include a benzene ring, a naphthalene ring and a heterocycle (for example, thiazole, pyrazole, thiophene and imidazole). The bulky substituent group of the invention is preferably introduced into a conjugation site of the azo group (for example, when the substituent group is a benzene ring or a pyridine ring, at position 2 or position 4 with respect to the azo group).

The following are specific examples of the azo dye represented by formula (9). However, the invention is not limited to these examples.

I-1

-continued

I-2

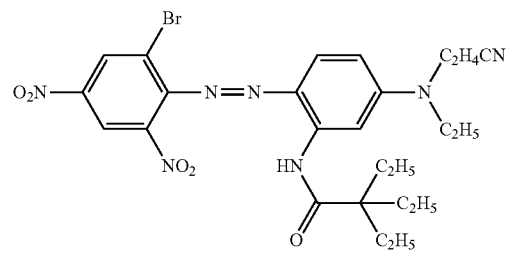

I-3

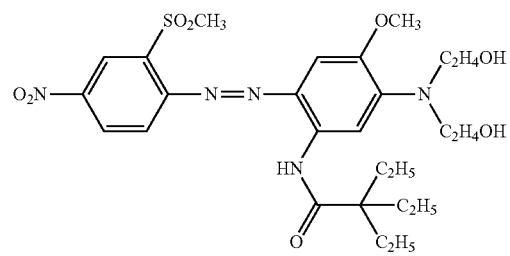

I-4

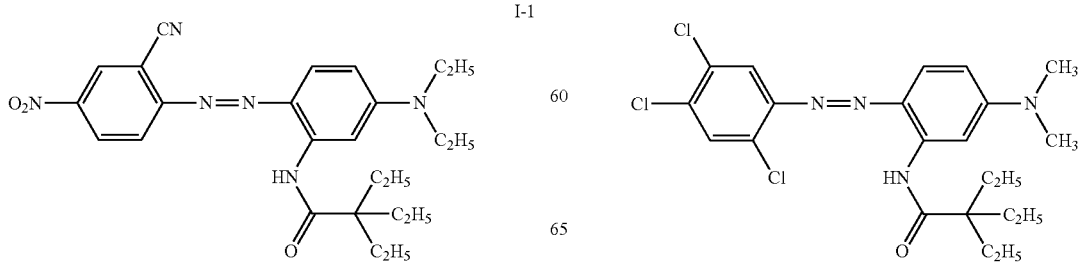

<Azomethine Dye>

The azomethine dye may be a compound having a structure represented by the following formula (10).

$$\begin{array}{c} R^{32} \quad R^{31} \\ X^5=N \diagup \diagdown E \\ \diagdown B^2=B^1 \diagup \end{array} \quad (10)$$

In formula (10), $R^{31}$ and $R^{32}$ each independently represent a hydrogen atom, a halogen atom, an aliphatic group, an aromatic group, a heterocyclic group, a cyano group, a hydroxyl group, a nitro group, an amino group, an alkylamino group, an alkoxy group, an aryloxy group, an amido group, an arylamino group, a ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group, an acyl group, a carboxyl group, or a sulfo group. E represents —NR$^{35}$R$^{36}$ or a hydroxyl group, R$^{35}$ and R$^{36}$ each independently represent a hydrogen atom, an aliphatic group, an aromatic group, or a heterocyclic group. E is preferably —NR$^{35}$R$^{36}$. R$^{35}$ and R$^{36}$ may be bonded to each other to form a ring. B$^1$ represents =C(R$^{33}$)— or =N—, and B$^2$ represents —C(R$^{34}$)= or —N=. Preferably, when B$^1$ or B$^2$ is —N=, the other one is not —N=. More preferably, B$^1$ is =C(R$^{33}$)— and B$^2$ is —C(R$^{34}$)=. R$^{33}$ and R$^{34}$ have the same definitions as the definitions of R$^{31}$ and R$^{32}$, respectively. A pair of R$^{31}$ and R$^{35}$, R$^{33}$ and R$^{36}$ and/or R$^{31}$ and R$^{32}$ may be bonded to each other to form an aromatic ring or a heterocyclic ring. X$^5$ represents a residue of active methylene compound.

In formula (10), $R^{32}$ is preferably a hydrogen atom, a halogen atom, an aliphatic group, an alkoxy group, an aryloxy group, an acylamino group, a ureido group, a sulfamoylamino group, an alkoxycarbonylamino group, or a sulfonamido group, among the substituent groups described above.

The following are specific examples of the azomethine dye represented by formula (10). However, the invention is not limited to them.

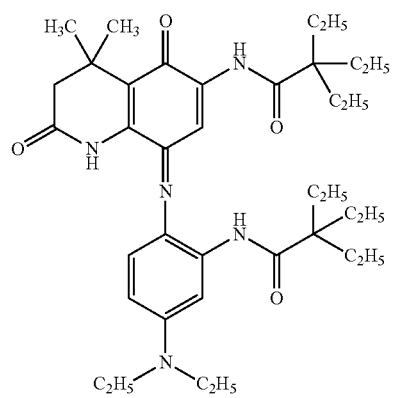

J-5

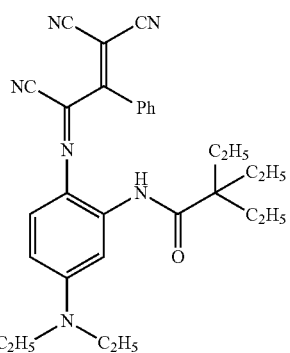

J-6

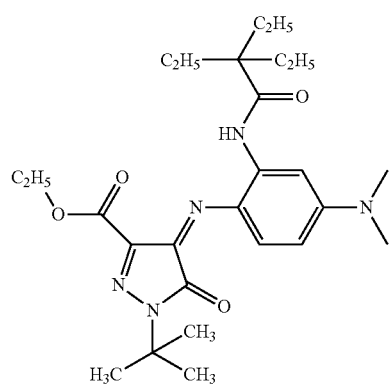

J-7

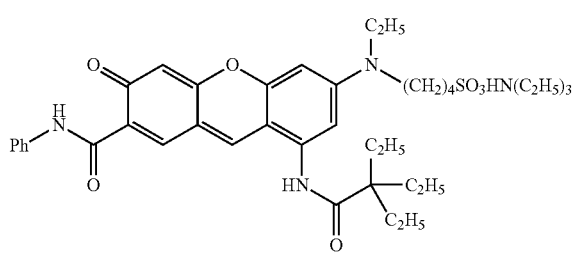

J-8

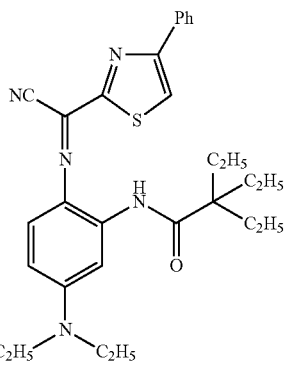

J-9

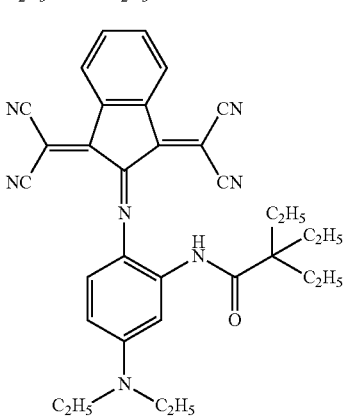

J-10

<Polymethine Dye>

The polymethine dye may be known dyes such as oxonol dyes, mellocyanine dyes, cyanine dyes, arylidene dyes, and styryl dyes represented by the following formulae.

The cyanine dyes include squarylium dyes and croconium dyes. Among these dyes, oxonol dyes and cyanine dyes are preferable, cyanine dyes are more preferably, and squarylium dyes are particularly preferable.

Cyanine dyes: Bs=Lo-Bo

Mellocyanine dyes: Bs=Le=Ak

Arylidene dyes: Ak=Lo-Ar

Styryl dyes: Bo-Le-Ar

Oxonol dyes: Ak=Lo-Ae

In the above formula, Bs represents a basic nucleus, Bo represents an onium body of a basic nucleus, Ak represents a keto type acidic nucleus, Ae represents an enol type acidic nucleus, Ar represents an aromatic nucleus, Lo represents a methine chain having odd numbers of methines, and Le represents a methine chain formed from even numbers of methines. In the invention, monomethine dyes in which Lo is formed from one methine is also included in the polymethine dyes.

The polymethine dye may be synthesized with reference to the descriptions of "Heterocyclic Compounds Cyanine Dyes and Related Compounds", F. M. Harmer, John Wiley and Sons, New York, London, 1964; "Heterocyclic Compounds-Special Topics in Heterocyclic Chemistry", D. M. Sturmer, Chapter 18, Section 14, and JP-A No. 6-313939.

The following are specific examples of the polymethine dye. However, the invention is not limited to these examples.

K-1
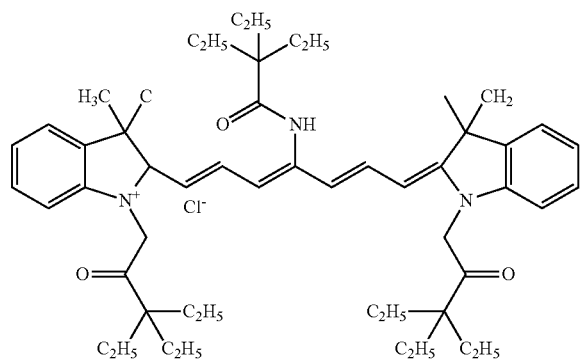
K-2
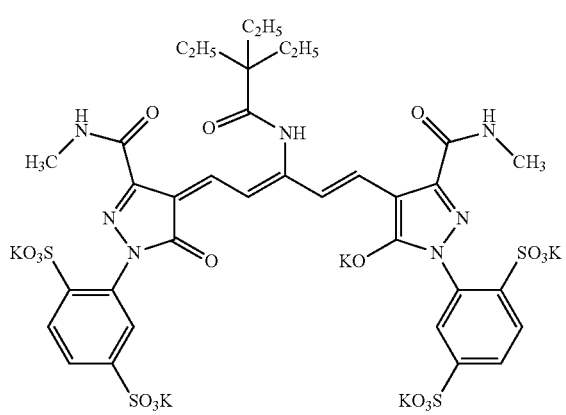
K-3
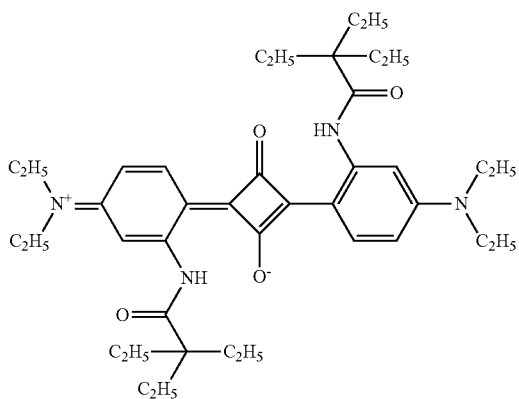
K-4
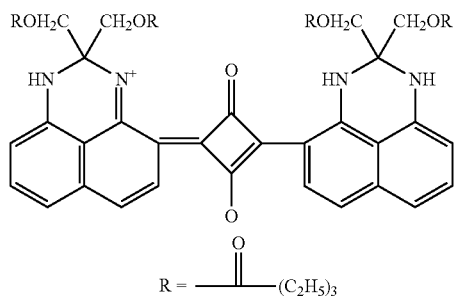

-continued

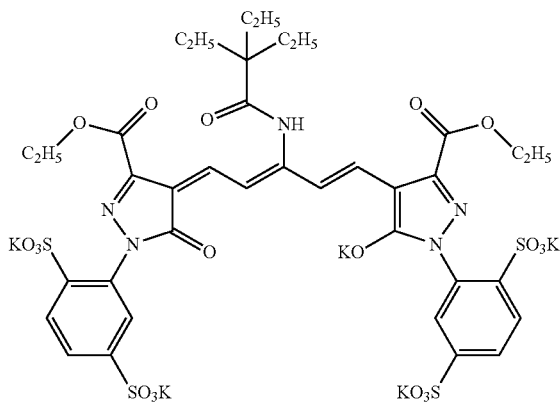
K-5

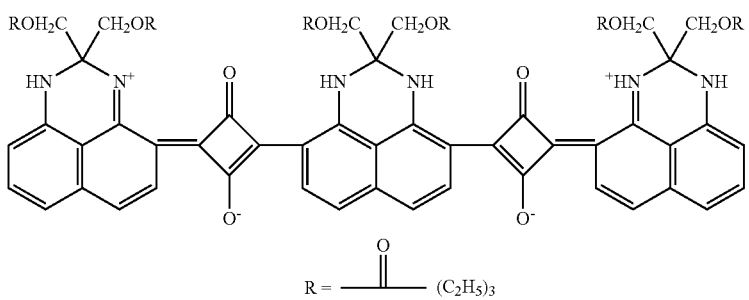
K-6

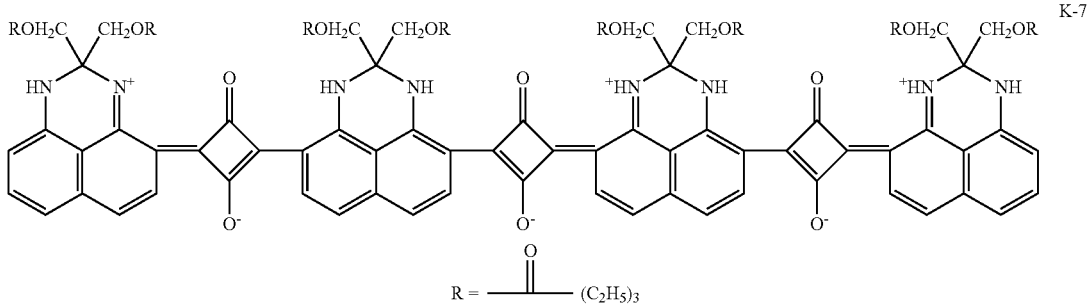
K-7

The dye compound of the invention preferably has a polymerizable group.

The method of introducing a polymerizable group into the dye compound of the invention is not specifically limited. For example, the introduction may be carried out by adding a polymerizable compound having an ethylenically unsaturated group (for example, a methacryloyl group, an acryloyl group or a styryl group) or a cyclic ether group (for example, an epoxy group or an oxetanyl group) to the dye compound.

Specifically, for example, a dye compound having a polymerizable group may be synthesized by adding a polymerizable compound (such as methacyloyl chloride, acryloyl chloride, 4-(chloromethyl) styrene, glycidyl methacrylate or methacryloxyethyl isocyanate) to a dye compound having a group that can react with the polymerizable compound (such as a hydroxyl group, an amino group or a carboxyl group).

By iniroducing a polymcrizablc group inio a dye compound, curability, heal fastness or solvent resistance can be improved.

The dye compound of the invention preferably has an alkali soluble group. By using a dye compound having an alkali soluble group in a colored composition, developability or the pattern shape of a color filter formed from the composition can be improved.

The method of introducing an alkali soluble group to a dye compound of the invention is not specifically limited. For example, the introduction may be carried out by adding a compound having an alkali soluble group to a dye compound.

Specifically, for example, a dye compound having an alkali soluble group may be synthesized by adding a compound having alkali solubility (such as thiomalic acid, thioglycolic acid, 5-mercaptoisophthalic acid, 3-mercaptobenzoic acid, malic acid, glycolic acid, 5-hydroxyisophthalic acid or 3-hydroxybenzoic acid) to a dye compound having a group that can react with the compound having alkali solubility (such as a halogenated alkyl group or a α-halogenated acyl group). By introducing an alkali soluble group to the dye compound, an ability of forming a colored pattern can be improved From the viewpoint of an ability of forming a colored pattern of a colored curable composition including the dye compound of the invention, the dye compound preferably contains alkali soluble groups so as to have an acid value of 10 to 400 mgKOH/g, more preferably an acid value of 30 to 300 mgKOH/g, and still more preferably an acid value of 50 to 200 mgKOH/g.

<<Dye Multimer>>

The dye compound of the invention is preferably a dye multimer including a dye structure described above as a partial structure of the dye moiety. In particular, the dye compound may be a dye multimer including a dye structure derived from a dipyrromethene compound as a partial structure of the dye moiety, or a dye multimer including a dye structure derived from a dipyrromethene metal complex compound as a partial structure of the dye moiety.

The method of introducing a dye skeleton derived from a dipyrromethene compound or a dipyrromethene metal complex compound into a dye multimer may be arbitrarily selected. For example, a dye skeleton may be introduced into a polymerizable monomer prior to polymerizing or copolymerizing the same to obtain a multimer, or a dye skeleton may be introduced into a multimer, after formation of the same, via polymerization reaction or the like.

Preferred embodiments of the dye multimer include a multimer containing at least one structural unit represented by any of formulae (A) to (C), a dye multimer represented by formula (D), and a multimer containing a dye monomer represented by formula (1) as a polymerizable component.

<Preferred Physical Properties of the Dye Multimer of the Invention>

Since the dye multimer of the invention exhibits excellent color purity, light fastness, heat fastness, and solvent resistance, and can form a cured film that exhibits suppressed color transfer and favorable ability of forming a pattern, it can be used for a colored curable composition suitable for forming a colored pattern of a color filter. From the viewpoint of improving an ability of forming a colored pattern, the dye multimer of the invention preferably has an alkali soluble group.

The method of introducing an alkali soluble group into the dye multimer of the invention is not specifically limited. For example, the introduction may be carried out by synthesizing a dye multimer from a monomer having an alkali soluble group, or by adding an alkali soluble group to a dye multimer after formation of the same.

In order to synthesize a dye multimer from a monomer having an alkali soluble group, it is sufficient when an alkali soluble group exists in at least one of a dye multimer containing at least one structural unit represented by formula (A), formula (B) or formula (C), a dye multimer represented by formula (D), a dye monomer represented by formula (1), or a monomer having a different structure from the dye monomer represented by formula (1) and having an ethylenically unsaturated terminal bond.

When the structural unit represented by formula (A), formula (B) or formula (C), or the dye monomer represented by formula (1) is a monomer having an alkali soluble group, an alkali soluble group may exist in the dye moiety (i.e., dye residue). From the viewpoint of synthesis suitability, the alkali soluble group is preferably included in a monomer having an ethylenically unsaturated bond used as a polymerization component, rather than in a monomer that forms a structural unit having the dye moiety (i.e., dye residue).

From the viewpoint of forming a colored pattern from a colored curable composition including the dye multimer of the invention, the dye multimer preferably includes alkali soluble groups so as to have an acid value of 10 to 400 mgKOH/g, more preferably an acid value of 30 to 300 mgKOH/g, and still more preferably an acid value of 50 to 200 mgKOH/g.

In the invention, the acid value is obtained by a method based on the JIS standard (JIS K 0070: 1992).

The dye multimer of the invention preferably has a solubility in an alkali solution as a developer (pH 9 to 15) of from 0.1% by mass to 80% by mass, more preferably from 0.5% by mass to 50% by mass, and still more preferably from 1% by mass to 30% by mass. When a dye multimer having a solubility within this range is used for the purposes accompanied by alkali development, such as a colored curable composition, a suitable pattern shape may be formed or the amount of residues on a substrate may be reduced.

Further, when the dye multimer of the invention is used for a colored curable composition, the dye multimer of the invention preferably has a polymerizable group from the viewpoint of inhibiting color transfer and improving an ability of forming a colored pattern. One or more kinds of polymerizable group may be included in the dye multimer.

Examples of the polymerizable group include an ethylenically unsaturated group (for example, a methacryloyl group, an acryloyl group, and a styryl group) or a cyclic ether group (for example, an epoxy group and an oxetanyl group). Among these, from the viewpoint of heat fastness and solvent resistance after polymerization, an ethylenically unsaturated group is preferable.

The dye multimer containing a polymerizable group preferably has, as a repeating unit, a structural unit having a polymerizable group and a structural unit having a group derived from a dye.

Further, the dye multimer containing a polymerizable group may have a structural unit other than a structural unit having a polymerizable group or a structural unit having a group derived from a dye.

From the viewpoint of reducing the thickness of a color filter, the dye multimer having a polymerizable group preferably contains a structural unit having a group derived from a dye in an amount of 60% by mass to 99% by mass, more preferably 70% by mass to 97% by mass, and still more preferably 80% by mass to 95% by mass.

Further, from the viewpoint of heat resistance and solvent resistance, the dye multimer containing a polymerizable group preferably contains a structural unit having a polymerizable group in an amount of 1% by mass to 40% by mass, more preferably 3% by mass to 30% by mass, and still more preferably 5% by mass to 20% by mass.

The structural unit having a polymerizable group may be introduced into a dye multimer having a polymerizable group according to a method as described below, for example.

In this method, specifically, a multimer is obtained by copolymerizing a dye compound as previously described and a polymerization component not having a dye skeleton (such as methacrylic acid, acrylic acid, or hydroxyethyl methacrylate), and subsequently adding, to the multimer, a polymerizable compound having a group that can react with a structural unit of the multimer derived from the polymerization component not having a dye skeleton (such as glycidyl methacrylate or methacryloyloxyethyl isocyanate), thereby introducing a structural unit having a polymerizable group.

It is also possible to obtain a polymerizable group-containing dye multimer by introducing, into a dye skeleton, a different polymerizable group from a polymerizable group that contributes to formation of a multimer from a dye compound, and then allowing the dye compound to polymerize.

The dye multimer of the invention is preferably dissolved in an organic solvent. Examples of the organic solvent include esters (for example, methyl 3-ethoxypropionate, ethyl 3-ethoxypropionate, ethyl lactate, butyl acetate, and methyl 3-methoxypropionate), ethers (for example, methyl cellosolve acetate, ethyl cellosolve acetate, propylene glycol monomethyl ether, and propylene glycol monomethyl ether acetate), ketones (for example, methyl ethyl ketone, cyclohexanone, 2-heptanone, and 3-heptanone), and aromatic hydrocarbons (for example, toluene and xylene). The dye multimer is preferably dissolved in an organic solvent an amount of 1% by mass to 50%, more preferably 5% by mass to 40% by mass, and still more preferably 10% by mass to 30% by mass. When a colored curable composition in which the amount of the dye multimer is within this range is used, a favorable coating surface may be obtained and reduction in concentration due to elution after application of a different color may be suppressed.

The Tg of the dye multimer of the invention is preferably 50° C. or more, and more preferably 100° C. or more. Further, the temperature at which the mass reduces by 5% according to thermogravimetric analysis (TGA) is preferably 120° C. or more, more preferably 150° C. or more, and still more preferably 200° C. or more. When a colored curable composition includes a dye multimer that satisfies the above ranges, changes in concentration due to a heating process may be reduced.

From the viewpoint of a coloring power, the molar absorption coefficient of the dye multimer of the invention is preferably as high as possible. Further, from the viewpoint of improving color purity, a maximum absorption wavelength (λmax) is preferably from 520 nm to 580 nm, and more preferably from 530 nm to 570 nm. When a maximum absorption wavelength (λmax) is within this range, a color filter that exhibits a favorable color reproducibility may be produced. Moreover, the dye multimer preferably has a molar absorption coefficient at a maximum absorption wavelength (λmax) being at least 1,000 times as great as a molar absorption coefficient at 450 nm, more preferably at least 10,000 times, further preferably at least 100,000 times. When the ratio is within this range, a color filter having an improved transmission, in particular a blue color filter, may be produced from a colored curable composition including the dye multimer of the invention. The maximum absorption wavelength and the molar absorption coefficient are measured by using a spectrophotometer (CARY5, trade name, manufactured by Varian Inc.)

The absorption coefficient per unit weight of the dye multimer of the invention (hereinbelow, described as ∈', unit: L/g·cm) is preferably 30 or more, more preferably 60 or more, and still more preferably 90 or more. When the absorption coefficient per unit weight of the dye multimer of the invention is within this range, a color filter that exhibits a favorable color reproducibility may be obtained when a color filter or the like is produced by using the dye multimer of the invention for a colored curable composition or the like.

It is more preferable that the dye multimer of the invention satisfies both the maximum absorption wavelength (λmax) and the absorption coefficient per unit weight of the dye multimer of the invention as described above.

<Structure of the Dye Multimer of the Invention>

The dye multimer of the invention is preferably a dye multimer having a dye skeleton derived from a dipyrromethene metal complex compound.

Examples of the dye multimer having a dye skeleton derived from a dipyrromethene metal complex compound include a dye multimer containing at least one structural unit represented by formula (A), formula (B) or formula (C), a dye multimer represented by formula (D), and a dye multimer containing a dye monomer represented by formula (1) as a polymerization component. In the following, these dye multimers are explained.

<Structural Unit Represented by Formula (A)>

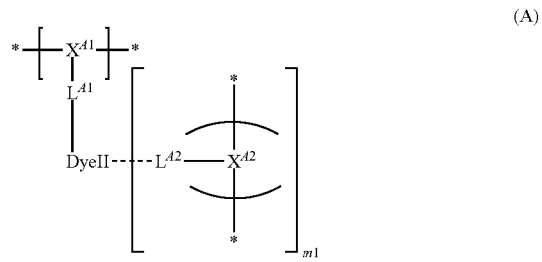

(In formula (A), $X^{A1}$ represents a linking group formed by polymerization, and $L^{A1}$ represents a single bond or a divalent linking group. Dye II represents a linking group having a partial structure represented by formula (5) from which from one to (m1+1) hydrogen atoms are removed, and Dye in formula (5) is a dye structure formed by removing one or two hydrogen atoms from a dipyrromethene metal complex compound obtained from a dipyrromethene compound represented by formula (M) and a metal or a metal compound. $X^{A2}$ represents a linking group formed by polymerization, $L^{A2}$ represents a single bond or a divalent linking group, and m1 represents an integer from 0 to 3. When m1 is 2 or more, the two or more structures in the brackets may be the same or different from each other. Dye II and $L^{A2}$ are linked to each other via covalent bonding, ionic bonding or coordinate bonding).

In formula (A), $X^{A1}$ and $X^{A2}$ each independently represent a linking group formed by polymerization, i.e., a moiety that forms a repeating unit corresponding to a main chain formed by polymerization reaction. Further, the moiety represented by a pair of * corresponds to a repeating unit. Examples of $X^{A1}$ and $X^{A2}$ include a linking group formed by polymerization of a substituted or unsubstituted unsaturated ethylene group and a linking group formed by ring-opening polymerization of a cyclic ether. Preferably, it is a linking group formed by polymerization of an unsaturated ethylene group. Specific examples include the linking groups described below. However, the linking group formed by polymerization of the invention is not limited to these examples.

In the following linking groups (X-1) to (X-15), * indicates a site to be linked to L.

(X-1)

(X-2)

(X-3)

(X-4)

(X-5) 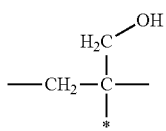

(X-6) 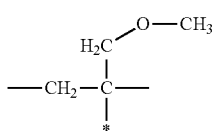

(X-7) 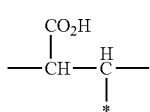

(X-8) 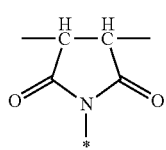

(X-9) 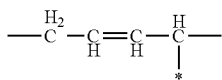

(X-10) 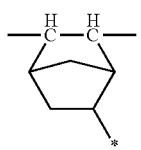

(X-11) 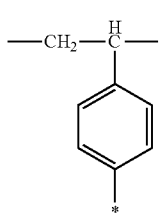

(X-12) 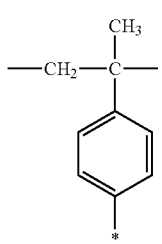

(X-13) 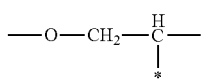

(X-14) 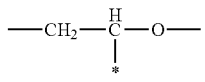

(X-15) 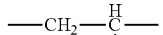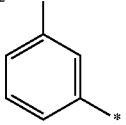

In formula (A), $L^{41}$ represents a single bond or a divalent linking group. Examples of the divalent linking group represented by $L^{41}$ include a substituted or unsubstituted alkylene group having 1 to 30 carbon atoms (for example, a methylene group, an ethylene group, a trimethylene group, a propylene group and a butylene group), a substituted or unsubstituted arylene group having 6 to 30 carbon atoms (for example, a phenylene group and a naphthalene group), a substituted or unsubstituted heterocyclic linking group, —CH═CH—, —O—, —S—, —NR— (each R independently represents a hydrogen atom, an alkyl group, an aryl group, or a heterocyclic group), —C(═O)—, —SO—, —SO$_2$—, a linking group represented by formula (2), a linking group represented by formula (3), and a linking group represented by formula (4)), which will be described later, and a linking group formed from two or more of these groups linked to each other.

The divalent liking group represented by formula (A) is not specifically limited, as long as the effect of the invention is achieved.

In formula (A), Dye II represents a group obtained by removing from one to (m1+1) hydrogen atoms from formula (5), which is a dye residue formed by removing any one or two hydrogen atoms from a dipyrromethene metal complex compound obtained from a dipyrromethene compound represented by formula (M) and a metal or a metal compound.

Preferably, Dye II is a dye structure obtained by removing any hydrogen atoms in a number of m1+1 from a dipyrromethene metal complex compound represented by formula (5) or formula (6).

In the following, specific examples of the structural unit represented by formula (A) are described. However, the invention is not limited to these examples.

(A-1)
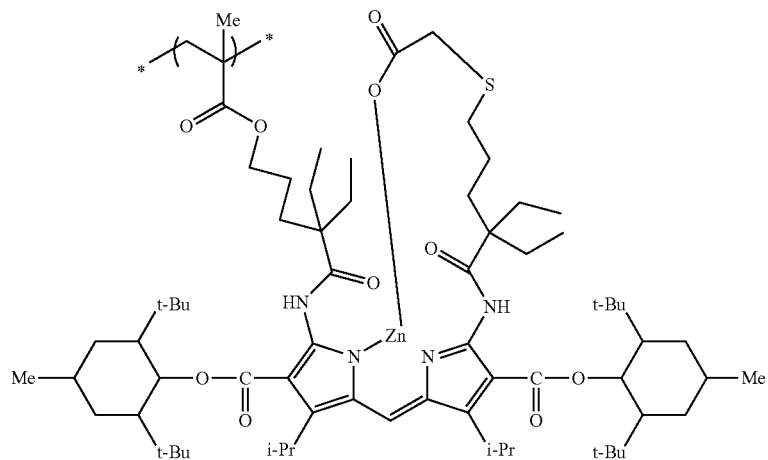
(A-2)
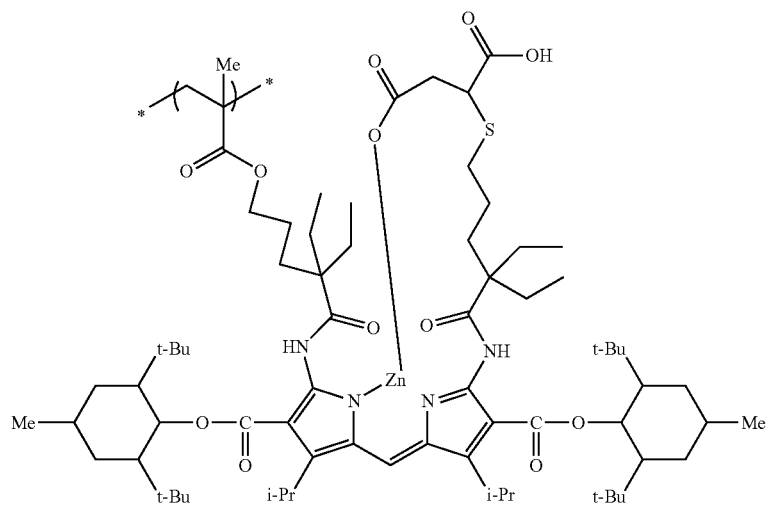
(A-3)
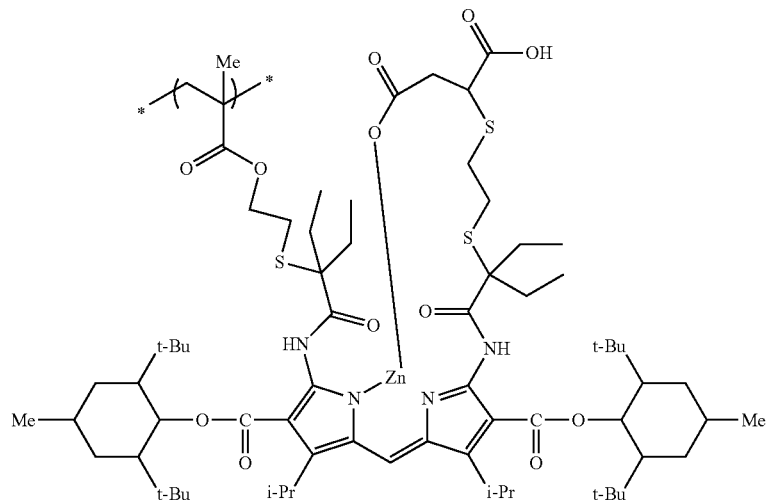

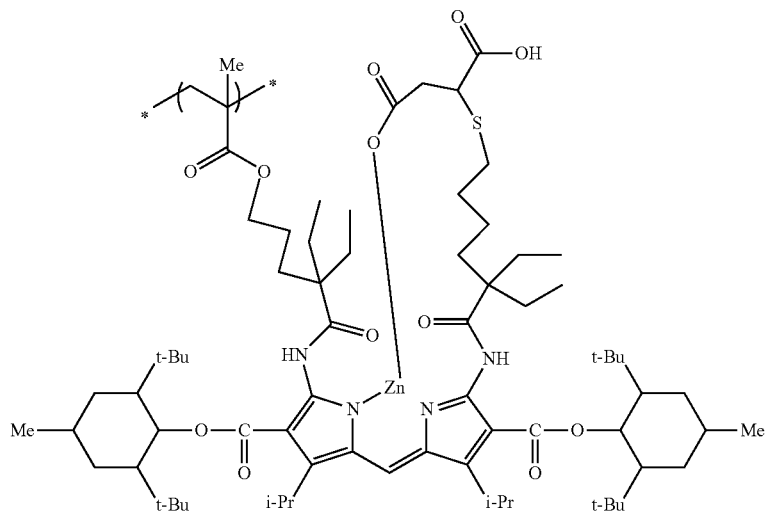
(A-4)
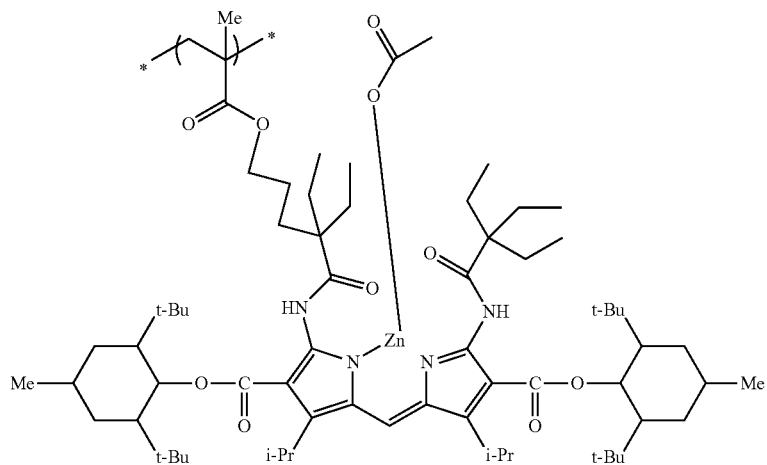
(A-5)
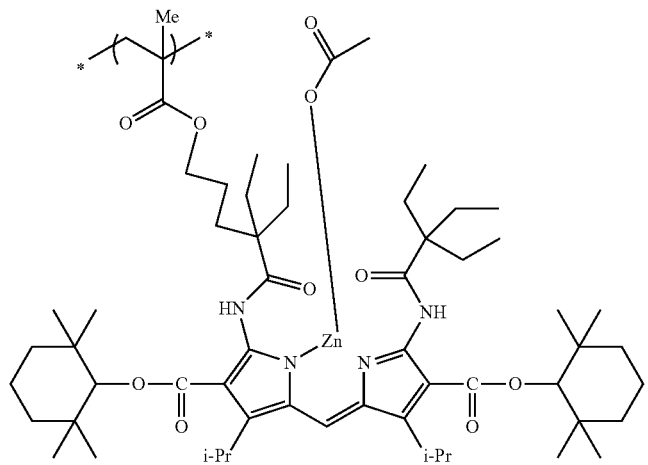
(A-6)

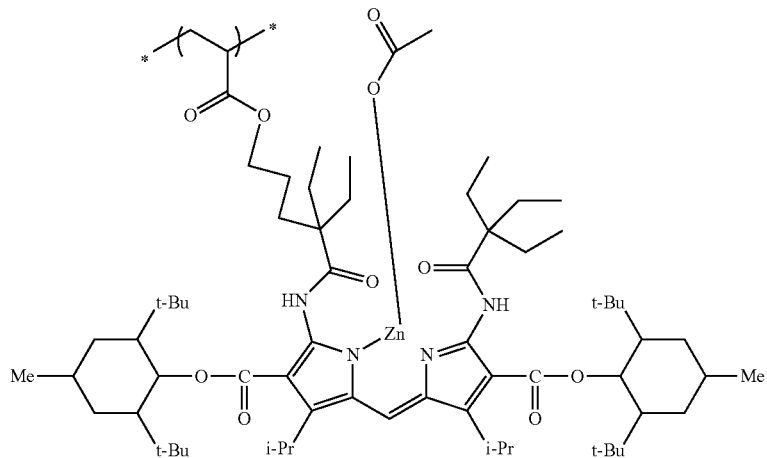
(A-7)
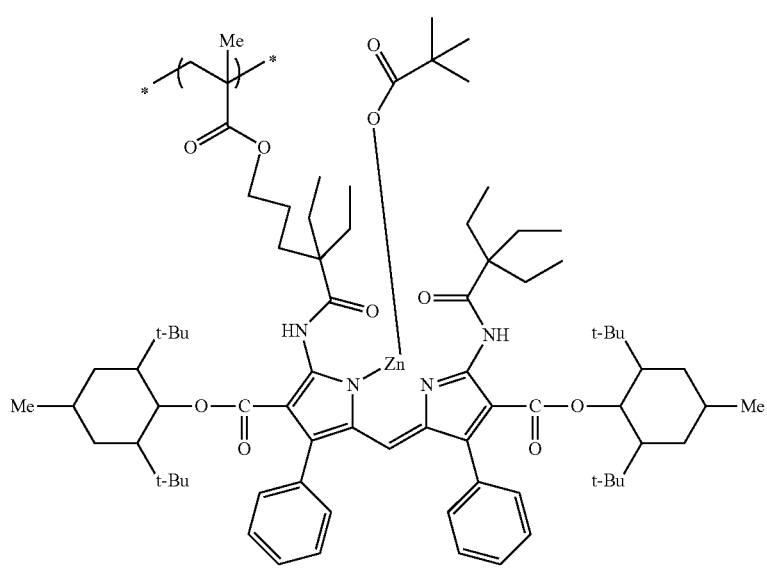
(A-8)
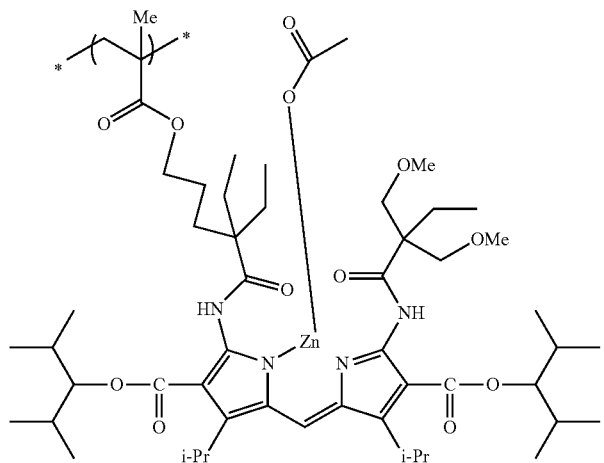
(A-9)

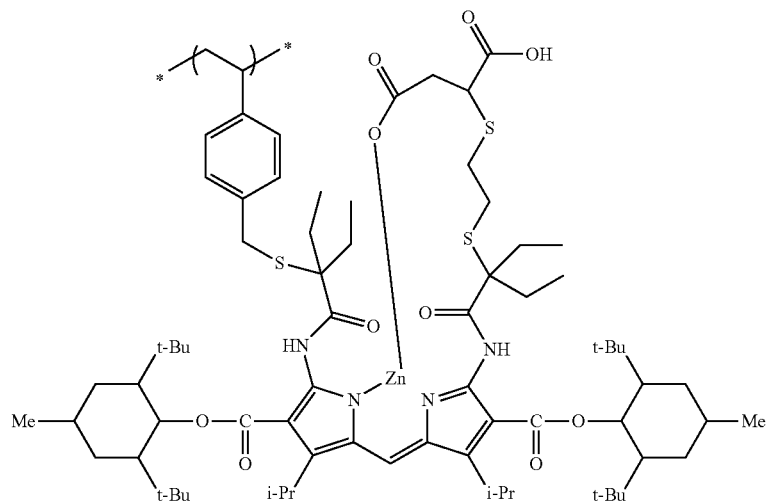
(A-10)
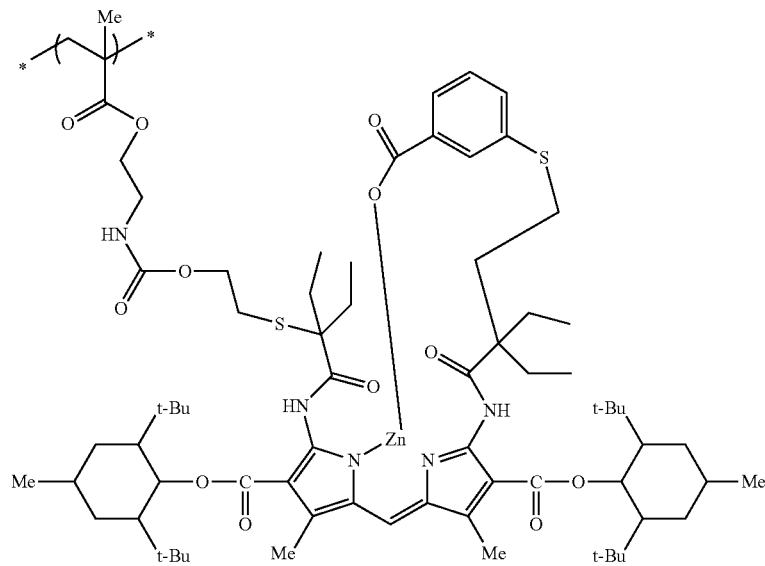
(A-11)

-continued
(A-12)
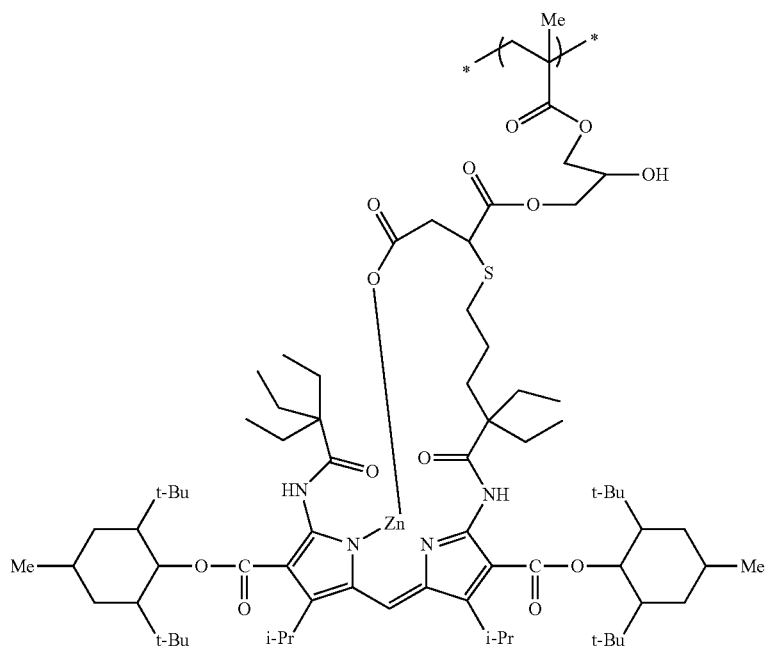
(A-13)
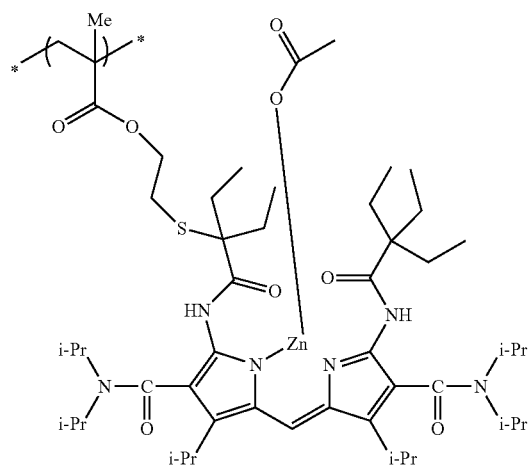
(A-14)
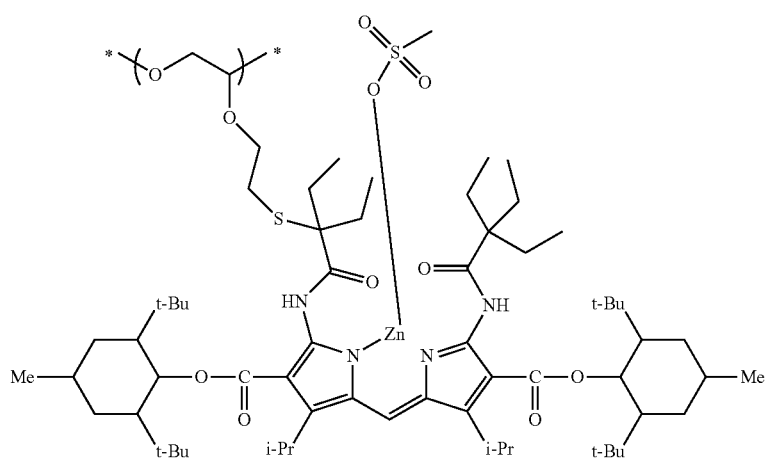

-continued
(A-15)
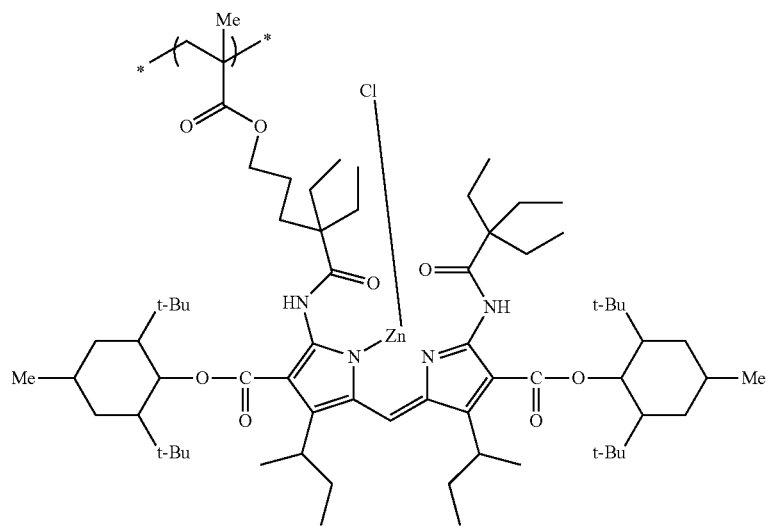
(A-16)
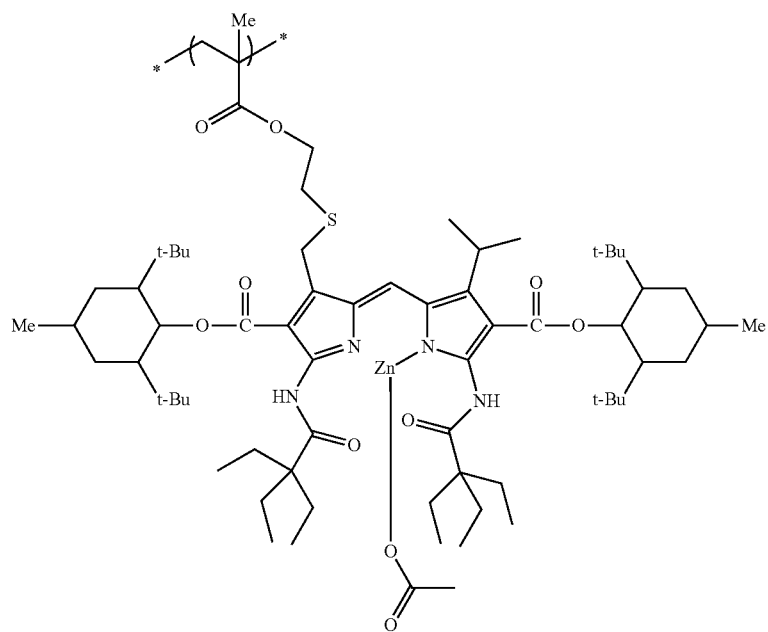
(A-17)
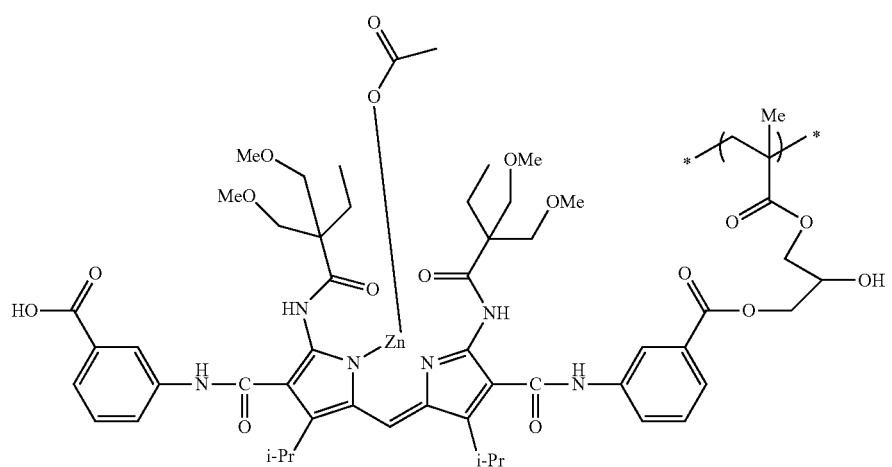

(A-18)
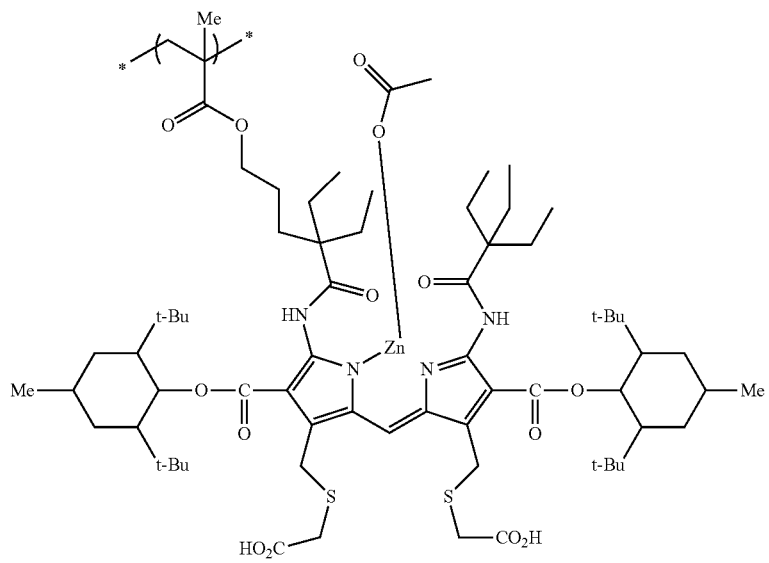
(A-19)
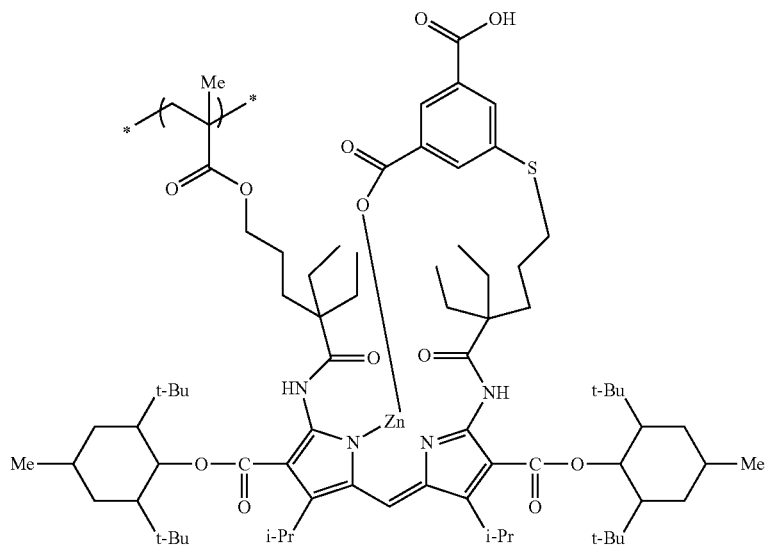
(A-20)
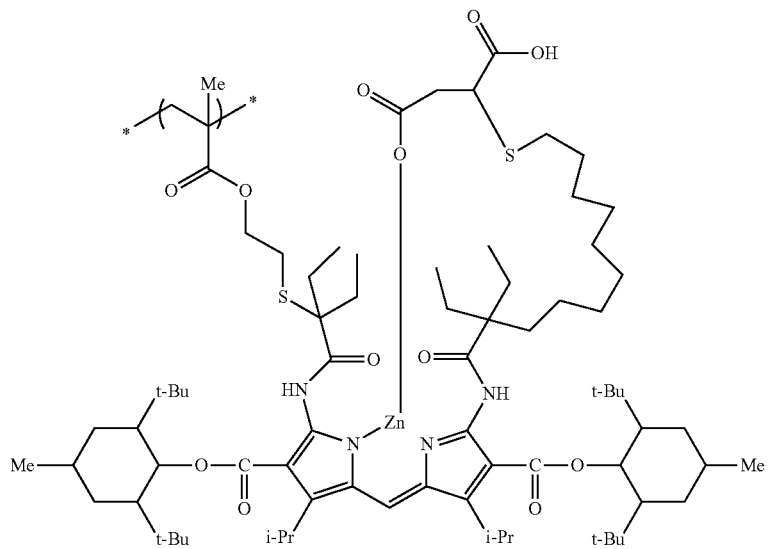

-continued
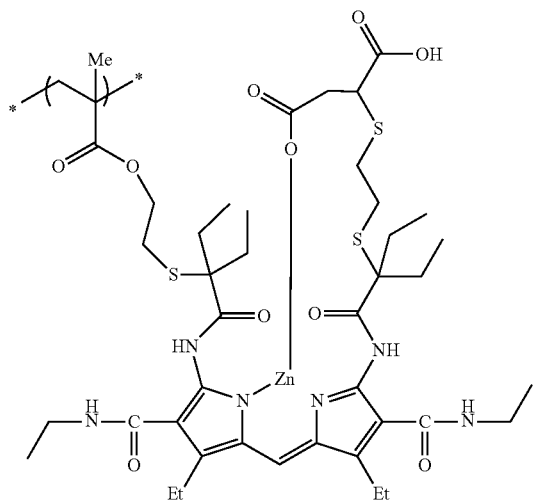
(A-21)
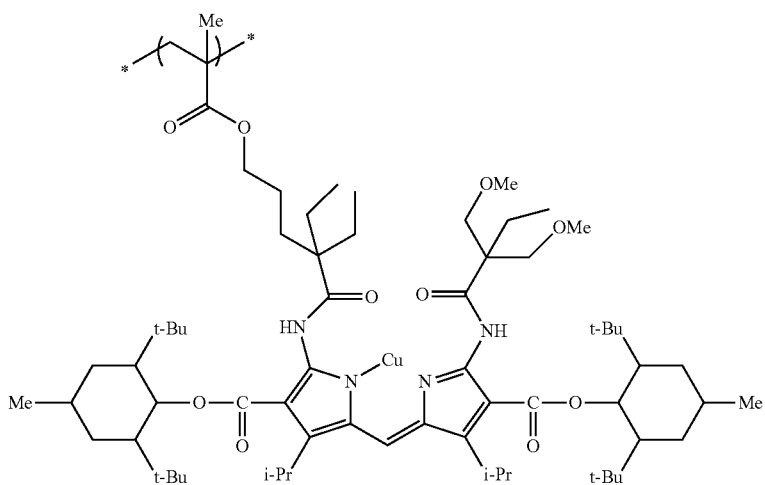
(A-22)
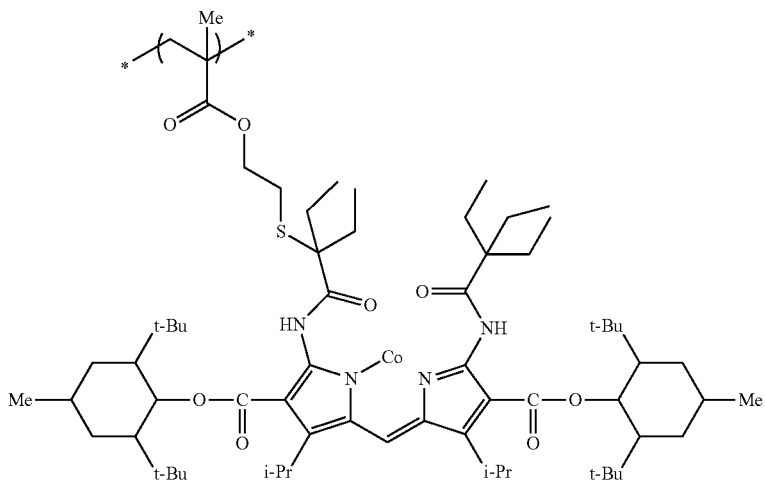
(A-23)

-continued
(A-24)
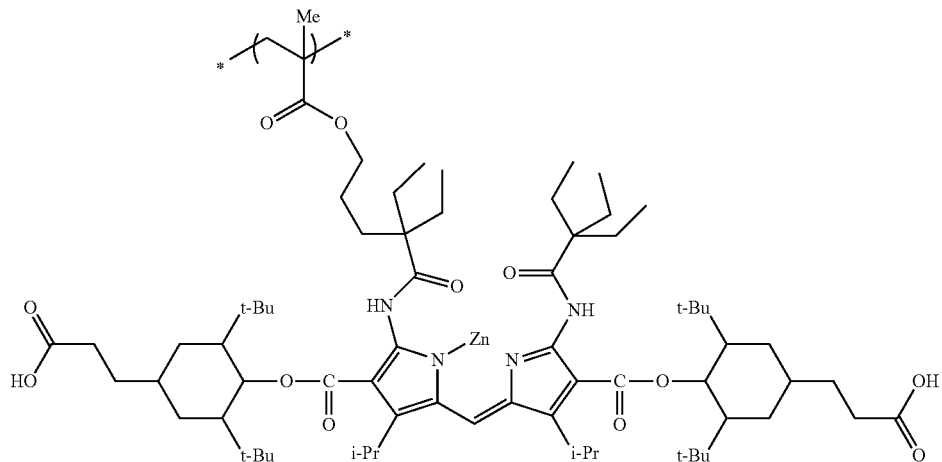
(A-25)
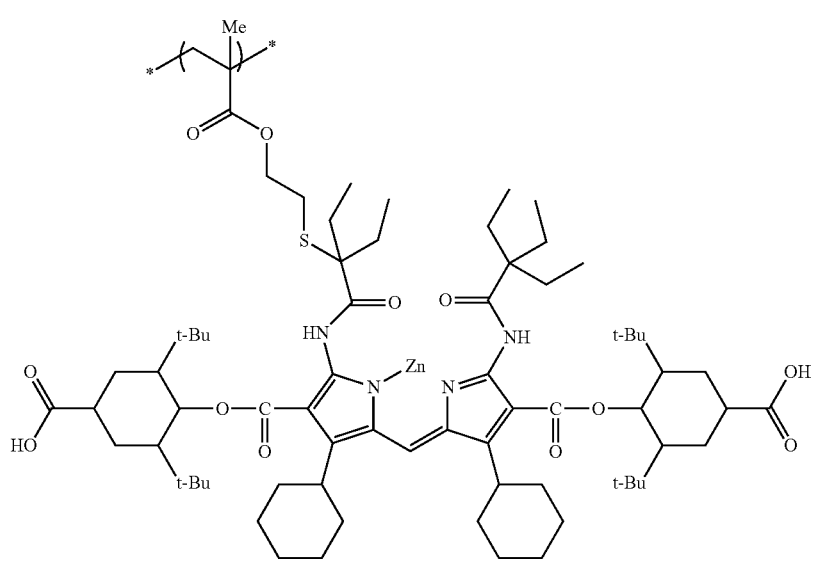
(A-26)
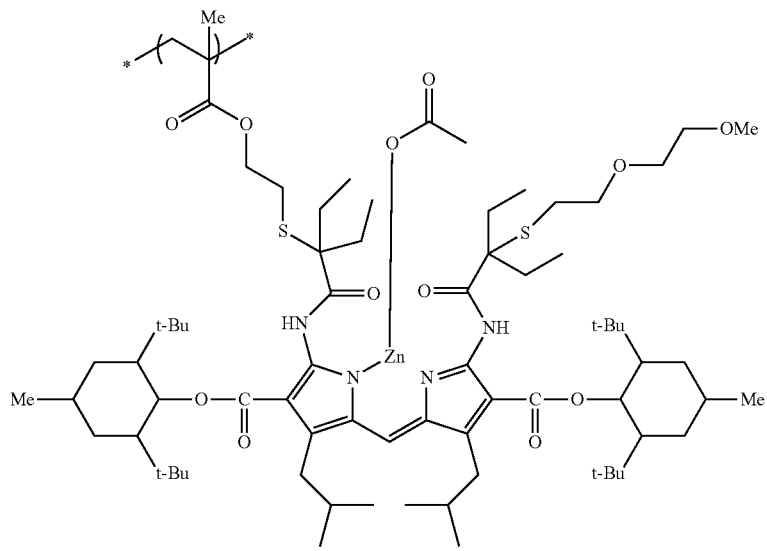

-continued
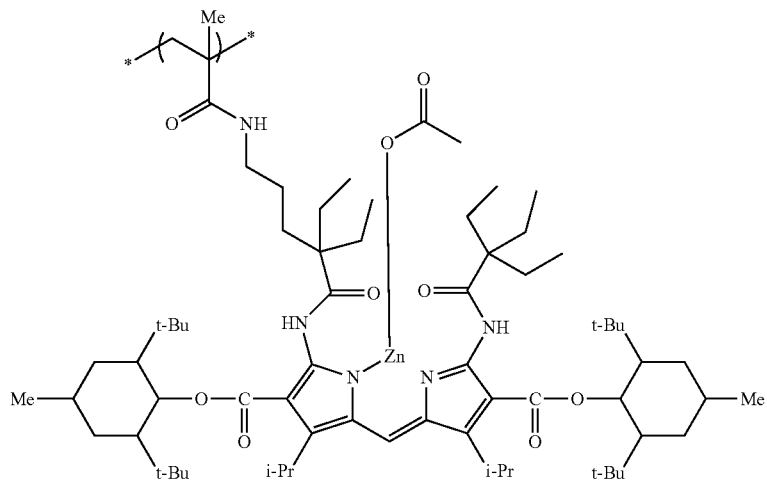
(A-27)
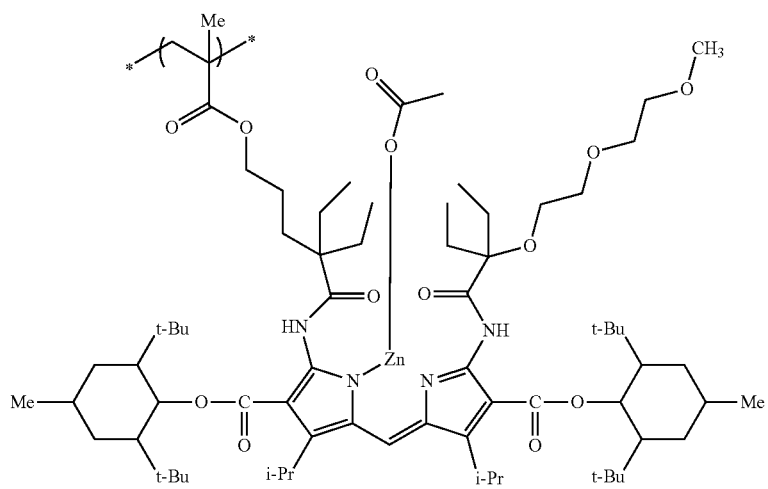
(A-28)
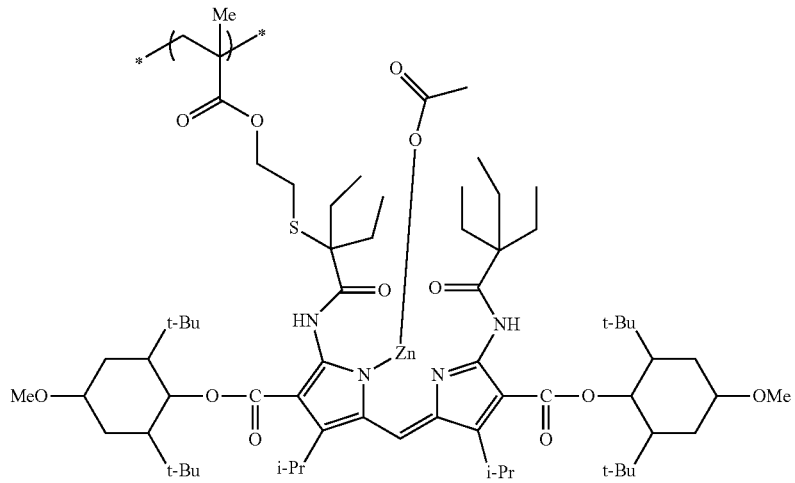
(A-29)

-continued
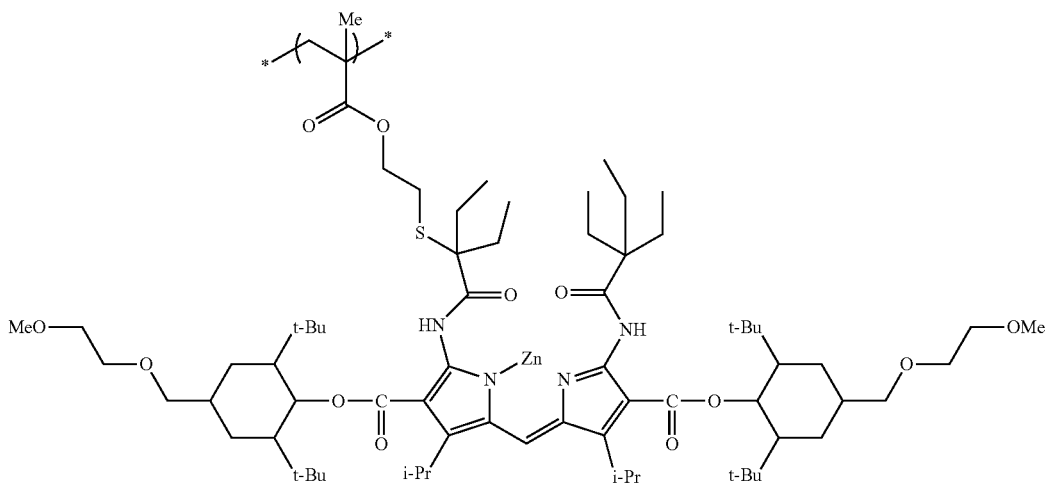
(A-30)
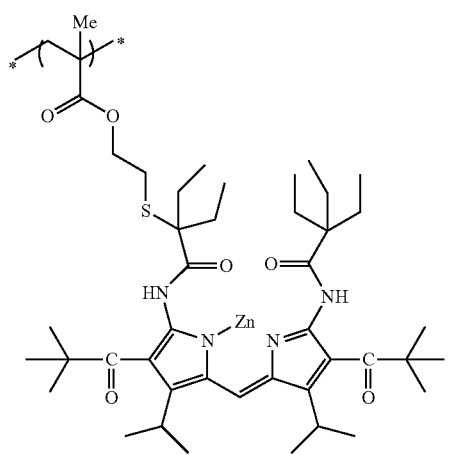
(A-31)
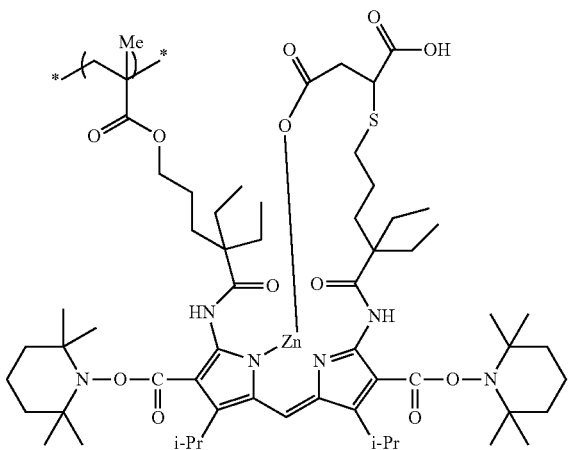
(A-32)
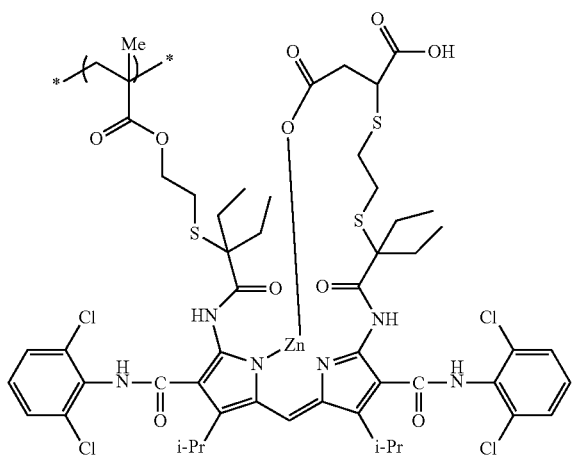
(A-33)

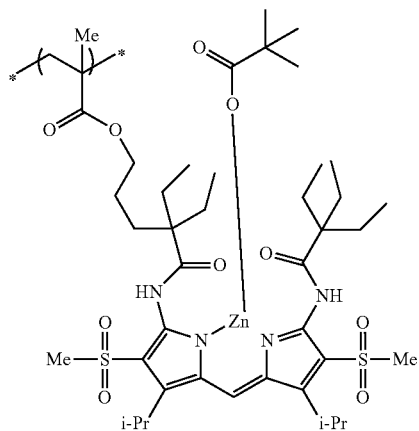
(A-34)
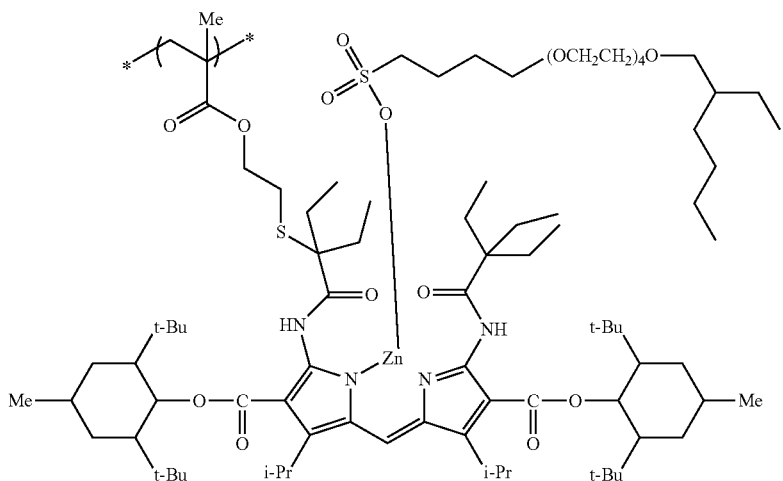
(A-35)
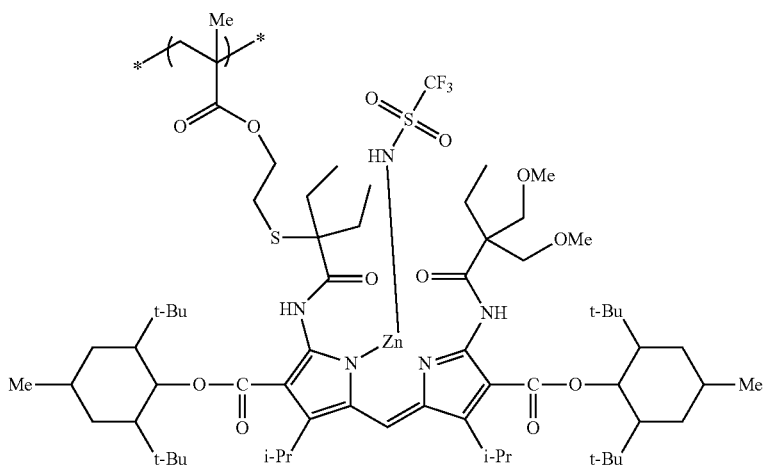
(A-36)

-continued
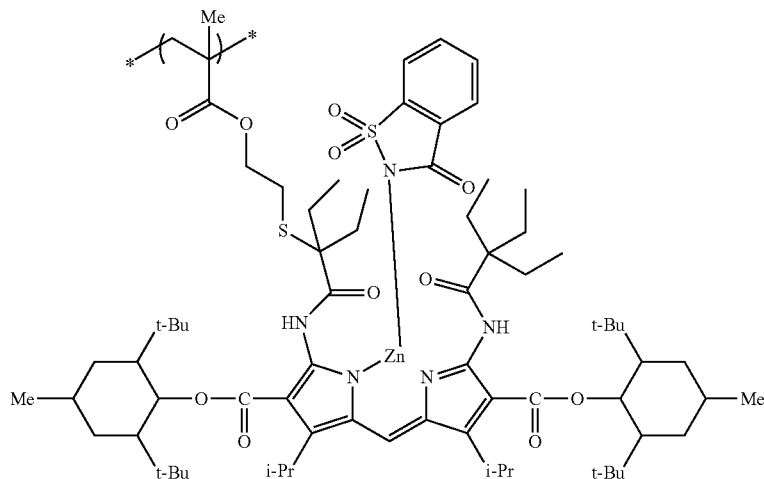
(A-37)
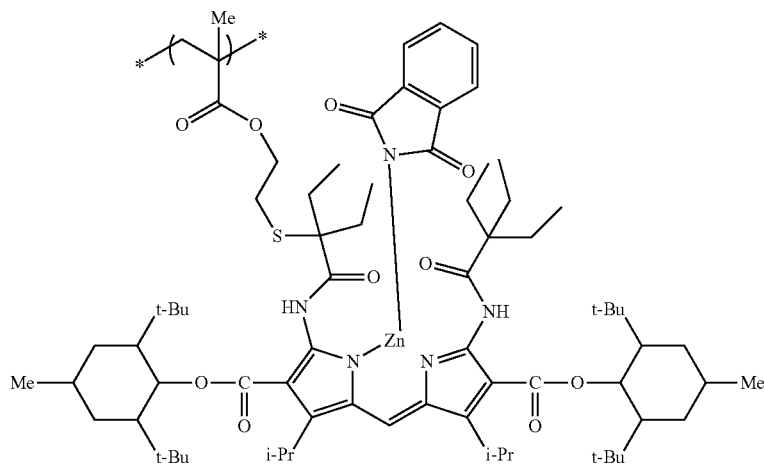
(A-38)
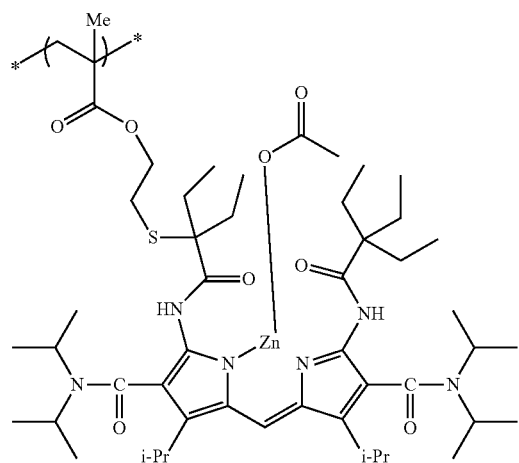
(A-39)

(A-40)
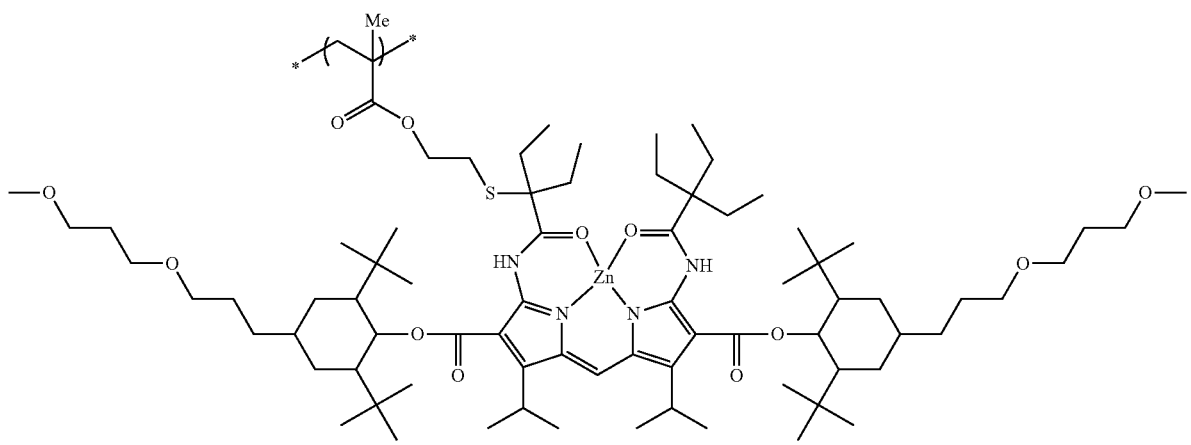
(A-41)
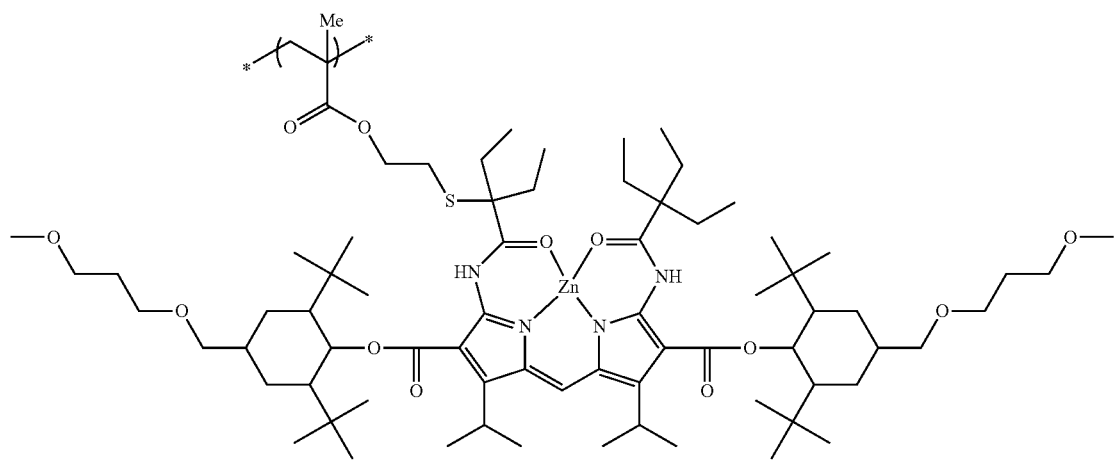
(A-42)
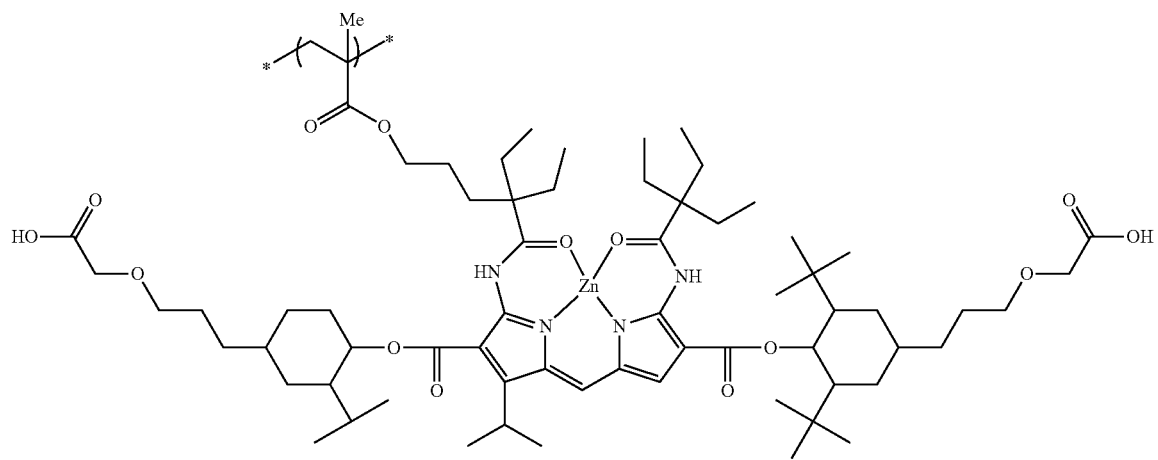

(A-43)
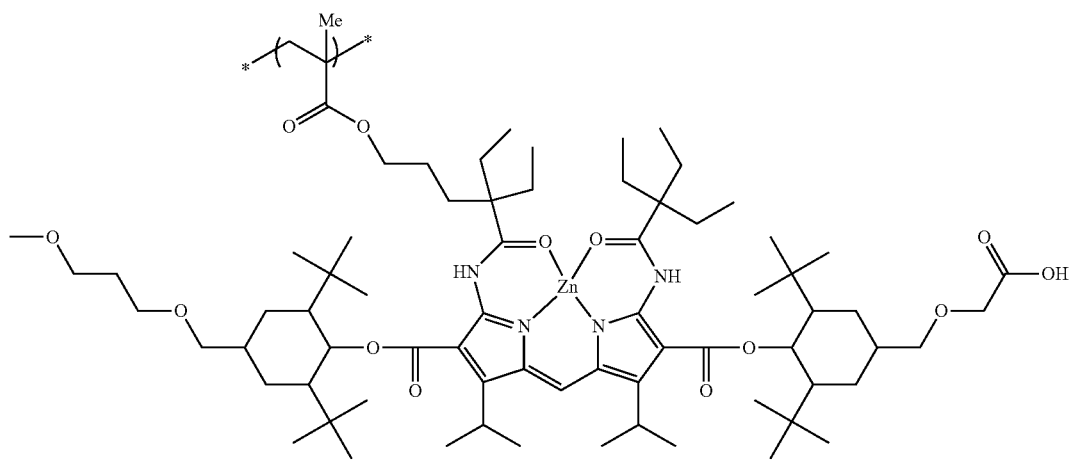
(A-44)
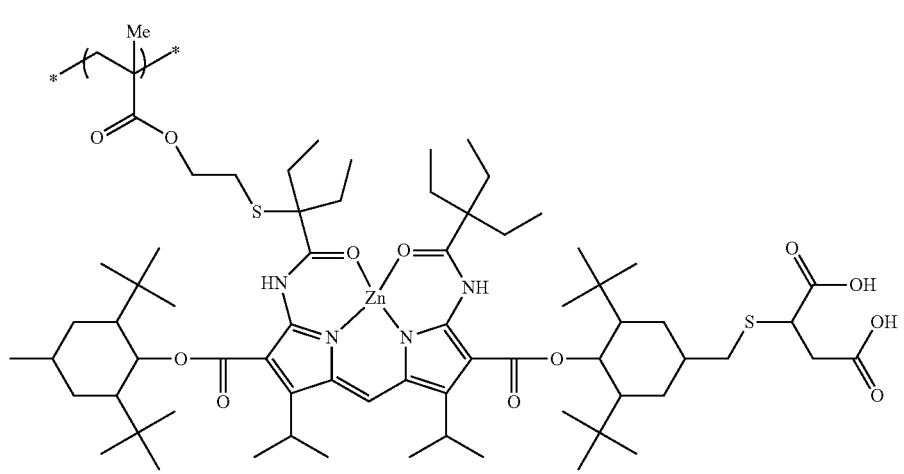
(A-45)
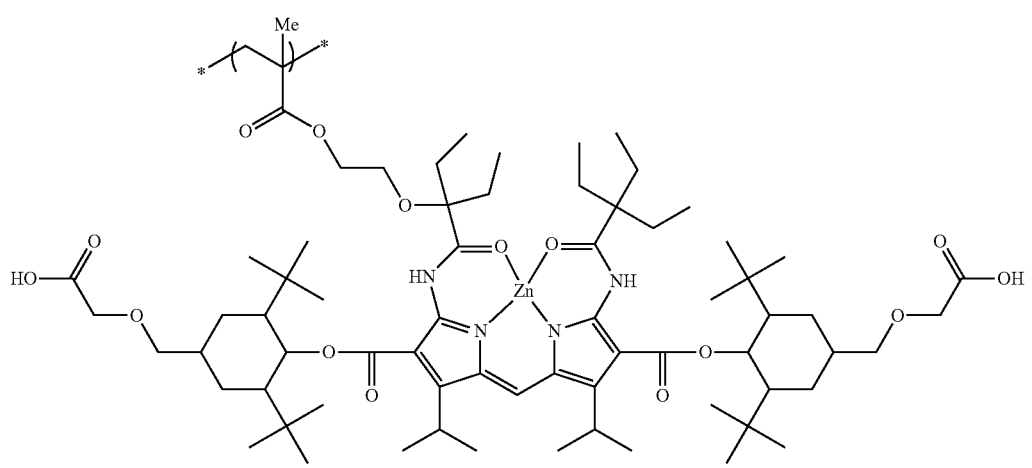

(A-46)
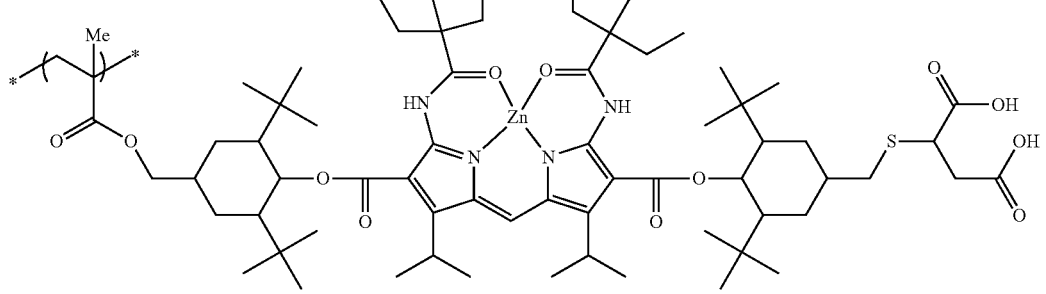
(A-47)
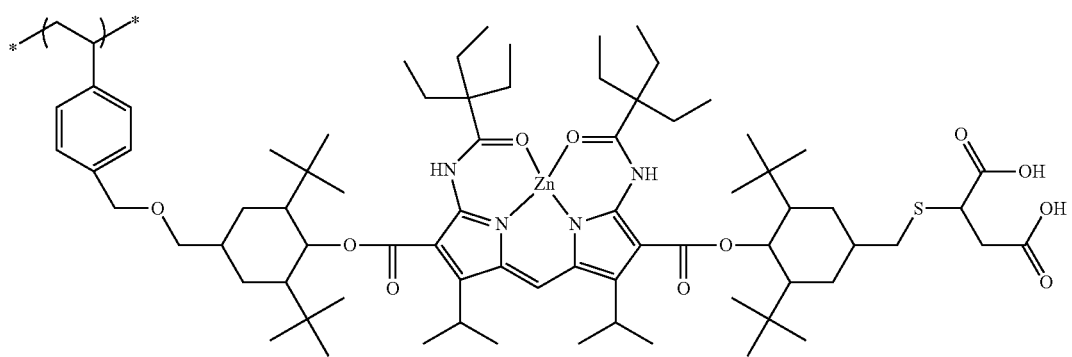
(A-48)
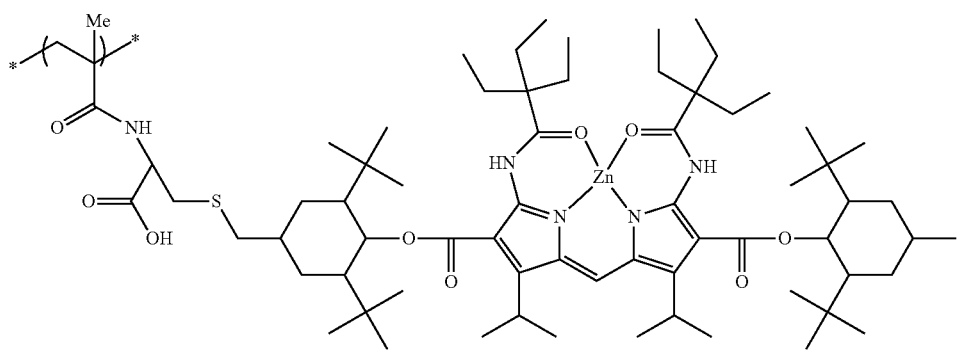
(A-49)
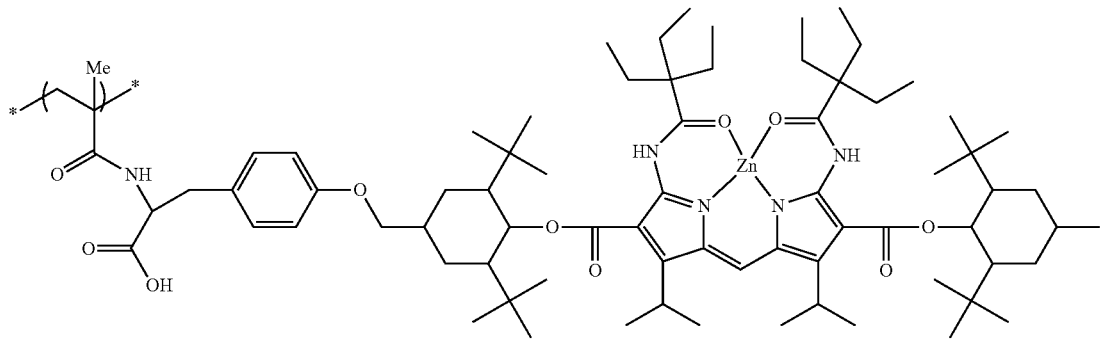

<Structural Unit Represented by Formula (B)>

In the following, the structural unit represented by formula (B) is explained in detail.

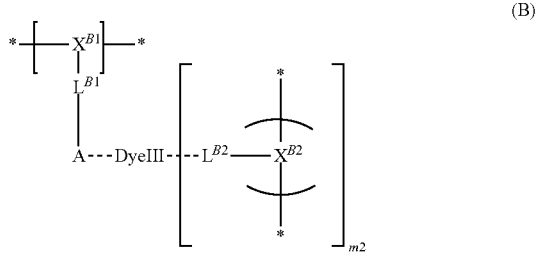

(In formula (B), $X^{B1}$ represents a linking group formed by polymerization, and $L^{B1}$ represents a single bond or a divalent linking group. A represents a group capable of being bonded to Dye III via ionic bonding or coordinate bonding. Dye III represents a linking group having a structure formed by removing from one to (m2+1) hydrogen atoms from a partial structure represented by formula (5), and Dye in formula (5) is a dye structure formed by removing any one or two hydrogen atoms from a dipyrromethene metal complex compound obtained from a dipyrromethene compound represented by formula (M) and a metal or a metal compound. $X^{B2}$ represents a linking group formed by polymerization, $L^{B2}$ represents a single bond or a divalent linking group, and m2 represents an integer from 0 to 3. When m2 is 2 or greater, the two or more structures in the brackets may be the same or different from each other. Dye III and $L^{B2}$ may be linked to each other via covalent bonding, ionic bonding or coordinate bonding).

In formula (B), definitions of $X^{B1}$ and $L^{B1}$ are the same as that of $X^{A1}$ and $L^{A1}$ in formula (A), respectively, and preferred embodiments are also the same.

The group represented by A in formula (B) may be any group as long as it can be bonded to Dye III via ionic bonding or coordinate bonding. The group capable of ionic bonding may be either an anionic group or a cationic group. The anionic group is preferably an anionic group having a pKa of 12 or less, such as a carboxyl group, a phospho group, a sulfo group, an acylsulfonamido group, and a sulfonimido group. More preferably, the anionic group has a pKa of 7 or less, and still more preferably 5 or less. The anionic group may be bonded to Ma or a heterocyclic group via ionic bonding or coordinate bonding, but is preferably bonded to Ma via ionic bonding.

The following are specific examples of preferred anionic groups, but the invention is not limited to these examples. In the anionic groups described below, each R independently represents a hydrogen atom, an alkyl group, an aryl group, or a heterocyclic group.

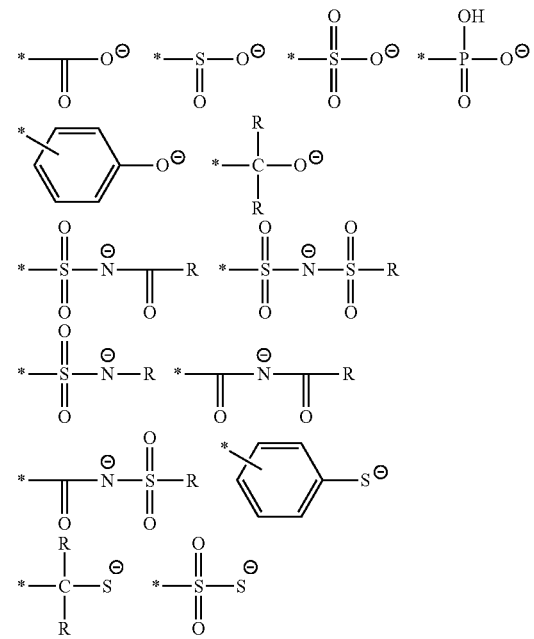

In formula (B), the cationic group represented by A is preferably a substituted or unsubstituted onium cation (for example, an ammonium group, a pyridinium group, an imidazolium group, a sulfonium group or a phosphonium group that may be substituted or unsubstituted). Among these, substituted ammonium group is particularly preferable.

The following are specific examples of the structural unit represented by formula (B), but the invention is not limited to these examples.

(B-1)

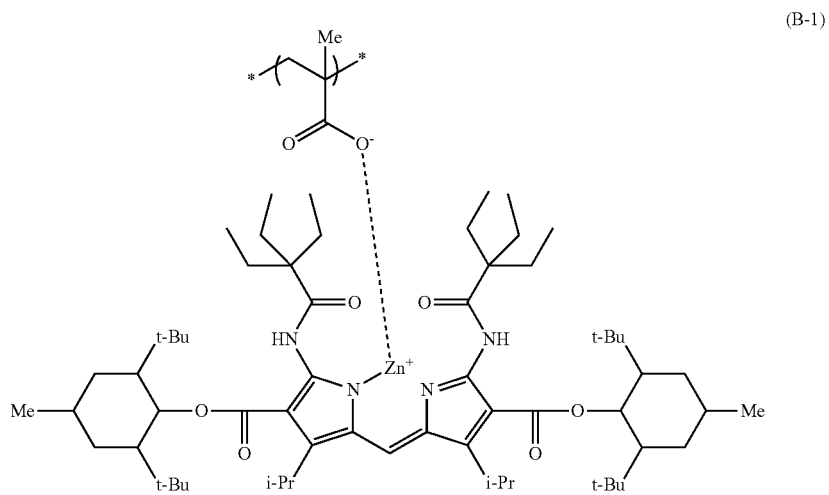

-continued
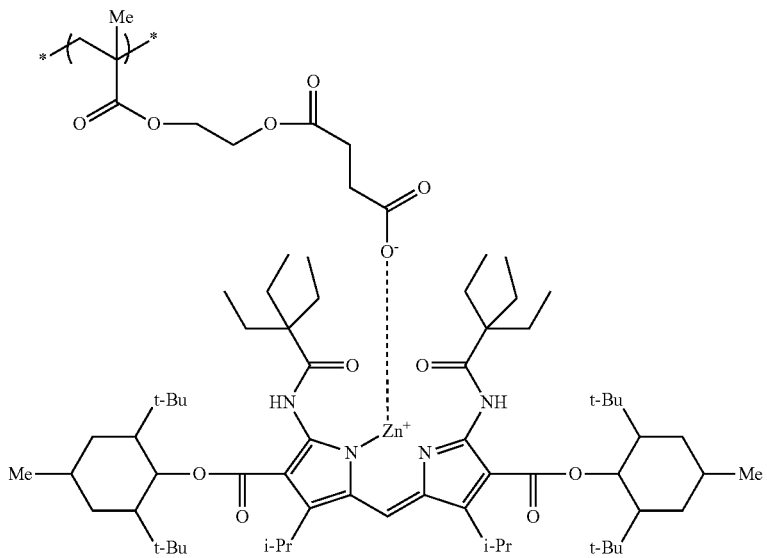
(B-2)
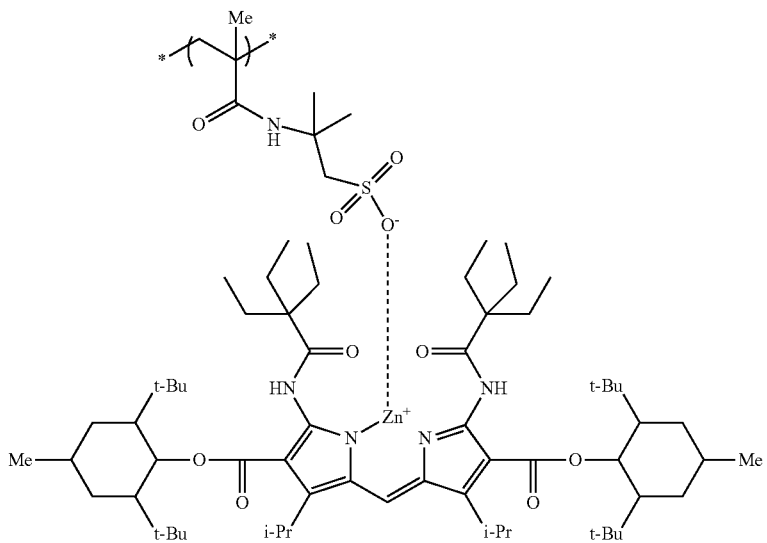
(B-3)
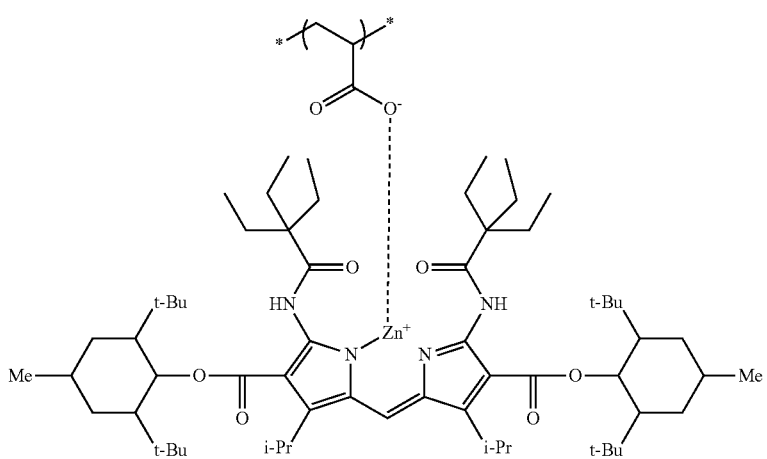
(B-4)

(B-5)
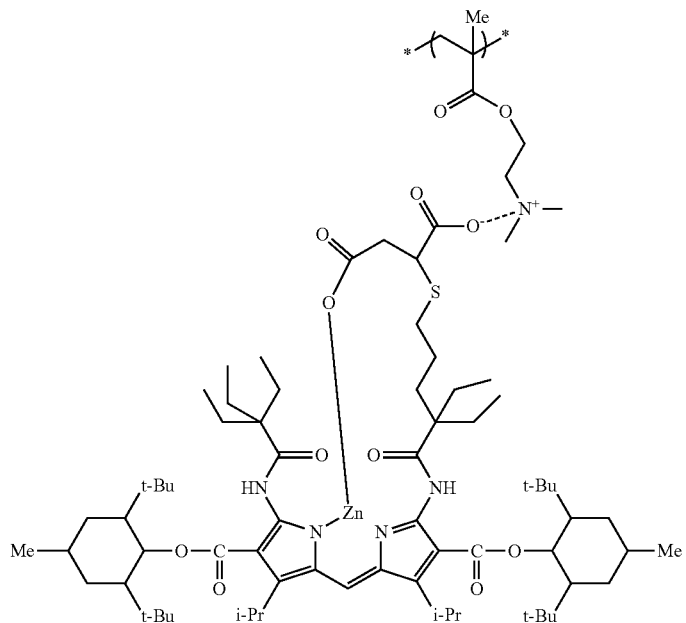
(B-6)
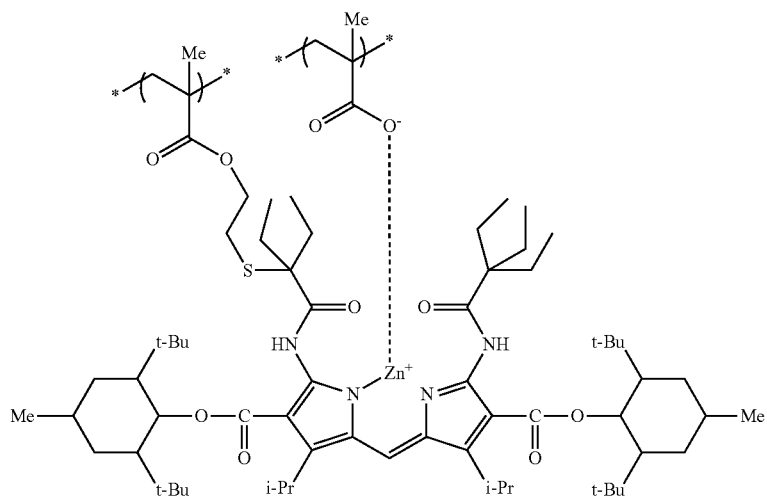
(B-7)
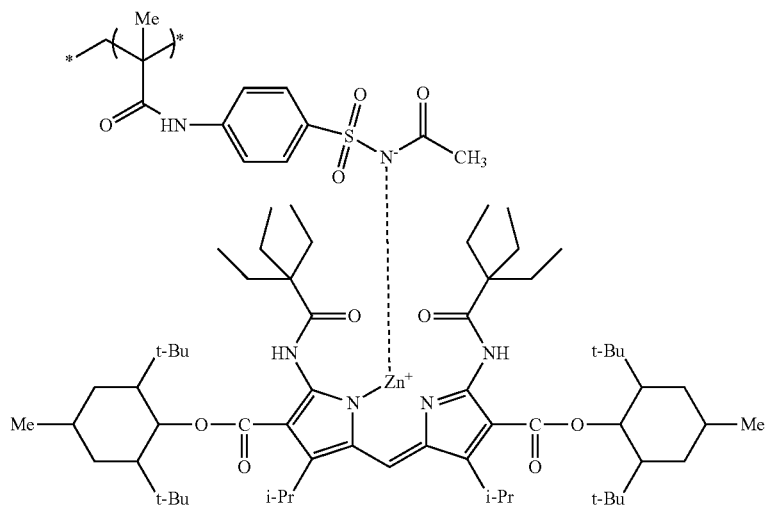

(B-8)

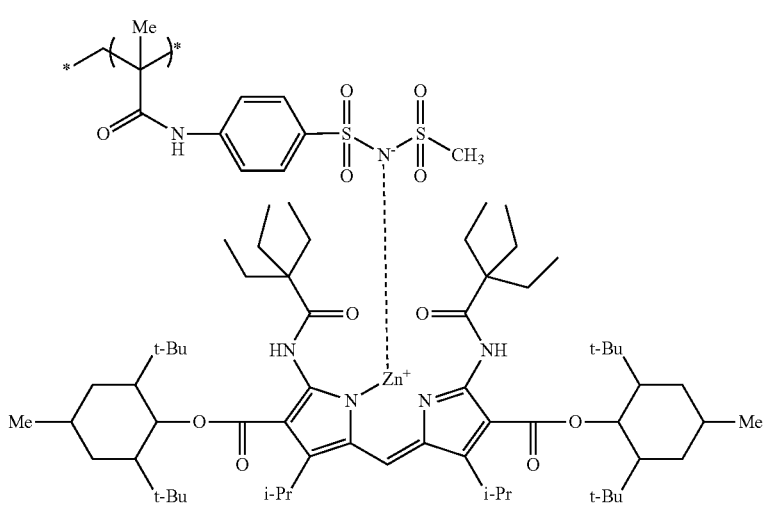

<Structural Unit Represented by Formula (C)>

In the following, the structural unit represented by formula (C) is explained in detail.

*─[─DyeIV-(L$^{C1}$)$_{m3}$─]─*   (C)

(In formula (C), L$^{C1}$ represents a single bond or a divalent linking group. Dye IV represents a linking group having a structure formed by removing two hydrogen atoms from a partial structure represented by formula (5), and Dye in formula (5) is a dye structure formed by removing any one or two hydrogen atoms from a dipyrromethene metal complex compound obtained from a dipyrromethene compound represented by formula (M) and a metal or a metal compound. m3 represents an integer from 1 to 4. When m3 is 2 or more, the two or more of L$^{C1}$ may be the same or different from each other).

In formula (C), examples of the divalent linking group represented by L$^{C1}$ include a substituted or unsubstituted linear, branched or cyclic alkylene group having 1 to 30 carbon atoms (for example, a methylene group, an ethylene group, a trimethylene group, a propylene group, and a butylene group), a substituted or unsubstituted arylene group having 6 to 30 carbon atoms (for example, a phenylene group and a naphthalene group), a substituted or unsubstituted heterocyclic linking group, —CH=CH—, —O—, —S—, —NR— (each R independently represents a hydrogen atom, an alkyl group, an aryl group, or a heterocyclic group), —C(=O)—, —SO—, —SO$_2$—, and a linking group in which two or more of these groups are linked to each other.

The following are specific examples suitably used as the divalent linking group represented by L$^{C1}$ in formula (C). However, L$^{C1}$ is not limited to these examples.

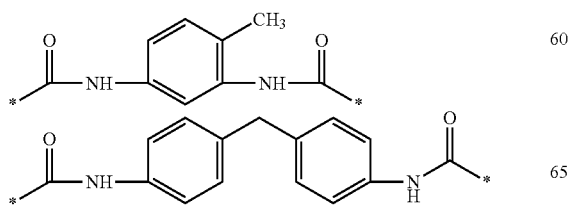

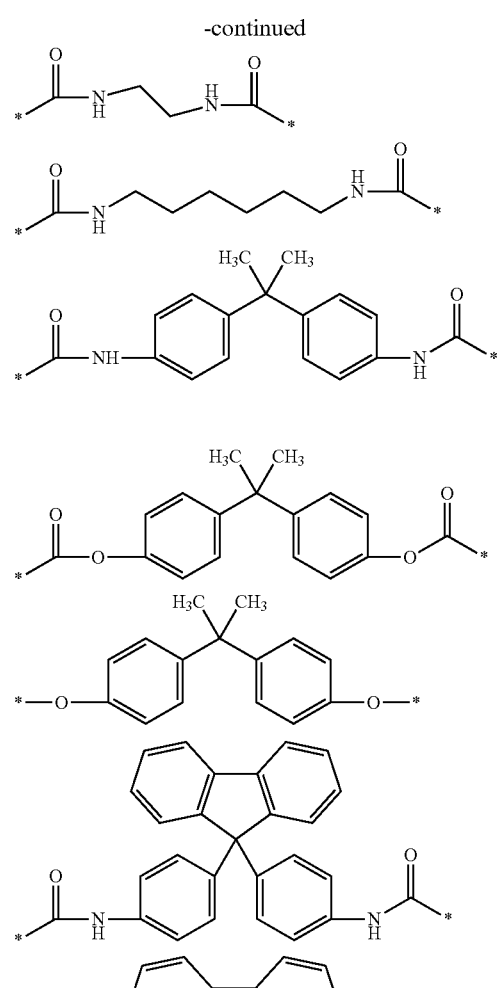

169
-continued
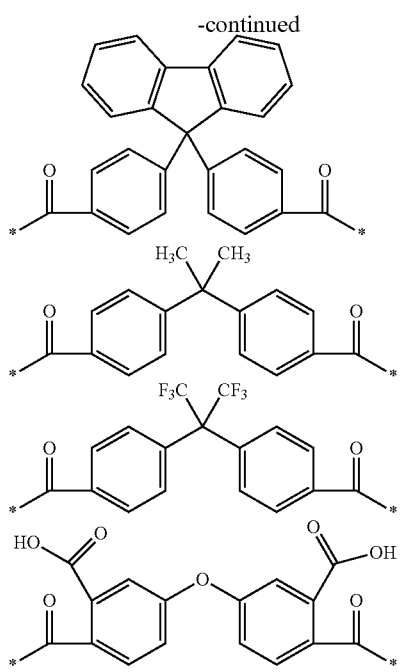
170
-continued
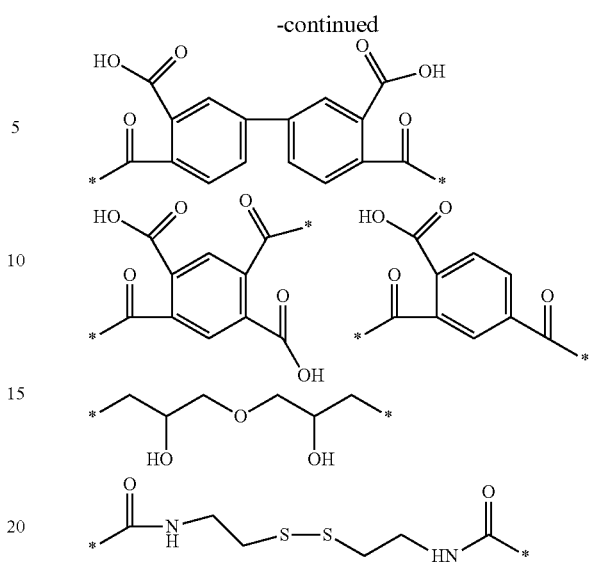
The following are specific examples of the structural unit represented by formula (C), but the invention is not limited to them.
(C-1)
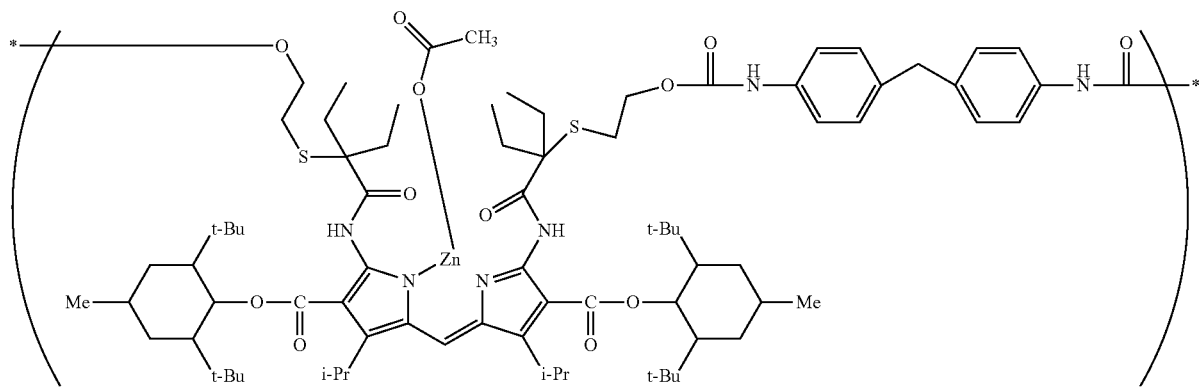
(C-2)
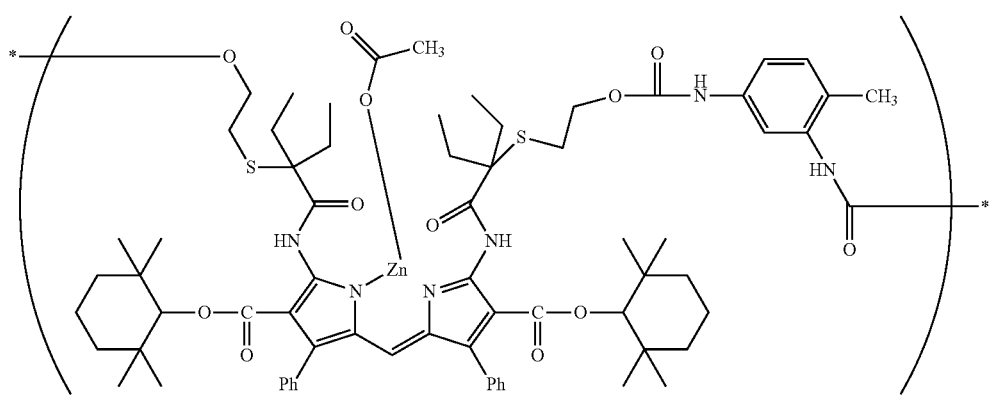

-continued
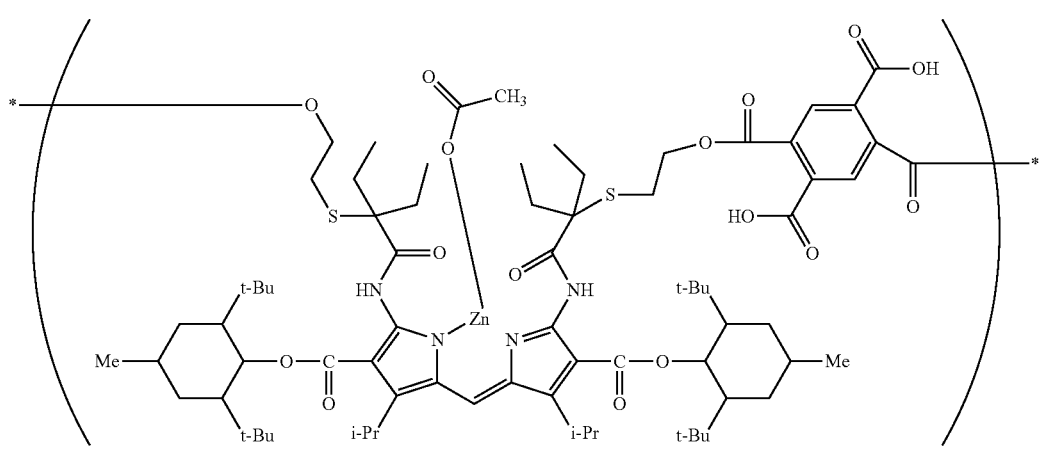
(C-3)
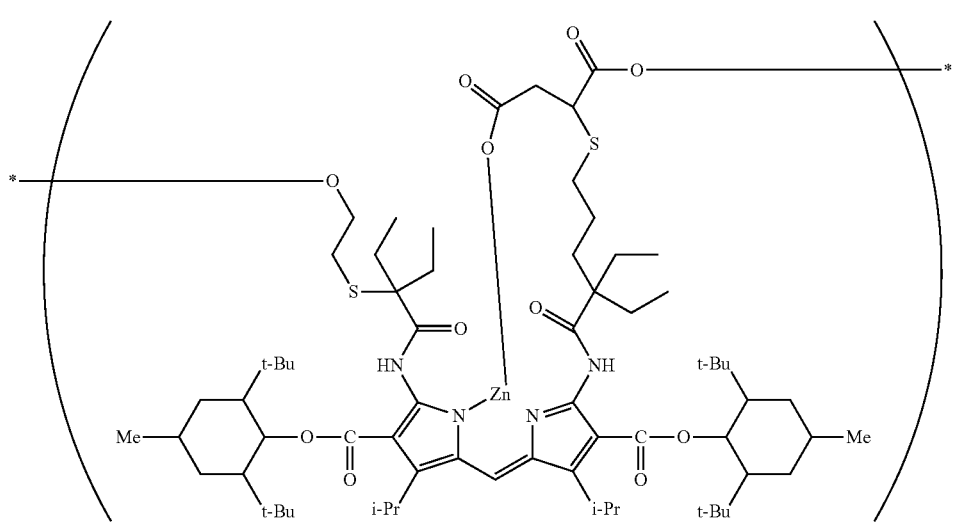
(C-4)
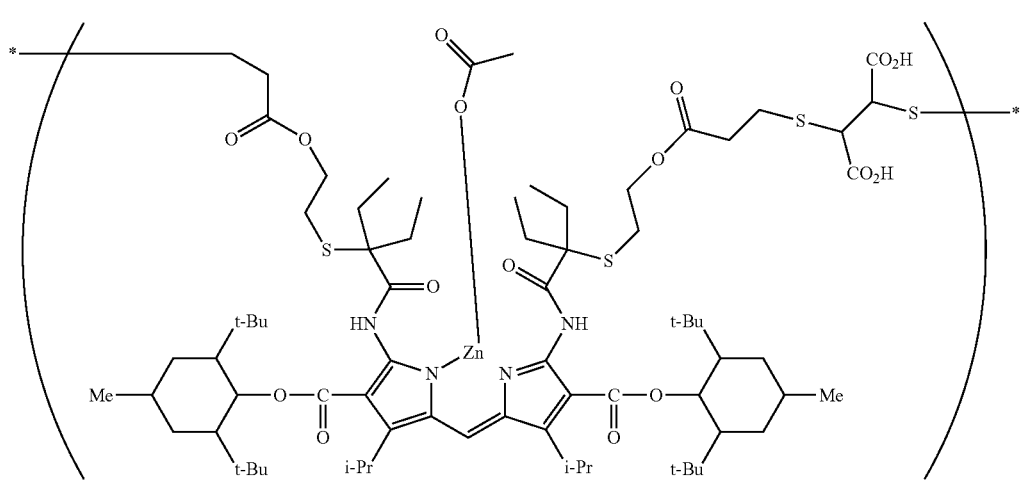
(C-5)
<Copolymerizable Component>
The dye multimer of the invention may be formed only from a structural unit represented by formula (A), formula (B) or formula (C), but the dye multimer may further include a structural unit other than the above. Examples of the other structural unit are described below, but the invention is not limited thereto.
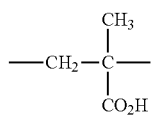
(H-1)

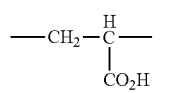 (H-2)
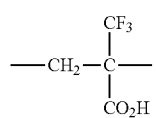 (H-3)
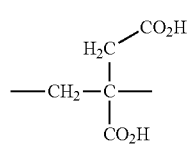 (H-4)
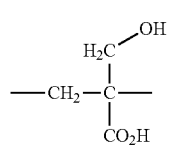 (H-5)
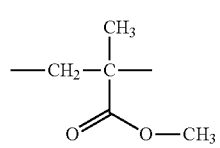 (H-6)
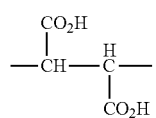 (H-7)
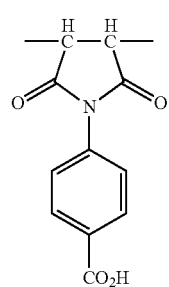 (H-8)
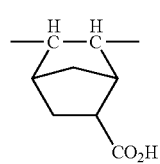 (H-9)
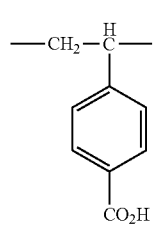 (H-10)
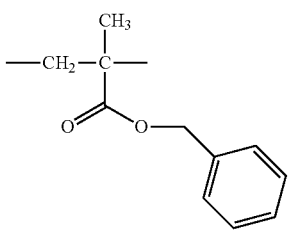 (H-11)
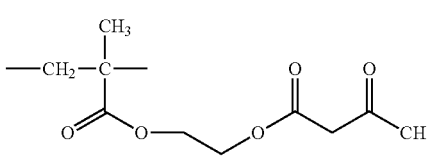 (H-12)
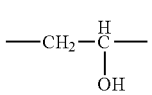 (H-13)
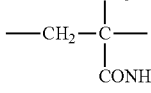 (H-14)
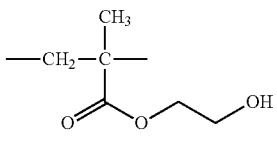 (H-15)
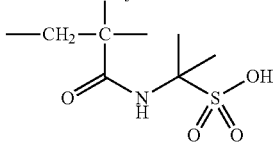 (H-16)
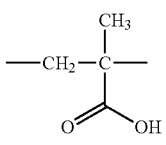 (H-17)
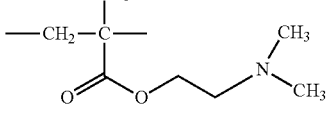 (H-18)
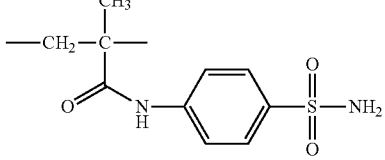 (H-19)
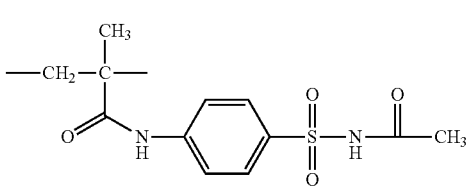 (H-20)

-continued

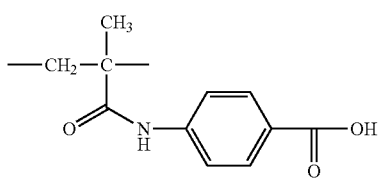
(H-21)

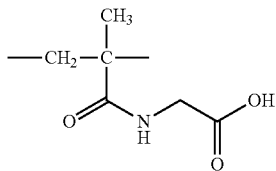
(H-22)

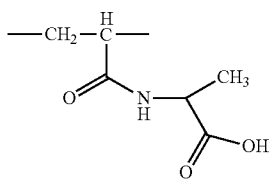
(H-23)

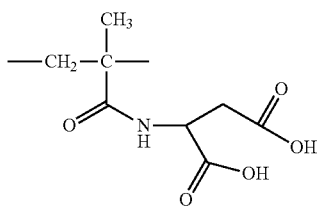
(H-24)

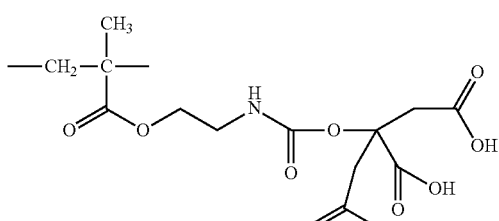
(H-24)

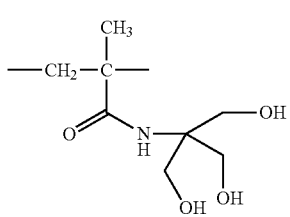
(H-25)

The other structural units may include a structural unit having a polymerizable group. Examples of the structural unit having a polymerizable group include the structural units given below.

Specifically, it is a structural unit obtained by adding, to a structural unit derived from the polymerizable component described above (for example, a methacrylic acid, acrylic acid, and hydroxy ethyl methacrylate), a polymerizable compound which reacts with the structural unit (for example, glycidyl methacrylate and a methacryloxy ethyl isocyanate).

The polymerizable group in the structural unit having a polymerizable group (hereinbelow, also referred to as a "polymerizable unit") is not specifically limited, and examples thereof include an ethylenically unsaturated group (for example, a methacryloyl group, an acryloyl group, and a styryl group) or a cyclic ether group (for example, an epoxy group and an oxetanyl group). Among these, from the viewpoint of heat resistance and solvent resistance, an ethylenically unsaturated group is preferable.

Specific examples of the structural unit having a polymerizable group include the following, but the invention is not limited thereto.

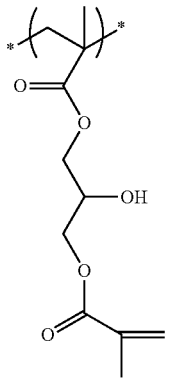
(G-1)

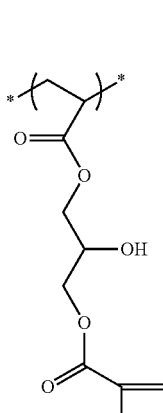
(G-2)

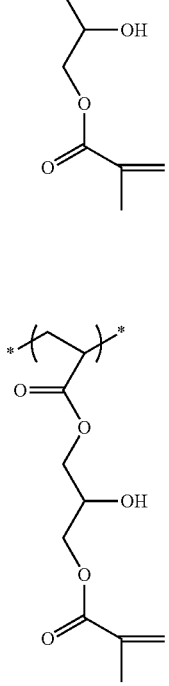
(G-3)

(G-4)
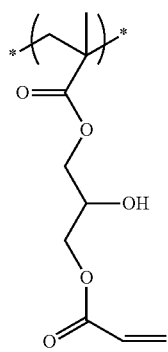

(G-5)
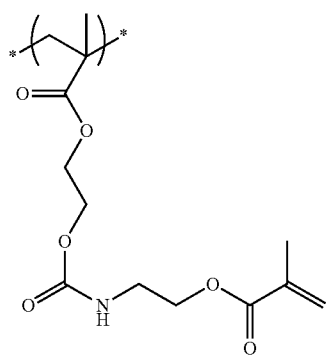

(G-6)
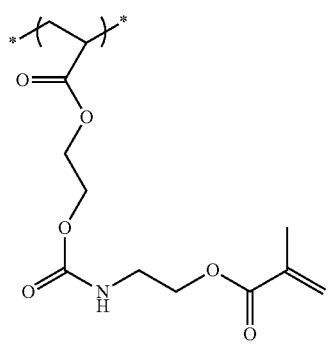

(G-7)
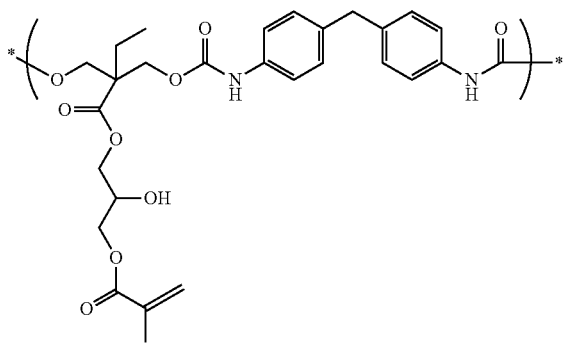

(G-8)
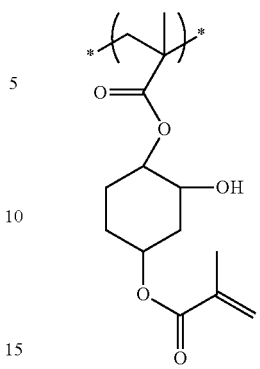

(G-9)
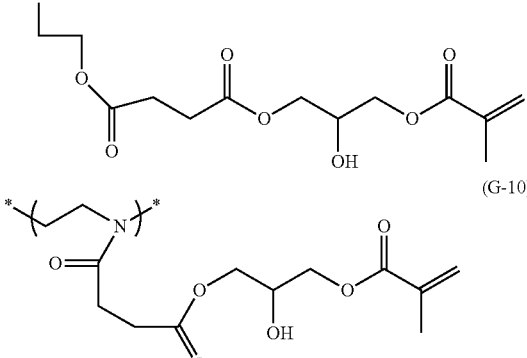

(G-10)
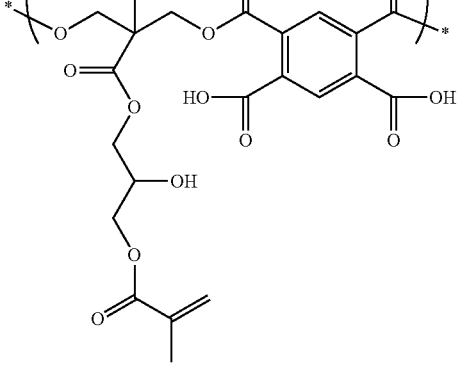

(G-11)

<Dye Multimer Represented by Formula (D)>
Next, the dye multimer represented by formula (D) is explained in detail.

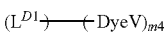 (D)

(In formula (D), $L^{D1}$ represents a linking group having a valency of m4. m4 represents an integer from 2 to 100. When m4 is 2 or more, the two or more structures of Dye V may be the same or different from each other. Dye V represents a linking group having a structure formed by removing one hydrogen atom from a partial structure represented by formula (5), and Dye in formula (5) is a dye structure formed by removing any one or two hydrogen atoms from a dipyrromethene metal complex compound obtained from a dipyrromethene compound represented by formula (M) and a metal or a metal compound.)

In formula (D), m4 is preferably 2 to 80, more preferably 2 to 40, and particularly preferably 2 to 10.

In formula (D), when m4 is 2, examples of the divalent linking group represented by $L^{D1}$ include a substituted or unsubstituted alkylene group having 1 to 30 carbon atoms (for example, a methylene group, an ethylene group, a trimethylene group, a propylene group, and a butylene group), a substituted or unsubstituted arylene group having 6 to 30 carbon atoms (for example, a phenylene group and a naphthalene group), a substituted or unsubstituted heterocyclic linking group, —CH=CH—, —O—, —S—, —NR— (each R independently represents a hydrogen atom, an alkyl group, an aryl group, or a heterocyclic group), —C(=O)—, —SO—, —SO$_2$—, and a linking group in which two or more of these groups are linked to each other.

When m4 is 3 or more, examples of the linking group having a valency of m4 include a linking group formed from a central nucleus substituted by a divalent linking group as mentioned above, and examples of the central nucleus include substituted or unsubstituted arylene groups (for example, a 1,3,5-phenylene group, a 1,2,4-phenylene group, and a 1,4,5,8-naphthalene group), heterocyclic linking groups (for example, a 1,3,5-triazine group), and alkylene linking groups.

The following are specific examples of the dye multimer represented by formula (D), but the invention is not limited thereto.

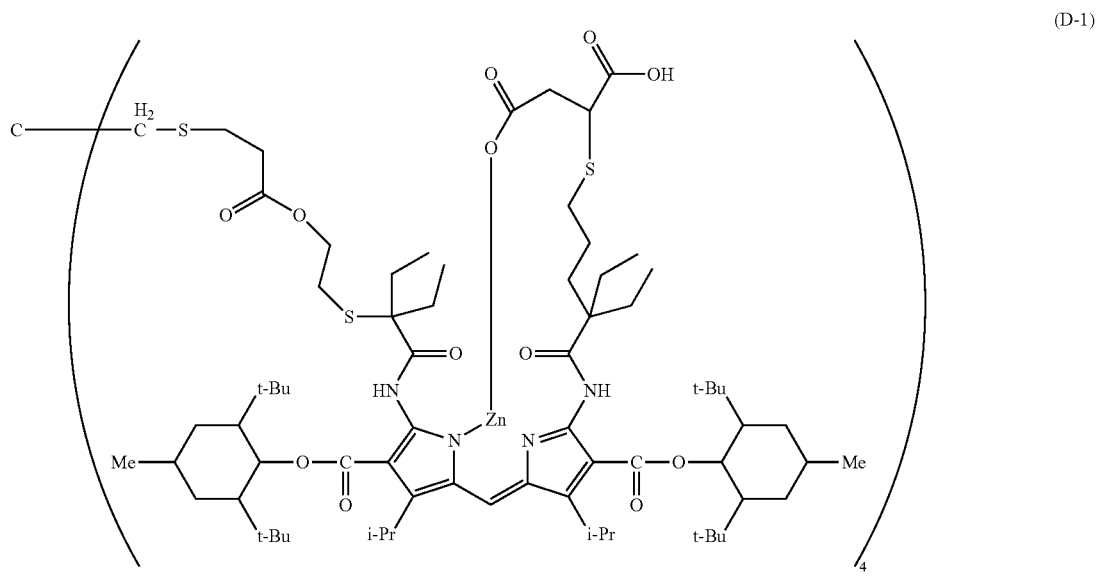

(D-1)

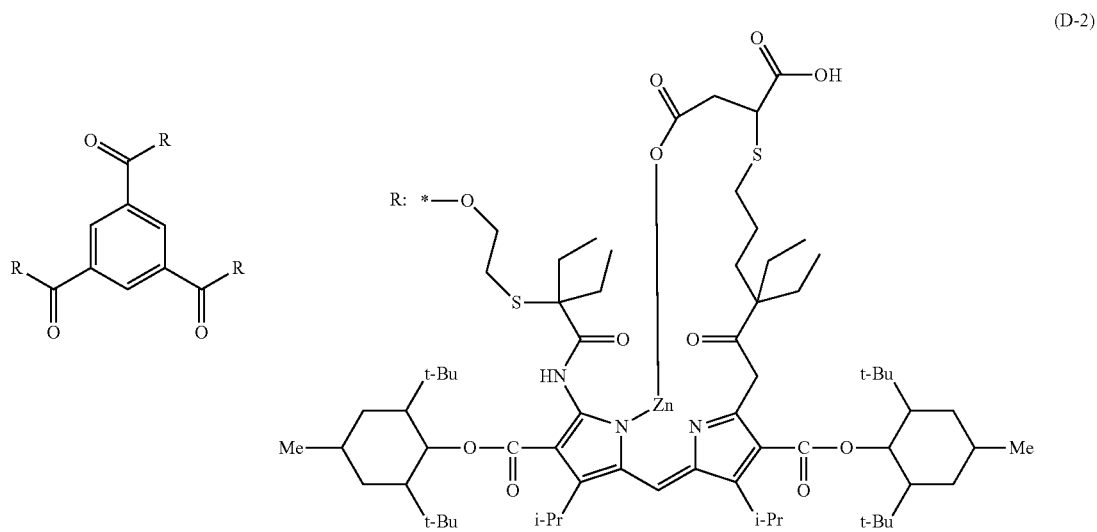

(D-2)

(D-3)
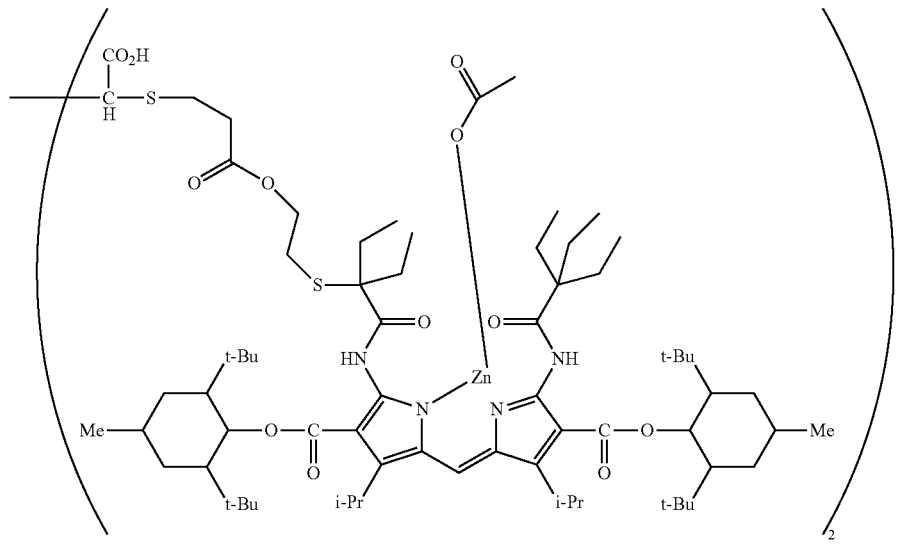
(D-4)
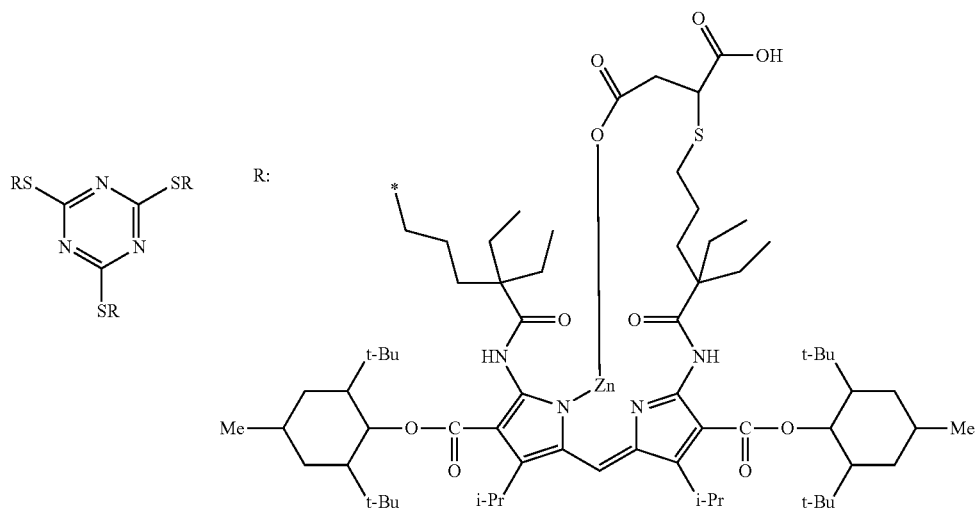
(D-5)
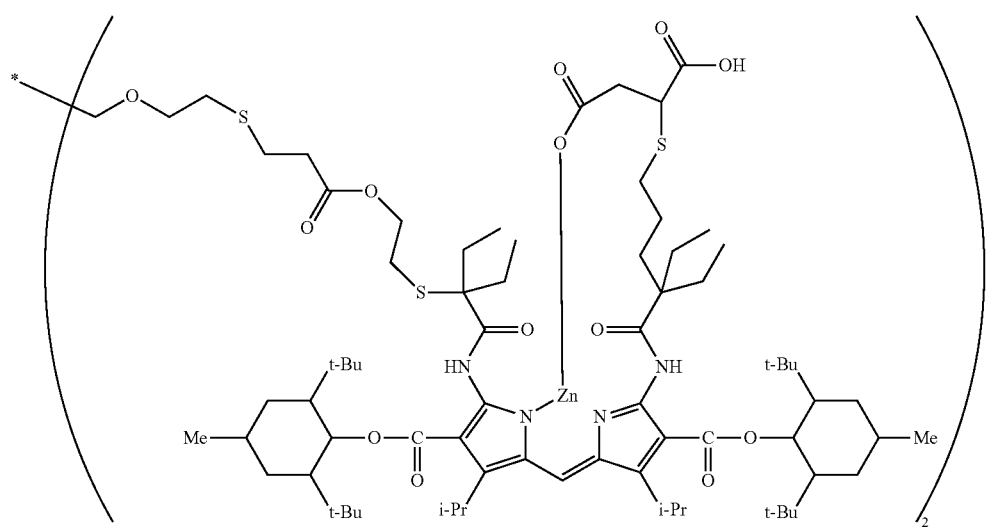

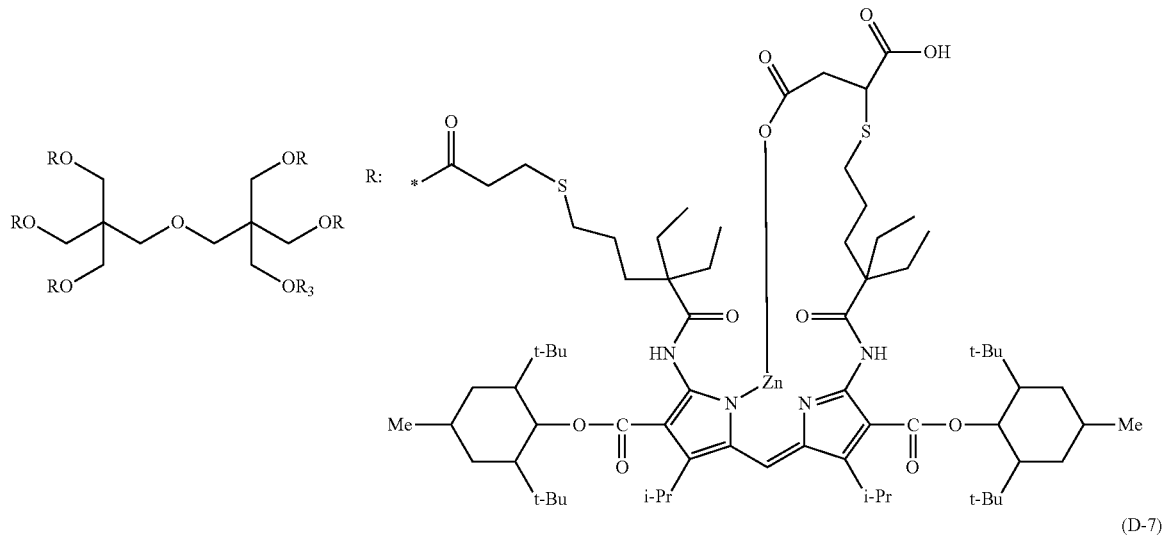

(D-6)

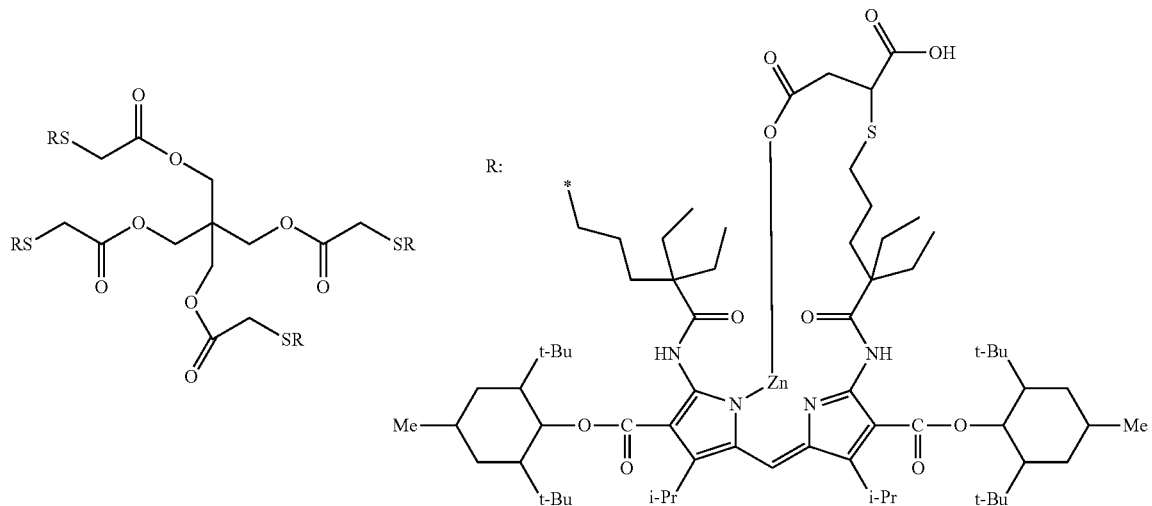

(D-7)

Preferred examples of the dye multimer of the invention are shown in the following Tables 4 and 5. In Tables 4 and 5, the type, the amount (% by mass), the weight average molecular weight and the dispersion degree of the structural units (described above) are described.

TABLE 4

| Exemplary Compound | Structural Unit 1 | | Structural Unit 2 | | Structural Unit 3 | | Mw | Mw/Mn |
|---|---|---|---|---|---|---|---|---|
| | Type | mass % | Type | mass % | Type | mass % | | |
| S-1 | A-1 | 88 | H-1 | 12 | — | | 8000 | 1.9 |
| S-2 | A-2 | 100 | — | | — | | 7200 | 2.3 |
| S-3 | A-2 | 88 | H-1 | 12 | — | | 9000 | 1.7 |
| S-4 | A-2 | 88 | H-1 | 12 | — | | 15000 | 1.8 |
| S-5 | A-2 | 82 | H-1 | 18 | — | | 5500 | 2.2 |
| S-6 | A-2 | 88 | H-1 | 6 | G-1 | 6 | 7800 | 1.8 |
| S-7 | A-2 | 88 | H-1 | 9 | G-1 | 3 | 8100 | 1.8 |
| S-8 | A-2 | 82 | H-1 | 12 | G-1 | 6 | 6400 | 2.6 |
| S-9 | A-2 | 82 | H-1 | 12 | H-3 | 6 | 7900 | 1.5 |

TABLE 4-continued

| Exemplary Compound | Structural Unit 1 | | Structural Unit 2 | | Structural Unit 3 | | Mw | Mw/Mn |
|---|---|---|---|---|---|---|---|---|
| | Type | mass % | Type | mass % | Type | mass % | | |
| S-10 | A-2 | 82 | H-1 | 12 | H-12 | 6 | 9100 | 1.8 |
| S-11 | A-2 | 82 | H-1 | 12 | H-20 | 6 | 10000 | 1.7 |
| S-12 | A-2 | 88 | H-3 | 12 | — | | 7400 | 2 |
| S-13 | A-2 | 88 | H-4 | 12 | — | | 6000 | 2.3 |
| S-14 | A-2 | 88 | H-12 | 12 | — | | 8500 | 1.8 |
| S-15 | A-2 | 88 | H-20 | 12 | — | | 8400 | 1.7 |
| S-16 | A-3 | 100 | — | | — | | 9600 | 1.9 |
| S-17 | A-3 | 88 | H-1 | 12 | — | | 5700 | 1.9 |
| S-18 | A-3 | 82 | H-1 | 18 | — | | 12000 | 2.1 |
| S-19 | A-3 | 88 | H-1 | 6 | G-1 | 6 | 9900 | 1.8 |
| S-20 | A-4 | 100 | — | | — | | 8700 | 2.3 |
| S-21 | A-4 | 88 | H-1 | 12 | — | | 7400 | 1.7 |
| S-22 | A-4 | 82 | H-1 | 18 | — | | 6300 | 2 |
| S-23 | A-4 | 88 | H-1 | 6 | G-1 | 6 | 7500 | 1.8 |
| S-24 | A-5 | 100 | — | | — | | 7600 | 1.8 |
| S-25 | A-5 | 88 | H-1 | 12 | — | | 14000 | 2 |

TABLE 4-continued

| Exemplary Compound | Structural Unit 1 Type | mass % | Structural Unit 2 Type | mass % | Structural Unit 3 Type | mass % | Mw | Mw/Mn |
|---|---|---|---|---|---|---|---|---|
| S-26 | A-5 | 88 | H-1 | 6 | G-1 | 6 | 6900 | 2.4 |
| S-27 | A-5 | 88 | H-1 | 9 | G-1 | 3 | 8400 | 1.9 |
| S-28 | A-5 | 82 | H-1 | 12 | H-3 | 6 | 9600 | 1.7 |
| S-29 | A-5 | 82 | H-1 | 12 | H-20 | 6 | 9400 | 1.7 |
| S-30 | A-5 | 88 | H-3 | 12 | — |  | 7600 | 2.1 |

TABLE 5

| Exemplary Compound | Structural Unit 1 Type | mass % | Structural Unit 2 Type | mass % | Structural Unit 3 Type | mass % | Mw | Mw/Mn |
|---|---|---|---|---|---|---|---|---|
| S-31 | A-5 | 88 | H-4 | 12 | — |  | 8000 | 1.9 |
| S-32 | A-7 | 88 | H-1 | 12 | — |  | 6000 | 1.9 |
| S-33 | A-8 | 88 | H-1 | 12 | — |  | 9400 | 1.6 |
| S-34 | A-9 | 88 | H-1 | 12 | — |  | 5900 | 2.1 |
| S-35 | A-10 | 88 | H-1 | 12 | — |  | 8300 | 1.9 |
| S-36 | A-15 | 88 | H-1 | 12 | — |  | 11000 | 1.7 |
| S-37 | A-19 | 88 | H-1 | 12 | — |  | 8700 | 1.8 |
| S-38 | A-24 | 88 | H-1 | 12 | — |  | 6600 | 2.2 |
| S-39 | A-26 | 88 | H-1 | 12 | — |  | 6800 | 2.1 |
| S-40 | A-27 | 88 | H-1 | 12 | — |  | 8800 | 1.8 |
| S-41 | A-37 | 88 | H-1 | 12 | — |  | 7600 | 1.7 |
| S-42 | A-41 | 88 | H-1 | 12 | — |  | 9400 | 2.3 |
| S-43 | A-44 | 88 | H-1 | 12 | — |  | 7200 | 1.9 |
| S-44 | A-45 | 88 | H-1 | 12 | — |  | 7500 | 1.9 |
| S-45 | A-46 | 88 | H-1 | 12 | — |  | 9000 | 2.2 |
| S-46 | B-1 | 88 | H-1 | 12 | — |  | 8600 | 2.2 |
| S-47 | B-1 | 82 | H-1 | 12 | H-6 | 6 | 7600 | 1.9 |
| S-48 | B-4 | 82 | H-1 | 12 | G-1 | 6 | 13200 | 1.8 |
| S-49 | B-5 | 82 | H-1 | 12 | H-18 | 6 | 9800 | 1.9 |
| S-50 | B-6 | 88 | H-1 | 12 | — |  | 7600 | 2.3 |
| S-51 | B-6 | 82 | A-6 | 6 | H-1 | 12 | 7900 | 2.1 |
| S-52 | C-1 | 100 | — |  | — |  | 5400 | 1.2 |
| S-53 | C-5 | 100 | — |  | — |  | 5900 | 1.3 |
| S-54 | D-1 | 100 | — |  | — |  | 4800 | 1.2 |
| S-55 | D-2 | 100 | — |  | — |  | 3700 | 1.4 |
| S-56 | D-4 | 100 | — |  | — |  | 4400 | 1.3 |
| S-57 | D-6 | 100 | — |  | — |  | 4900 | 1.1 |
| S-58 | D-7 | 100 | — |  | — |  | 5900 | 1.2 |

The dye multimer of the invention preferably includes a structural unit represented by formula (A), formula (B), or formula (C). Among these, the dye multimer preferably includes a structural unit represented by formula (A).

In addition, the structural unit represented by formula (A) is preferably formed by using a dye monomer represented by the following formula (1) as a polymerization component.

Hereinbelow, the dye monomer represented by formula (1) is explained in detail.

<Dye Monomer Represented by Formula (1)>

The dye monomer included in the dye multimer of the invention as a polymerization component is explained in detail.

The dye monomer is a compound represented by formula (1).

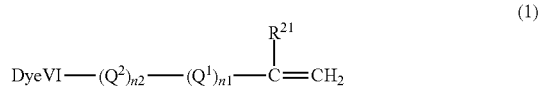

(1)

(In formula (1), $R^{21}$ represents a hydrogen atom, a halogen atom, an alkyl group, or an aryl group. $Q^1$ represents —N($R^2$)C(=O)—, —OC(=O)—, —C(=O)N($R^2$)—, —C(=O)O—, a group represented by formula (2), a group represented by formula (3), or a group represented by formula (4). $Q^2$ represents a divalent linking group. n1 and n2 each independently represent 0 or 1. Dye VI represents a linking group having a structure formed by removing two hydrogen atoms from a partial structure represented by formula (5), and Dye in formula (5) is a dye structure formed by removing any one or two hydrogen atoms from a dipyrromethene metal complex compound obtained from a dipyrromethene compound represented by the following formula (7) or (8) and a metal or a metal compound. $R^2$ represents a hydrogen atom, an alkyl group, an aryl group, or a heterocyclic group).

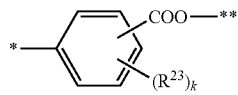

(2)

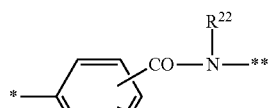

(3)

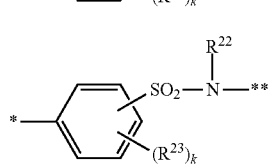

(4)

(In formula (2) to (4), $R^{22}$ represents a hydrogen atom, an alkyl group, an aryl group, or a heterocyclic group. Each of plural $R^{23}$ independently represents a hydrogen atom or a monovalent substituent group. k represents an integer from 0 to 4. When k is 2 or more, the two or more of $R^{23}$ may be the same or different from each other. * indicates a bonding site to the —C($R^{21}$)=CH$_2$ group in formula (1), and ** indicates a bonding site to $Q^2$ or Dye VI (when n2=0) in formula (1)).

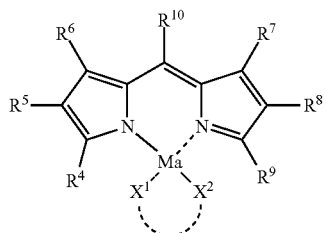

(7)

In formula (7), $R^4$ to $R^9$ each independently represent a hydrogen atom or a substituent group, and $R^{10}$ represents a hydrogen atom, a halogen atom, an alkyl group, an aryl group, or a heterocyclic group. Ma represents a metal atom or a metal compound. $X^1$ represents a group capable of being bonded to Ma, $X^2$ represents a group that neutralizes a charge of Ma, $X^1$ and $X^2$ may be bonded to each other to form a 5-membered, 6-membered or 7-membered ring together with Ma, and $R^4$ and $R^9$ are not bonded to each other to form a ring.

The dipyrromethene metal complex compound represented by formula (7) includes a tautomer.

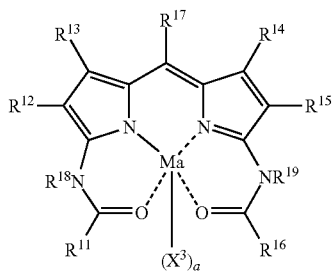

(8)

In formula (8), $R^{11}$ and $R^{16}$ each independently represent an alkyl group, an alkenyl group, an aryl group, a heterocyclic group, an alkoxy group, an aryloxy group, an alkylamino group, an arylamino group, or a heterocyclic amino group. $R^{12}$ to $R^{15}$ each independently represent a hydrogen atom or a monovalent substituent group. $R^{17}$ represents a hydrogen atom, a halogen atom, an alkyl group, an aryl group, or a heterocyclic group. Ma represents a metal atom or a metal compound. $R^{18}$ and $R^{19}$ each independently represent a hydrogen atom, an alkyl group, an alkenyl group, an aryl group, a heterocyclic group, an acyl group, an alkylsulfonyl group, or an arylsulfonyl group. $R^{11}$ and $R^{18}$ may be bonded to each other to form a 5-membered, 6-membered or 7-membered ring, and $R^{16}$ and $R^{19}$ may be bonded to each other to form a 5-membered, 6-membered or 7-membered ring. $X^3$ represents a group capable of being bonded to Ma, and a represents 0, 1, or 2.

The dipyrromethene metal complex compound represented by formula (8) includes a tautomer.

Specifically, the dye monomer represented by formula (1) is a compound obtained by adding a polymerizable group represented by -$(Q^2)$n2-$(Q^1)$n1-$C(R^{21})$=$CH_2$, in formula (1), to a dipyrromethene metal complex compound represented by formula (7) or formula (8).

When both n1 and n2 are 0, the —$C(R^{21})$=$CH_2$ group is directly introduced into a dipyrromethene metal complex compound. Definitions of $Q^1$, $Q^2$ and $R^{21}$ are the same as that of $Q^1$, $Q^2$ and $R^{21}$ in formula (1), respectively.

In the dipyrromethene metal complex compound represented by formula (7), the site at which the polymerizable group is to be introduced is not specifically limited. However, from the viewpoint of synthesis suitability, the site for introduction is preferably any one of $R^4$ to $R^9$, more preferably any one of $R^4$, $R^6$, $R^7$ and $R^9$, still more preferably $R^4$ or $R^9$.

In the dipyrromethene metal complex compound represented by formula (8), the site at which the polymerizable group is to be introduced is any one of $R^{11}$ to $R^{17}$, $X^1$, $Y^1$ and $Y^2$. Among these, from the viewpoint of synthesis suitability, the polymerizable group is preferably introduced into any one of $R^{11}$ to $R^{16}$ and $X^1$, more preferably any one of $R^{11}$, $R^{13}$, $R^{14}$ and $R^{16}$, still more preferably $R^{11}$ or $R^{16}$.

In formula (1), $R^{21}$ represents a hydrogen atom, a halogen atom, an alkyl group, or an aryl group. When $R^{21}$ is an alkyl group or an aryl group, it may be substituted or unsubstituted.

When $R^{21}$ is an alkyl group, the alkyl group is preferably a substituted or unsubstituted alkyl group having 1 to 36 carbon atoms, and more preferably 1 to 6 carbon atoms. Examples of the alkyl group include a methyl group, an ethyl group, a propyl group, a butyl group, an octyl group, an isopropyl group, and a cyclohexyl group.

When $R^{21}$ is an aryl group, the aryl group is preferably a substituted or unsubstituted aryl group having preferably 6 to 18 carbon atoms, more preferably 6 to 14 carbon atoms, and still more preferably 6 to 12 carbon atoms. Examples of the aryl group include a phenyl group and a naphthyl group.

When $R^{21}$ is a substituted alkyl group or a substituted aryl group, examples of the substituent group include a halogen atom (for example, a fluorine atom, a chlorine atom, a bromine atom, and an iodine atom), an alkyl group (an alkyl group having preferably 1 to 24 carbon atoms, and more preferably 1 to 12 carbon atoms, such as methyl, ethyl, propyl, butyl, isopropyl, t-butyl, 2-ethylhexyl, dodecyl, cyclopropyl, cyclopentyl, cyclohexyl, or adamantyl), an aryl group (an aryl group having preferably 6 to 24 carbon atoms, and more preferably 6 to 12 carbon atoms, such as phenyl or naphthyl), a heterocyclic group (a heterocyclic group having preferably 1 to 24 carbon atoms, and more preferably 1 to 12 carbon atoms, such as 2-thienyl, 4-pyridyl, 2-furyl, 2-pyrimidinyl, 1-pyridyl, 2-benzothiazolyl, 1-imidazolyl, 1-pyrazolyl, or benzotriazol-1-yl), a silyl group (a silyl group having preferably 3 to 24 carbon atoms, and more preferably 3 to 12 carbon atoms, such as trimethylsilyl, triethylsilyl, tributylsilyl, t-butyldimethylsilyl, or t-hexyldimethylsilyl), a hydroxyl group, a cyano group, a nitro group, a sulfonic acid group, a phosphonic acid group, a carboxyl group, an alkoxy group (an alkoxy group having preferably 1 to 24 carbon atoms, more preferably 1 to 12 carbon atoms, and still more preferably 1 to 6 carbon atoms such as methoxy, ethoxy, 1-butoxy, 2-butoxy, isopropoxy, t-butoxy, dodecyloxy, or cycloalkyloxy group including cyclopentyloxy or cyclohexyloxy), an aryloxy group (an aryloxy group having preferably 6 to 24 carbon atoms, and more preferably 6 to 12 carbon atoms, such as phenoxy or 1-naphthoxy), a heterocyclic oxy group (a heterocyclic oxy group having preferably 1 to 24 carbon atoms, and more preferably 1 to 12 carbon atoms, such as 1-phenyltetrazol-5-oxy or 2-tetrahydropyranyloxy), a silyloxy group (a silyloxy group having preferably 1 to 24 carbon atoms, and more preferably 1 to 12 carbon atoms, such as trimethylsilyloxy, t-butyldimethylsilyloxy, or diphenylmethylsilyloxy), an acyloxy group (an acyloxy group having preferably 2 to 24 carbon atoms, and more preferably 2 to 12 carbon atoms, such as acetoxy, pivaloyloxy, benzoyloxy, or dodecanoyloxy), an alkoxycarbonyloxy group (an alkoxycarbonyloxy group having preferably 2 to 24 carbon atoms, more preferably 2 to 12 carbon atoms, and still more preferably 2 to 6 carbon atoms, such as ethoxycarbonyloxy or t-butoxycarbonyloxy), a cycloalkyloxycarbonyloxy group (for example, cyclohexyloxycarbonyloxy), an aryloxycarbonyloxy group (an aryloxycarbonyloxy group having preferably 7 to 24 carbon atoms, and more preferably 7 to 12 carbon atoms, such as phenoxycarbonyloxy), a carbamoyloxy group (a carbamoyloxy group having preferably 1 to 24 carbon atoms, more preferably 1 to 12 carbon atoms, and still more preferably 1 to 6 carbon atoms, such as N,N-dimethylcarbamoyloxy, N-butylcarbamoyloxy, N-phenylcarbamoyloxy, N-ethyl-N-phenylcarbamoyloxy), a sulfamoyloxy group (a sulfamoyloxy group having preferably 1 to 24 carbon atoms, more preferably 1 to 12 carbon atoms, and still more preferably 1 to 6 carbon atoms, such as N,N-diethylsulfamoyloxy or N-propylsulfamoyloxy), an alkylsulfonyloxy group (an alkylsulfonyloxy group having preferably 1 to 24 carbon atoms, more preferably 1 to 12 carbon atoms, and still more preferably 1 to 6 carbon atoms, such as methylsulfonyloxy, hexadecylsulfonyloxy, or cyclohexylsulfonyloxy), an arylsulfonyloxy group (an arylsulfonyloxy group having preferably 6 to 24 carbon atoms, and more preferably 6 to 12 carbon atoms, such as phenylsulfonyloxy), an acyl group (an acyl group having preferably 1 to 24 carbon atoms, and more preferably 1 to 12 carbon atoms, such as formyl acetyl, pivaloyl, benzoyl, tetradecanoyl, or cyclohexanoyl), an alkoxycarbonyl group (an alkoxycarbonyl group having preferably 2 to 24 carbon atoms, more preferably 2 to 12 carbon atoms, and still more preferably 2 to 6 carbon atoms, such as methoxycarbonyl, ethoxycarbonyl, octadecyloxycarbonyl, or cyclohexyloxycarbonyl), an aryloxycarbonyl group (an aryloxycarbonyl group having preferably 7 to 24 carbon atoms, and more preferably 7 to 12 carbon atoms, such as phenoxycarbonyl), a carbamoyl group (a carbamoyl group having preferably 1 to 24 carbon atoms, and more preferably 1 to 12 carbon atoms, such as carbamoyl, N,N-diethylcarbamoyl, N-ethyl-N-octylcarbamoyl, N,N-dibutylcarbamoyl, N-propylcarbamoyl, N-phenylcarbamoyl, N-methyl-N-phenylcarbamoyl, or N,N-dicyclohexyl carbamoyl), an amino group (an amino group having preferably 24 or less carbon atoms, and more preferably 12 or less carbon atoms, such as amino, methylamino, N,N-dibutylamino, tetradecylamino, 2-ethylhexylamino, or cyclohexylamino), an anilino group (an anilino group having preferably 6 to 24 carbon atoms, and more preferably 6 to 12 carbon atoms, such as anilino or N-methylanilino), a heterocyclic amino group (a heterocyclic amino group having preferably 1 to 24 carbon atoms, and more preferably 1 to 12 carbon atoms such as 4-pyridylamino), a carbonamido group (a carbonamido group having preferably 2 to 24 carbon atoms, and more preferably 2 to 12 carbon atoms, such as acetamide, benzamide, tetradecaneamido, pivaloylamido, or cyclohexaneamido), a ureido group (a ureido group having preferably 1 to 24 carbon atoms, and more preferably 1 to 12 carbon atoms, such as ureido, N,N-dimethylureido, or N-phenylureido), an imido group (an imido group having preferably 20 or less carbon atoms, and more preferably 12 or less carbon atoms, such as N-succinimido or N-phthalimido), an alkoxycarbonylamino group (an alkoxycarbonylamino group having preferably 2 to 24 carbon atoms, and more preferably 2 to 12 carbon atoms, such as methoxycarbonylamino, ethoxycarbonylamino, t-butoxycarbonylamino, octadecyloxycarbonylamino, or cyclohexyloxycarbonylamino), an aryloxycarbonylamino group (an aryloxycarbonylamino group having preferably 7 to 24 carbon atoms, and more preferably 7 to 12 carbon atoms, such as phenoxycarbonylamino), a sulfonamido group (a sulfonamido group having preferably 1 to 24 carbon atoms, and more preferably 1 to 12 carbon atoms, such as methanesulfonamido, butanesulfonamido, benzenesulfonamido, hexadecanesulfonamido, or cyclohexanesulfonamido), a sulfamoylamino group (a sulfamoylamino group having preferably 1 to 24 carbon atoms, and more preferably 1 to 12 carbon atoms, such as N,N-dipropylsulfamoylamino or N-ethyl-N-dodecylsulfamoylamino), an azo group (an azo group having preferably 1 to 24 carbon atoms, and more preferably 1 to 12 carbon atoms, such as phenylazo or 3-pyrazolylazo), an alkylthio group (an alkylthio group having preferably 1 to 24 carbon atoms, and more preferably 1 to 12 carbon atoms, such as methylthio, ethylthio, octylthio, or cyclohexylthio), an arylthio group (an arylthio group having preferably 6 to 24 carbon atoms, and more preferably 6 to 12 carbon atoms, such as phenylthio), a heterocyclic thio group (a heterocyclic thio group having preferably 1 to 24 carbon atoms, and more preferably 1 to 12 carbon atoms, such as 2-benzothiazolylthio, 2-pyridylthio, or 1-phenyltetrazolylthio), an alkylsulfinyl group (an alkylsulfinyl group having preferably 1 to 24 carbon atoms, and more preferably 1 to 12 carbon atoms, such as dodecylsulfinyl), an arylsulfinyl group (an arylsulfinyl group having preferably 6 to 24 carbon atoms, and more preferably 6 to 12 carbon atoms, such as phenylsulfinyl), an alkylsulfonyl group (an alkylsulfonyl group having preferably 1 to 24 carbon atoms, and more preferably 1 to 12 carbon atoms, such as methylsulfonyl, ethylsulfonyl, propylsulfonyl, butylsulfonyl, isopropylsulfonyl, 2-ethylhexylsulfonyl, hexadecylsulfonyl, octylsulfonyl, or cyclohexylsulfonyl), an arylsulfonyl group (an arylsulfonyl group having preferably 6 to 24 carbon atoms, and more preferably 6 to 12 carbon atoms, such as phenylsulfonyl and 1-naphthylsulfonyl), a sulfamoyl group (a sulfamoyl group having preferably 24 or less carbon atoms, and more preferably 16 or less carbon atoms, such as sulfamoyl, N,N-dipropylsulfamoyl, N-ethyl-N-dodecylsulfamoyl, N-ethyl-N-phenylsulfamoyl, or N-cyclohexylsulfamoyl), a sulfo group, a phosphonyl group (a phosphonyl group having preferably 1 to 24 carbon atoms, and more preferably 1 to 12 carbon atoms, such as phenoxyphosphonyl, octyloxyphosphonyl, or phenylphosphonyl), a phosphinoylamino group (a phosphinoylamino group having preferably 1 to 24 carbon atoms, and more preferably 1 to 12 carbon atoms, such as diethoxyphosphinoylamino or dioctyloxyphosphinoylamino).

Among the above substituent groups, a halogen atom, an alkyl group, an aryl group, a hydroxyl group, a sulfonic acid group, a phosphonic acid group, a carboxylic acid group, an alkoxy group, an aryloxy group, an alkoxycarbonyloxy group, a cycloalkylcarbonyloxy group, an aryloxycarbonyloxy group, a carbamoyloxy group, a sulfamoyloxy group, an alkylsulfonyloxy group, an arylsulfonyloxy group, an acyl group, an alkoxycarbonyl group, an aryloxycarbonyl group, a carbamoyl group, a carbonamido group, an imido group, a sulfonamido group, a sulfamoylamino group, and a sulfamoyl group are preferable. An alkyl group, an aryl group, a hydroxyl group, a sulfonic acid group, a phosphonic acid group, a carboxylic acid group, an alkoxy group, an aryloxy group, an alkoxycarbonyloxy group, an aryloxycarbonyloxy group, a carbamoyloxy group, a sulfamoyloxy group, an alkylsulfonyloxy group, an arylsulfonyloxy group, an acyl group, an alkoxy carbonyl group, an aryloxycarbonyl group, a carbamoyl group, a carbonamido group, a sulfonamido group, a sulfamoylamino group, and a sulfamoyl group are more preferable. A hydroxyl group, a sulfonic acid group, a phosphonic acid group, a carboxylic acid group, an alkoxy group, an aryloxy group, an alkoxycarbonyloxy group, an aryloxycarbonyloxy group, a carbamoyloxy group, a sulfamoyloxy group, an alkylsulfonyloxy group, an arylsulfonyloxy group, an acyl group, an alkoxycarbonyl group, and an aryloxycarbonyl group are still more preferable. A hydroxyl group, a sulfonic acid group, a carboxylic acid group, an alkoxy group, an alkoxycarbonyloxy group, a carbamoyloxy group, a sulfamoyloxy group, an alkylsulfonyloxy group, an acyl group, and an alkoxy carbonyl group are particularly preferable.

Among the particularly preferable substituent groups, a sulfonic acid group, a carboxylic acid group, an alkoxy group, an alkoxycarbonyloxy group, an alkylsulfonyloxy group, and an alkoxycarbonyl group are more preferable. A sulfonic acid group, a carboxylic acid group, an alkoxy group, and an alkoxycarbonyl group are still more preferable. A sulfonic acid group, a carboxylic acid group, and an alkoxy group are particularly preferable.

$R^{21}$ is preferably a hydrogen atom, an alkyl group, or an aryl group, and particularly preferably a hydrogen atom or an alkyl group.

When the substituent group for a substituted alkyl group or a substituted aryl group represented by $R^{21}$ is a group that can have a further substituent group, the further substituent group may be selected from the substituent groups mentioned above, and when there are two or more substituent groups, the substituent groups may be the same or different from each other.

In formula (1), $Q^1$ represents —N($R^2$)C(=O)—, —OC(=O)—, —C(=O)N($R^2$)—, —C(=O)O—, a group represented by formula (2), a group represented by formula (3), or a group represented by formula (4). $R^2$ represents a hydrogen atom, an alkyl group, an aryl group, or a heterocyclic group.

$R^2$ represents an alkyl group, an aryl group, or a heterocyclic group, and examples of the alkyl group, aryl group and heterocyclic group may be the same as the alkyl group, aryl group or heterocyclic group mentioned above as the substituent groups for the substituted alkyl group and the substituted aryl group represented by $R^{21}$. Preferred embodiments thereof are also the same.

The alkyl group, aryl group and, heterocyclic group represented by $R^2$ may be substituted by a substituent group explained above as the substituent group for $R^{21}$, and when there are two or more substituent groups, they may be the same or different from each other.

In the following, a group represented by formula (2), a group represented by formula (3), and a group represented by formula (4), corresponding to $Q^1$ in formula (1), are explained.

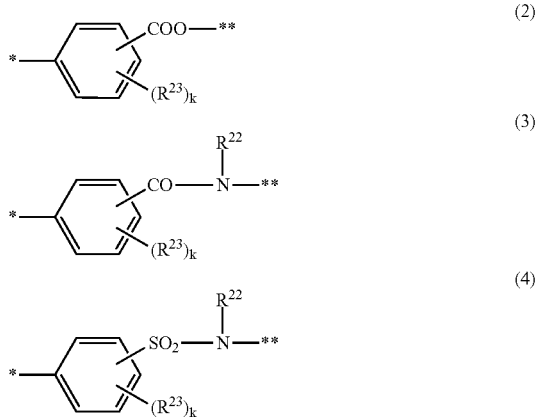

In formulas (2) to (4), $R^{22}$ represents a hydrogen atom, an alkyl group, an aryl group, or a heterocyclic group, $R^{23}$ represents a hydrogen atom or a substituent group, and k represents an integer from 0 to 4. When k is 2 or more, the two or more of $R^{23}$ may be the same or different from each other. * indicates a bonding site to the —C($R^{21}$)=$CH_2$ group in formula (1), and ** indicates a bonding site to $Q^2$ or Dye VI (when n2=0) in formula (1).

$R^{22}$ in formulas (3) and (4) has the same definitions as that of $R^2$ in formula (1), and preferred embodiments thereof are also the same.

In formulas (2) to (4), $R^{23}$ represents a hydrogen atom or a substituent group, and examples of the substituent group represented by $R^{23}$ may be the substituent groups mentioned above as a substituent group for the substituted alkyl group and the substituted aryl group represented by $R^{21}$ in formula (1). Preferred embodiments thereof are also the same. k represents an integer from 0 to 4. When k is 2 or more, the two or more of $R^{23}$ may be the same or different from each other.

When $R^{23}$ in formulas (2) to (4) is a group that can have a further substituent group, the substituent group may be selected from the substituent groups explained above with respect to $R^{21}$ in formula (1). When there are two or more substituent groups, they may be the same or different from each other.

From the viewpoint of synthesis suitability, $Q^1$ in formula (1) is preferably —N($R^2$)C(=O)—, —OC(=O)—, —C(=O)N($R^2$)—, or —C(=O)O—, more preferably —OC(=O)—, —C(=O)N($R^2$)—, or —C(=O)O—, and still more preferably —C(=O)N($R^2$)— or —C(=O)O—. $R^2$ represents a hydrogen atom, an alkyl group, an aryl group, or a heterocyclic group.

In formula (1), when n1=0, $Q^2$ represents a divalent linking group that connects the —C($R^{21}$)=$CH_2$ group to Dye.

$Q^2$ is preferably an alkylene group, an arylalkylene group, an arylene group, —O—, —C(=O)—, —OC(=O)—, OC(=O)O—, —O$SO_2$—, —OC(=O)N($R^{50}$)—, —N($R^{50}$)—, —N($R^{50}$)C(=O)—, —N($R^{50}$)C(=O)O—, —N($R^{50}$)C(=O)N($R^{51}$)—, —N($R^{50}$)$SO_2$—, —N($R^{50}$)$SO_2$N($R^{51}$)—, —S—, —S—S—, —SO—, —$SO_2$—, —$SO_2$N($R^{50}$)—, or —$SO_2$O—. Two or more of these divalent linking groups may be linked to each other to form a divalent linking group.

Here, $R^{50}$ and $R^{51}$ each independently represent a hydrogen atom, an alkyl group, an aryl group, or a heterocyclic group. Examples of the alkyl group, aryl group, and heterocyclic group represented by $R^{50}$ and $R^{51}$ include an alkyl group, an aryl group, and a heterocyclic group explained above as a substituent group for $R^{21}$ in formula (1). Preferred embodiments are also the same. The alkyl group, aryl group and heterocyclic group represented by $R^{50}$ and $R^{51}$ may be substituted with a substituent group explained as a substituent group for $R^{21}$ in formula (1). When there are two or more substituent groups, they may be the same or different from each other.

When $Q^2$ in formula (1) is an alkylene group, an arylalkylene group, or an arylene group, it may be unsubstituted or substituted, and when it is substituted, the substituent group may be the substituent group for $R^1$. When there are two or more substituent groups, they may be the same or different from each other.

When $Q^2$ is an alkylene group, an arylalkylene group, or an arylene group, $Q^2$ is preferably an alkylene group having 1 to 12 carbon atoms, an arylalkylene group having 6 to 18 carbon atoms, or an arylene group having 6 to 18 carbon atoms; more preferably, an alkylene group having 1 to 8 carbon atoms, an arylalkylene group having 6 to 16 carbon atoms, or an arylene group having 6 to 12 carbon atoms; and still more preferably, an alkylene group having 1 to 6 carbon atoms or an arylalkylene group having 6 to 12 carbon atoms.

Preferred combinations of $Q^1$ and $Q^2$ include an embodiment in which $Q^1$ is —N($R^2$)C(=O)—, —OC(=O)—, —C(=O)N($R^2$)— or —C(=O)O— and $Q^2$ is an alkylene group having 1 to 12 carbon atoms, an arylalkylene group having 6 to 18 carbon atoms, an arylene group having 6 to 18 carbon atoms, an alkylthioether group having 2 to 18 carbon atoms, an alkylcarbonamido group having 2 to 18 carbon atoms, or an alkylaminocarbonyl group having 2 to 18 carbon atoms. Among these, an embodiment in which $Q^1$ is —OC(=O)—, —C(=O)N($R^2$)— or —C(=O)O— and $Q^2$ is an alkylene group having 1 to 8 carbon atoms, an arylalkylene group having 6 to 16 carbon atoms, an arylene group having 6 to 12 carbon atoms, an alkylthioether group having 2 to 12 carbon atoms, an alkylcarbonamido group having 2 to 12 carbon atoms or an alkylaminocarbonyl group having 2 to 12 carbon atoms is more preferable. An embodiment in which $Q^1$ is —C(=O)N($R^2$)— or —C(=O)O— and $Q^2$ is an alkylene group having 1 to 6 carbon atoms, an arylalkylene group having 6 to 12 carbon atoms, an alkylthioether group having 2 to 6 carbon atoms, an alkylcarbonamido group having 2 to 6 carbon atoms, or an alkylaminocarbonyl group having 2 to 6 carbon atoms is still more preferable.

The following are examples of the polymerizable group represented by -(Q²)n2-(Q¹)n1-C(R²¹)=CH₂ in formula (1). However, the invention is not limited to these examples.

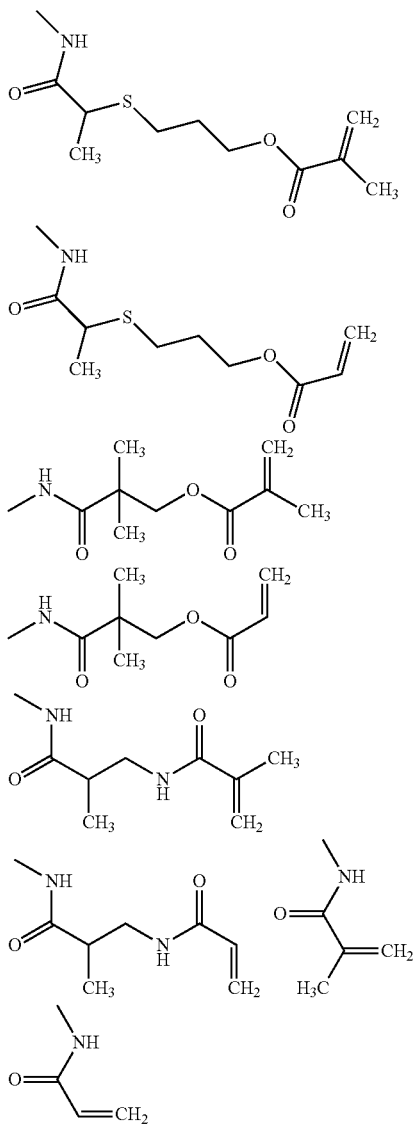

(Dipyrromethene Metal Complex Compound)

The dye monomer represented by formula (1) has a dye residue formed by removing an arbitrarily selected hydrogen atom from a dipyrromethene metal complex compound represented by formula (7), or a dye residue formed by removing a hydrogen atom of any one of substituent groups represented by $R^{11}$ to $R^{19}$ and $X^3$ from a dipyrromethene metal complex compound represented by formula (8). In other words, the dye monomer represented by formula (1) is a dipyrromethene metal complex compound represented by formula (7) or formula (8) to which a polymerizable group, represented by -(Q²)n2-(Q¹)n1-C(R²¹)=CH₂, is introduced. In addition, when both n1 and n2 are 0, the —C(R²¹)=CH₂ group is directly introduced into the dipyrromethene metal complex compound.

The dipyrromethene metal complex compound to be introduced to formula (1) is a dipyrromethene metal complex compound represented by formula (7) or formula (8).

The dye monomer represented by formula (1) may be used alone or in a combination of two or more kinds The dye multimer of the invention may further contain, as a copolymerizable component, a monomer having a different structure from the dye monomer represented by formula (1) and a terminal ethylenically unsaturated bond. One or more kinds of the monomer may be contained. When the monomer includes a further monomer as a copolymerization compound, the copolymerization monomer may be used alone or in a combination of two or more kinds The monomer having a different structure from a dye monomer represented by formula (1) and a terminal ethylenically unsaturated bond is described below.

The dye multimer of the invention may be formed only from a structural unit represented by formula (A), formula (B) or formula (C), or from a dye monomer represented by formula (1), i.e., from these structural units by 100% by mass.

From the viewpoint of a coloring power, the dye multimer of the invention preferably includes a structural unit represented by formula (A), formula (B) or formula (C) in an amount of 10% by mass to 100% by mass, more preferably 20% by mass to 100% by mass, and still more preferably 30% by mass to 100% by mass.

<Monomer Having a Structure Different from the Dye Monomer Represented by Formula (1) and a Terminal Ethylenically Unsaturated Bond>

In addition to a structural unit represented by formula (A), formula (B), or formula (C), or a dye monomer represented by formula (1) as a preferred embodiment thereof, the dye multimer of the invention may further contain, as a copolymerizable component, a monomer having a structure different from the dye monomer represented by formula (1) and a terminal ethylenically unsaturated bond (hereinbelow, also referred to as a "further monomer with an ethylenically unsaturated bond"). The dye multimer may further include a monomer having a structure different from the further monomer with an ethylenically unsaturated bond as a copolymerizable component.

Accordingly, the dye multimer of the invention may be a copolymer of a dye monomer that may form a structural unit represented by formula (A), formula (B), or formula (C), a dye monomer represented by formula (1), and a further monomer with an ethylenically unsaturated bond. In that case, the copolymer may include only one kind of the specific dye monomer according to the invention, or two or more kinds thereof in combination. Also, the copolymer may include only one kind of a further monomer with an ethylenically unsaturated bond, or two or more kinds thereof in combination.

The further monomer with an ethylenically unsaturated bond is not particularly limited as long as it is a compound having an ethylenically unsaturated bond at least at its terminal, and a structure different from that of the dye monomer which may form the structural unit represented by formula (A), formula (B) or formula (C), or the dye monomer represented by formula (1).

When the dye multimer of the invention is used for a colored curable composition, from the viewpoint of improving an ability of forming a colored pattern, the further monomer with an ethylenically unsaturated bond is preferably a monomer having an alkali soluble group, in addition to an ethylenically unsaturated bond at its terminal.

Examples of the monomer with ethylenically unsaturated bond having an alkali soluble group include a vinyl monomer having a carboxyl group, a vinyl monomer having a sulfonic acid group, and a monomer having a phosphoric acid group.

Examples of the vinyl monomer having a carboxyl group include (meth)acrylic acid, vinyl benzoic acid, maleic acid, maleic acid monoalkyl ester, fumaric acid, itaconic acid, crotonic acid, cinnamic acid, and acrylic acid dimer. Further, an addition product of a monomer having a hydroxyl group, such as 2-hydroxyethyl(meth)acrylate, and a cyclic anhydride, such as maleic anhydride, phthalic anhydride or cyclohexane dicarboxylic acid anhydride, and ω-carboxy-polycaprolactone mono(meth)acrylate, or the like, may also be used. Further, as a precursor of a carboxyl group, a monomer including an anhydride, such as maleic anhydride, itaconic anhydride, and citraconic anhydride, may be used. Among these, from the viewpoint of copolymerization properties, costs, solubility or the like, (meth)acrylic acid is particularly preferable.

Further, examples of the vinyl monomer having a sulfonic acid group include 2-acrylamide-2-methylpropane sulfonic acid. Examples of the vinyl monomer having a phosphoric acid group include mono(2-acryloyloxyethyl ester) phosphate and mono(1-methyl-2-acryloyloxyethyl ester) phosphate.

The dye multimer of the invention preferably contains a repeating unit derived from a vinyl monomer having an alkali soluble group as described above. By using a dye multimer including a repeating unit derived from a vinyl monomer having an alkali soluble group in a colored curable composition, a favorable removability of unexposed portions during development may be achieved In the dye multimer of the invention, the content of a repeating unit derived from a vinyl monomer having an alkali soluble group, in terms of an acid value of the dye multimer, is preferably 50 mgKOH/g or more, and more preferably from 50 mgKOH/g to 200 mgKOH/g. When the content is within the range, formation of precipitates in a developer may be suppressed.

Further, when a colored curable composition includes the dye multimer of the invention and a pigment in combination and has an acid value within this range, formation of secondary aggregates, which are aggregates of primary particles of a pigment, may be effectively suppressed, or the aggregation force of the secondary aggregates may be effectively weakened.

The vinyl monomer that may be used for the copolymerization with the dye monomer of the invention is not specifically limited. Preferred examples of the vinyl monomer include (meth)acrylic acid esters, crotonic acid esters, vinyl esters, maleic acid diesters, fumaric acid diesters, itaconic acid diesters, (meth)acrylamides, vinyl ethers, vinyl alcohol esters, styrenes, and (meth)acrylonitriles. Specific examples of the vinyl monomer include the compounds described below. In the present specification, either one or both of acrylic and methacrylic may be collectively referred to as "(meth)acrylic".

Examples of the (meth)acrylic acid esters include methyl (meth)acrylate, ethyl(meth)acrylate, n-propyl(meth)acrylate, isopropyl(meth)acrylate, n-butyl(meth)acrylate, isobutyl (meth)acrylate, t-butyl(meth)acrylate, n-hexyl(meth)acrylate, cyclohexyl(meth)acrylate, t-butyl cyclohexyl(meth) acrylate, 2-ethylhexyl(meth)acrylate, t-octyl(meth)acrylate, dodecyl(meth)acrylate, octadecyl(meth)acrylate, acetoxyethyl(meth)acrylate, phenyl(meth)acrylate, 2-hydroxyethyl (meth)acrylate, 2-methoxy ethyl(meth)acrylate, 2-ethoxyethyl(meth)acrylate, 2-(2-methoxyethoxy)ethyl(meth) acrylate, 3-phenoxy-2-hydroxy propyl(meth)acrylate, benzyl (meth)acrylate, diethylene glycol monomethyl ether(meth) acrylate, diethylene glycol monoethyl ether(meth)acrylate, triethylene glycol monomethyl ether(meth)acrylate, triethylene glycol monoethyl ether(meth)acrylate, polyethylene glycol monomethyl ether(meth)acrylate, polyethylene glycol monoethyl ether(meth)acrylate, β-phenoxy ethoxy ethyl (meth)acrylate, nonyl phenoxy polyethylene glycol(meth) acrylate, dicyclopentenyl(meth)acrylate, dicyclopentenyloxyethyl(meth)acrylate, trifluoroethyl(meth)acrylate, octafluoropentyl(meth)acrylate, perfluorooctylethyl(meth) acrylate, dicyclopentanyl(meth)acrylate, tribromo phenyl (meth)acrylate, and tribromo phenyloxy ethyl(meth)acrylate.

Examples of the crotonic acid esters include butyl crotonate and hexyl crotonate.

Examples of the vinyl esters include vinyl acetate, vinyl propionate, vinyl butyrate, vinyl methoxyacetate, and vinyl benzoate.

Examples of the maleic acid diesters include dimethyl maleate, diethyl maleate, and dibutyl maleate.

Examples of the fumaric acid diesters include dimethyl fumarate, diethyl fumarate, and dibutyl fumarate.

Examples of the itaconic acid diesters include dimethyl itaconate, diethyl itaconate, and dibutyl itaconate.

Examples of the (meth)acrylamides include (meth)acrylamide, N-methyl(meth)acrylamide, N-ethyl(meth)acrylamide, N-propyl(meth)acrylamide, N-isopropyl(meth)acrylamide, N-n-butyl acryl(meth)amide, N-t-butyl(meth) acrylamide, N-cyclohexyl(meth)acrylamide, N-(2-methoxy ethyl)(meth)acrylamide, N,N-dimethyl(meth)acrylamide, N,N-diethyl(meth)acrylamide, N-phenyl(meth)acrylamide, N-benzyl(meth)acrylamide, (meth)acryloyl morpholine, and diacetone acrylamide.

Examples of the vinyl ethers include methylvinyl ether, butylvinyl ether, hexylvinyl ether, and methoxyethylvinyl ether.

Examples of the styrenes include styrene, methylstyrene, dimethylstyrene, trimethylstyrene, ethylstyrene, isopropylstyrene, butylstyrene, hydroxystyrene, methoxystyrene, butoxystyrene, acetoxystyrene, chlorostyrene, dichlorostyrene, bromostyrene, chloromethylstyrene, hydroxystyrene protected with a group that can be de-protected with an acidic material (for example, t-Boc), methyl vinyl benzoate, and α-methylstyrene.

In the following, specific examples of the further monomer with an ethylenically unsaturated bond are described, but the invention is not limited thereto.

(b-1)

(b-2)

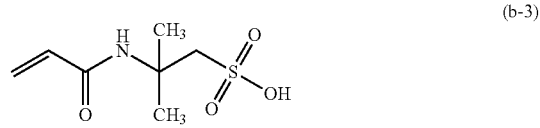

(b-3)

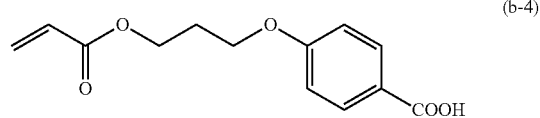

(b-4)

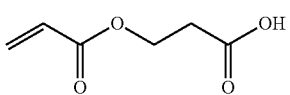 (b-5)

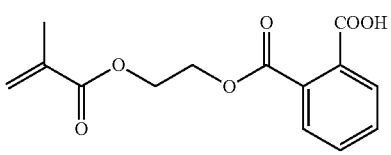 (b-6)

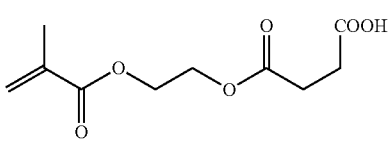 (b-7)

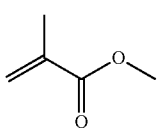 (b-8)

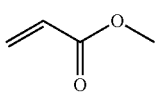 (b-9)

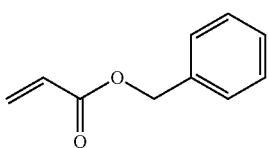 (b-10)

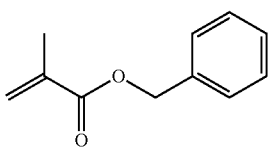 (b-11)

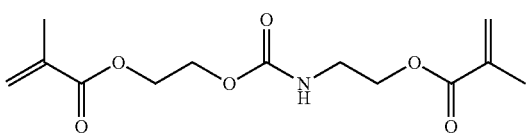 (b-12)

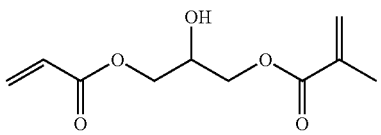 (b-13)

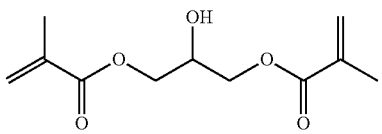 (b-14)

The dye compound of the invention may also include a group that reacts with a substituent group of the dye compound, and a polymerizable group that is introduced by adding a compound having a polymerizable group to the dye compound.

Examples of the group that reacts with a substituent group of the dye compound include a group that reacts with a monovalent leaving group of the dye compound (for example, a chlorine atom, a bromine atom, an iodine atom, an alkylcarbonyloxy group having 2 to 6 carbon atoms, a cycloalkylcarbonyloxy group having 4 to 9 carbon atoms, an arylcarbonyloxy group having 7 to 12 carbon atoms, a hydroxyl group, an alkoxy group having 1 to 5 carbon atoms, and a triflate), an acid group (for example, carboxylic acid, sulfonic acid, and phosphoric acid), or a substituent group such as a hydroxyl group and a primary or a secondary amino group, and specific examples of the group which reacts with a hydroxyl group of the dye compound include an epoxy group, a monovalent leaving group (examples thereof are the same as the monovalent leaving group described above), and an isocyanate group. Specific examples of the group that reacts with a chlorine atom of the dye compound include a thiol group, a hydroxyl group, a primary or secondary amino group, and a carbonyl group. Examples of the polymerizable group include an ethylenically unsaturated group, an epoxy ring, and an oxetane ring.

Examples of the compound having a polymerizable group and a group that reacts with a substituent group of the dye compound include glycidyl(meth)acrylate, aryl bromide, para vinyl phenyl bromide, and a methacryloyloxy ethyl isocyanate. Preferred examples include glycidyl(meth)acrylate and methacryloyloxy ethyl isocyanate.

Examples of the dye compound that includes a group that reacts with a substituent group of the dye compound and a polymerizable group that is introduced by adding a compound having a polymerizable group to the dye compound include the following.

The dye compound having a polymerizable compound may include a dye compound into which a polymerizable group has not been introduced yet.

199    200
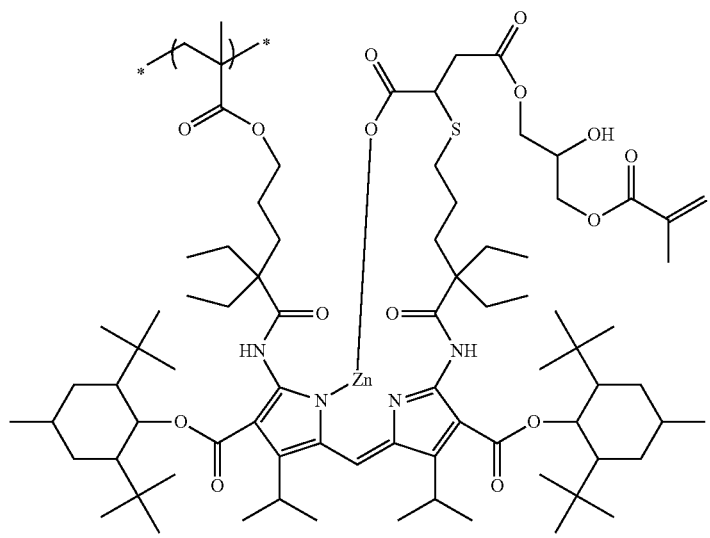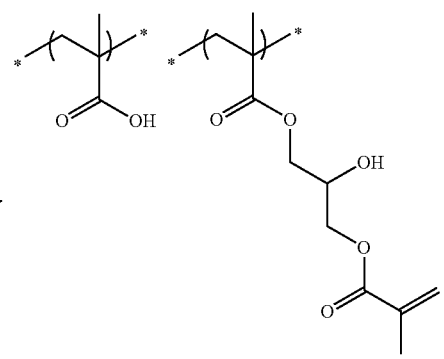
P-101
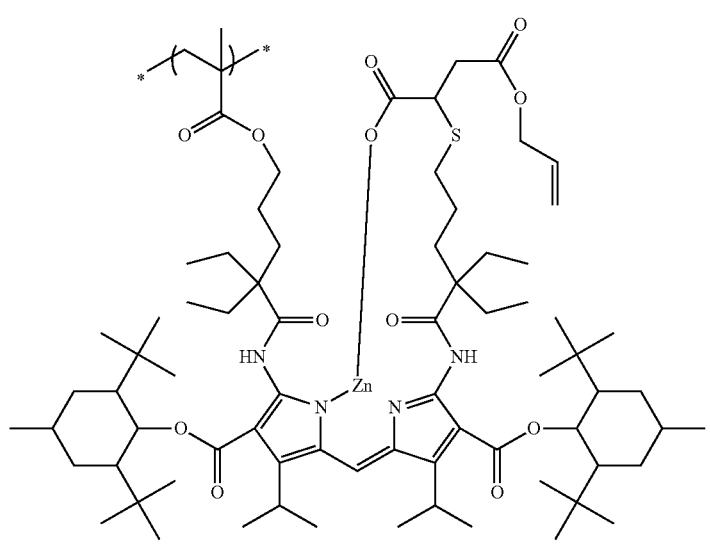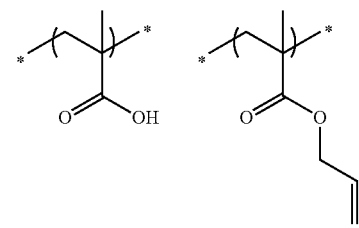
P-102
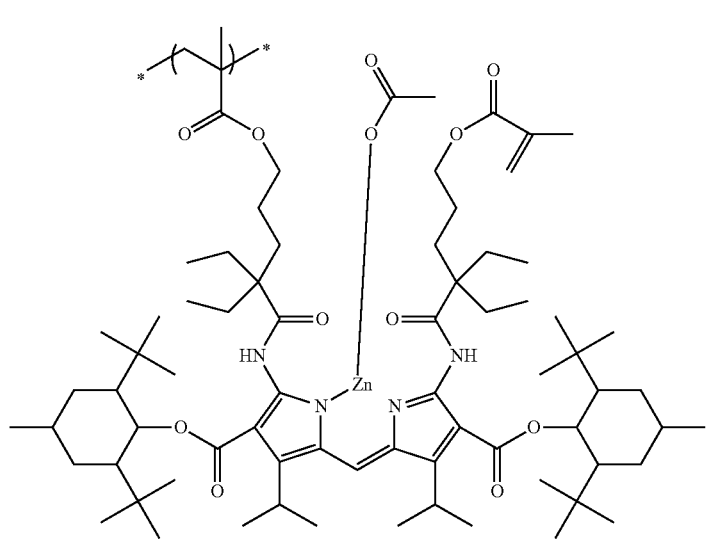
P-103

-continued
201
202
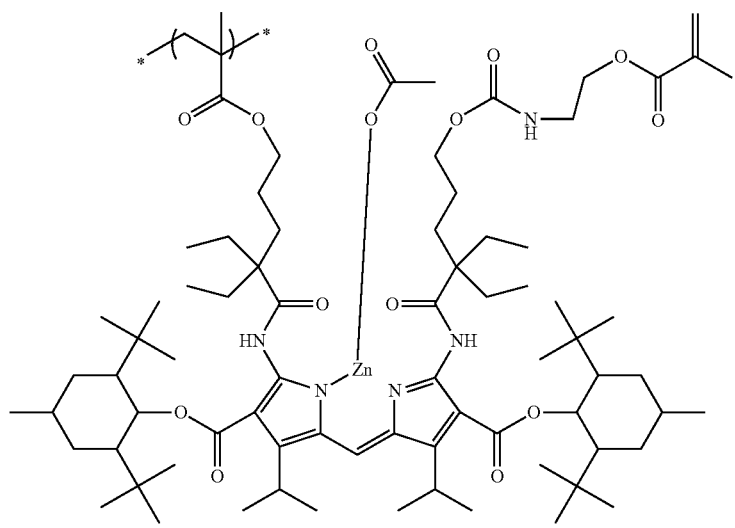
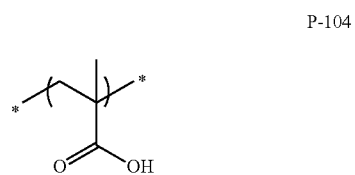
P-104
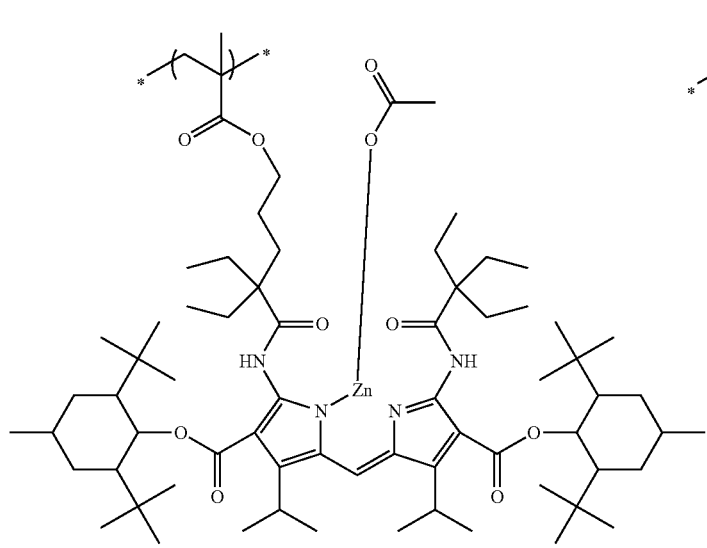
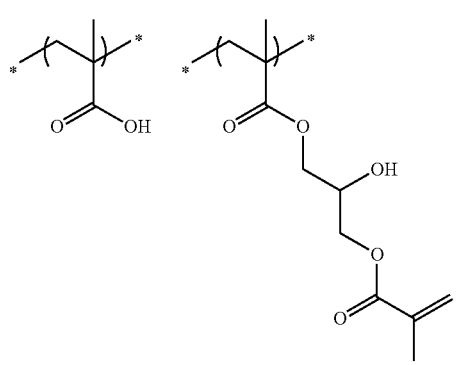
P-105
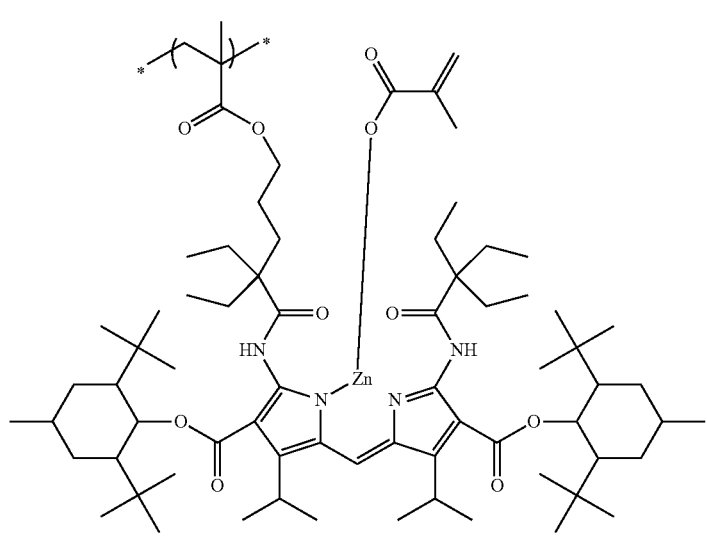
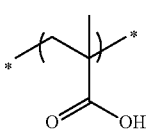
P-106

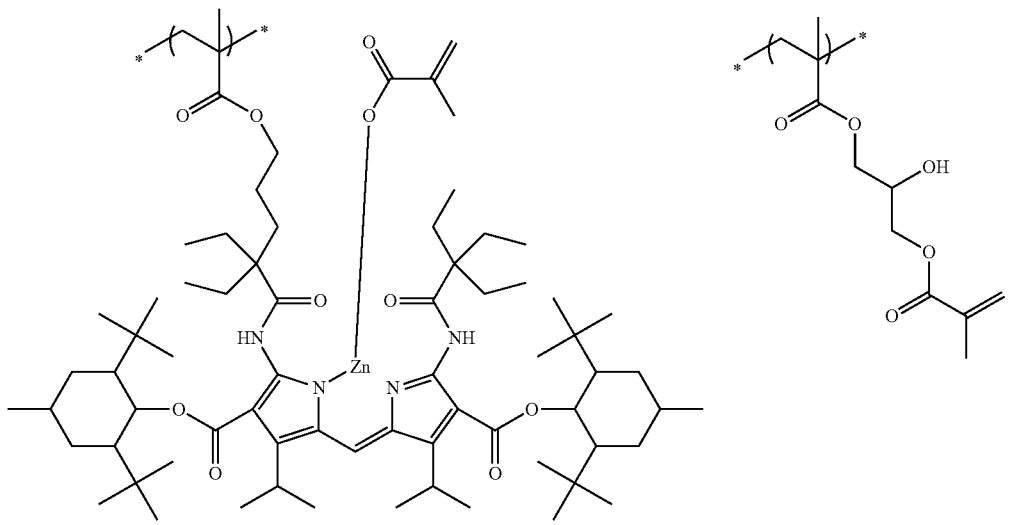

P-107

(Specific Examples of the Dye Multimer)

The following are specific examples of the dye multimer of the invention, but the invention is not limited thereto. In the following Tables 6 to 8, the compound numbers of monomer a correspond to the specific examples of the dye monomer, and the compound numbers of monomer b correspond to the specific examples of the monomer with an ethylenically unsaturated bond.

The dye multimer may be produced by radical polymerization, photoradical polymerization or thermal polymerization, preferably by radical polymerization, from a dye multimer including a structural unit derived from a dye monomer represented by formula (1) alone, or from a combination of a dye multimer including a structural unit derived from a dye monomer represented by formula (1) and a monomer with an ethylenically unsaturated bond.

TABLE 6

| Exemplary Compound | Monomer a | | Monomer b | | Mw | Mw/Mn |
|---|---|---|---|---|---|---|
| | Type | mass % | Type | mass % | | |
| P1 | M-48 | 100 | — | 0 | 8000 | 1.7 |
| P2 | M-48 | 100 | — | 0 | 6000 | 1.5 |
| P3 | M-48 | 100 | — | 0 | 9000 | 2.4 |
| P4 | M-48 | 100 | — | 0 | 13000 | 2.1 |
| P5 | M-48 | 93.5 | b-2 | 6.5 | 9000 | 1.3 |
| P6 | M-48 | 93.5 | b-2 | 6.5 | 18000 | 2.4 |
| P7 | M-48 | 93.5 | b-2 | 6.5 | 10000 | 1.8 |
| P8 | M-48 | 93.5 | b-2 | 6.5 | 8000 | 1.8 |
| P9 | M-48 | 87.8 | b-2 | 12.2 | 9000 | 2 |
| P10 | M-48 | 87.8 | b-2 | 12.2 | 6000 | 1.9 |
| P11 | M-48 | 87.8 | b-2 | 12.2 | 12000 | 2.5 |
| P12 | M-48 | 87.8 | b-2 | 12.2 | 10000 | 1.7 |
| P13 | M-48 | 82.7 | b-2 | 17.3 | 17000 | 1.2 |
| P14 | M-48 | 82.7 | b-2 | 17.3 | 6000 | 1.4 |
| P15 | M-48 | 82.7 | b-2 | 17.3 | 8000 | 1.8 |
| P16 | M-48 | 82.7 | b-2 | 17.3 | 9000 | 2.4 |
| P17 | M-48 | 78.2 | b-2 | 21.8 | 8000 | 2.2 |
| P18 | M-48 | 78.2 | b-2 | 21.8 | 6000 | 1.8 |
| P19 | M-48 | 78.2 | b-2 | 21.8 | 14000 | 1.7 |
| P20 | M-48 | 78.2 | b-2 | 21.8 | 9000 | 2.7 |
| P21 | M-48 | 74.2 | b-2 | 25.8 | 9000 | 2.4 |
| P22 | M-48 | 74.2 | b-2 | 25.8 | 6000 | 2.1 |
| P23 | M-48 | 74.2 | b-2 | 25.8 | 11000 | 1.7 |
| P24 | M-48 | 74.2 | b-2 | 25.8 | 21000 | 1.5 |
| P25 | M-48 | 93.5 | b-1 | 6.5 | 5000 | 1.4 |

TABLE 6-continued

| Exemplary Compound | Monomer a | | Monomer b | | Mw | Mw/Mn |
|---|---|---|---|---|---|---|
| | Type | mass % | Type | mass % | | |
| P26 | M-48 | 87.8 | b-1 | 12.2 | 11000 | 2.4 |
| P27 | M-48 | 82.7 | b-1 | 17.3 | 8000 | 2.8 |
| P28 | M-48 | 78.2 | b-1 | 21.8 | 6000 | 1.7 |
| P29 | M-48 | 74.2 | b-1 | 25.8 | 7000 | 2.2 |
| P30 | M-48 | 93.5 | b-3 | 6.5 | 9000 | 2.7 |

TABLE 7

| Exemplary Compound | Monomer a | | Monomer b | | Mw | Mw/Mn |
|---|---|---|---|---|---|---|
| | Type | mass % | Type | mass % | | |
| P31 | M-48 | 82.7 | b-4 | 17.3 | 12000 | 2.1 |
| P32 | M-48 | 78.2 | b-5 | 21.8 | 20000 | 2.3 |
| P33 | M-48 | 87.8 | b-6 | 12.2 | 9000 | 1.9 |
| P34 | M-48 | 74.2 | b-7 | 25.8 | 7000 | 1.6 |
| P35 | M-48 | 93.5 | b-8 | 6.5 | 14000 | 1.8 |
| P36 | M-48 | 78.2 | b-9 | 21.8 | 8000 | 2.1 |
| P37 | M-48 | 74.2 | b-10 | 25.8 | 8000 | 2 |
| P38 | M-48 | 82.7 | b-11 | 17.3 | 10000 | 1.9 |
| P39 | M-48 | 87.8 | b-12 | 12.2 | 17000 | 2.6 |
| P40 | M-48 | 93.5 | b-13 | 6.5 | 8000 | 3.1 |
| P41 | M-48 | 78.2 | b-14 | 21.8 | 9000 | 2.4 |
| P42 | M-48 | 74.2 | b-15 | 25.8 | 8000 | 2.4 |
| P43 | M-48 | 87.8 | b-16 | 12.2 | 15000 | 2.1 |
| P44 | M-48 | 74.2 | b-17 | 25.8 | 10000 | 1.8 |
| P45 | M-48 | 82.7 | b-18 | 17.3 | 7000 | 1.8 |
| P46 | M-53 | 100 | — | 0 | 9000 | 1.8 |
| P47 | M-53 | 100 | — | 0 | 11000 | 2.2 |
| P48 | M-53 | 100 | — | 0 | 7000 | 2.2 |
| P49 | M-53 | 100 | — | 0 | 8000 | 2.1 |
| P50 | M-53 | 94 | b-2 | 6 | 10000 | 1.9 |
| P51 | M-53 | 94 | b-2 | 6 | 7000 | 1.7 |
| P52 | M-53 | 94 | b-2 | 6 | 8000 | 1.8 |
| P53 | M-53 | 94 | b-2 | 6 | 12000 | 2.8 |
| P54 | M-53 | 88.6 | b-2 | 11.4 | 8000 | 2.4 |
| P55 | M-53 | 88.6 | b-2 | 11.4 | 15000 | 2.7 |
| P56 | M-53 | 88.6 | b-2 | 11.4 | 11000 | 1.6 |
| P57 | M-53 | 88.6 | b-2 | 11.4 | 9000 | 1.7 |
| P58 | M-53 | 83.8 | b-2 | 16.2 | 12000 | 2 |
| P59 | M-53 | 83.8 | b-2 | 16.2 | 7000 | 1.9 |
| P60 | M-53 | 83.8 | b-2 | 16.2 | 8000 | 2.4 |

TABLE 8

| Exemplary Compound | Monomer a Type | Monomer a mass % | Monomer b Type | Monomer b mass % | Mw | Mw/Mn |
|---|---|---|---|---|---|---|
| P61 | M-53 | 83.8 | b-2 | 16.2 | 10000 | 2.4 |
| P62 | M-53 | 79.5 | b-2 | 20.5 | 7000 | 2.1 |
| P63 | M-53 | 79.5 | b-2 | 20.5 | 8000 | 2.5 |
| P64 | M-53 | 79.5 | b-2 | 20.5 | 9000 | 1.5 |
| P65 | M-53 | 79.5 | b-2 | 20.5 | 7000 | 1.9 |
| P66 | M-53 | 75.7 | b-2 | 24.3 | 7000 | 1.7 |
| P67 | M-53 | 75.7 | b-2 | 24.3 | 20000 | 2 |
| P68 | M-53 | 75.7 | b-2 | 24.3 | 18000 | 2.4 |
| P69 | M-53 | 75.7 | b-2 | 24.3 | 9000 | 2.5 |
| P70 | M-53 | 94 | b-1 | 6 | 7000 | 2.3 |
| P71 | M-53 | 88.6 | b-1 | 11.4 | 17000 | 1.9 |
| P72 | M-53 | 83.8 | b-1 | 16.2 | 9000 | 2.7 |
| P73 | M-53 | 79.5 | b-1 | 20.5 | 8000 | 1.9 |
| P74 | M-53 | 75.7 | b-1 | 24.3 | 10000 | 1.5 |
| P75 | M-53 | 88.6 | b-3 | 11.4 | 8000 | 1.3 |
| P76 | M-53 | 83.8 | b-4 | 16.2 | 7000 | 1.2 |
| P77 | M-53 | 94 | b-5 | 6 | 12000 | 1.9 |
| P78 | M-53 | 75.7 | b-6 | 24.3 | 9000 | 2.7 |
| P79 | M-53 | 88.6 | b-7 | 11.4 | 9000 | 1.7 |
| P80 | M-53 | 75.7 | b-8 | 24.3 | 7000 | 1.9 |
| P81 | M-53 | 83.8 | b-9 | 16.2 | 10000 | 1.5 |
| P82 | M-53 | 94 | b-10 | 6 | 8000 | 1.7 |
| P83 | M-53 | 79.5 | b-11 | 20.5 | 13000 | 1.8 |
| P84 | M-53 | 83.8 | b-12 | 16.2 | 11000 | 1.9 |
| P85 | M-53 | 75.7 | b-13 | 24.3 | 9000 | 1.8 |
| P86 | M-53 | 79.5 | b-14 | 20.5 | 8000 | 2.1 |
| P87 | M-53 | 94 | b-15 | 6 | 7000 | 2.3 |
| P88 | M-53 | 79.5 | b-16 | 20.5 | 11000 | 1.8 |
| P89 | M-53 | 75.7 | b-17 | 24.3 | 8000 | 2 |
| P90 | M-53 | 88.6 | b-18 | 11.4 | 9000 | 1.9 |

The dye multimer of the invention preferably has a weight average molecular weight (Mw) in the range of from 5000 to 30000 and a number average molecular weight (Mn) in the range of from 3000 to 20000, more preferably a weight average molecular weight (Mw) in the range of from 5000 to 25000 and a number average molecular weight (Mn) in the range of from 3000 to 17000, particularly preferably a weight average molecular weight (Mw) in the range of from 5000 to 20000 and a number average molecular weight (Mn) in the range of from 3000 to 15000.

When the dye multimer of the invention is used for a colored curable composition for producing a color filter, the weight average molecular weight (Mw) of the dye multimer is preferably 20000 or less, from the viewpoint of developability.

(Method of Producing the Dipyrromethene Metal Complex Compound)

Method of producing the dipyrromethene metal complex compound of the invention is described hereinbelow.

(Complexation Reaction)

The dipyrromethene metal complex compound of the invention, represented by the following formula (1), may be obtained by allowing a dipyrromethene compound represented by the following formula (XI) to react with a metal derivative represented by formula (XIII) (hereinbelow, the reaction is also referred to as "complexation reaction").

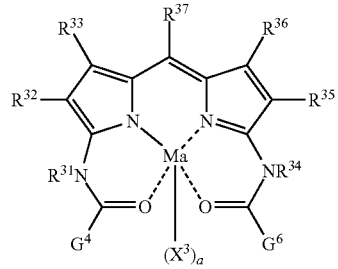

(I)

(In formula (1), $G^4$ and $G^6$ each independently represent a monovalent substituent group having a steric parameter (–Es' value) of 1.5 or more. $R^{32}$, $R^{33}$, $R^{35}$ and $R^{36}$ each independently represent a hydrogen atom or a monovalent substituent group. $R^{37}$ represents a hydrogen atom, a halogen atom, an alkyl group, an aryl group, or a heterocyclic group. $R^{31}$ and $R^{34}$ each independently represent a hydrogen atom, an alkyl group, an alkenyl group, an aryl group, a heterocyclic group, an acyl group, an alkylsulfonyl group, or an arylsulfonyl group. Ma represents a metal atom or a metal compound. $X^3$ represents a group capable of being bonded to Ma, and a represents 0, 1 or 2).

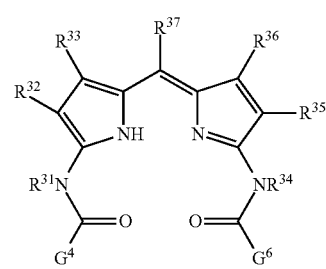

(XI)

(In formula (XI), $R^{31}$ to $R^{37}$, $G^4$ and $G^6$ each have the same definitions as that of $R^{31}$ to $R^{37}$, $G^4$ and $G^6$ in formula (1), respectively).

$$Ma(X^1)_b \quad (XIII)$$

(In formula (XIII), Ma and $X^1$ have the same definitions as that of Ma and $X^3$ in formula (1), respectively. b represents an integer from 0 to 4).

In the dipyrromethene metal complex compound represented by formula (1), $R^{32}$, $R^{33}$, $R^{35}$ and $R^{36}$ each have the same definitions as that of $R^5$, $R^6$, $R^8$ and $R^7$ in formula (M), respectively, and the preferred embodiments are also the same. $R^{37}$ has the same definitions as that of $R^{10}$ in formula (M), and the preferred embodiments are also the same. Ma has the same definitions as that of Ma in formula (7), and the preferred embodiments are also the same. $R^{31}$, $R^{34}$ and $X^3$ each have the same definitions as that of $R^{18}$, $R^{19}$ and $X^3$ in formula (8), respectively, and the preferred embodiments are also the same.

More specifically, among $R^{32}$, $R^{33}$, $R^{35}$ and $R^{36}$ in formula (1), $R^{32}$ and $R^{35}$ are preferably an alkoxycarbonyl group, an aryloxycarbonyl group, a carbamoyl group, an alkylsulfonyl group, an arylsulfonyl group, a nitrile group, an imido group, or a carbamoylsulfonyl group, more preferably an alkoxycarbonyl group, an aryloxycarbonyl group, a carbamoyl group, an alkylsulfonyl group, a nitrile group, an imido group, or a carbamoylsulfonyl group, still more preferably an alkoxycarbonyl group, an aryloxycarbonyl group, a carbamoyl group, a nitrile group, an imido group, or a carbamoylsulfonyl group, and particularly preferably an alkoxycarbonyl group, an aryloxycarbonyl group, or a carbamoyl group.

Further, $R^{33}$ and $R^{36}$ are preferably a substituted or unsubstituted alkyl group, a substituted or unsubstituted aryl group, or a substituted or unsubstituted heterocyclic group, more preferably a substituted or unsubstituted alkyl group or a substituted or unsubstituted aryl group. Specific examples of the more preferred alkyl group, an aryl group, and heterocyclic group are the same as the specific examples represented by $R^6$ and $R^7$ in formula (M).

Among the above, $R^{31}$ and $R^{34}$ are preferably a hydrogen atom, an alkyl group, an alkenyl group, an aryl group, or a heterocyclic group, more preferably a hydrogen atom or an alkyl group, and particularly preferably a hydrogen atom.

In formula (1), $G^4$ and $G^6$ each independently represent a monovalent substituent group having a steric parameter (–Es' value) of 1.5 or more, and specific examples thereof include an alkyl group (a branched or cyclic alkyl group having preferably 1 to 36 carbon atoms, and more preferably 1 to 12 carbon atoms, and examples thereof include the substituent groups described in Table 1, i.e., a 2-ethylhexyl group, a 1-adamantyl group, and a triethylmethyl group), an alkenyl group (an alkenyl group having preferably 2 to 24 carbon atoms, and more preferably 2 to 12 carbon atoms, and examples thereof include a vinyl group, an allyl group, and a 3-buten-1-yl group), an aryl group (an aryl group having preferably 6 to 36 carbon atoms, and more preferably 6 to 18 carbon atoms, and examples thereof include a phenyl group, an o-tolyl group, and a naphthyl group), a heterocyclic group (a heterocyclic group having preferably 1 to 24 carbon atoms, and more preferably 1 to 12 carbon atoms, and examples thereof include a 2-thienyl group, a 4-pyridyl group, a 2-furyl group, a 2-pyrimidinyl group, a 2-pyridyl group, a 2-benzothiazolyl group, a 1-imidazolyl group, a 1-pyrazolyl group, and a benzotriazol-1-yl group).

Among the above, $G^4$ and $G^6$ are preferably an alkyl group, an alkenyl group, or an aryl group, more preferably an alkyl group or an alkenyl group, and particularly preferably an alkyl group.

In formula (8), examples of the group represented by $X^3$, which can be bonded to Ma, include a halogen atom, a hydroxyl group, a carboxylic acid group, a phosphoric acid group, a sulfonic acid group, and compounds described in "Metal Chelate" ([1] Sakaguchi Takeichi, Ueno Keihei (1995, Nankodo Co., Ltd.), [2] (1996), and [3] (1997), etc.). Among them, from the viewpoint of producibility, a halogen atom, a hydroxyl group, a carboxylic acid group, and a sulfonic acid group are preferable, and a halogen atom, a hydroxyl group, and a carboxylic acid group are more preferable. a indicates 0, 1, or 2. When a is 2, the structures of the two of $X^3$ may be the same or different from each other.

In formula (1), $R^{31}$ and $G^4$ may be bonded to each other to form, together with the carbon atom, a 5-membered ring (for example, cyclopentane, pyrrolidine, tetrahydrofuran, dioxolan, tetrahydrothiophene, pyrrole, furan, thiophene, indole, benzofuran, and benzothiophene), a 6-membered ring (for example, cyclohexane, piperidine, piperazine, morpholine, tetrahydropyran, dioxane, pentamethylene sulfide, dithiane, benzene, piperidine, piperazine, pyridazine, quinoline, and quinazoline), or a 7-membered ring (for example, cycloheptane and hexamethylene imine).

In formula (1), $R^{34}$ and $G^6$ may be bonded to each other to form, together with the carbon atom, a 5-membered ring (for example, cyclopentane, pyrrolidine, tetrahydrofuran, dioxolan, tetrahydrothiophene, pyrrole, furan, thiophene, indole, benzofuran, and benzothiophene), a 6-membered ring (for example, cyclohexane, piperidine, piperazine, morpholine, tetrahydropyran, dioxane, pentamethylene sulfide, dithiane, benzene, piperidine, piperazine, pyridazine, quinoline, and quinazoline), or a 7-membered ring (for example, cycloheptane and hexamethylene imine).

In formula (1), $G^4$ and $G^6$ each independently represent a monovalent substituent group having a steric parameter (–Es' value) of 1.5 or more. More preferably, $G^4$ and $G^6$ each independently have an Es' value of 2.0 or more, still more preferably 3.5 or more, and particularly preferably 5.0 or more.

In the preferred embodiments of the compound represented by formula (1), $R^{32}$, $R^{33}$, $R^{35}$ and $R^{36}$ each independently are the preferred embodiments of $R^5$, $R^6$, $R^8$ and $R^7$ of formula (M), $R^{37}$ is a preferred embodiment of $R^{10}$ of formula (M), $R^{31}$ and $R^{34}$ each independently are a hydrogen atom or an alkyl group, $G^4$ and $G^6$ each independently are an alkyl group, an alkenyl group, or an aryl group having an –Es' value of 2.0 or more, Ma is Zn, Cu, Co, or V=O, $X^1$ is a group bonded to Ma via an oxygen atom, and a is 0 or 1.

With regard to a more preferred embodiment of the compound represented by formula (1), $R^{32}$, $R^{33}$, $R^{35}$ and $R^{36}$ each independently have the embodiment that is described above as the preferred embodiment for explaining $R^5$, $R^6$, $R^8$, and $R^7$ of formula (M), $R^{37}$ has the embodiment that is described above as the preferred embodiment for explaining $R^{10}$ of formula (M), $R^{31}$ and $R^{34}$ each independently represent a hydrogen atom or an alkyl group, $G^4$ and $G^6$ each independently represent an alkyl group or alkenyl group having –Es' value of 3.5 or more, Ma is Zn, $X^3$ is a group bonded to Ma via an oxygen atom, and a is 0 or 1.

The site at which the dipyrromethene metal complex compound represented by formula (1) is introduced into a dye multimer described below is not specifically limited, as long as the effect of the invention is not impaired. However, the site for introduction is preferably any one of $R^{31}$ to $R^{36}$, $X^3$, $G^4$ and $G^6$. Among these, from the viewpoint of synthesis suitability, the site for introduction is preferably any one of $R^{32}$, $R^{33}$, $R^{35}$, $R^{36}$, $X^3$, $G^4$ and $G^6$, more preferably any one of $R^{32}$, $R^{35}$, $X^3$, $G^4$ and $G^6$, and still more preferably $G^4$ or $G^6$.

With regard to a method of introducing an alkali soluble group to the dye compound of the invention, when a dye monomer or a structural unit having an alkali soluble group is used, an alkali soluble group may be introduced into at least one substituent group of $R^{31}$ to $R^{37}$, $X^3$, $G^4$ and $G^6$ of the dipyrromethene metal complex compound represented by formula (1). Among these substituent groups, any one of $R^{32}$, $R^{33}$, $R^{35}$, $R^{36}$, $X^3$, $G^4$ and $G^6$ is preferable, and any one of $R^{32}$, $R^{35}$, $G^4$ and $G^6$ is more preferable, and $G^4$ or $G^6$ is still more preferable.

The dipyrromethene metal complex compound represented by formula (1) may include a functional group other than an alkali soluble group, as long as the effect of the invention is not impaired.

The organic solvent used for the complexation reaction is not specifically limited. However, from the viewpoint of solubility of the metal derivative represented by formula (XIII), the reaction is preferably carried out in a polar protic solvent or a polar aprotic solvent. In particular, examples of a suitable solvent include a polar solvent such as an alcoholic organic solvent (for example, methanol, ethanol, and isopropyl alcohol), ether solvent (for example, tetrahydrofuran, dioxane, and cyclopentyl methyl ether), acetone, acetonitrile, N,N-dimethylformamide, and N-methyl-2-pyrrolidone. The solvent may be used alone or in combination of two or more kinds The reaction temperature for the complexation reaction may be selected from a temperature range of from 0° C. to less than the boiling temperature of the solvent, depending on the raw materials used, etc.

The molar ratio between the dipyrromethene compound represented by formula (XI) and the metal derivative represented by formula (XIII), i.e., the dipyrromethene compound represented by formula (XI): the metal derivative represented by formula (XIII), is preferably 1:10 to 10:1, more preferably 1:3 to 3:1, still more preferably 1.2:1 to 1:1.2, and particularly preferably 1:1.

(Coupling Reaction A)

The dipyrromethene compound represented by formula (XI) may be obtained by allowing a substituted pyrrole compound represented by formula (V) to react with a substituted pyrrole compound represented by formula (X) (hereinbelow, this reaction is referred to as "coupling reaction A").

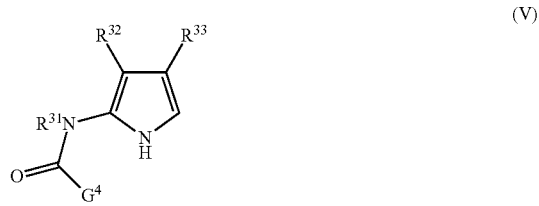

(V)

In formula (V), $R^{31}$, $R^{32}$, $R^{33}$ and $G^4$ each have the same definitions as that of $R^{31}$, $R^{32}$, $R^{33}$ and $G^4$ of formula (1), respectively, and preferred embodiments thereof are also the same.

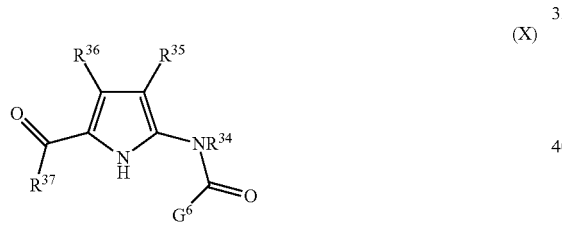

(X)

In formula (X), $R^{34}$, $R^{35}$, $R^{36}$, $R^{37}$ and $G^6$ each have the same definitions as $R^{34}$, $R^{35}$, $R^{36}$, $R^{37}$ and $G^6$ of formula (1), respectively, and the preferred embodiment is also the same.

Coupling reaction A may be carried out by a method described in Aust. J. Chem, 1965, 11, 1835-45, U.S. Pat. No. 4,774,339, JP-A Nos. 2008-292970 and 2009-227639, for example.

From the viewpoint of synthesis suitability, coupling reaction A is preferably carried out in the presence of an acid. Specific examples of the acid include hydrogen bromide acid, hydrogen chloride acid, acetic acid, trifluoroacetic acid, methane sulfonic acid, and para toluenesulfonic acid. The amount of the acid is not particularly limited, but preferably used in an amount of 1 to 200 equivalents with respect to the substituted pyrrole compound represented by formula (X), more preferably 1 to 10 equivalents. The acid may be used also as a solvent.

From the viewpoint of synthesis suitability, a dehydrating agent may be used in coupling reaction A. Specific examples of the dehydrating agent include acid anhydrides (for example, acetic anhydride, trifluoroacetic anhydride, and trifluoro methane sulfonic anhydride), trimethyl silyl chloride, and oxy phosphorus chloride. The amount of the dehydrating agent is not specifically limited, but is preferably used in an amount of 1 to 200 equivalents with respect to the substituted pyrrole compound represented by formula (X). The dehydrating agent may be used also as a solvent.

The organic solvent used in coupling reaction A is not specifically limited, as long as the reaction is not impaired. When the reaction is carried out in the presence of an acid, a solvent that does not react with an acid is preferable. Preferred examples of the solvent include a halogen-based solvent (for example, dichloromethane), toluene, acetonitrile, and an alcohol-based solvent (for example, methanol, ethanol, isopropyl alcohol). Further, the acid or the dehydrating agent, used as a reacting material, may be used as a solvent. The organic solvent may be used alone or in combination of two or more kinds The reaction temperature for coupling reaction A may be selected from the temperature range of from –50° C. to 200° C., depending on the raw materials used, etc. The temperature range is preferably from –10° C. to 150° C., and more preferably 0° C. to 100° C.

The molar ratio between the substituted pyrrole compound represented by formula (V) and the substituted pyrrole compound represented by formula (X), i.e., the substituted pyrrole compound represented by formula (V): the substituted pyrrole compound represented by formula (X), is preferably 1:10 to 10:1, more preferably 1:3 to 3:1, still more preferably 1.2:1 to 1:1.2, and particularly preferably 1:1.

(Acylation)

The compound represented by formula (X) may be obtained by allowing the compound represented by the following formula (IX) to react with an acylating agent (including a formylating agent), and a dipyrromethene compound may be obtained using the compound represented by formula (X).

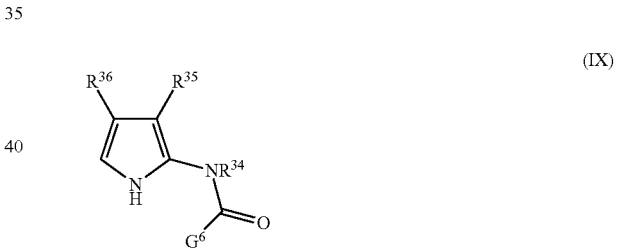

(IX)

In formula (IX), $R^{34}$, $R^{35}$, $R^{36}$ and $G^6$ each have the same definitions as that of $R^{34}$, $R^{35}$, $R^{36}$ and $G^6$ of formula (1), respectively, and the preferred embodiments are also the same.

Acylation of pyrrole may be carried out according to a kwon method described in, for example, Yamanaka Hiroshi, Hino Toni, Nakagawa Masako, Sakamoto Hisao, Basics of Heterocyclic Compounds, New Edition, published on Mar. 1, 2004 (Kodansha Scientific Ltd., Chapter 1, pages 31 to 32). Examples of the method include Gattermann reaction, Vilsmeier reaction, Houben-Hoesch reaction, Friedel-Crafts reaction or the like. Among these, from the viewpoint of production applicability, Vilsmeier reaction and Friedel-Crafts reaction are preferred.

(Vilsmeier Reaction)

The Vilsmeier reaction of pyrrole may be carried out by a method described in, for example, Jones, G., Stanforth, S. P., The Vilsmeier reaction of fully conjugated carbocycles and heterocycles. Org. React. 1997, 49, pages 1 to 330. In addition, an example of applying Vilsmeier reaction for synthesis of a dipyrromethene metal complex compound is described in JP-A No. 2001-240761.

In the Vilsmeier reaction, a Vilsmeier reacting agent is prepared from N,N-disubstituted amide and acid chloride. However, a reacting agent that is commonly suitably used may be used for the invention. Specific examples of the N,N-disubstituted amide include N,N-dimethylformamide, N-methylformanilide and acetanilide. Further, examples of the acid chloride include oxy phosphorus chloride, thionyl chloride, oxalyl chloride, and 2,4,6-trichloro-1,3,5-triazine.

The organic solvent used for Vilsmeier reaction is not specifically limited, as long as the reaction is not impaired. A solvent that does not react with an acid is preferable. Preferred examples of the solvent include a halogen-based solvent (for example, dichloromethane), toluene, acetonitrile, oxy phosphorus chloride, and N,N-dimethylformamide. The solvent may be used alone or in combination of two or more kinds.

The reaction temperature for Vilsmeier reaction may be selected from the temperature range of from −50° C. to 200° C., depending on the raw materials used, etc. The temperature range is preferably from 0° C. to 100° C., and more preferably 10° C. to 60° C.

The molar ratio of the Vilsmeier reacting agent with respect to the substituted pyrrole compound represented by formula (IX), i.e., substituted pyrrole compound represented by formula (IX): Vilsmeier reacting agent, is preferably from 1:1 to 1:10, more preferably from 1:1 to 1:5, and still more preferably from 1:1 to 1:2.

(Friedel-Crafts Reaction)

The Friedel-Crafts reaction of pyrrole may be carried out by a method described in, for example, Yamanaka Hiroshi, Hino Tom, Nakagawa Masako, Sakamoto Hisao, Basics of Heterocyclic Compounds, New Edition, published on Mar. 1, 2004 (Kodansha Scientific Ltd., Chapter 1, pages 31 to 32).

In the Friedel-Crafts reaction, an acylating agent represented by formula (XV) is used. In formula (XV), $R^{37}$ has the same definitions as $R^{37}$ in formula (1), and the preferred embodiments are also the same. X represents a leaving group. Specific examples thereof include a chlorine atom, a bromine atom, an iodine atom, and a triflate. From the viewpoint of production suitability, a chlorine atom is preferable.

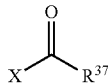

(XV)

In the Friedel-Crafts reaction, any Lewis acid catalyst commonly suitably used may be used. Specific examples of the Lewis acid catalyst include aluminum chloride, aluminum bromide, lanthanoid triflate, sulfuric acid, phosphoric acid, iron trichloride, zinc dichloride, and polyphosphoric acid. The lewis acid catalyst may be used alone or in combination of two or more kinds The organic solvent used in the Friedel-Crafts reaction is not specifically limited as long as the reaction is not impaired. Preferred examples of the solvent include a halogen-based solvent (for example, dichloromethane) and nitrobenzene. The organic solvent may be used alone or in combination of two or more kinds The reaction temperature for the Friedel-Crafts reaction may be selected from the temperature range of from −50° C. to 200° C., depending on the raw materials used, etc. The temperature range is preferably from −10° C. to 100° C., and more preferably 0° C. to 60° C.

The molar ratio of the acylating agent represented by formula (XV) with respect to the substituted pyrrole compound represented by formula (IX), i.e., substituted pyrrole compound represented by formula (IX): acylating agent represented by formula (XV), is preferably from 1:1 to 1:10, more preferably from 1:1 to 1:5, and still more preferably from 1:1 to 1:2. Further, the molar ratio of the Lewis acid catalyst with respect to the substituted pyrrole compound represented by formula (IX), i.e., substituted pyrrole compound represented by formula (IX): Lewis acid catalyst, is preferably from 1:1 to 1:10, more preferably from 1:1 to 1:5, and still more preferably from 1:1 to 1:2.

(Coupling Reaction B)

The dipyrromethene compound represented by formula (XI) may be obtained by allowing a compound represented by the following formula (V) to react with a compound represented by formula (IX) and a compound represented by the following formula (XII) (hereinbelow, this reaction is referred to as "coupling reaction B").

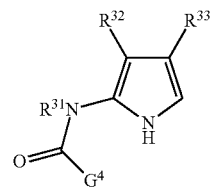

(V)

In formula (V), $R^{31}$, $R^{32}$, $R^{33}$ and $G^4$ each have the same definitions as that of $R^{31}$, $R^{32}$, $R^{33}$ and $G^4$ of formula (1), respectively, and the preferred embodiments are also the same.

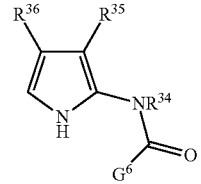

(IX)

In formula (IX), $R^{34}$, $R^{35}$, $R^{36}$ and $G^6$ each have the same definitions as that of $R^{34}$, $R^{35}$, $R^{36}$ and $G^6$ of formula (1), respectively, and the preferred embodiments are also the same.

$$R^{37}C(OR^{38})_3 \quad\quad (XII)$$

In formula (XII), $R^{37}$ has the same definitions as that of $R^{37}$ of formula (1), and the preferred embodiments are also the same. $R^{38}$ represents an alkyl group or an aryl group.

More specifically, $R^{38}$ in formula (XII) represents an alkyl group (i.e., a linear, branched, or cyclic alkyl group having preferably 1 to 36 carbon atoms, and more preferably 1 to 12 carbon atoms, such as methyl, ethyl, propyl, isopropyl, butyl, isobutyl, t-butyl, hexyl, 2-ethylhexyl, dodecyl, cyclopropyl, cyclopentyl, cyclohexyl, and 1-adamantyl), or an aryl group (i.e., an aryl group having preferably 6 to 36 carbon atoms, and more preferably 6 to 18 carbon atoms, such as phenyl and naphthyl).

In formula (XII), $R^{38}$ preferably represents an alkyl group, and more preferably a methyl group or an ethyl group.

Coupling reaction B may be carried out with reference to the method described in JP-A Nos. 2008-292970 and 2009-227639, for example.

From the viewpoint of synthesis suitability, coupling reaction B is preferably carried out in the presence of an acid. Specific examples of the acid include hydrogen bromide acid, hydrogen chloride acid, acetic acid, trifluoroacetic acid, methane sulfonic acid, and para toluenesulfonic acid. The amount of the acid is not particularly limited. However, it is preferably used in an amount of 1 to 200 equivalents with respect to the substituted pyrrole compound represented by formula (X), more preferably 1 to 10 equivalents. The acid may be used also as a solvent.

From the viewpoint of synthesis suitability, a dehydrating agent may be used for coupling reaction B. Specific examples of the dehydrating agent include acid anhydrides (acetic anhydride, trifluoroacetic anhydride, and trifluoro methane sulfonic anhydride, or the like), trimethyl silyl chloride, and oxy phosphorus chloride. The amount of the dehydrating agent is not specifically limited. However, it is preferably used in an amount of 1 to 200 equivalents with respect to the substituted pyrrole compound represented by formula (X), more preferably 1 to 10 equivalents. The dehydrating agent may be used also as a solvent.

The organic solvent used for coupling reaction B is not specifically limited, as long as the reaction is not impaired. When the reaction is carried out in the presence of an acid, a solvent which does not react with an acid is preferable. Preferred examples of the solvent include a halogen-based solvent (for example, dichloromethane), toluene, acetonitrile, and an alcohol-based solvent (for example, methanol, ethanol, and isopropyl alcohol). Further, the acid or dehydrating agent as a reacting material may be used as a solvent. It may be used alone or in combination of two or more kinds The reaction temperature for coupling reaction B may be selected from the temperature range of from −50° C. to 200° C., depending on the raw materials used, etc. The temperature range is preferably from −10° C. to 150° C., and more preferably 0° C. to 100° C.

The molar ratio between the substituted pyrrole compound represented by formula (V) and the substituted pyrrole compound represented by formula (IX) is, i.e., substituted pyrrole compound represented by formula (V): substituted pyrrole compound represented by formula (IX), is preferably 1:10 to 10:1, more preferably 1:3 to 3:1, still more preferably 1.2:1 to 1:1.2, and particularly preferably 1:1.

Further, the molar ratio of the compound represented by formula (XII) with respect to the total amount of the substituted pyrrole compounds represented by formula (V) and formula (IX), i.e., the total amount:the amount of the compound represented by formula (XII), is preferably from 1:0.1 to 1:2.5, more preferably from 1:0.3 to 1:1, and still more preferably from 1:0.5.

The substituted pyrrole compounds represented by formula (V) may be obtained by chemically converting the leaving group $X^{11}$ in the compound represented by the following formula (IV), and thereby forming the substituent group $G^4$ in the compound represented by formula (V).

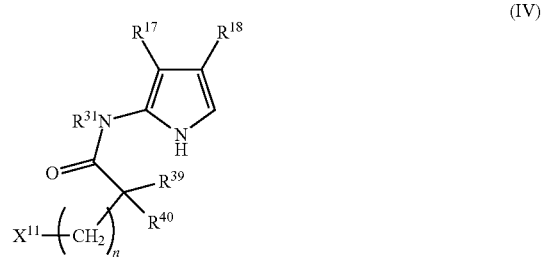

In formula (IV), $R^{31}$, $R^{32}$ and $R^{33}$ each have the same definitions as that of $R^{31}$, $R^{32}$, and $R^{33}$ of formula (1), respectively. $R^{39}$ and $R^{40}$ each independently represent an alkyl group, an alkenyl group, an aryl group, a heterocyclic group, each having two or more carbon atoms. $X^{11}$ represents a monovalent leaving group. n represents from 0 to 10.

(Amidation)

The substituted pyrrole compound represented by formula (IV) may be obtained by allowing the compound represented by the following formula (II) to react with an acid halide represented by the following formula (III) (hereinbelow, this reaction is referred to as "amidation").

In formula (II), $R^{31}$, $R^{32}$ and $R^{33}$ each have the same definitions as that of $R^{31}$, $R^{32}$, and $R^{33}$ of formula (1), respectively.

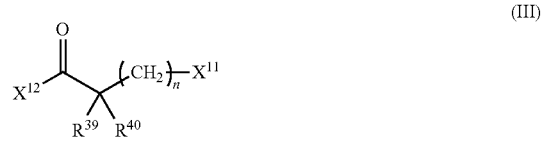

In formula (III), $R^{39}$, $R^{40}$, $X^{11}$ and n each have the same definitions as that of $R^{39}$, $R^{40}$, $X^{11}$ and n of formula (IV), respectively. $X^{12}$ represents a monovalent leaving group.

In formula (III), $X^{12}$ may be a chlorine atom, a bromine atom, an iodine atom, an alkylcarbonyloxy group having 2 to 6 carbon atoms, a cycloalkylcarbonyloxy group having 4 to 9 carbon atoms, an arylcarbonyloxy group having 7 to 12 carbon atoms, a hydroxyl group, an alkoxy group having 1 to 5 carbon atoms, or a triflate. From the viewpoint of production suitability, an alkylcarbonyloxy group having 2 to 6 carbon atoms, a chlorine atom, or a bromine atom is preferred, and a methylcarbonyloxy group or a chlorine atom is most preferred.

The amidation may be carried out by a method described in, for example, "The Fourth Edition, Experimental Chemistry Course 22, Organic Synthesis IV, pages 137 to 151".

In the amidation, as necessary, a base is preferably used. Specific examples of the base include triethylamine, diisopropylamine, diisopropylethylamine, and 1,8-diazabicyclo [5.4.0]undec-7-ene. The amount of the base is not specifically limited, but it is preferably in an amount of 0.01 to 5 equivalents, and more preferably in an amount of 0.1 to 3 equivalents, with respect to the acid halide represented by formula (III). The base may be used alone or in combination of two or more kinds.

The organic solvent used for amidation is not specifically limited, as long as the reaction is not impaired. Examples of suitable solvent include a halogen-based solvent (for example, dichloromethane) and acetonitrile. The organic solvent may be used alone or in combination of two or more kinds The reaction temperature for amidation may be selected from the temperature range of from −50° C. to 150° C., depending on the raw materials used, etc. The temperature range is preferably from −10° C. to 120° C., and more preferably 0° C. to 100° C.

The molar ratio between the substituted pyrrole compound represented by formula (II) and the acid halide represented by formula (III), i.e., the substituted pyrrole compound represented by formula (II): the acid halide represented by formula (III), is preferably 1:10 to 10:1, more preferably 1:3 to 3:1, still more preferably 1.2:1 to 1:1.2, and particularly preferably 1:1.

By using the thus obtained substituted pyrrole compound, the dipyrromethene metal complex compound, which is particularly preferred in the invention, may be prepared.

(Radical Polymerization)

By subjecting a dye monomer represented by the following formula (1) to radical polymerization, a dye multimer including a structural unit derived from the dye monomer represented by formula (1) may be synthesized (hereinbelow, this reaction is referred to as "radical polymerization").

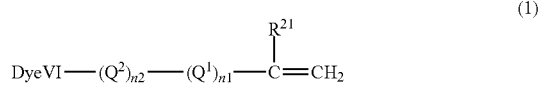

(1)

(In formula (1), $R^{21}$ represents a hydrogen atom, a halogen atom, an alkyl group, or an aryl group. $Q^1$ represents —N($R^2$)C(=O)—, —OC(=O)—, —C(=O)N($R^2$)—, —C(=O)O—, a group represented by the following formula (2), a group represented by the following formula (3), or a group represented by the following formula (4). $Q^2$ represents a divalent linking group. n1 and n2 each independently represent 0 or 1. Dye VI represents a linking group having a structure formed by removing two hydrogen atoms from the partial structure represented by formula (5), and Dye in formula (5) is a dye structure formed by removing any one or two hydrogen atoms from the dipyrromethene metal complex compound obtained from a dipyrromethene compound represented by formula (M) and a metal or a metal compound. $R^2$ represents a hydrogen atom, an alkyl group, an aryl group, or a heterocyclic group).

The radical polymerization may be carried out by a method described in, for example, "The Fourth Edition, Experimental Chemistry Course 28, Polymer Synthesis".

The radical polymerization is preferably carried out by using a radical polymerization initiator. Specific examples of the radical polymerization initiator include an azo initiator (for example, azoisobutyronitrile, dimethyl 2,2-azobisisobutyrate, and dimethyl 2,2'-azobis(2-methylpropionate)) and a peroxide initiator (for example, benzoyl peroxide and di-t-butyl peroxide).

The amount of the radical polymerization initiator is not specifically limited, but is preferably used in an amount of 0.01 to 0.5 equivalents, and more preferably in an amount of 0.03 to 0.3 equivalents, with respect to the dye monomer represented by formula (1). The radical polymerization initiator may be used alone or in combination of two or more kinds From the viewpoint of controlling the reaction, a chain transfer agent may be used in the radical polymerization. Specific examples of the chain transfer agent include thiols (for example, dodecane thiol and thiomalic acid), disulfides (for example, diphenyl disulfide), and carbon tetrachloride.

The amount of the chain transfer agent is not specifically limited. However, the chain transfer agent is used preferably in an amount of 0.01 to 0.5 equivalents, and more preferably in an amount of 0.03 to 0.3 equivalents, with respect to the dye monomer represented by formula (1). The chain transfer agent may be used alone or in combination of two or more kinds.

The organic solvent used for radical polymerization is not specifically limited, as long as the reaction is not impaired. Preferred examples of the solvent include propylene glycol methyl ether acetate (PGMEA), N-methylpyrrolidone (NMP), cyclohexanone, butyl acetate, a halogen-based solvent (for example, dichloromethane) and acetonitrile. The organic solvent may be used alone or in combination of two or more kinds The reaction temperature for radical polymerization may be selected from the temperature range of from 0° C. to 150° C., depending on the raw materials used, etc. The temperature range is preferably from 30° C. to 120° C., and more preferably 40° C. to 100° C.

In the radical polymerization, a monomer having a different structure from that of the dye monomer represented by formula (1) and a terminal ethylenically unsaturated bond may be used, in addition to the dye monomer represented by formula (1). Examples of the monomer having a different structure from that of the dye monomer represented by formula (1) and a terminal ethylenically unsaturated bond include the vinyl monomers described in the present specification, but it is not specifically limited.

The amount of the monomer having a structure different from that of the dye monomer represented by formula (1) and a terminal ethylenically unsaturated bond is not specifically limited, but it is used preferably in an amount of 0.1 to 10 equivalents, and more preferably in an amount of 0.2 to 5 equivalents, with respect to the dye monomer represented by formula (1). These monomers may be used alone or in combination of two or more kinds, respectively.

The polymerization may be carried out by a solution polymerization, a suspension polymerization, an emulsion polymerization or the like, but from the viewpoint of reaction control, a solution polymerization is preferable. Further, the polymerization may be carried out by a process in which raw materials except an initiator or a polymerization catalyst are mixed at once at an initial stage, and then polymerization is initiated by adding an initiator and a polymerization catalyst; or a process in which raw materials are dropped over plural hours; and a process in which part of raw materials are mixed in advance, and the remainder is added thereto by dropping.

(Polymerizable Group-Introduction)

A dye multimer having a polymerizable group may be synthesized by forming a multimer via homopolymerization of a dye monomer represented by formula (1), or copolymerization of the dye monomer represented by formula (1) and a monomer having a structure different from that of the dye monomer represented by formula (1) and a terminal ethylenically unsaturated bond, and then adding, to the multimer, a compound having a copolymerizable group and a group that can react with the multimer (hereinbelow, this reaction is referred to as a "polymerizable group-introduction").

The reaction for introducing a polymerizable group may be carried out by, for example, a process in which exemplary compound P51 having a carboxylic acid moiety and glycidyl methacrylate are allowed to react in the presence of a catalyst such as ammonium salt (hereinbelow, this reaction is referred to as a "GMA reaction"), or by a process in which the halogen group in the multimer is converted to a terminal ethylenically unsaturated bond by dehydrohalogenation.

(GMA Reaction)

The GMA reaction is preferably carried out with a catalyst. Specific examples of the catalyst include ammonium salts (for example, tetrabutyl ammonium bromide or tetrabutyl ammonium chloride), amines (for example, N,N-dimethyldodecylamine or diisopropylethylamine), phosphorus compounds (for example, triphenylphosphine), and betaines (for example, trimethyl glycine).

The amount of the catalyst such as an ammonium salt is not specifically limited. However, the catalyst is used preferably in an amount of 0.01 to 0.5 equivalents, and more preferably in an amount of 0.03 to 0.3 equivalents, with respect to the dye monomer represented by formula (1). The catalyst may be used alone or in combination of two or more kinds The organic solvent used for GMA reaction is not specifically limited, as long as the reaction is not impaired. Preferred examples of the solvent include propylene glycol methyl ether acetate, N-methylpyrrolidone, cyclohexanone, butyl acetate, a halogen-based solvent (for example, dichloromethane) and acetonitrile. The solvent may be used alone or in combination of two or more kinds The reaction temperature for GMA reaction may be selected from the temperature range of from 0° C. to 150° C., depending on the raw materials used, etc. The temperature range is preferably from 30° C. to 120° C., and more preferably 40° C. to 100° C.

The substituted pyrrole compound of the invention is a compound represented by the following formula (V) or (X).

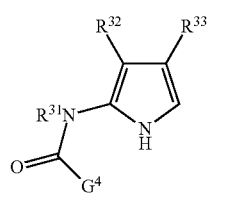

(V)

(In formula (V), $R^{32}$ and $R^{33}$ each independently represent a hydrogen atom or a monovalent substituent group. $R^{31}$ represents a hydrogen atom, an alkyl group, an alkenyl group, an aryl group, a heterocyclic group, an acyl group, an alkylsulfonyl group, or an arylsulfonyl group. $G^4$ represents a monovalent substituent group having a steric parameter (–Es' value) of 1.5 or more).

In formula (V), $R^{31}$, $R^{32}$, $R^{33}$ and $G^4$ each have the same definitions as that of $R^{31}$, $R^{32}$, $R^{33}$ and $G^4$ in formula (1), respectively, and the preferred embodiments are also the same.

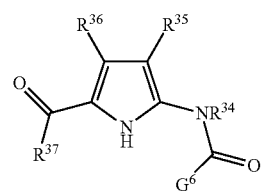

(X)

(In formula (X), $R^{35}$ and $R^{36}$ each independently represent a hydrogen atom or a monovalent substituent group. $R^{34}$ represents a hydrogen atom, an alkyl group, an alkenyl group, an aryl group, a heterocyclic group, an acyl group, an alkylsulfonyl group, or an arylsulfonyl group. $R^{37}$ represents a hydrogen atom, a halogen atom, an alkyl group, an aryl group, or a heterocyclic group. $G^6$ represents a monovalent substituent group having a steric parameter (–Es' value) of 1.5 or more).

In formula (X), $R^{34}$, $R^{35}$, $R^{36}$, $R^{37}$ and $G^6$ each have the same definitions as that of $R^{34}$, $R^{35}$, $R^{36}$, $R^{37}$ and $G^6$ in formula (1), respectively, and the preferred embodiments are also the same.

$G^4$ and $G^6$ each preferably have a steric parameter (–Es' value) of 2.0 or more, more preferably 3.0 or more, still more preferably 4.0 or more, and particularly preferably 5.0 or more.

Specific examples of the substituent group having a steric parameter (–Es' value) of 1.5 or more are described in Table 1 to Table 3, but the invention is not limited thereto.

(Specific Examples of Substituted Pyrrole Compound)

The following are specific examples of the substituted pyrrole compound of the invention, but the invention is not limited thereto.

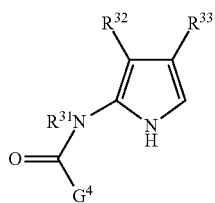
| Exemplary Compound | G⁴ | R³¹ | R³² | R³³ |
|---|---|---|---|---|
| N-1 | C(Et)₃ | H | 2,6-di-t-Bu-4-methylcyclohexyl-O-C(=O)- | i-Pr |
| N-2 | C(Et)₃ | H | 2,6-di-t-Bu-4-methylcyclohexyl-O-C(=O)- | —Ph |
| N-3 | C(Et)₃ | H | 2,6-di-t-Bu-4-methylcyclohexyl-O-C(=O)- | —Me |
| N-4 | C(Et)₃ | H | 2,6-di-t-Bu-4-methylcyclohexyl-O-C(=O)- | —Et |
| N-5 | C(Et)₃ | H | 2,6-di-t-Bu-4-methylcyclohexyl-O-C(=O)- | —Bu |
| N-6 | C(Et)₃ | H | EtO-C(=O)- | i-Pr |
| N-7 | C(Et)₃ | H | EtO-C(=O)- | —Ph |
| N-8 | C(Et)₃ | H | EtO-C(=O)- | —Me |
| N-9 | C(Et)₃ | H | —CN | —Me |

-continued
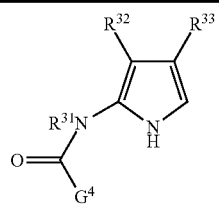
| Exemplary Compound | G⁴ | R³¹ | R³² | R³³ |
|---|---|---|---|---|
| N-10 | C(Et)₃ | H | -C(O)NH-Ph | —Me |
| N-11 | -CH₂-t-Bu | H | -C(O)O-(2,6-di-t-Bu-4-Me-cyclohexyl) | -i-Pr (isobutyl) |
| N-12 | -CH₂-t-Bu | H | -C(O)O-(2,6-di-t-Bu-4-Me-cyclohexyl) | 2,4,5-trimethylphenyl |
| N-13 | -CH₂-t-Bu | H | -C(O)O-(2,6-di-t-Bu-4-Me-cyclohexyl) | —Ph |
| N-14 | -CH(Et)(Bu) | H | -C(O)O-(2,6-di-t-Bu-4-Me-cyclohexyl) | isobutyl |
| N-15 | -CH(Et)(Bu) | H | -C(O)O-(2,6-di-t-Bu-4-Me-cyclohexyl) | —Bu |
| N-16 | -CH(Et)(Bu) | H | -C(O)O-(2,6-di-t-Bu-4-Me-cyclohexyl) | —Et |
| N-17 | -CH(Et)(Bu) | H | -C(O)O-(2,6-di-t-Bu-4-Me-cyclohexyl) | isobutyl |

-continued

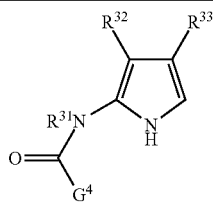

| Exemplary Compound | G⁴ | R³¹ | R³² | R³³ |
|---|---|---|---|---|
| N-18 | CH(Et)(Bu) | H | C(=O)O-(2,2,6,6-tetramethyl-4-methylcyclohexyl) | -iPr |
| N-19 | CH(Et)(Bu) | H | C(=O)O-(2-t-Bu-4,6-dimethylcyclohexyl) | —Ph |
| N-20 | 2,4,6-trimethylheptan-4-yl | H | C(=O)O-(2,6-di-t-Bu-4-methylcyclohexyl) | -iPr |
| N-21 | 2,4,6-trimethylheptan-4-yl | H | C(=O)O-(2,6-di-t-Bu-4-methylcyclohexyl) | —Ph |
| N-22 | 2,4,6-trimethylheptan-4-yl | H | C(=O)O—Et | —Ph |
| N-23 | CH(t-Bu)(iBu) | H | C(=O)O-(2,6-di-t-Bu-4-methylcyclohexyl) | -iPr |
| N-24 | CH(t-Bu)(iBu) | H | —CN | —Me |
| N-25 | CH(t-Bu)(iBu) | H | C(=O)NH₂ | —Me |

-continued

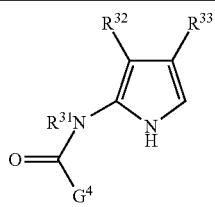

| Exemplary Compound | G⁴ | R³¹ | R³² | R³³ |
|---|---|---|---|---|
| N-26 | (2,3-dimethylbutyl group) | H | (3,5-di-t-Bu-cyclohexyloxycarbonyl) | i-Pr |
| N-27 | (2,2,3-trimethylbutyl/neopentyl-isopropyl group) | H | (3,5-di-t-Bu-cyclohexyloxycarbonyl) | i-Pr |
| N-28 | (tolyl/phenyl-CH₂) | H | (3,5-di-t-Bu-cyclohexyloxycarbonyl) | i-Pr |
| N-29 | (2-methylphenyl-CH₂) | H | (3,5-di-t-Bu-cyclohexyloxycarbonyl) | i-Pr |
| N-30 | (2-phenylphenyl-CH₂) | H | (3,5-di-t-Bu-cyclohexyloxycarbonyl) | i-Pr |
| N-31 | CHPh₃ | H | (3,5-di-t-Bu-cyclohexyloxycarbonyl) | i-Pr |
| N-32 | (2,2-bis(methoxymethyl)propyl) | H | (3,5-di-t-Bu-cyclohexyloxycarbonyl) | i-Pr |

-continued

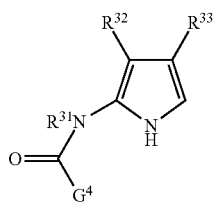

| Exemplary Compound | G⁴ | R³¹ | R³² | R³³ |
|---|---|---|---|---|
| N-33 | HOCH₂-C(Me)-CH₂OH (2-methyl-2-(hydroxymethyl)propane-1,3-diol type) | H | 2,6-di-t-Bu-cyclohexyl ester (acetoxy) | i-Pr |
| N-34 | Et₂(Me)C- | H | 2,6-di-t-Bu-cyclohexyl ester (acetoxy) | i-Pr |
| N-35 | —Ad | H | 2,6-di-t-Bu-cyclohexyl ester (acetoxy) | i-Pr |
| N-36 | Et₃C- | H | 3,5-di-t-Bu-4-acetoxy-cyclohexyl-CH₂-S-CH(COOH)₂ | i-Pr |
| N-37 | Et₃C- | H | 3,5-di-t-Bu-4-acetoxy-cyclohexyl-CH₂-O-C(=O)-C(Me)=CH₂ | i-Pr |
| N-38 | MeOCH₂CH₂-O-CH₂-C(Me)-CH₂-O-CH₂CH₂OMe | H | 2,6-di-t-Bu-cyclohexyl ester (acetoxy) | Ph |
| N-39 | Et₂C(Me)-CH₂CH₂-O-CH₂-OMe | H | 2,6-di-t-Bu-cyclohexyl ester (acetoxy) | i-Pr |

-continued
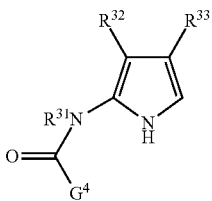
| Exemplary Compound | G⁴ | R³¹ | R³² | R³³ |
|---|---|---|---|---|
| N-40 | 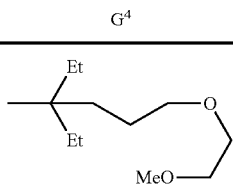 | H | 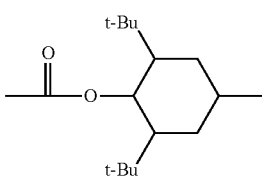 | <img/> |
| N-41 | 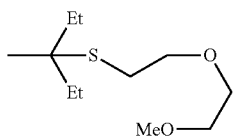 | H | 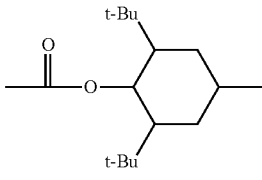 | <img/> |
| N-42 | 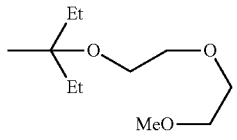 | H | 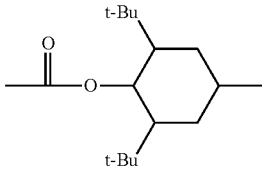 | <img/> |
| N-43 | 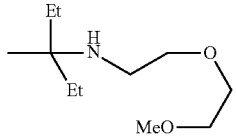 | H | 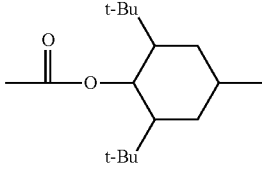 | <img/> |
| N-44 | 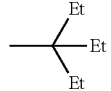 | Me | 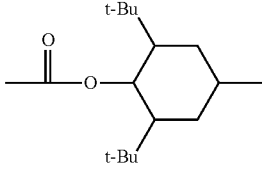 | <img/> |
| N-45 | 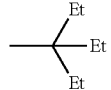 | Me | 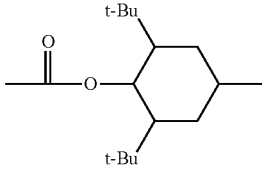 | —Ph |
| N-46 | 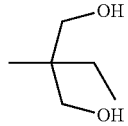 | Me | <img/> | —Ph |

-continued

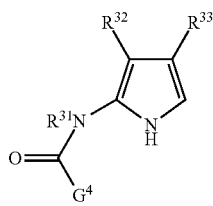

| Exemplary Compound | G⁴ | R³¹ | R³² | R³³ |
|---|---|---|---|---|
| N-47 | 2,3-dimethylphenyl | Me | 2,6-di-t-Bu-4-methylcyclohexyl-O-C(O)- | —Ph |
| N-48 | —C(Et)₃ | Et | 2,6-di-t-Bu-4-methylcyclohexyl-O-C(O)- | i-Pr |
| N-49 | —C(Et)₃ | i-Pr | 2,6-di-t-Bu-4-methylcyclohexyl-O-C(O)- | i-Pr |
| N-50 | —C(Et)₃ | —Ph | 2,6-di-t-Bu-4-methylcyclohexyl-O-C(O)- | i-Pr |
| N-51 | —C(CH₂OCH₂COOH)₂(CH₃) | H | 2,6-di-t-Bu-4-methylcyclohexyl-O-C(O)- | i-Pr |
| N-52 | —C(Et)₂CH₂CH₂CH₂-S-CH(COOH)CH₂COOH | H | 2,6-di-t-Bu-4-methylcyclohexyl-O-C(O)- | i-Pr |
| N-53 | —C(Et)₂CH₂CH₂CH₂-S-CH₂COOH | H | 2,6-di-t-Bu-4-methylcyclohexyl-O-C(O)- | —Me |

-continued

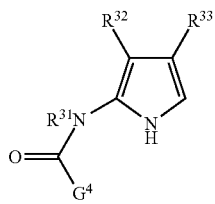

| Exemplary Compound | G⁴ | R³¹ | R³² | R³³ |
|---|---|---|---|---|
| N-54 | Et₂C(Et)CH₂CH₂CH₂-O-CH(COOH)CH₂COOH | H | 2,6-di-t-Bu-cyclohexyl ester (4-Me) | —Et |
| N-55 | (Et)(Et)(Me)C-S-CH(COOH)CH₂COOH | H | 2,6-di-t-Bu-cyclohexyl ester (4-Me) | —Ph |
| N-56 | (Et)(Et)(Me)C-S-CH₂CH₂-S-CH(COOH)CH₂COOH | H | 2,6-di-t-Bu-cyclohexyl ester (4-Me) | —iPr |
| N-57 | Et₂C(Et)CH₂CH₂CH₂-S-CH₂CH(COOH)CH₂COOH | H | 2,6-di-t-Bu-cyclohexyl ester (4-Me) | —iPr |
| N-58 | Me₂C(Me)CH₂-O-CH₂CH₂CH₂-OMe | H | —C(=O)-O-Et | —Me |
| N-59 | Me₂C(Me)CH₂CH₂CH₂-S-CH(COOH)CH₂COOH | H | —CN | —Me |
| N-60 | (iPr)(Me)CH-CH(Me)CH₂CH₂-S-CH(COOH)COOH | H | —C(=O)-NH-Ph | —Me |

-continued

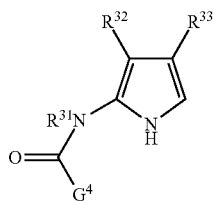

| Exemplary Compound | G⁴ | R³¹ | R³² | R³³ |
|---|---|---|---|---|
| N-61 | Et₂C(Et)CH₂CH₂OC(O)C(=CH₂)CH₃ | H | 2,6-di-t-Bu-4-methylcyclohexyl-OC(O)– | i-Bu |
| N-62 | 3,5-di(COOH)phenyl-O-CH₂CH₂C(Et)₂ | H | 2,6-di-t-Bu-4-methylcyclohexyl-OC(O)– | 2,4,6-trimethylphenyl |
| N-63 | (Et)₂C(CH₃)CH₂COOH | H | 3,5-di-t-Bu-4-(OC(O)–)-cyclohexylmethyl-O-CH₂CH₂CH₂-OMe | —Ph |
| N-64 | Et₂C(S–CH₂CH₂-OC(O)C(=CH₂)CH₃) | H | 2,6-di-t-Bu-4-methylcyclohexyl-OC(O)– | i-Bu |
| N-65 | Et₂C(O–CH₂CH₂-OC(O)C(=CH₂)CH₃) | H | 2,6-di-t-Bu-4-methylcyclohexyl-OC(O)– | i-Bu |
| N-66 | CH₂=CH– | H | 2,6-di-t-Bu-4-methylcyclohexyl-OC(O)– | i-Bu |

-continued

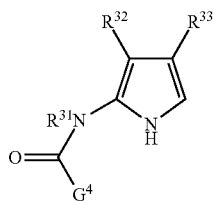

| Exemplary Compound | G⁴ | R³¹ | R³² | R³³ |
|---|---|---|---|---|
| N-67 | isopropenyl | H | 2,6-di-t-Bu-4-methylcyclohexyl ester | i-Pr |
| N-68 | -C(Et)₂-CH₂CH₂-O-C(O)-CH=CH₂ | H | 2,6-di-t-Bu-4-methylcyclohexyl ester | i-Pr |
| N-69 | -C(Me)₂-S-CH₂CH₂-O-C(O)-C(Me)=CH₂ | H | 2,6-di-t-Bu-4-methylcyclohexyl ester | —Ph |
| N-70 | -C(Me)₂-CH₂-S-CH₂CH₂-S-CH(COOH)-CH₂-COOH | H | 2,6-di-t-Bu-4-methylcyclohexyl ester | i-Pr |
| N-71 | -C(Me)₂-CH₂-S-CH₂CH₂-O-C(O)-C(Me)=CH₂ | H | 2,6-di-t-Bu-4-methylcyclohexyl ester | i-Pr |
| N-72 | -C(Me)₂-CH₂CH₂CH₂-O-C(O)-C(Me)=CH₂ | Me | 2,6-di-t-Bu-4-methylcyclohexyl ester | i-Pr |

-continued
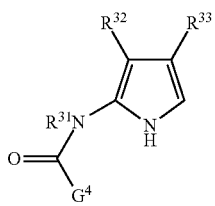
| Exemplary Compound | G⁴ | R³¹ | R³² | R³³ |
|---|---|---|---|---|
| N-73 |  |  | 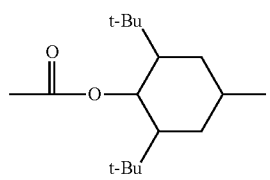 |  |
| N-74 |  | 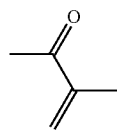 | 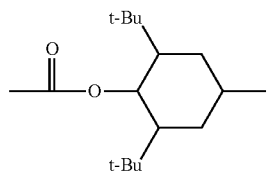 |  |
| N-75 | 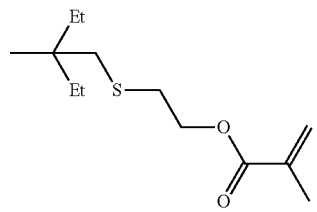 | H | 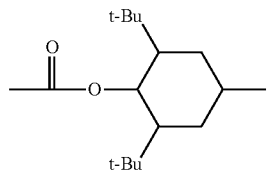 |  |
| N-76 | 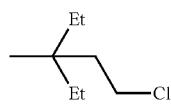 | H | 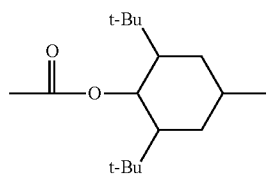 |  |
| N-77 | 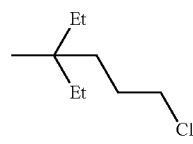 | H | 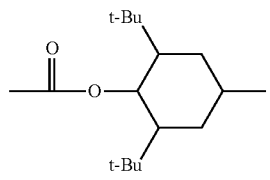 |  |
| N-78 | 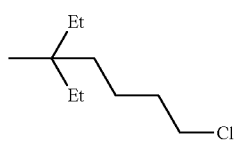 | H | 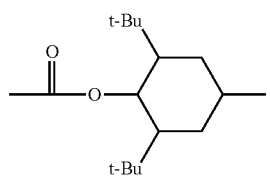 |  |

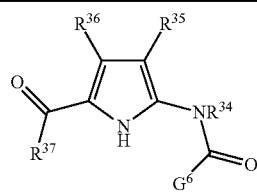
| Exemplary Compound | G⁶ | R³⁴ | R³⁵ | R³⁶ | R³⁶ |
|---|---|---|---|---|---|
| 0-1 | C(Et)(Et)(Et) | H | 2,6-di-t-Bu-4-Me-cyclohexyl ester (—C(=O)O-cyclohexyl) | i-Pr | H |
| 0-2 | C(Et)(Et)(Et) | H | 2,6-di-t-Bu-4-Me-cyclohexyl ester | —Ph | H |
| 0-3 | C(Et)(Et)(Et) | H | 2,6-di-t-Bu-4-Me-cyclohexyl ester | —Me | H |
| 0-4 | C(Et)(Et)(Et) | H | 2,6-di-t-Bu-4-Me-cyclohexyl ester | —Et | H |
| 0-5 | C(Et)(Et)(Et) | H | 2,6-di-t-Bu-4-Me-cyclohexyl ester | —Bu | H |
| 0-6 | C(Et)(Et)(Et) | H | —C(=O)O—Et | i-Pr | H |
| 0-7 | C(Et)(Et)(Et) | H | —C(=O)O—Et | —Ph | H |
| 0-8 | C(Et)(Et)(Et) | H | —C(=O)O—Et | —Me | H |
| 0-9 | C(Et)(Et)(Et) | H | —CN | —Me | H |

-continued
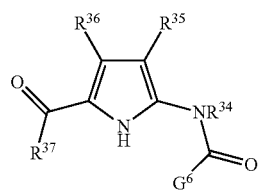
| | $G^6$ | $R^{34}$ | $R^{35}$ | $R^{36}$ | $R^{37}$ |
|---|---|---|---|---|---|
| 0-10 | C(Et)(Et)Et | H | CH₂C(O)NHPh | —Me | H |
| 0-11 | CH(t-Bu)CH₃ | H | 2,6-di-t-Bu-4-Me-cyclohexyl ester | i-Pr | H |
| 0-12 | CH(t-Bu)CH₃ | H | 2,6-di-t-Bu-4-Me-cyclohexyl ester | 2,4,6-trimethylphenyl | H |
| 0-13 | CH(t-Bu)CH₃ | H | 2,6-di-t-Bu-4-Me-cyclohexyl ester | —Ph | H |
| Exemplary Compound | $G^6$ | $R^{34}$ | $R^{35}$ | $R^{36}$ | $R^{37}$ |
|---|---|---|---|---|---|
| 0-14 | CH(Et)Bu | H | 2,6-di-t-Bu-4-Me-cyclohexyl ester | i-Bu | H |
| 0-15 | CH(Et)Bu | H | 2,6-di-t-Bu-4-Me-cyclohexyl ester | —Bu | H |
| 0-16 | CH(Et)Bu | H | 2,6-di-t-Bu-4-Me-cyclohexyl ester | —Et | H |

-continued
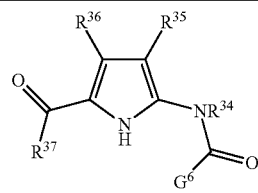
| | R36 | R35 | | | |
|---|---|---|---|---|---|
| 0-17 | 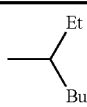 Et / Bu | H | 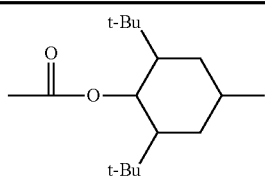 t-Bu / t-Bu (ester on cyclohexyl) |  | H |
| 0-18 | 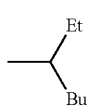 Et / Bu | H | 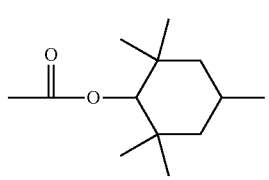 | 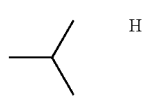 | H |
| 0-19 | 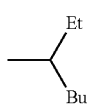 Et / Bu | H | 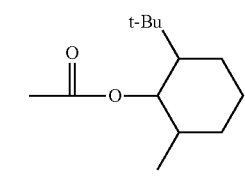 t-Bu | —Ph | H |
| 0-20 | 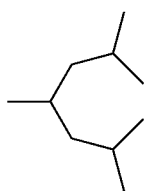 | H | 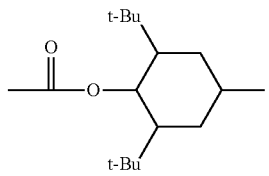 t-Bu / t-Bu | 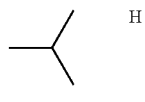 | H |
| 0-21 | 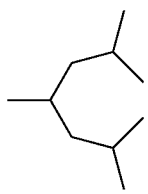 | H | 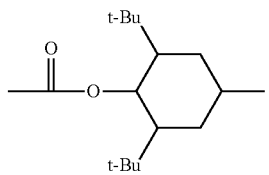 t-Bu / t-Bu | —Ph | H |
| 0-22 | 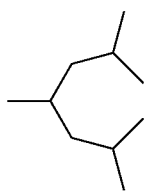 | H | 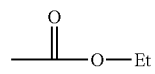 O—Et | —Ph | H |
| 0-23 | 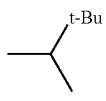 t-Bu | H | 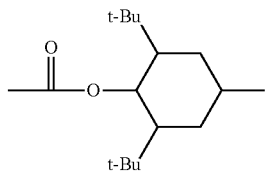 t-Bu / t-Bu | 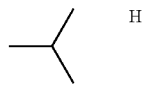 | H |
| 0-24 | 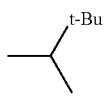 t-Bu | H | —CN | —Me | H |

-continued

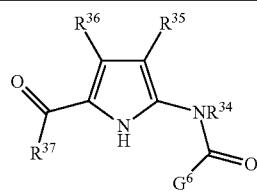

| No. | R37 | R36 | C(O)G6 | R34 | R35 |
|---|---|---|---|---|---|
| O-25 | t-Bu / isobutyl | H | —C(O)—NH$_2$ | —Me | H |
| O-26 | 2,3-dimethylbutyl | H | 2,6-di-t-Bu-4-methylcyclohexyl ester | isopropyl | H |
| O-27 | 2,2,3-trimethyl-3-isopropyl | H | 2,6-di-t-Bu-4-methylcyclohexyl ester | isopropyl | H |
| O-28 | phenyl (o-Me) | H | 2,6-di-t-Bu-4-methylcyclohexyl ester | isopropyl | H |
| O-29 | 2,3-dimethylphenyl | H | 2,6-di-t-Bu-4-methylcyclohexyl ester | isopropyl | H |
| O-30 | 2-biphenyl (o-Me) | H | 2,6-di-t-Bu-4-methylcyclohexyl ester | isopropyl | H |
| O-31 | CHPh$_3$ | H | 2,6-di-t-Bu-4-methylcyclohexyl ester | isopropyl | H |
| O-32 | CH(CH$_2$OMe)$_2$-Me | H | 2,6-di-t-Bu-4-methylcyclohexyl ester | isopropyl | H |

-continued
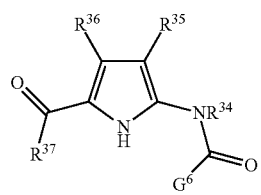
| | | | | | |
|---|---|---|---|---|---|
| 0-33 | 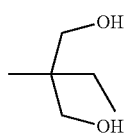 | H | 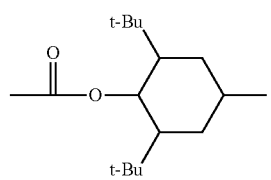 | | H |
| 0-34 | 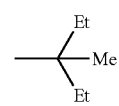 | H | 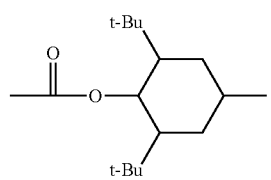 | | H |
| 0-35 | —Ad | H | 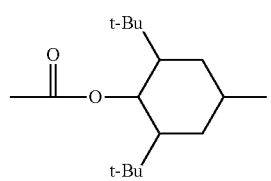 | | H |
| 0-36 | 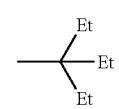 | H | 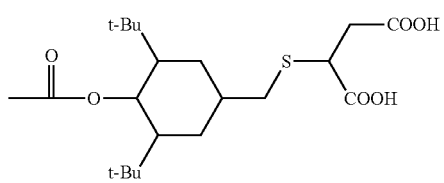 | | H |
| 0-37 | 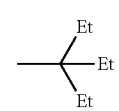 | H | 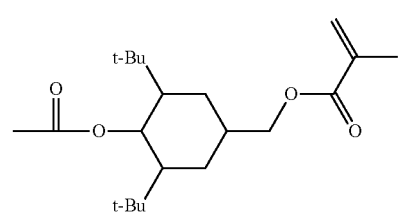 | | H |
| 0-38 | 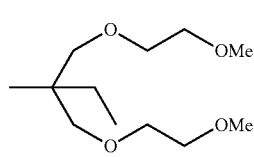 | H | 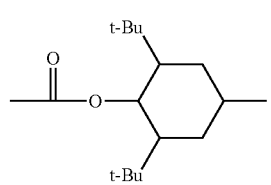 | 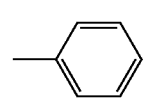 | H |
| 0-39 | 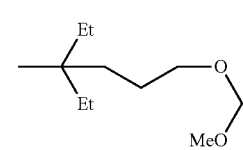 | H | 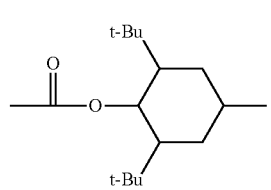 | 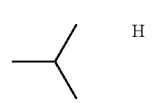 | H |

-continued

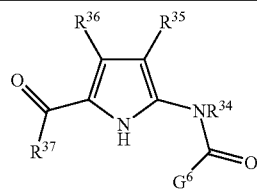

| | R37 | R36 | R35 | G6 | R34 |
|---|---|---|---|---|---|
| O-40 | Et₂C(Me)CH₂CH₂OCH₂CH₂OMe | H | | 2,6-di-t-Bu-4-Me-cyclohexyl-O-C(O)- | i-Pr | H |
| O-41 | Et₂C(Me)SCH₂CH₂OMe | H | | 2,6-di-t-Bu-4-Me-cyclohexyl-O-C(O)- | i-Pr | H |
| O-42 | Et₂C(Me)OCH₂CH₂OMe | H | | 2,6-di-t-Bu-4-Me-cyclohexyl-O-C(O)- | i-Pr | H |
| O-43 | Et₂C(Me)NHCH₂CH₂OMe | H | | 2,6-di-t-Bu-4-Me-cyclohexyl-O-C(O)- | i-Pr | H |
| O-44 | Et₃C | Me | | 2,6-di-t-Bu-4-Me-cyclohexyl-O-C(O)- | i-Pr | H |
| O-45 | Et₃C | Me | | 2,6-di-t-Bu-4-Me-cyclohexyl-O-C(O)- | —Ph | H |
| O-46 | (HOCH₂)₂C(Me)- | Me | | 2,6-di-t-Bu-4-Me-cyclohexyl-O-C(O)- | —Ph | H |
| O-47 | 2-Me-phenyl | Me | | 2,6-di-t-Bu-4-Me-cyclohexyl-O-C(O)- | —Ph | H |

-continued
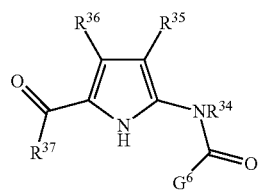
| Exemplary Compound | G⁶ | R³⁴ | R³⁵ | R³⁶ | R³⁷ |
|---|---|---|---|---|---|
| 0-48 | 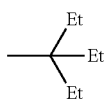 | Et | 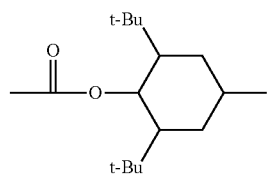 |  | H |
| 0-49 | 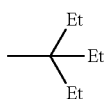 |  | 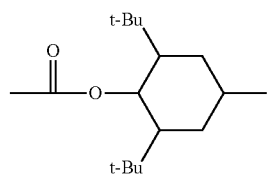 |  | H |
| 0-50 | 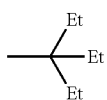 | —Ph | 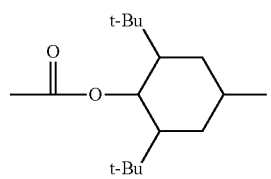 |  | H |
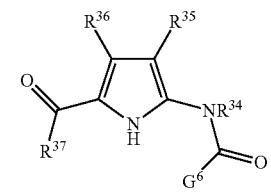
| Exemplary Compound | G⁶ | R³⁴ | R³⁵ | R³⁶ | R³⁷ |
|---|---|---|---|---|---|
| 0-51 | 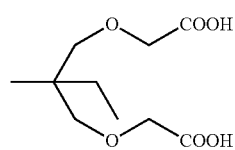 | H | 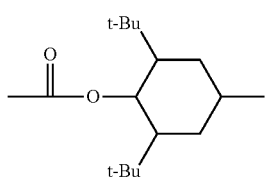 | 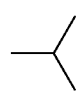 | H |
| 0-52 | 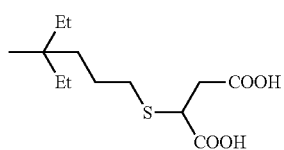 | H | 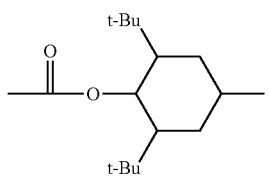 | 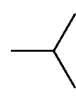 | H |

-continued

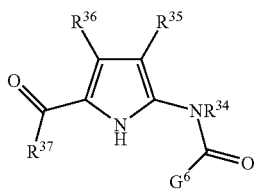

| Exemplary Compound | G⁶ | R³⁴ | R³⁵ | R³⁶ | R³⁷ |
|---|---|---|---|---|---|
| 0-53 | Et₂C(Et)CH₂CH₂CH₂-S-CH₂COOH | H | 2,6-di-t-Bu-4-Me-cyclohexyl-O-C(=O)- | —Me | H |
| 0-54 | Et₂C(Et)CH₂CH₂CH₂-O-CH(COOH)COOH | H | 2,6-di-t-Bu-4-Me-cyclohexyl-O-C(=O)- | —Et | H |
| 0-55 | Et₃C-S-CH(COOH)CH₂COOH | H | 2,6-di-t-Bu-4-Me-cyclohexyl-O-C(=O)- | —Ph | H |
| 0-56 | Et₃C-S-CH₂CH₂-S-CH(COOH)CH₂COOH (shown as Et₂C(Et)CH₂CH₂-S-CH(COOH)COOH) | H | 2,6-di-t-Bu-4-Me-cyclohexyl-O-C(=O)- | i-Pr | H |
| 0-57 | Et₂C(Et)CH₂CH₂CH₂-S-CH₂CH(COOH)CH₂COOH | H | 2,6-di-t-Bu-4-Me-cyclohexyl-O-C(=O)- | i-Pr | H |
| 0-58 | Me₂C(Me)CH₂-O-CH₂CH₂CH₂-OMe | H | EtO-C(=O)- | —Me | H |
| 0-59 | Me₂C(Me)CH₂CH₂CH₂-S-CH(COOH)COOH | H | —CN | —Me | H |

-continued

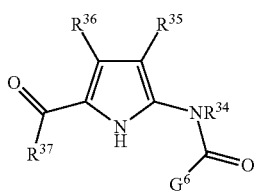

| Exemplary Compound | G⁶ | R³⁴ | R³⁵ | R³⁶ | R³⁷ |
|---|---|---|---|---|---|
| O-60 | (isobutyl-methyl-CH-CH(CH₃)-CH₂-CH₂-S-CH(COOH)-CH₂-COOH) | H | -C(=O)-NH-Ph | —Me | H |
| O-61 | Et₂C(Me)-CH₂-CH₂-CH₂-O-C(=O)-C(Me)=CH₂ | H | -C(=O)-O-(2,6-di-t-Bu-4-Me-cyclohexyl) | i-Pr | H |
| O-62 | Et₂C(Me)-CH₂-CH₂-CH₂-O-(3,5-di-COOH-phenyl) | H | -C(=O)-O-(2,6-di-t-Bu-4-Me-cyclohexyl) | 2-Me-phenyl | H |
| O-63 | Et₂C(Me)-CH₂-CH₂-COOH | H | -C(=O)-O-(2,6-di-t-Bu-4-(CH₂OCH₂CH₂OMe)-cyclohexyl) | —Ph | H |
| O-64 | Et₂C(Me)-S-CH₂-CH₂-O-C(=O)-C(Me)=CH₂ | H | -C(=O)-O-(2,6-di-t-Bu-4-Me-cyclohexyl) | i-Pr | H |
| O-65 | Et₂C(Me)-O-CH₂-CH₂-O-C(=O)-C(Me)=CH₂ | H | -C(=O)-O-(2,6-di-t-Bu-4-Me-cyclohexyl) | i-Pr | H |

-continued

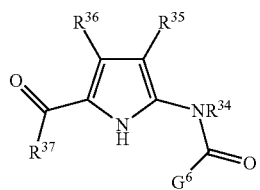

| Exemplary Compound | G⁶ | R³⁴ | R³⁵ | R³⁶ | R³⁷ |
|---|---|---|---|---|---|
| O-66 | allyl | H | menthyl ester with 2,6-di-t-Bu, 4-Me | isopropyl | H |
| O-67 | isopropenyl | H | menthyl ester with 2,6-di-t-Bu, 4-Me | isopropyl | H |
| O-68 | 4,4-diethyl acrylate ester chain | H | menthyl ester with 2,6-di-t-Bu, 4-Me | isopropyl | H |
| O-69 | Me₂C(S-CH₂CH₂-O-C(=O)-C(Me)=CH₂) | H | menthyl ester with 2,6-di-t-Bu, 4-Me | —Ph | H |
| O-70 | Me₂C-CH₂-S-CH(COOH)CH₂COOH | H | menthyl ester with 2,6-di-t-Bu, 4-Me | isopropyl | H |
| O-71 | Me₂C-CH₂-S-CH₂CH₂-O-C(=O)-C(Me)=CH₂ | H | menthyl ester with 2,6-di-t-Bu, 4-Me | isopropyl | H |

-continued

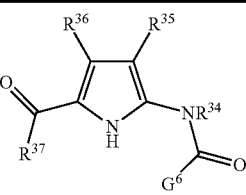

| Exemplary Compound | G⁶ | R³⁴ | R³⁵ | R³⁶ | R³⁷ |
|---|---|---|---|---|---|
| 0-72 | Me₂C(CH₂)₃OC(O)C(Me)=CH₂ | Me | 2,6-di-t-Bu-4-Me-cyclohexyl-O-C(O)- | i-Pr | H |
| 0-73 | isobutenyl | i-Pr | 2,6-di-t-Bu-4-Me-cyclohexyl-O-C(O)- | i-Pr | H |
| 0-74 | isobutenyl | methacryloyl | 2,6-di-t-Bu-4-Me-cyclohexyl-O-C(O)- | i-Pr | H |
| 0-75 | Me₂C(CH₂)₃OC(O)C(Me)=CH₂ | Me | 2,6-di-t-Bu-4-Me-cyclohexyl-O-C(O)- | i-Pr | H |
| 0-76 | Et₃C- | H | 2,6-di-t-Bu-4-Me-cyclohexyl-O-C(O)- | i-Pr | Me |
| 0-77 | Et₃C- | H | 2,6-di-t-Bu-4-Me-cyclohexyl-O-C(O)- | —Ph | Me |
| 0-78 | Et₃C- | H | 2,6-di-t-Bu-4-Me-cyclohexyl-O-C(O)- | i-Pr | CF₃ |

-continued
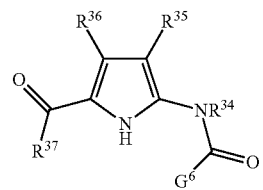
| Exemplary Compound | G⁶ | R³⁴ | R³⁵ | R³⁶ | R³⁷ |
|---|---|---|---|---|---|
| O-79 | C(Et)(Et)Et | H | 2,6-di-t-Bu-4-Me-cyclohexyl-O-C(=O)- | —Ph | CF₃ |
| O-80 | C(Et)(Et)Et | H | 2,6-di-t-Bu-4-Me-cyclohexyl-O-C(=O)- | —Ph | Ph |
| O-81 | C(Et)(Et)Et | H | 2,6-di-t-Bu-4-Me-cyclohexyl-O-C(=O)- | —Ph | 2-pyridyl |
| O-82 | C(Et)(Et)Et | H | 2,6-di-t-Bu-4-Me-cyclohexyl-O-C(=O)- | —Me | 2-naphthyl |
| O-83 | C(Et)(Et)Et | H | 2,6-di-t-Bu-4-Me-cyclohexyl-O-C(=O)- | —Me | Cl |
| O-84 | C(Et)(Et)Et | H | 2,6-di-t-Bu-4-Me-cyclohexyl-O-C(=O)- | —Me | Br |
| O-85 | C(Et)(Et)Et | H | 2,6-di-t-Bu-4-Me-cyclohexyl-O-C(=O)- | —Me | Cl |

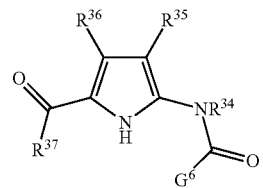

| Exemplary Compound | $G^6$ | $R^{34}$ | $R^{35}$ | $R^{36}$ | $R^{37}$ |
|---|---|---|---|---|---|
| 0-86 | Et₃C— | H | 2,6-di-t-Bu-4-Me-phenyl ester | i-Pr | —O—CH₂—C(=O)—O—CH₂Ph |
| 0-87 | Et₃C— | H | —C(=O)—NH—Ph | —Me | Me |
| 0-88 | i-Bu(Et)CH— | Me | —CN | —Ph | Me |

<<Colored Curable Composition>>

The colored curable composition of the invention includes at least one kind of a dye compound described above as a colorant, and a polymerizable compound. The colored curable composition of the invention cures with heat, light or a combination thereof, and may include other components as necessary, such as a photopolymerization initiator, a solvent, or a binder.

The colored curable composition of the invention forms a pixel pattern in the form of a thin film (for example, with a thickness of 1 μm or less) due to the characteristics of the dye compound having a specific structure. Accordingly, the colored curable composition of the invention is particularly suitable for producing a color filter for solid-state image sensors that require a high precision of a size of 2 μm or less (for example, a pixel pattern having a side length of 0.5 to 2.0 μm when viewed in a normal direction against the substrate) and a favorable rectangular cross-section profile.

In the colored curable composition of the invention, the dye compound may be used alone or in a combination of two or more kinds The content of the dye compound in the colored curable composition of the invention is, although it varies according to the molecular weight and the molar absorption coefficient of the dye compound, preferably from 10 to 70% by mass, more preferably from 10 to 50% by mass, and most preferably from 10 to 30% by mass, with respect to the total solid content of the colored curable composition.

In the present specification, the total solid content refers to the total content of the components of the colored curable composition, except a solvent.

The colored curable composition of the invention, and a color filter formed from the colored curable composition, may include a colorant other than the dye compound of the invention as long as the effect of the invention is not impaired. Examples include triaryl methane dyes having a maximum absorption in 550 nm to 650 nm (for example, C.I. Acid Blue 7, C.I. Acid Blue 83, C.I. Acid Blue 90, C.I. Solvent Blue 38, C.I. Acid Violet 17, C.I. Acid Violet 49 and C.I. Acid Green 3), xanthene dyes having a maximum absorption in 500 nm to 600 nm (for example, C.I. Acid Red 289).

The content of the triaryl methane dye may be determined within a range in which the effect of the invention is not impaired, and preferably from 0.5 to 50% by mass with respect to the total solid content of the colored curable composition of the invention.

When a blue filter array is produced, it is preferred to use at least one kind of the dye compound of the invention and a phthalocyanine pigment in combination.

(Phthalocyanine Pigment)

The phthalocyanine pigment that can be used in the invention is not particularly limited as long as it is a pigment having a phthalocyanine skeleton. The central metal included in the phthalocyanine pigment is not particularly limited as long as it is metal that can constitute a phthalocyanine skeleton. Among these metals that can be used as the central metal, magnesium, titanium, iron, cobalt, nickel, copper, zinc or aluminum is preferably used.

Specific examples of the phthalocyanine pigment include C.I. Pigment Blue 15, C.I. Pigment Blue 15:1, C.I. Pigment Blue 15:2, C.I. Pigment Blue 15:3, C.I. Pigment Blue 15:4, C.I. Pigment Blue 15:5, C.I. Pigment Blue 15:6, C.I. Pigment Blue 16, C.I. Pigment Blue 17:1, C.I. Pigment Blue 75, C.I. Pigment Blue 79, C.I. Pigment Green 7, C.I. Pigment Green 36, C.I. Pigment Green 37, C.I. Pigment Green 58, chloroaluminum phthalocyanine, hydroxyaluminum phthalocyanine, aluminum phthalocyanine oxide, and zinc phthalocyanine Among these, from the viewpoint of light fastness and coloring power, C.I. Pigment Blue 15, C.I. Pigment Blue 15:6, C.I. Pigment Blue 15:1 and C.I. Pigment Blue 15:2 are preferred, and C.I. Pigment Blue 15:6 is more preferred.

The content of the phthalocyanine pigment in the colored curable composition of the invention with respect to the total solid content of the composition is preferably from 10 to 70% by mass, more preferably from 20 to 60% by mass, and most preferably from 35 to 50% by mass.

The content ratio of the dye compound of the invention to the phthalocyanine pigment is, for example, in the case of phthalocyanine pigment:dipyrromethene metal complex compound, it is preferably from 100:5 to 100:100, more preferably from 100:15 to 100:75, further preferably from 100:25 to 100:50, on the mass basis.

(Dispersant)

When the colored curable composition of the invention includes a pigment, a dispersant may be included therein.

Examples of the pigment dispersant that can be used in the invention include polymer dispersants (such as polyamide amine and a salt thereof, polycarboxylic acid and a salt thereof, high molecular weight unsaturated acid ester, modified polyurethane, modified polyester, modified poly(meth)acrylate, (meth)acrylic copolymer, naphthalene sulfonic acid formalin condensate), surfactants such as polyoxyethylene alkyl phosphoric acid ester, polyoxyethylene alkyl amine and alkanol amine, and pigment derivatives.

The polymer dispersants may be classified into linear polymer, terminal-modified polymer, graft polymer and block polymer, in terms of the structure.

Examples of the terminal-modified polymer having an anchoring site to the pigment surface include polymers having a phosphoric acid group at a terminal, such as those described in JP-A No. 3-112992 and Japanese National Publication No. 2003-533455; polymers having a sulfonic acid group at a terminal, such as those described in JP-A No. 2002-273191; and polymers having a partial skeleton of an organic dye or a heterocycle such as those described in JP-A No. 9-77994. Polymers having terminals into which two or more anchoring sites to the pigment surface are introduced (such as an acidic group, a basic group, a partial skeleton of an organic dye or a heterocycle), such as those described in JP-A No. 2007-277514, exhibit favorable dispersion stability and are also preferable.

Examples of the graft polymer having an anchoring site to the pigment surface include reaction products of poly(lower alkelene imine) and polyester, such as those described in JP-A No. 54-37082, Japanese National Publication No. 8-507960 and JP-A No. 2009-258668; reaction products of polyallylamine and polyester, such as those described in JP-A No. 9-169821; copolymers of a macromonomer and a nitrogen-containing monomer, such as those described in JP-A No. 10-339949 and JP-A No. 2004-37986; graft polymers having a partial skeleton of an organic dye or a heterocycle, such as those described in JP-A No. 2003-238837, JP-A No. 2008-9426 and JP-A No. 2008-81732; and copolymers of a macromonomer and an acidic group-containing monomer, such as those described in JP-A No. 2010-106268. Amphoteric dispersant resins having a basic group and an acidic group, described in JP-A No. 2009-203462, are particularly preferred from the viewpoint of dispersibility and dispersion stability of a pigment dispersion, and developability of a colored curable composition in which the pigment dispersant is used.

The macromonomer used for producing a graft polymer having an anchoring site to the pigment surface by radical polymerization may be selected from known macromonomers, such as AA-6 (polymethyl methacrylate having a methacryloyl group at terminals), AS-6 (polystyrene having a methacryloyl group at terminals), AN-6S (styrene-acrylonitrile copolymer having a methacryloyl group at terminals) and AB-6 (polybutyl acrylate having a methacryloyl group at terminals), all manufactured by Toagosei Co., Ltd.; PLACCEL FM5 (trade name, a product in which 5 mol-equivalent of 8-caprolactone is added to 2-hydroxyethyl methacrylate), FA10L (trade name, a product in which 10 mol-equivalent of 8-caprolactone is added to 2-hydroxyethyl acrylate), all manufactured by Daicel Chemical Industries, Ltd.; and a polyester macromer described in JP-A No. 2-0272009. Among these, polyester macromers are particularly preferred in view of flexibility, solvent compatibility, and developability of a colored curable composition in which the pigment dispersant is used. Further, polyester macromonomers described in JP-A No. 2-272009 are most preferred.

In the following, the dispersant described in JP-A No. 2010-106268, which is suitably used in the invention, will be described.

Examples of the preferred dispersant includes graft copolymers having 40 to 10,000 atoms other than hydrogen and including, in its molecule, a graft chain selected from a polyester structure, a polyether structure or a polyacrylate structure. The graft copolymer preferably include at least one of the structural units represented by the following formula (1) to (4), more preferably at least one of the structural units represented by the following formula (2A), formula (3A), formula (3B) and formula (4).

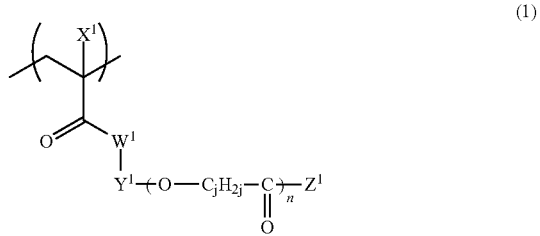

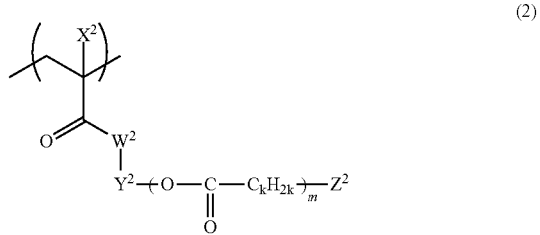

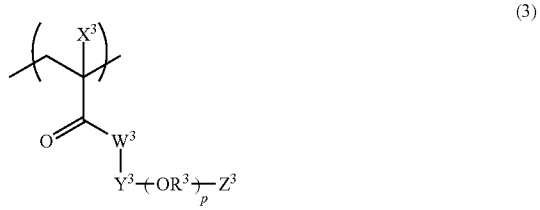

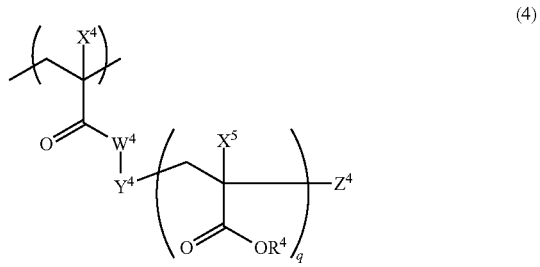

In formulas (1) to (4), $X^1$, $X^2$, $X^3$, $X^4$ and $X^5$ each independently represents a hydrogen atom or a monovalent organic group. From the viewpoint of the restriction on synthesis, $X^1$, $X^2$, $X^3$, $X^4$ and $X^5$ are preferably a hydrogen atom or an alkyl group having 1 to 12 carbon atoms, more preferably a hydrogen atom or a methyl group, particularly preferably a methyl group.

In formulas (1) to (4), $W^1$, $W^2$, $W^3$ and $W^4$ each independently represents O or NH.

In formulas (1) to (4), $Y^1$, $Y^2$, $Y^3$ and $Y^4$ each independently represents a divalent linking group, and the structure thereof is not particularly limited. Specific examples include the following linking group (Y-1) to (Y-21). In the following structures, A and B represent a bonding site to the left terminal group and bonding site to the right terminal group in formulas (1) to (4), respectively. Among these structures, (Y-2) and (Y-13) are more preferred in view of ease of synthesis.

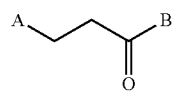 (Y-1)

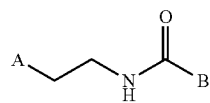 (Y-2)

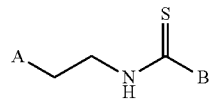 (Y-3)

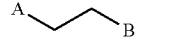 (Y-4)

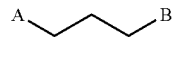 (Y-5)

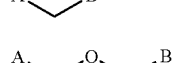 (Y-6)

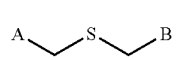 (Y-7)

 (Y-8)

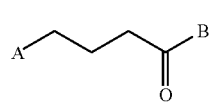 (Y-9)

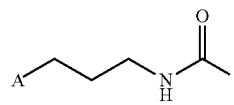 (Y-10)

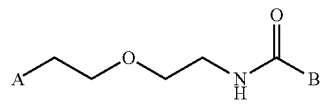 (Y-11)

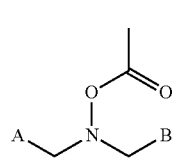 (Y-12)

-continued

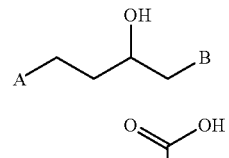 (Y-14)

(Y-15)

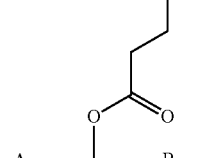 (Y-16)

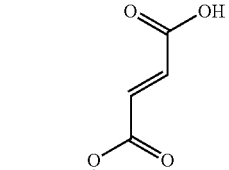 (Y-17)

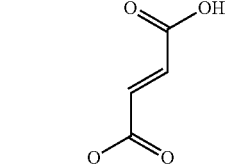 (Y-18)

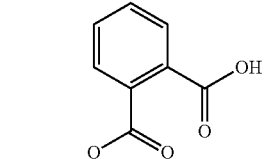 (Y-19)

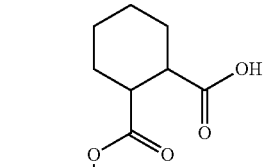 (Y-20)

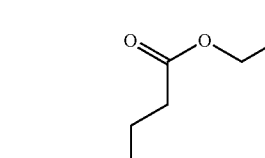 (Y-21)

In formulas (1) to (4), $Z^1$, $Z^2$, $Z^3$ and $Z^4$ each independently represents a monovalent organic group, and the structure thereof is not particularly limited. Specific examples include an alkyl group, a hydroxyl group, an alkoxy group, an aryloxy group, a heteroaryloxy group, an alkyl thioether group, an aryl thioether group, a heteroaryl thioether group, and an amino group. Among these, the monovalent organic group represented by $Z^1$, $Z^2$, $Z^3$ and $Z^4$ preferably exhibits a steric repulsion effect, particularly in view of improving dispersibility, and the organic group represented by $Z^1$ to $Z^3$ is preferably independently an alkyl group having 5 to 24 carbon atoms or an alkoxy group having 5 to 24 carbon atoms. Among these, an alkoxy group having 5 to 24 carbon atoms and having a branched alkyl group, and an alkoxy group having 5 to 24 carbon atoms having a cyclic alkyl group are preferred. The organic group represented by $Z^4$ is preferably independently an alkyl group having 5 to 24 carbon atoms. Among these, a branched alkyl group having 5 to 24 carbon atoms and a cyclic alkyl group having 5 to 24 carbon atoms are preferred.

In formulas (1) to (4), n, m, p and q each independently is an integer from 1 to 500.

In formulas (1) and (2), j and k each independently is an integer from 2 to 8. From the viewpoint of dispersion stability and developability, j and k in formulas (1) and (2) is preferably an integer from 4 to 6, most preferably 5.

In formula (3), $R^3$ represents a linear or branched alkylene group, more preferably an alkylene group having 1 to 10 carbon atoms, more preferably an alkylene group having 2 or 3 carbon atoms.

In formula (4), $R^4$ represents a hydrogen atom or a monovalent organic group, and the structure of the monovalent organic group is not particularly limited. $R^4$ is preferably a hydrogen atom, an alkyl group, an aryl group or a heteroaryl group, more preferably a hydrogen atom or an alkyl group. When $R^4$ is an alkyl group, it is preferably a linear alkyl group having 1 to 20 carbon atoms, a branched alkyl group having 3 to 20 carbon atoms, or a cyclic alkyl group having 5 to 20 carbon atoms. $R^4$ is more preferably a linear alkyl group having 1 to 20 carbon atoms, particularly preferably a linear alkyl group having 1 to 6 carbon atoms. In formula (4), two or more kinds of $R^4$ having different structures may be used in the graft copolymer.

In the graft copolymer, the structural unit represented by formulas (1) to (4) is preferably included in an amount of 10% to 90% with respect to the total mass of the graft copolymer, more preferably from 30% to 70%. When the amount of the structural unit represented by formulas (1) to (4) in the graft copolymer is within this range, favorable dispersibility of the pigment and developability during forming a light-shielding film may be achieved.

Further, in the graft copolymer, two or more kinds of graft copolymers having different structures may be included.

The structural unit represented by formula (1) is more preferably a structural unit represented by the following formula (1A) from the viewpoint of dispersion stability and developability.

The structural unit represented by formula (2) is more preferably a structural unit represented by the following formula (2A) from the viewpoint of dispersion stability and developability.

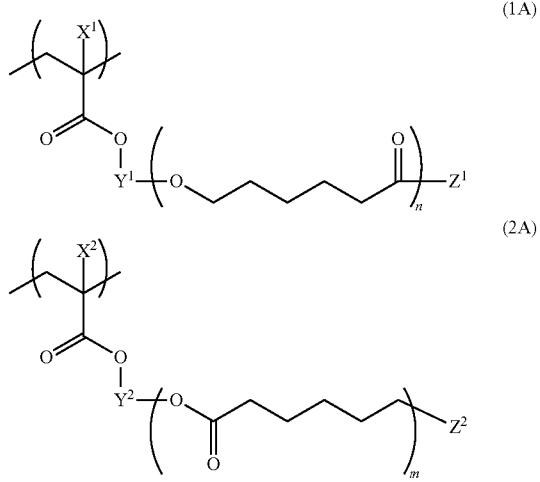

In formula (1A), definitions of $X^1$, $Y^1$ and $Z^1$ are the same as that of $X^1$, $Y^1$ and $Z^1$ in formula (1), respectively, and preferred embodiments are also the same.

In formula (2A), definitions of $X^2$, $Y^2$ and $Z^2$ are the same as that of $X^2$, $Y^2$ and $Z^2$ in formula (2), respectively, and preferred embodiments are also the same.

Further, the structural unit represented by formula (3) is preferably a structural unit represented by the following formula (3A) or formula (3B) from the viewpoint of dispersion stability and developability.

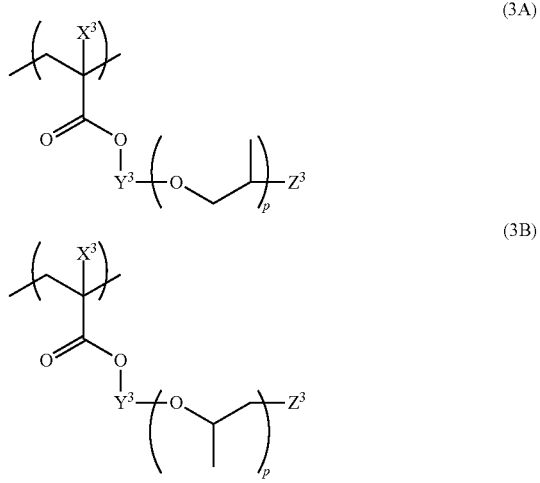

In formulas (3A) and (3B), definitions of $X^3$, $Y^3$, $Z^3$ and p are the same as that of $X^3$, $Y^3$, $Z^3$ and p in formula (3), respectively, and preferred embodiments are also the same.

In a preferred embodiment, the graft copolymer has a structural unit represented by formula (1A).

The graft copolymer having a graft chain preferably has a functional group that exhibits alkali solubility. In order to have a functional group that exhibits alkali solubility, it is necessary to include an acidic group in the molecule. Preferred acidic groups include carboxylic acid, phosphoric acid, monophosphoric acid ester, sulfonic acid, sulfinic acid, a sulfonamido group, a phenolic hydroxyl group, a thio group, an alkyl acetoacetate group, and a derivative of these groups.

From the viewpoint of sensitivity, stability and developability, the acidic group is preferably a carboxylic group.

When the graft copolymer having a graft chain include an alkali soluble group, the graft copolymer preferably has an acid value of from 5 mgKOH/g to 150 mgKOH/g, more preferably from 30 mgKOH/g to 130 mgKOH/g.

The functional group that exhibits alkali solubility can be introduced into the graft copolymer by, in case of radical polymerization, polymerizing a compound having an acidic group and a polymerizable group such as an ethylene group, such as methacrylic acid, acrylic acid, vinyl benzoate and vinyl phenol. The introduction may also be performed by polymerizing acetoxyvinyl phenol and hydrolyzing the same.

In the case of a urethane binder, an acidic group may be introduced by way of polycondensation of diol having carboxylic acid with a diisocyanate compound.

When the polymer that forms a main chain of the graft copolymer having a graft chain is a (meth)acrylic polymer, the polymer having a carboxylic acid group may be obtained by radical polymerization.

Example of the acid group-containing monomer that may be used in radical polymerization include acrylic acid, methacrylic acid, itaconic acid, crotonic acid, maleic acid, fumaric acid, phthalic monohydroxyethyl acrylate, Ω-carboxy polycaprolactone monoacrylate, β-carboxyethyl acrylate, 2-acryloyloxyethyl succinic acid, 2-acryloyloxyethyl hexahydrophthalic acid, phthalic acid monohydroxyethyl methacrylate, Ω-carboxy polycaprolactone monomethacrylate, β-carboxyethyl methacrylate, 2-methacryloyloxyethyl succinic acid, 2-methacryloyloxyethyl hexahydrophthalic acid, and 4-carboxyl styrene. Examples of the monomer having an acid anhydride include maleic anhydride. It is also possible to use other monomers.

The following are examples of a monomer that can be copolymerized with an acid group-containing monomer.

(1) acrylic acid esters and methacrylic acid esters having an aliphatic hydroxyl group, such as 2-hyeroxyethyl acrylate, 2-hydroxypropyl acrylate, 3-hydroxypropyl acrylate, 4-hydroxybutyl acrylate, 2-hydroxyethyl methacrylate, 2-hydroxypropyl methacrylate, 3-hydroxypropyl methacrylate and 4-hydroxybutyl methacrylate.

(2) alkyl acrylates such as methyl acrylate, ethyl acrylate, propyl acrylate, butyl acrylate, isobutyl acrylate, amyl acrylate, hexyl acrylate, 2-ethylhexyl acrylate, octyl acrylate, benzyl acrylate, 2-chloroethyl acrylate, glycidyl acrylate, 3,4-epoxycyclohexyl methyl acrylate, vinyl acrylate, 2-phenylvinyl acrylate, 1-propenyl acrylate, allyl acrylate, 2-allyloxyethyl acrylate and propargyl acrylate.

(3) alkyl methacrylates such as methyl methacrylate, ethyl methacrylate, propyl methacrylate, butyl methacrylate, isobutyl methacrylate, amyl methacrylate, hexyl methacrylate, 2-ethylhexyl methacrylate, cyclohexyl methacrylate, benzyl methacrylate, 2-chloroethyl methacrylate, glycidyl methacrylate, 3,4-epoxycyclohexyl methyl methacrylate, vinyl methacrylate, 2-phenyl vinyl methacrylate, 1-propenyl methacrylate, allyl methacrylate, 2-allyloxyethyl methacrylate and propargyl methacrylate.

(4) acrylamides and methacrylamides such as acrylamide, methacrylamice, N-methylol acrylamide, N-ethyl acrylamide, N-hexyl methacrylamide, N-cyclohexyl acrylamide, N-hydroxyethyl acrylamide, N-phenyl acrylamide, N-nitrophenyl acrylamide, N-ethyl-N-phenyl acrylamide, vinyl acrylamide, vinyl methacrylamide, N,N-diallyl acrylamide, N,N-diallyl methacrylatmide, allyl acrylamide and allyl methacrylamide.

(5) vinyl ethers such as ethyl vinyl ether, 2-chloroethyl vinyl ether, hydroxyethyl vinyl ether, propyl vinyl ether, butyl vinyl ether, octyl vinyl ether, and phenyl vinyl ether.

(6) vinyl esters such as vinyl acetate, vinyl chloroacetate, vinyl butylate and vinyl benzoate.

(7) styrenes such as styrene, α-methyl styrene, methyl styrene, chloromethyl styrene and p-acetoxy styrene.

(8) vinyl ketones such as methyl vinyl ketone, ethyl vinyl ketone, propyl vinyl ketone, and phenyl vinyl ketone.

(9) olefins such as ethylene, propylene, isobutylene, butadiene and isoprene.

(10) N-vinyl pyrrolidone, acrylonitrile, methacrylonitrile, and the like.

(11) unsaturated imides such as maleimide, N-acryloyl acrylamice, N-acetyl methacrylamide, N-propionyl methacrylamide and N-(p-chlorobenzoyl)methacrylamide.

(12) methacrylic acid-based monomer with a hetero atom bonded thereto at α-position, such as those described in JP-A No. 2002-309057 and JP-A No. 2002-311569.

The following are specific examples of the graft copolymer. In the exemplary compounds, the values indicate the content of each structural unit (wt %).

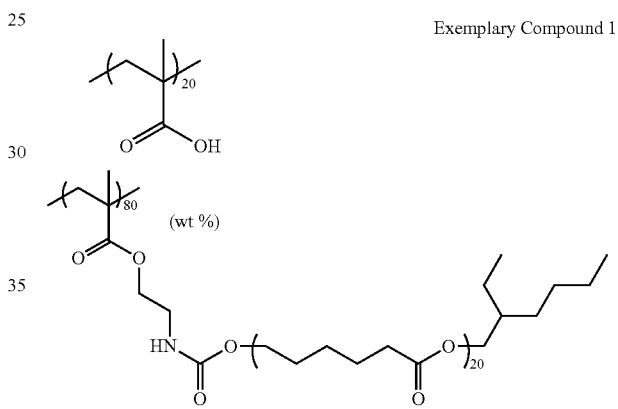

Exemplary Compound 1

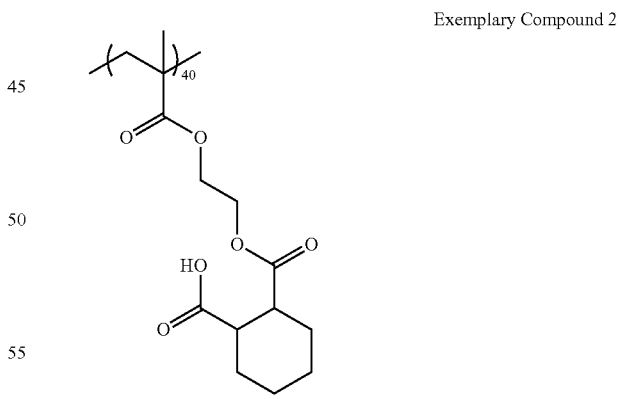

Exemplary Compound 2

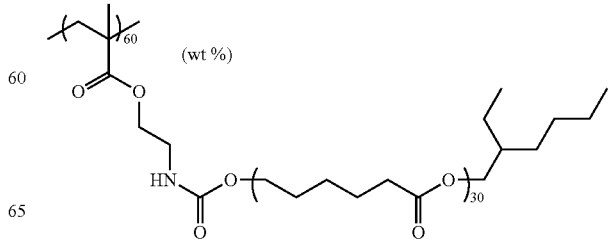

Exemplary Compound 3
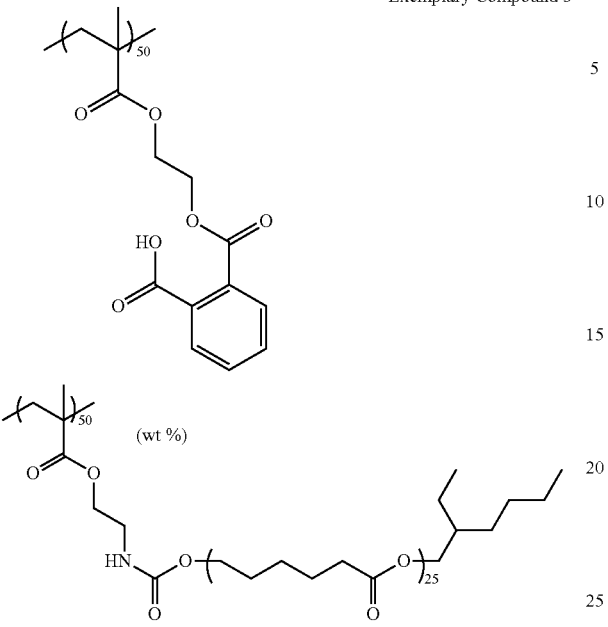
Exemplary Compound 4
Exemplary Compound 5
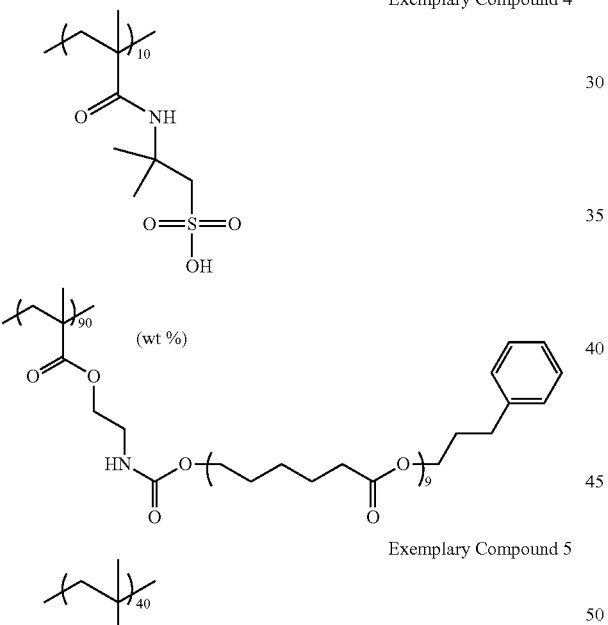
Exemplary Compound 6
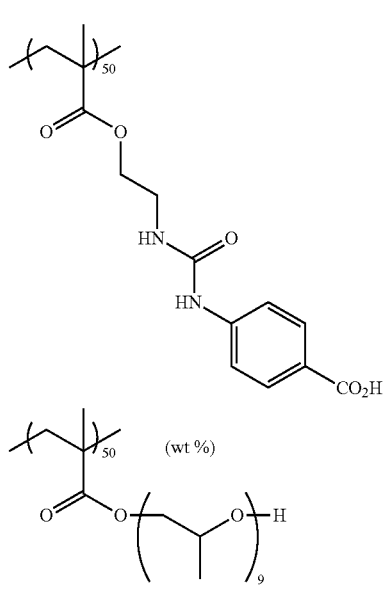
Exemplary Compound 7
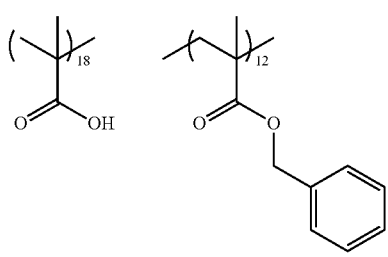
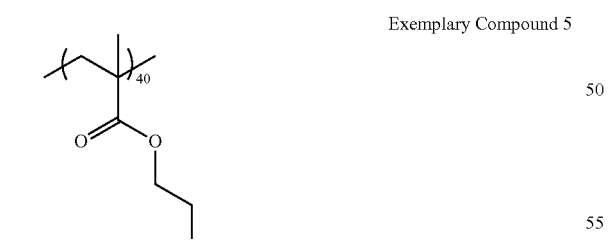
Exemplary Compound 8
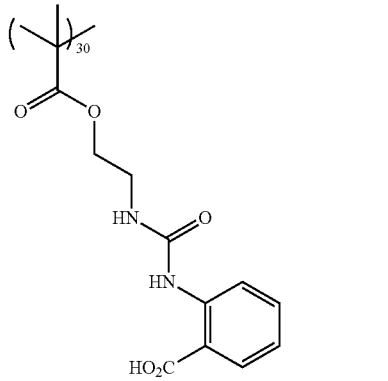

-continued

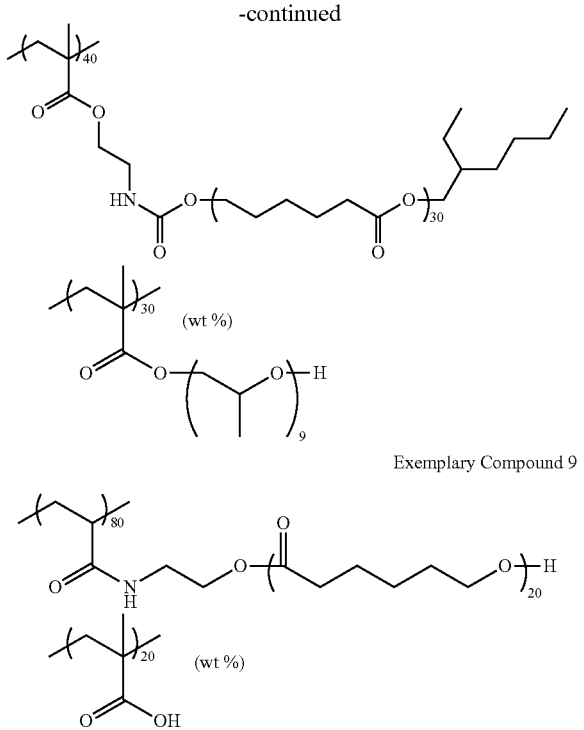

Exemplary Compound 9

In the invention, the dispersant is preferably a compound having a polyester chain and carboxylic acid, such as exemplary compounds 1, 2, 3, 7 and 8.

<Synthesis of Exemplary Compound 1>

In a 500-mL three-neck flask, 600.0 g of 8-caprolactone and 22.8 g of 2-ethyl-1-hexanol were placed and stirred to dissolve while introducing nitrogen. Further, 0.1 g of monobutyl tin oxide were added and heated to 100° C. Eight hours after, disappearance of the raw materials was confirmed by gas chromatography, and cooled to 80° C. After adding 0.1 g of 2,6-di-t-butyl-4-methylphenol, 27.2 g of 2-methacryloyloxyethyl isocyanate were added. Five hours after, disappearance of the raw materials was confirmed by $^1$H-NMR, and cooled to room temperature. 200 g of a precursor compound in a solid state, having the following structure, were obtained. Determination of whether the compound was a precursor was performed by $^1$H-NMR and mass analysis.

Precursor Compound

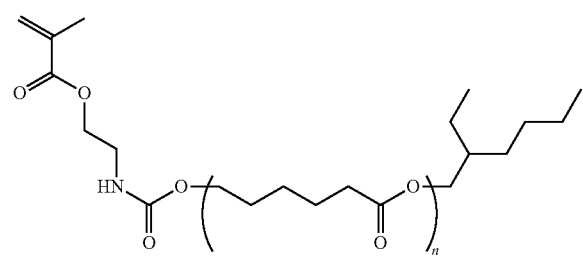

80.0 g of the precursor compound, 20.0 g of methacrylic acid, 2.3 g of dodecylmercaptan and 233.3 g of propylene glycol monomethyl ether acetate were placed in a nitrogen-purged three-neck flask, and stirred with a stirrer (THREE-ONE MOTOR, trade name, manufactured by Shinto Scientific Co., Ltd.) and heated to 75° C. while introducing nitrogen. To the resultant, 0.2 g of 2,2-azobis(2,4-dimethylvaleronitrile) (V-65, trade name, manufactured by Wako Pure Chemical Industries, Ltd.) were added and heated while stirring for 2 hours at 75° C. Two hours after, 0.2 g of V-65 were further added and stirred for 3 hours while heating. A 30% solution of specific resin 1 (exemplary compound 1) was obtained.

Exemplary compounds 2 to 8 were synthesized in a similar manner to that of exemplary compound 1.

The block polymer having an anchoring site to the pigment surface is preferably those described in JP-A No. 2003-49110 and JP-A No. 2009-52010.

The pigment dispersants that may be used in the invention are also available as commercial products, and specific examples thereof include DISPERBYK-101 (polyamide amine phosphate), 107 (carboxylic acid ester), 110 (acid group-containing copolymer), 130 (polyamide), 161, 162, 163, 164, 165, 166, 170 and BYK-161 (high-molecular-weight copolymer), BYK-P 104, P105 (high-molecular-weight unsaturated polycarboxylic acid), which are manufactured by BYK Chemie;

EFKA 4047, 4050-4010-4165 (polyurethane-based), EFKA 4330-4340 (block copolymer), 4400-4402 (modified polyacrylate), 5010 (polyester amide), 5765 (high-molecular-weight polycarboxylate), 6220 (fatty acid polyester), 6745 (high-molecular-weight polycarboxylate), 6750 (azo pigment derivative), which are manufactured by EFKA;

AJISPER PB821, PB822, PB880 and PB881, which are manufactured by Ajinomoto Fine-Techno Co., Inc.;

FLOWLENE TG-710 (urethane oligomer), POLYFLOW No. 50E and No. 300 (acrylic copolymer), which are manufactured by Kyoeisha Chemical Co., Ltd.;

DISPALON KS-860, 873SN, 874, #2150 (aliphatic polycarboxylic acid), #7004 (polyether ester), DA-703-50, DA-705, DA-725, which are manufactured by Kusumoto Chemicals, Ltd.;

DEMOL RN, N (naphthalene sulfonic acid formalin polycondensate), MS, C, SN-B (aromatic sulfonic acid formalin polycondensate), HOMOGENOL L-18 (high-molecular polycarboxylic acid), EMERGEN 920, 930, 935 and 985 (polyoxyethylene nonyl phenyl ether), ACETAMIN 86 (stearyl amine acetate), which are manufactured by Kao Corporation;

SOLSPERSE 5000 (phthalocyanine derivative), 22000 (azo pigment derivative), 13240 (polyester amine), 3000, 17000 and 27000 (polymer having a functional moiety at a terminal), 24000, 28000, 32000 and 38500 (graft polymer), which are manufactured by the Lubrizol Corporation;

NIKOL T106 (polyoxyethylene sorbitan monooleate), MYS-IEX (polyoxyethylene monostearate), manufactured by Nikko Chemicals, Co., Ltd.;

HINOACT T-8000E, manufactured by Kawaken Fine Chemicals Ltd.;

KP341 (organosiloxane polymer) manufactured by Shin-Etsu Chemical Co., Ltd.;

WO01 (cationic surfactant), polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid ester (nonionic surfactants), WO04, WO05 and WO17 (anionic surfactants) available from Yusho;

EFKA-46, EFKA-47, EFKA-47EA, EFKA POLYMER 100, EFKA POLYMER 400, EFKA POLYMER 401, EFKA POLYMER 450, manufactured by Morishita Sangyo Kabusiki Kaisha;

DISPERSEAID 6, DISPERSEAID 8, DISPERSEAID 15, DISPERSEAID 9100 (polymer dispersants) manufactured by San Nopco Limited;

ADEKA PLURONIC L31, F38, L42, L44, L61, L64, F68, L62, P95, F77, P84, F87, P94, L101, P103, F108, L121 and P-123, manufactured by Adeka Corporation; and IONET S-20, manufactured by Sanyo Chemical Industries, Ltd.

These pigment dispersants may be used alone or in a combination of two or more kinds. In the present invention, in particular, a combination of a pigment derivative and a polymer dispersant is preferably used. The pigment dispersant may be a combination of a terminal-modified polymer, a graft polymer or a block copolymer with an alkali-soluble resin. Examples of the alkali-soluble resin include (meth)acrylic acid copolymer, itaconic acid copolymer, crotonic acid copolymer, maleic acid copolymer, partially esterified maleic acid copolymer, acidic cellulose derivative having a carboxylic acid in a side chain, and a resin obtained by modifying a polymer having a hydroxyl group with an acid anhydride. Among these, (meth)acrylic acid copolymer is preferred. In addition, copolymers of N position-substituted maleimide monomer described in JP-A No. 10-300922, ether dimer copolymers described in JP-A No. 2004-300204, and alkali soluble resins having a polymerizable group described in JP-A No. 7-319161 are also preferred.

The content of the pigment dispersant in the colored curable composition is preferably from 1 to 80 parts by mass, more preferably from 5 to 70 parts by mass, further preferably from 10 to 60 parts by mass, with respect to 100 parts by mass of a pigment used as a colorant.

Specifically, when a polymer dispersant is used, the amount thereof is preferably from 5 to 100 parts by mass, more preferably from 10 to 80 parts by mass, with respect to 100 parts by mass of a pigment.

When a pigment derivative is used, the amount thereof is preferably from 1 to 30 parts by mass, more preferably from 3 to 20 parts by mass, further preferably from 5 to 15 parts by mass, with respect to 100 parts by mass of a pigment.

When a pigment dispersant is used in combination with a pigment used as a colorant, the total amount thereof is preferably from 30 to 90% by mass, more preferably from 40 to 85% by mass, further preferably from 50 to 80% by mass, with respect to the total solid content of the components that constitute the colored curable composition, from the viewpoint of curing sensitivity and color density.

(Polymerizable Compound)

The colored curable composition of the invention includes a polymerizable compound.

Examples of the polymerizable compound include addition-polymerizable compounds having at least one ethylenically unsaturated bond, specifically, compounds having one or more, preferably two or more, terminal ethylenically unsaturated bonds. These compounds are widely known in the field of the art, and any one of these compounds may be used in the invention without being particularly limited. The compounds may have a chemical form selected from a monomer, a prepolymer (a dimer, a trimer or an oligomer), a mixture thereof, or a (co)polymer thereof.

Specific examples of the monomers or the (co)polymers include those described in paragraphs [0058] to [0065] of JP-A No. 2008-224982.

Other examples include aliphatic alcohol-based esters described in Japanese Examined Patent Publication No. 51-47334 and JP-A No. 57-196231, compounds having an aromatic skeleton described in JP-A No. 59-5240, JP-A No. 59-5241 and JP-A No. 2-226149, and compounds having an amino group described in JP-A No. 1-165613.

Details of how to use the polymerizable compound, such as the structure, the number of kinds of the polymerizable compound, the amount or the like, may be arbitrarily selected in view of the eventual characteristics of the colored curable composition. For example, from the viewpoint of sensitivity, a structure including more unsaturated groups per molecule, typically two or more unsaturated groups, is preferred. From the viewpoint of increasing the strength of a colored cured film, at least trifunctional compounds are preferred. It is also effective to adjust both sensitivity and strength by combining compounds having different numbers of functional groups or different types of polymerizable group (such as acrylic acid ester, methacrylic acid ester, styrene compound or vinyl ether compound). The selection and the use of the polymerizable compound is an important factor also in terms of compatibility with other compounds included in the colored curable composition (such as a photopolymerization initiator, a colorant (pigment) or a binder), or dispersibility. For example, compatibility may be improved by using a compound having a low purity or using two or more kinds of compounds in combination. A specific structure may be selected and used from the viewpoint of improving adhesiveness with respect to a hard surface, such as a support.

The content of the polymerizable compound in the total solid content of the colored curable composition (when two or more kinds of polymerizable compounds are used, the total content thereof) is not particularly limited, and is preferably from 10 to 80% by mass, more preferably from 15 to 75% by mass, particularly preferably from 20 to 60% by mass, from the viewpoint of achieving the effect of the invention more efficiently.

(Photopolymerization Initiator)

The colored curable composition of the invention may include a photopolymerization initiator.

The photopolymerization initiator is not particularly limited as long as it can polymerize the polymerizable compound, and preferably selected in view of its characteristics, initiation efficacy, absorption wavelength, availability, costs or the like.

Examples of the photopolymerization initiator include active halogen compounds selected from halomethyl oxadiazole compounds and halomethyl-s-triazine compounds, 3-aryl substituted coumarin compounds, lophine dimers, benzopheone compounds, acetophenone compounds and a derivative thereof, and cyclopentadinene-benzene-iron complexes and a salt thereof. Specific examples of the photopolymerization initiator include those described in paragraphs [0070] to [0077] of JP-A No. 2004-295116. Among these, from the viewpoint of achieving a rapid polymerization reaction, oxime compounds are preferred.

The oxime compounds are not particularly limited, and examples include oxime compounds described in JP-A No. 2000-80068, WO02/100906A1 and JP-A No. 2001-233842. Specific examples include 2-(o-benzoyloxime)-1-[4-(phenylthio)phenyl]-1,2-butanedione, 2-(o-benzoyloxime)-1-[4-(phenylthio)phenyl]-1,2-pentandione, 2-(o-benzoyloxime)-1-[4-(phenylthio)phenyl]-1,2-hexanedione, 2-(o-benzoyloxime)-1-[4-(phenylthio)phenyl]-1,2-heptanedione, 2-(o-benzoyloxime)-1-[4-(phenylthio)phenyl]-1,2-octanedione, 2-(o-benzoyloxime)-1-[4-(methylphenylthio)phenyl]-1,2-butanedione, 2-(o-benzoyloxime)-1-[4-(butylphenylthio)phenyl]-1,2-butanedione, 1-(o-acetyloxime)-1-[9-ethyl-6-(2-methylbenzoyl)-9H-carbazol-3-yl]ethanone, 1-(o-acetyloxime)-1-[9-methyl-6-(2-methylbenzoyl)-9H-carbazol-3-yl]ethanone, 1-(o-acetyloxime)-1-[9-propyl-6-

(2-methylbenzoyl)-9H-carbazol-3-yl]ethanone, 1-(o-acetyloxime)-1-[9-ethyl-6-(2-ethylbenzoyl)-9H-carbazol-3-yl]ethanone, and 1-(o-acetyloxime)-1-[9-ethyl-6-(2-buhylbenzoyl)-9H-carbazol-3-yl]ethanone. However, the oxime compounds are not particularly limited to these examples.

Among these, from the viewpoint of forming a pattern having a favorable shape (rectangularity of a pattern for solid-state image sensors), oxime-o-acyl compounds such as 2-(o-benzoyloxime)-1-[4-(phenylthio)phenyl]-1,2-octandione and 1-(o-acetyloxime)-1-[9-ethyl-6-(2-methylbenzoyl)-9H-carbazol-3-yl]ethanone are particularly preferred, and specific examples include IRGACURE-OXE01 and IRGACURE-OXE02 (trade name, manufactured by BASF Ltd.)

Further, in the invention, from the viewpoint of sensitivity, temporal stability and coloration during post heating, an oxime compound represented by the following formula (E) or (F) is more preferred.

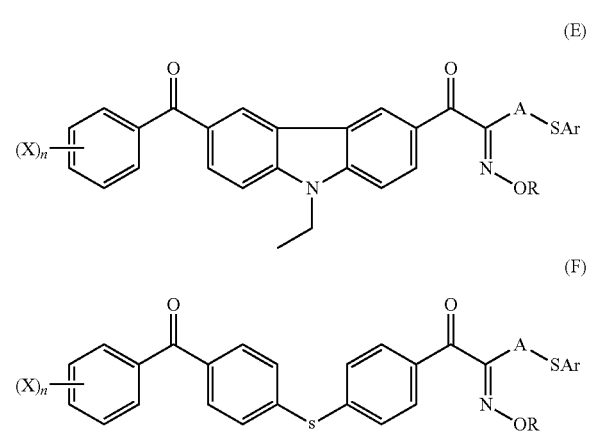

In formulas (E) and (F), each of R and X independently represents a monovalent substituent, A represents a divalent organic group, Ar represents an aryl group, and n represents an integer from 1 to 5.

From the viewpoint of increasing the sensitivity, R is preferably an acyl group, specifically an acetyl group, a propionyl group, a benzoyl group or a toluoyl group.

From the viewpoint of increasing the sensitivity and suppressing the coloration, A is preferably an unsubstituted alkylene group, an alkylene group substituted by an alkyl group (such as a methyl group, an ethyl group, a tert-butyl group or a dodecyl group), or an alkylene group substituted by an aryl group (such as a phenyl group, a p-tolyl group, a xylyl group, a cumenyl group, a naphthyl group, an anthryl group, a phenanthryl group or a styryl group).

From the viewpoint of increasing the sensitivity and suppressing the coloration by heating with time, Ar is preferably a substituted or unsubstituted phenyl group. When the phenyl group is substituted, the substituent group is preferably a halogen atom such as a fluorine atom, a chlorine atom, a bromine atom or an iodine atom.

From the viewpoint of improving the solubility in a solvent and the absorption efficacy in a long wavelength region, X is preferably an alkyl group that may have a substituent group, an aryl group that may have a substituent group, an alkenyl group that may have a substituent group, an alkynyl group that may have a substituent group, an alkoxy group that may have a substituent group, an aryloxy group that that may have a substituent group, an alkylthioxy group that may have a substituent group, an arylthioxy group that may have a substituent group, or an amino group that may have a substituent group.

In formula (E) or (F), p is preferably an integer of 1 or 2.

The following are specific examples of the compounds represented by formula (E) or (F). However, the invention is not limited to these examples.

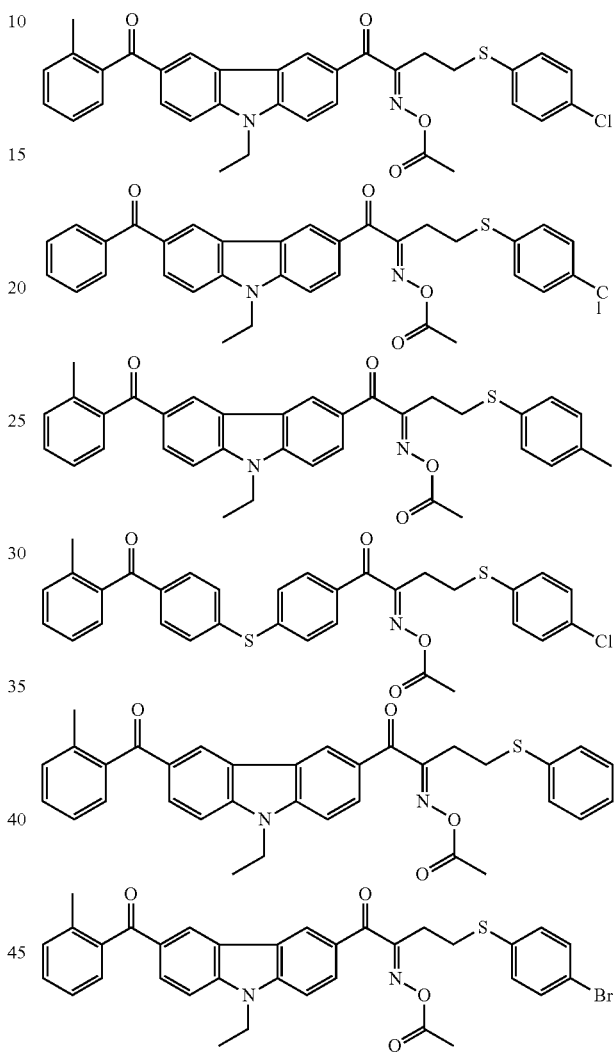

The colored curable composition of the invention may include other known photopolymerization initiator such as those described in paragraph [0079] of JP-A No. 2004-295116, instead of the photopolymerization initiators as mentioned above.

The photopolymerization initiator may be used alone or as a combination of two or more kinds The content of the photopolymerization initiator in the total solid content of the colored curable composition (when two or more kinds are used, the total content thereof) is, from the viewpoint of achieving the effect of the invention more efficiently, preferably from 3 to 20% by mass, more preferably from 4 to 19% by mass, particularly preferably from 5 to 18% by mass.

(Organic Solvent)

The colored curable composition of the invention may include an organic solvent. The organic solvent is not particularly limited as long as it satisfies the solubility of the components in the composition or coatability of the composition. In particular, the organic solvent is preferably selected in consideration of solubility of a binder, coatability and safety.

Specific examples of the organic solvent include esters, ethers, ketones, and aromatic hydrocarbons.

Esters include ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, alkyl oxyacetate (such as methyl oxyacetate, ethyl oxyacetate, butyl oxyacetate; specifically, methyl methoxy acetate, ethyl methoxyacetate, butyl methoxyacetate, methyl ethoxyacetate, and ethyl ethoxyacetate), alkyl 3-oxypropionate (such as methyl 3-oxypropionate, ethyl 3-oxypropionate; specifically, methyl 3-methoxypropionate, ethyl 3-methoxypropionate, methyl 3-ethoxypropionate, and ethyl 3-ethoxypropionate), alkyl 2-oxypropionate (such as methyl 2-oxypropionate, ethyl 2-oxypropionate, propyl 2-methoxypropionate, specifically, methyl 2-methoxypropionate, ethyl 2-methoxypropionate, propyl 2-methoxypropionate, methyl 2-ethoxypropionate, and ethyl 2-ethoxypropionate), methyl 2-oxy-2-methylpropionate, ethyl 2-oxy-2-methylpropionate (specifically, methyl 2-methocy-2-methylpropionate and ethyl 2-ethoxy-2-methyl propionate), methyl pyruvate, methyl acetoacetate, ethyl acetoacetate, methyl 2-oxobutanate, and ethyl 2-oxobutanate.

Ethers include diethylene glycol dimethyl ether, teterahydrofuran, ethylene glycol monomethyl ether, ethylene glycol monoethyl ether, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monomethyl ether, diethylene glycol monobutyl ether, propylene glycol monomethyl ether, propylene glycol monomethyl ether acetate, propylene glycol monomethyl ether acetate, propylene glycol monoethyl ether acetate, and propylene glycol monopropyl ether acetate.

Ketones include methyl ethyl ketone, cyclohexanone, 2-heptanone and 3-heptanone.

Aromatic hydrocarbons include toluene and xylene.

These organic solvents may be used in combination of two or more kinds, from the viewpoint of improving the solubility of the components as mentioned above, solubility of an alkali soluble binder (when used) or a state of a coated surface. In that case, the combination of organic solvent is particularly preferably a combination of at least two selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol methyl ether acetate.

The content of the organic solvent in the colored curable composition is preferably determined such that the total solid content concentration of the composition from 10 to 80% by mass, more preferably from 15 to 60% by mass.

(Other Components)

The colored curable composition of the invention may include other components, such as an alkali soluble binder or a crosslinking agent, in addition to the above components, as long as the effect of the invention is not impaired.

<Alkali Soluble Binder>

The alkali soluble binder is not particularly limited, and preferably selected in view of heat fastness, developability, availability or the like.

The alkali soluble binder is preferably a linear organic polymer that is soluble in an organic solvent and capable of being developed with a weak aqueous alkali solution. Examples of the linear organic polymer include polymers having a carboxyl group in a side chain, such as methacrylic acid copolymers, acrylic acid copolymers, itaconic acid copolymers, crotonic acid copolymers, maleic acid copolymers, partially esterified maleic acid copolymers, and acidic cellulose derivatives having a carboxyl group in a side chain described in JP-A No. 59-44615, Japanese Examined Patent Publication No. 54-34327, Japanese Examined Patent Publication No. 58-12577, Japanese Examined Patent Publication No. 54-25957, JP-A No. 59-53836 and JP-A No. 59-71048. Polymers obtained by polymerizing a compound having a specific structure, which is an ether dimer of 2-(hydroxyalkyl)acrylic acid ester (such as compounds described in JP-A No. 2004-300203) are also usable.

Other preferred examples of the binder that may be used in the invention include a polymer including, as a polymerization component, a structure derived from a compound represented by the following formula (ED).

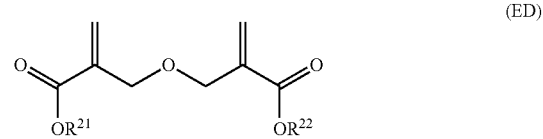

(ED)

In formula (ED), $R^{21}$ and $R^{22}$ each independently represents a hydrogen atom or a hydrocarbon group having 1 to 25 carbon atoms which may have a substituent.

By using a binder including a structural unit derived from an ether dimer, the polymerizable composition of the invention may have an advantage in that a cured film that exhibits excellent heat fastness and transparency can be formed.

In formula (ED) representing an ether dimer, the hydrocarbon group having 1 to 25 carbon atoms which may have a substituent, represented by $R^{21}$ and $R^{22}$, is not particularly limited, and examples thereof include a linear or branched alkyl group such as a methyl group, an ethyl group, an n-propyl group, an isopropyl group, an n-butyl group, an isobutyl group, a t-butyl group, a t-amyl group, a stearyl group, a lauryl group or a 2-ethyl hexyl group; an aryl group such as a phenyl group; a cycloaliphatic group such as a cyclohexyl group, a t-butyl cyclohexyl group, a dicyclopentadienyl group, a tricyclodecanyl group, an isobornyl group, an adamantyl group or a 2-methyl-2-adamantyl group; an alkoxy group-substituted alkyl group such as a 1-methoxyethyl group or a 1-ethoxyethyl group; and an aryl group-substituted alkyl group such as a benzyl group. Among these, the substituent is particularly preferably a group of primary or secondary carbon, which is hardly detachable by acid or heat, such as a methyl group, an ethyl group, a cyclohexyl group or a benzyl group, is preferable from the viewpoints of heat resistance.

Specific examples of the ether dimer include: dimethyl-2,2'-[oxybis(methylene)]bis-2-propenoate, diethyl-2,2'-[oxybis(methylene)]bis-2-propenoate, di(n-propyl)-2,2'-[oxybis(methylene)]bis-2-propenoate, di(isopropyl)-2,2'-[oxybis(methylene)]bis-2-propenoate, di(n-butyl)-2,2'-[oxybis(methylene)]bis-2-propenoate, di(isobutyl)-2,2'-[oxybis(methylene)]bis-2-propenoate, di(t-butyl)-2,2'-[oxybis(methylene)bis-2-propenoate, di(t-amyl)-2,2'-[oxybis(methylene)]bis-2-propenoate, di(stearyl)-2,2'-[oxybis(methylene)]bis-2-propenoate, di(lauryl)-2,2'-[oxybis(methylene)]bis-2-propenoate, di(2-ethylhexyl)-2,2'-[oxybis(methylene)]bis-2-propenoate, di(1-methoxyethyl)-2,2'-

[oxybis(methylene)]bis-2-propenoate, di(1-ethoxyethyl)-2,2'-[oxybis(methylene)]bis-2-propenoate, dibenzyl-2,2'-[oxybis(methylene)]bis-2-propenoate, diphenyl-2,2'-[oxybis(methylene)]bis-2-propenoate, dicyclohexyl-2,2'-[oxybis(methylene)]bis-2-propenoate, di(t-butylcyclohexyl)-2,2'-[oxybis(methylene)]bis-2-propenoate, di(dicyclopentadienyl)-2,2'-[oxybis(methylene)]bis-2-propenoate, di(tricyclodecanyl)-2,2'-[oxybis(methylene)]bis-2-propenoate, di(isobornyl)-2,2'-[oxybis(methylene)]bis-2-propenoate, diadamantyl-2,2'-[oxybis(methylene)]bis-2-propenoate, di(2-methyl-2-adamantyl)-2,2'-[oxybis(methylene)]bis-2-propenoate, and the like.

Among these, dimethyl-2,2'-[oxybis(methylene)]bis-2-propenoate, diethyl-2,2'-[oxybis(methylene)]bis-2-propenoate, dicyclohexyl-2,2'-[oxybis(methylene)]bis-2-propenoate, and dibenzyl-2,2'-[oxybis(methylene)]bis-2-propenoate are preferred.

These ether dimers may be used alone or in a combination of two or more thereof.

The structure derived from a compound represented by formula (ED) may be formed by including other monomers for copolymerization. Other monomers that may be used include the monomers mentioned above as other components for structural unit, and these monomers may be used within a range in that the characteristics of the ether dimer is not impaired.

In addition to the above, the alkali soluble binder in the invention may include a compound obtained by adding an acid anhydride to a polymer having a hydroxyl group, a polyhydroxystyrene resin, a polysiloxane resin, a poly(2-hydroxyethykl(meth)acrylate, polyvinyl pyrrolidone, polyethylene oxide, polyvinyl alcohol, and the like. Further, the linear organic polymer may be obtained by copolymerizing a monomer having hydrophilicity, such as alkoxyalkyl(meth)acrylate, hydroxylalkyl(meth)acrylate, glycellol(meth)acrylate, (meth)acrylamide, N-methylol acrylamide, secondary or tertiary alkyl acrylamide, dialkylaminoalkyl(meth)acrylate, morpholine(meth)acrylate, N-vinyl pyrrolidone, N-vinyl caprolactam, vinyl imidazole, vinyl triazole, methyl(meth)acrylate, ethyl(meth)acrylate, branched or linear propyl (meth)acrylate, branched or linear butyl(meth)acrylate, or phenoxyhydroxypropyl(meth)acrylate. Further, examples of monoemers having hydrophilicity include monomers having a teterahydrofurfuryl group, a phospholic acid group, a phosphoric acid ester group, a quaternary ammonium salt group, an ethylene oxy chain, a propylene oxy chain, a sulfonic acid group or a group derived from a salt thereof, or a morpholinoethyl group.

The alkali soluble binder may have a polymerizable group in a side chain in order to improve crosslinking efficacy, such as polymers having an allyl group, a (meth)acryloyl group, or an allyloxyalkyl group in a side chain. Examples of the polymers having a polymerizable group include DIANAL NR series (trade name, manufactured by Mitsubishi Rayon Co., Ltd.), PHOTOMER 6173 (COOH-containing polyurethane acrylic oligomer, trade name, manufactured by Diamond Shamrock Co., Ltd.), VISCOTE R-264, KS RESIST 106 (trade name, manufactured by Osaka Organic Chemical Industry Ltd.), CYCLOMER P series and PLACEL CF200 series (trade names, manufactured by DAICEL Chemical Industries, Ltd.), and EVBCRYL 3800 (trade name, manufactured by DAICEL UCB). In order to improve the strength of a cured film, alcohol-soluble nylon or polyether of 2,2-bis-(4-hydroxyphenyl)-propane with epichlorohydrin are also usable.

Among these alkali soluble binders, from the viewpoint of heat fastness, polyhydroxy styrene resins, polysiloxane resins, acrylic resins, acrylamide resins, acryl/acrylamide resins, and acryl/akrylamide copolymer resins are preferred. From the viewpoint of controlling developability, acrylic resins, acrylamide resins and acryl/acrylamide copolymer resins are preferred.

The acrylic resin is preferably a copolymer formed from a monomer selected from benzyl(meth)acrylate, (meth)acrylic acid, hydroxyethyl(meth)acrylate, (meth)acrylamide or the like, PHOTOMER 6176, KE RESIST-106 or CYCLOMER P series. Among these, benzyl methacrylate/2-hydroxyethyl methacrylate copolymer and benzyl methacrylate/methacrylic acid copolymer are preferred.

From the viewpoint of developability and liquid viscosity, the alkali soluble binder preferably has a weight average molecular weight (in terms of polystyrene measured by GPC) of 1,000 to 200,000, more preferably from 2,000 to 100,000, particularly preferably from 5,000 to 50,000.

The colored curable composition may include a crosslinking agent in order to improve the hardness of a colored cured film formed by curing the colored curable composition.

The crosslinking agent is not particularly limited as long as it can cure a film via crosslinking reaction, and examples include: (a) an epoxy resin; (b) a melamine compound, a guanamine compound, a glycoluryl compound or a urea compound, each of which is substituted by at least one selected from a methylol group, an alkoxymethyl group and an acyloxymethyl group; and (c) a phenol compound, a naphthol compound or a hydroxyanthracene compound, each of which is substituted by at least one selected from a methylol group, an alkoxymethyl group and an acyloxymethyl group. Among them, a polyfunctional epoxy resin is preferable as the crosslinking agent.

Details of the crosslinking agent, such as specific examples, are described in paragraphs [0134] to [0147] of JP-A No. 2004-295116.

<Polymerization Inhibitor>

The colored curable composition of the invention may include a small amount of polymerization inhibitor for suppressing undesired thermal polymerization of a polymerizable compound during the production or storage of the colored composition.

Examples of the polymerization inhibitor that can be used in the present invention include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylene bis(4-methyl-6-t-butylphenol), and an N-nitrosophenylhydroxyamine cerium (I) salt.

The amount of the polymerization inhibitor is preferably from about 0.01% by mass to about 5% by mass with respect to the total mass of the composition.

<Surfactant>

The colored curable composition may include a surfactant. Various surfactants such as a fluorosurfactant, a nonionic surfactant, a cationic surfactant, an anionic surfactant, and a silicone surfactant may be used as the surfactant.

In particular, when the colored composition of the present invention contains a fluorosurfactant, liquid properties (in particular, fluidity) of the colored composition when it is prepared as a coating solution may be further improved. As a result, uniformity in coating thickness may be further improved and the amount of the liquid to be used may be further decreased.

In other words, when a film is formed using a coating solution which is a colored composition containing a fluorosurfactant, a surface tension of the coating solution with respect to a surface to be coated is decreased and wettability with respect to the surface to be coated is improved, thereby improving coatability of the coating solution. Accordingly, a film having a thickness with suppressed unevenness can be suitably formed even when a thin film having a thickness of several micrometers is formed with a small liquid amount.

The content of fluorine in the fluorosurfactant is preferably in the range of from 3% by mass to 40% by mass, more preferably from 5% by mass to 30% by mass, and particularly preferably from 7% by mass to 25% by mass. A fluorosurfactant containing fluorine in an amount within the above range is effective in terms of forming a coating film with suppressed thickness unevenness and reducing the amount of the coating solution to be used, and also exhibits favorable solubility in the colored composition.

Examples of the fluorosurfactant include MEGAFAC F171, MEGAFAC F172, MEGAFAC F173, MEGAFAC F176, MEGAFAC F177, MEGAFAC F141, MEGAFAC F142, MEGAFAC F143, MEGAFAC F144, MEGAFAC R30, MEGAFAC F437, MEGAFAC F479, MEGAFAC F482, MEGAFAC F780, MEGAFAC F781 (all trade names, manufactured by DIC Corporation), FLUORAD FC430, FLUORAD FC431, FLUORAD FC171 (all trade names, manufactured by Sumitomo 3M Limited.), SURFLON S-382, SURFLON SC-101, SURFLON SC-103, SURFLON SC-104, SURFLON SC-105, SURFLON SC-1068, SUR-FLON SC-381, SURFLON SC-383, SURFLON SC393, SURFLON KH-40 (all trade names, manufactured by Asahi Glass Co., Ltd.)

Specific examples of the cationic surfactant include phthalocyanine derivatives (trade name: EFKA-745, manufactured by Morishita & Co., Ltd.), organosiloxane polymer KP341 (trade name, manufactured by Shin-Etsu Chemical Co., Ltd.), (meth)acrylic (co)polymers POLYFLOW No. 75, No. 90 and No. 95 (trade name, manufactured by Kyoeisha Chemical Co., Ltd.), and W001 (trade name, available from Yusho Co., Ltd.)

Specific examples of the nonionic surfactant include glycerol, trimethylol propane, trimethylol ethane, and an ethoxylate or a propoxylate thereof (such as glycerol propoxylate or glycerin ethoxylate), polyoxyethylene lauryl ether, polyoxyethylene stearyl ether, polyoxyethylene oleyl ether, polyoxyethylene octylphenyl ether, polyoxyethylene nonylphenyl ether, polyethylene glycol dilaurate, polyethylene glycol distearate, sorbitan fatty acid ester (PLURONIC L10, L31, L61, L62, 10R5, 17R2, 25R2, TETRONIC 304, 701, 704, 901, 904, 150R1, all trade names, manufactured by BASF Japan).

Specific examples of the anionic surfactant include WO04, WO05, and WO17 (all trade names, available from Yusho Co., Ltd.).

Examples of the silicone surfactant include TORAY SILICONE DC3PA, TORAY SILICONE SH7PA, TORAY SILICONE DC11PA, TORAY SILICONE SH21PA, TORAY SILICONE SH28PA, TORAY SILICONE SH29PA, TORAY SILICONE SH30PA, TORAY SILICONE SH8400 (all trade names, manufactured by Toray Silicone Co., Ltd.), TSF-4440, TSF-4300, TSF-4445, TSF-444(4)(5)(6)(7)$_6$, TSF-4460, TSF-4452 (all trade names, manufactured by Momentive Performance Materials Inc.), KP341 (trade name, manufactured by Shin-Etsu Silicone Co., Ltd.), and BYK323, BYK330 (all trade names, manufactured by BYK Chemie).

The surfactants may be used alone or in a combination of two or more kinds thereof.

<Other Additives>

The colored composition of the present invention may contain various additives as necessary, for example, a filler, an adhesion promoter, an antioxidant, an ultraviolet absorbent, and an aggregation inhibitor. Examples of these additives include additives described in paragraph numbers [0155] to [0156] of JP-A No. 2004-295116.

The colored curable composition of the invention may include a sensitizer or a photostabilizer described in paragraph [0078] of JP-A No. 2004-295116, or a thermal polymerization inhibitor described in paragraph [0081] of JP-A No. 2004-295116.

In order to promote the alkali solubility in unexposed portions or the developability of the colored curable composition, it is preferred to add an organic carboxylic acid, preferably having a low molecular weight of 1,000 or less, in the composition.

Specific examples include an aliphatic monocarboxylic acid such as formic acid, acetic acid, propionic acid, butyric acid, pyvalic acid, caproic acid, diethyl acetic acid, enanthic acid, and capric acid; aliphatic dicarboxylic acid such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetramethylsuccinic acid, and citraconic acid; aliphatic tricarboxylic acid such as tricarbaryl acid, anicot acid, and camphoronic acid; aromatic monocarboxylic acid such as benzoic acid, toluic acid, cuminic acid, hemellitic acid, and mesitylenic acid; aromatic polycarboxylic acid such as phthalic acid, isophthalic acid, terephthalic acid, trimellitic acid, trimesic acid, mellophanic acid, and pyrromellitic acid; and other carboxylic acids such as phenyl acetic acid, hydroatropic acid, hydrocinnamic acid, methylcinnamic acid, benzylcynnamic acid, cinnamylidene acetic acid, and umbellic acid.

<Preparation Method of Colored Composition>

The colored curable composition of the present invention can be prepared by mixing the components as mentioned above. The components may be mixed together, or may be mixed after dissolving or dispersing each component in a solvent. The order of adding the components or operation conditions to prepare the composition is not particularly limited. For example, all of the components may be dissolved in a solvent in a single step to prepare a composition, or each of the components may be prepared as two or more solutions such that these solutions are mixed to prepare the composition when it is used (applied).

The thus prepared composition may be subjected to filtration before it is used, with a filter having a pore diameter of preferably from 0.01 µm to 3.0 µm, and more preferably a pore diameter of from 0.05 µm to 0.5 µm.

The colored curable composition of the present invention is suitably used in the formation of colored pixels of color filters or the like for liquid crystal displays (LCDs) or solid-state image sensors (for example, CCD or CMOS), printing inks, inkjet inks or paints. In particular, the colored composition is suitably used in the formation of color filters for solid-state image sensors such as CCD and CMOS.

<Color Filter and Fabrication Method Thereof>

In the following, the method of producing a color filter from the colored curable composition is described.

In the method of producing the color filter of the invention, a colored curable composition layer is formed by applying the colored curable composition on a support by spin coating, cast coating, roll coating, inkjetting, spray coating or the like. There after, the colored curable composition is dried by performing pre-baking, as necessary.

Examples of the support used in the method of fabricating a color filter in accordance with the present invention include supports to be used for liquid crystal display devices and the like, for example, alkali-free glass, soda-lime glass, borosilicate glass (PYREX (registered trademark) glass), quartz glass, and supports with a transparent conductive film deposited thereon; photoelectric conversion device substrates to be used for image sensors and the like, for example, silicon substrates. These substrates may have a black stripe that defines the pixels from each other. An undercoat layer may be optionally formed on these supports for the purpose of improving adhesion with respect to an upper layer, suppressing diffusion of substances, or flattening the surface of the substrate.

When the colored composition is applied onto a support by spin-coating, it is possible to drop a suitable organic solvent on the support and rotate the support prior to dropping the colored composition, in order to improve compatibility of the colored composition with respect to the support to reduce the amount of the colored composition used for the application.

During application of the colored curable composition of the invention, even when the colored curable composition adheres to nozzles of ejection ports of the application device, piping of the application device or inside the application device, the colored curable composition may be readily removed with a known cleaner. In order to perform the cleaning efficiently, the solvent mentioned above as the solvent that may be used in the colored curable composition is preferably used.

Cleaning liquids described in JP-A No. 7-128867, JP-A No. 7-146562, JP-A No. 8-278637, JP-A No. 2000-273370, JP-A No. 2006-85140, JP-A No. 2006-291191, JP-A No. 2007-2101, JP-A No. 2007-2102 and JP-A No. 2007-281523 are also suitably used for removing the colored curable composition of the invention.

The cleaning liquid is preferably alkylene glycol alkyl ether carboxylate or alkylene glycol monoalkyl ether.

These solvents may be used alone or in a combination of two or more kinds.

When solvents are mixed, a mixture of a solvent having a hydroxyl group and a solvent not having a hydroxyl group is preferred. The mass ratio of a solvent having a hydroxyl group and a solvent not having a hydroxyl group is from 1/99 to 99/1, preferably 10/90 to 90/10, more preferably 20/80 to 80/20. The mixture is particularly preferably a combination of propylene glycol monomethyl ether acetate (PGMEA) and propylene glycol monomethyl ether (PGME) mixed at a mass ratio of 60/40.

In order to improve permeability of the cleaning liquid with respect to the colored curable composition, a surfactant as mentioned above as the surfactant that may be included in the colored curable composition may be added.

The pre-baking may be performed, for example, by heating the support using a hot plate or an oven at 70° C. to 130° C. for about 0.5 minutes to 15 minutes.

The thickness of the colored curable composition layer may be arbitrarily selected depending on the purposes, but is typically in the range of 0.2 μm to 5.0 μm, more preferably 0.3 μm to 2.5 μm, and most preferably 0.3 μm to 1.5 μm. The thickness of the colored curable composition layer mentioned here is a film thickness measured after performing the pre-baking Next, the colored curable composition layer formed on the support is exposed to light or radiation through a mask (exposure step).

The light or radiation used for the exposure is preferably g-line, h-line, i-line, KrF or ArF, and particularly preferably i-line. When i-line is used for the exposure, the exposure dose is preferably from 100 mJ/cm$^2$ to 10,000 mJ/cm$^2$.

The exposed colored curable composition layer may be heated using a hot plate or an oven at 70° C. to 180° C. for 0.5 minutes to 15 minutes, prior to the subsequent development treatment.

Further, exposure may be performed while allowing a nitrogen gas to flow in a chamber so as to suppress coloration due to oxidation of the dye in the colored curable composition layer.

Subsequently, the exposed colored curable composition layer is developed using a developer (development step). In this way, a negative-type or positive-type colored pattern (resist pattern) may be formed.

The developer may be a combination of various organic solvents or an alkali aqueous solution, as long as it dissolves uncured portions (unexposed portions) and does not dissolve cured portions in the colored layer. When the developer is an alkali aqueous solution, it is preferable to adjust the alkali concentration such that the pH is from 11 to 13, more preferably from 11.5 to 12.5. Specifically, an alkali aqueous solution in which the concentration of tetramethylammonium hydroxide is adjusted to from 0.001% by mass to 10% by mass, preferably from 0.01% by mass to 5% by mass, may be used as a developer.

The development time is preferably in the range of from 30 seconds to 300 seconds, more preferably from 30 seconds to 120 seconds. The development temperature is preferably 20° C. to 40° C., and more preferably 23° C.

The development may be performed by using a paddle system, a shower system, a spray system or the like.

It is preferable to perform washing with water after the development with an alkali aqueous solution. The method for washing is appropriately selected according to the purpose, and one example is to perform a rinse treatment by supplying purified water in shower form while rotating a support such as a silicon wafer substrate at a rotation speed of 10 rpm to 500 rpm, from ejection nozzles positioned above the rotational center of the support.

Thereafter, the colored pattern may be optionally subjected to post-heating and/or post-exposure to accelerate the curing of the colored pattern (post-curing step).

—Ultraviolet Irradiation Step—

In the ultraviolet irradiation step, curing of a pattern by post-exposure is carried out.

Specifically, the pattern which has been subjected to a development treatment in the pattern-forming step is irradiated, for example, with ultraviolet light at an irradiation dose [mJ/cm$^2$] of at least 10 times the exposure dose [mJ/cm$^2$] in the exposure treatment prior to the development. By irradiating the developed pattern with ultraviolet light for a predetermined time period, between the development treatment in the pattern-forming step and the heating treatment to be described hereinafter, color transfer during the subsequent heating may be effectively suppressed and light fastness may be improved.

The light source for irradiating ultraviolet light may be, for example, an ultra high pressure mercury lamp, a high pressure mercury lamp, a low pressure mercury lamp, a deep ultraviolet lamp or the like. Among them, a light source that irradiates ultraviolet light including light at a wavelength of 275 nm or less, and may irradiate light in which an irradiation illuminance [mW/cm$^2$] of the light at a wavelength of 275 nm or less is 5% or more with respect to the integral irradiation illuminance of the light at all wavelengths in the ultraviolet light is preferable. By adjusting the irradiation illuminance of the light at a wavelength of 275 nm or less in the ultraviolet light to be 5% or more, the effect of suppressing color transfer between the colored pixels or the adjacent upper and lower layers, and the effect of improving light fastness may be further improved. From these viewpoints, it is preferable that the post-exposure by ultraviolet irradiation is performed by using a light source that differs from the light source used in the exposure performed at the pattern-forming step (a bright line such as i-line). Specifically, a high pressure mercury lamp, a low pressure mercury lamp or the like is suitably used. For the similar reasons, the irradiation illuminance [mW/cm²] of the light at a wavelength of 275 nm or less is preferably 7% or more with respect to the integral irradiation illuminance of the light at all wavelengths in the ultraviolet light. Further, it is desirable that the upper limit of the irradiation illuminance of the light at a wavelength of 275 nm or less is 25% or less.

The "integral irradiation illuminance" refers to the sum (area) of illuminances of respective wavelengths of light included in the irradiated light, which is expressed by the area of a curve drawn in a graph in which the illuminance at each spectral wavelength (radiation energy passing through a unit area/unit time; [mW/m²]) represents the vertical axis and the wavelength [nm] of the light represents the horizontal axis.

The UV irradiation is performed with an irradiation illuminance [mW/cm²] of at least 10 times the exposure dose of light used in the previous process of forming a pattern. When the illuminance in this process is less than 10 times, the effect of suppressing color transfer between the colored pixels or the adjacent upper and lower layers, or the effect of improving light fastness, may be insufficient.

In particular, the irradiation illuminance of UV light is preferably from 12 times to 200 times the exposure dose of light used in the previous process of forming a pattern, more preferably from 15 times to 100 times.

The integral irradiation illuminance of ultraviolet light used in the post-exposure is preferably 200 mW/cm² or more. If the integral irradiation illuminance is 200 mW/cm² or more, effects of suppressing color transfer between the colored pixels or between the adjacent upper and lower layers, and improving light fastness may be improved more effectively. The integral irradiation illuminance is preferably 250 mW/cm² to 2,000 mW/cm², more preferably 300 mW/cm² to 1,000 mW/cm².

Further, the post-heating is preferably carried out with a hot plate or an oven at a temperature of 100° C. to 300° C., and more preferably 150° C. to 250° C. The time for post-heating is preferably in the range of 30 seconds to 30,000 seconds, and more preferably 60 seconds to 1,000 seconds.

In the post-curing step, either the post-exposure or the post-heating may be carried out first. However, it is preferred to perform post-exposure prior to post-curing, since deformation of the pattern shape due to thermal sagging or hemming bottom, which may occur during the post-heating step, can be suppressed by promoting curing of the pattern by performing post-exposure.

The thus obtained colored pattern constitutes the colored pixels of the color filter.

A color filter having pixels of plural colors can be formed by performing a series of steps including a colored layer formation step, an exposure step and a development step (and optionally a post-curing step) for a number of times corresponding to the number of colors to be used in the color filter.

The color filter, obtained from the method of producing the same according to the invention, exhibits excellent light fastness.

Accordingly, the color filter of the present invention can be suitably used for liquid crystal display devices, organic EL display devices, solid-state image sensors such as CCD image sensors and CMOS image sensors, and a camera system in which the solid-state image sensor is used. In particular, the color filter of the invention is suitably used for CCD devices or CMOS devices having a high resolution such as more than one million pixels, in which a colored pattern needs to have a microscopic size and a small thickness, in addition to a favorable rectangular profile.

<Solid-State Image Sensor>

The solid-state image sensor of the present invention includes the color filter of the present invention. The color filter of the invention exhibits high heat fastness and light fastness. The solid-state image sensor including the color filter enables favorable color reproduction.

The configuration of the solid-state image sensor is not specifically limited as long as it includes the color filter of the present invention and functions as a solid-state image sensor, and an example thereof is a configuration including a support, plural photodiodes that constitute a light receiving area and transfer electrodes made of polysilicon or the like formed on the support, the color filter of the present invention formed thereon, and a microlens formed thereon.

Further, in the camera system having the color filter of the present invention, a camera lens or an IR cut film is preferably provided with a dichroic-coated cover glass, a microlens or the like, in view of the discoloration of the dye. Further, the material for the cover glass or the microlens desirably has an optical property of absorbing part or all of ultraviolet light of 400 nm or less. Moreover, in order to suppress discoloration due to oxidization of the dye, the camera system preferably has a structure in which oxygen permeability to the color filter is reduced. For example, part or the entire body of the camera system is preferably sealed with a nitrogen gas.

<Display Device>

The display device of the present invention includes the color filter of the present invention.

Examples of the display device of the present invention include, specifically, liquid crystal display devices (LCD), organic EL display devices, liquid crystal projectors, display devices for game machines, display devices for portable terminals such as mobile phones, display devices for digital cameras and display devices for car navigators. In particular, color display devices are particularly suitable.

The definition of a display device and the explanation of each display device are described, for example, in "Electronic Display Device (Akio Sasaki, Kogyo Chosakai Publishing Co., Ltd., 1990", "Display Device (Sumiaki Ibuki, Sangyo Tosho Publishing Co., Ltd., 1989)" and the like.

Liquid crystal display devices are described, for example, in "Next Generation Liquid Crystal Display Techniques (Tatsuo Uchida, Kogyo Chosakai Publishing Co., Ltd., 1994)". The liquid crystal display device to which the present invention may be applied is not particularly limited, and the present invention may be applied to various liquid crystal display devices described, for example, in "Next Generation Liquid Crystal Display Techniques".

The color filter of the present invention is particularly effectively used in a color TFT liquid crystal display device. Color TFT liquid crystal display devices are described, for example, in "Color TFT Liquid Crystal Display (Kyoritsu Shuppan Co., Ltd., 1996)". Further, the present invention may be applied to a liquid crystal display device with a wider view angle such as an in-plane switching (IPS) system or a multi-domain vertical alignment (MVA) system, or STN, TN, VA, OCS, FFS, R—OCB and the like.

The color filter of the present invention may also be applied to a COA (Color-filter On Array) system, which has high brightness and high definition. In the COA type liquid crystal display device, the color filter layer needs to satisfy the properties required for an interlayer dielectric film, such as a low dielectric constant and a resistance to a removing liquid, in addition to the ordinary requirements as mentioned above. It is thought that the transmissivity of the color filter with respect to ultraviolet laser used as an exposure light can be increased by selecting the method of performing exposure or selecting the color or the film thickness of the colored pixels. As a result, curability of the colored pixels is improved and the colored pixels can be formed without chipping, peeling or unevenness, thereby improving the resistance to a removing liquid of the colored layer provided directly or indirectly on the TFT substrate. For these reasons, the color filter of the present invention is useful for a COA type liquid crystal display device. In order to achieve a low dielectric constant, a resin coating may be provided on the color filter layer.

In the colored layer formed by the COA system, in order to electrically connect the ITO electrode disposed on the colored layer with the terminal of a driving substrate disposed under the colored layer, an electrically-conducting path such as a rectangular through hole having a side length of about 1 μm to 15 μm or a U-shaped depressed area needs to be formed. The size (i.e., the side length) of the electrically-conducting path is preferably 5 μm or less, and an electrically-conducting path having a size of 5 μm or less can be formed according to the present invention, These image display systems are described, for example, on page 43 of "EL, PDP, LCD Display—Latest Trends of Technology and Markets (Research Study Division of Toray Research Center, Inc., 2001)" and the like.

The liquid crystal display device of the present invention includes, in addition to the color filter of the present invention, various kinds of other members such as an electrode substrate, a polarization film, a phase difference film, a back light, a spacer, and a view angle compensation film. The color filter of the present invention can be applied to a liquid crystal display device including these known members.

Details of these members are described, for example, in "94 Market of Liquid Crystal Display Related Materials And Chemicals (Kentaro Shima, CMC Publishing Co., Ltd., 1994)" and "2003 Current State And Perspective Of Liquid Crystal Related Market (the second volume, Ryokichi Omote, Fuji Chimera Research Institute, Inc., 2003)".

Back lights are described, for example, in SID meeting Digest 1380 (2005) (A. Konno et al) and Monthly Display, 2005 December, pages 18-24 (Hiroyasu Shima) and pages 25-30 (Takaaki Yagi).

When the color filter of the present invention is used in a liquid crystal display device, a high contrast may be obtained when combined with a known three-wavelength cold-cathode tube. However, when combined with an LED light source of red, green and blue is used as a back light, a liquid crystal display device that exhibits high brightness, high color purity, and excellent color reproducibility can be achieved.

Moreover, when combined with an organic EL display device, an organic EL display device that exhibits a high contrast and favorable color reproducibility with high color purity can be provided.

EXAMPLES

Hereinbelow, examples of the method of synthesizing the dye compound represented by formula (5) are given, but the invention is not limited thereto.

The exemplary compound M-7 was synthesized according to a process of the following synthetic scheme.

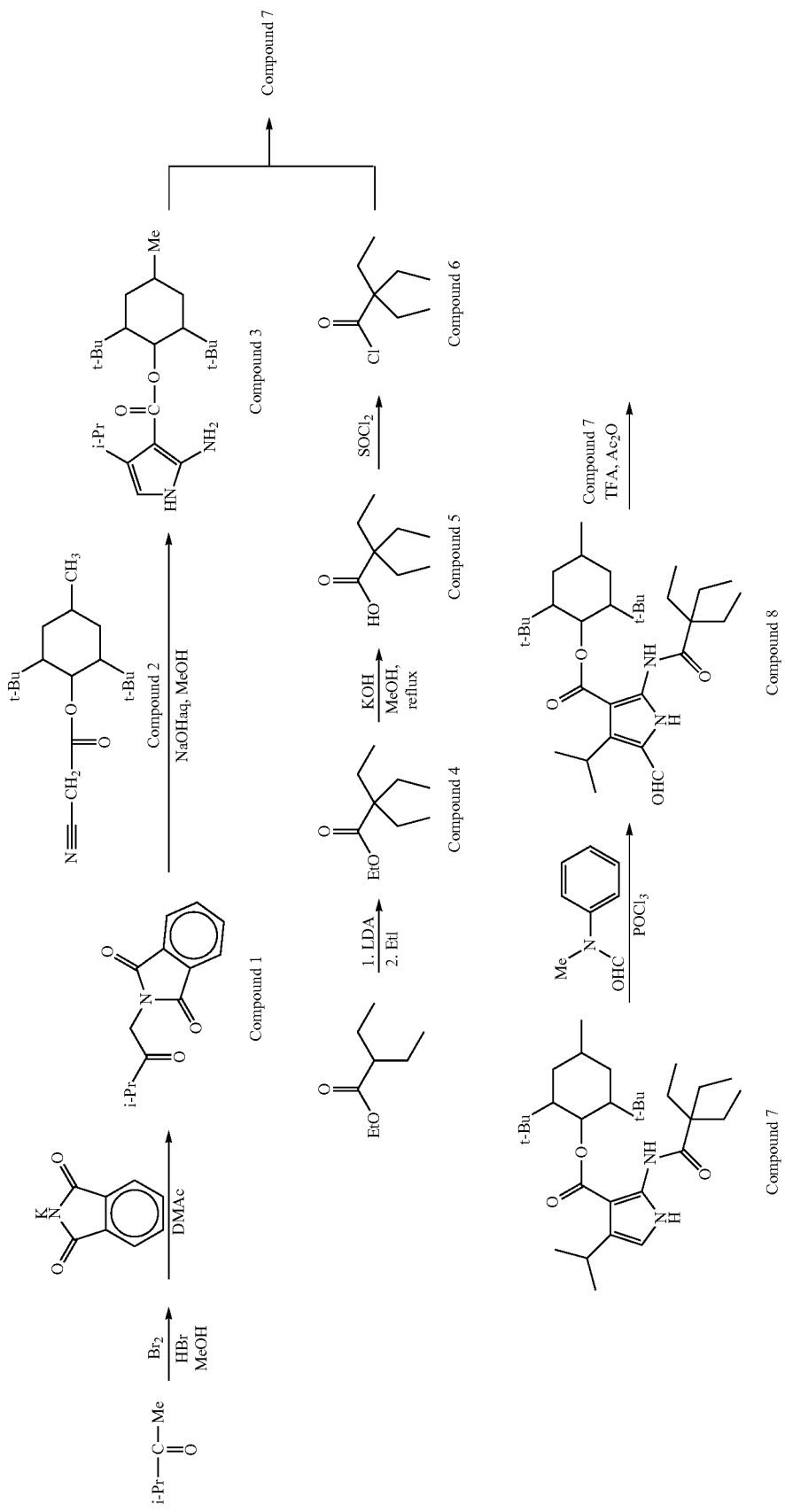

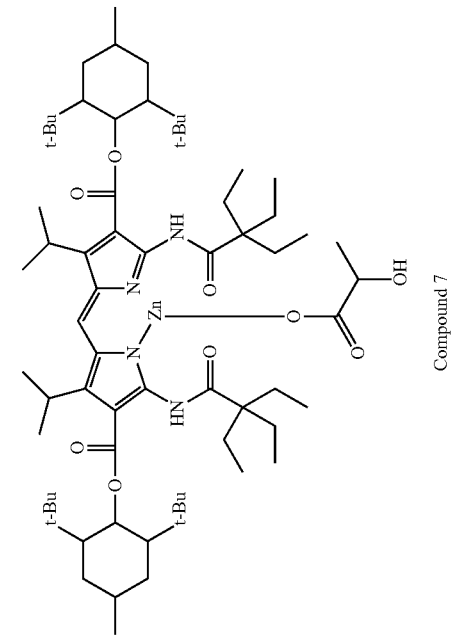
Compound 7
-continued
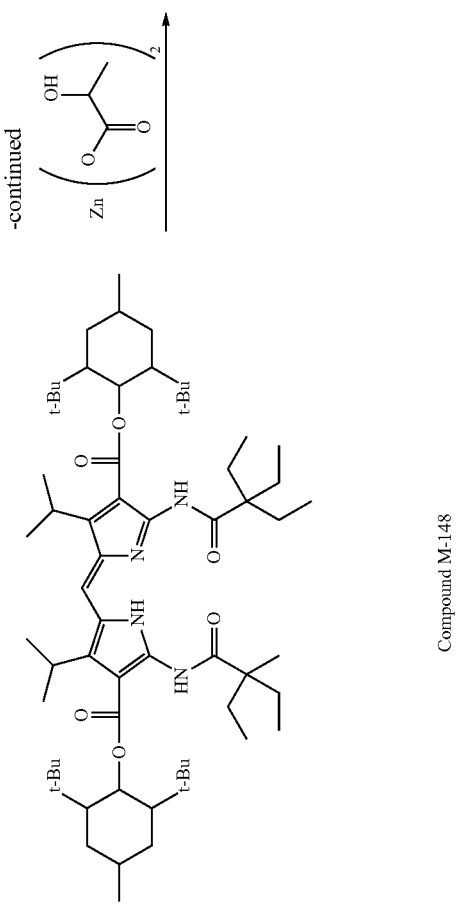
Compound M-148

<Synthesis of Compound 1>

206.4 g of isopropyl methyl ketone was stirred in methanol (1 L), 7 mL of hydrogen bromide acid (47 to 49% aqueous solution) were added thereto, and bromine was dropped over 3 hours at 30 to 34° C. The mixture was stirred for 30 minutes at 30° C. After neutralizing the mixture with an aqueous solution of sodium hydrogen carbonate (124 g) dissolved in 1.3 L of water, an aqueous solution of sodium chloride (400 g) dissolved in 1.3 L of water was added, and a reaction product in the form of a liquid state that had been separated was collected.

Separately from the above process, 222 g of potassium phthalimide were stirred in 800 mL of dimethyl acetamide (DMAc), and the reaction product collected in the above process was dropped under water cooling, and stirred at room temperature for 4 hours. Thereafter, water (720 mL) was added under water cooling and a precipitated crystal was collected by filtration. The crystal was suspended in 1.5 L of toluene to filter undissolved matters, and the filtrate was concentrated to obtain Compound 1 (100 g).

Compound 1: $^{1}$H-NMR, 400 MHz, δ (CDCl$_3$) ppm: 1.21-1.23 (6H, d), 2.74-2.79 (1H, m), 4.56 (2H, s), 7.72-7.74 (2H, d), 7.85-7.87 (2H, d).

<Synthesis of Compound 2>

Compound 2 was synthesized according to a method described in paragraph [0134] of JP-A No. 2008-292970.

<Synthesis of Compound 3>

Compound 2 (293 g) and Compound 1 (231 g) were stirred in methanol (1.4 L) under a nitrogen atmosphere. Sodium hydroxide (88 g) was dissolved in water (400 mL) and added dropwise to the mixture at room temperature. Thereafter, the mixture was refluxed for 8 hours. After cooling to room temperature, the precipitated crystal was collected by filtration, and washed with methanol (100 mL) to obtain Compound 9 (299 g).

Compound 3: $^{1}$H-NMR, 400 MHz, δ (CDCl$_3$) ppm: 0.88-0.95 (18H, s), 1.00-1.03 (3H, d), 1.17-1.19 (6H, d), 1.20-1.66 (7H, m), 3.38-3.43 (1H, m), 5.19-5.24 (2H, br), 5.95 (1H, br), 6.00 (1H, s), 7.39-7.45 (1H, br).

<Synthesis of Compound 4>

N,N-diisopropylamine (11.1 g) was stirred in dehydrated tetrahydrofuran (80 mL) under a nitrogen atmosphere, and a butyl lithium hexane solution (1.6 mol/L, 66 mL) was dropped over 10 minutes at −40° C. After stirring for 1 hour, ethyl 2-ethyl butyric acid (14.4 g) was added dropwise over 15 minutes at −20° C. and the temperature was raised to 0° C. After stirring for 1 hour, ethyl iodide (17.2 g) was added dropwise over 10 minutes. After the completion of the reaction, 40 mL of 1 M aqueous hydrochloric acid solution were added, extracted with ethyl acetate (100 mL), and washed with water (80 mL) and saturated brine (80 mL). The organic layer was dehydrated by using 15 g of magnesium sulfate and filtered. The filtrate was concentrated and dried, thereby obtaining Compound 4 (17.9 g).

Compound 4: $^{1}$H-NMR, 400 MHz, δ (CDCl$_3$) ppm: 0.76 (9H, t), 1.25 (3H, t), 1.57 (6H, q), 4.13 (2H, q)

<Synthesis of Compound 5>

Compound 4 (17.6 g) and potassium hydroxide (16.8 g) were dissolved in water (5 mL) and ethanol (30 mL), and refluxed for 8 hours while heating and stirring. Thereafter, water (20 mL) was added and concentrated hydrochloric acid was added until pH of the aqueous layer was about 1. The solution was extracted with ethyl acetate (100 mL) and washed with water (80 mL) and saturated brine (80 mL). The organic layer was dehydrated with 20 g of sodium sulfate, and filtered. The filtrate was concentrated and dried, thereby obtaining Compound 5 (13.0 g).

Compound 5: $^{1}$H-NMR, 400 MHz, δ (CDCl$_3$) ppm: 0.81 (9H, t), 1.60 (6H, q)

<Synthesis of Compound 6>

Compound 5 (2.6 g) was stirred in methylene chloride (3 mL), and thionyl chloride (2.6 g) were dropped at room temperature over 10 minutes. After one hour, the reaction solution was distilled at 8000 Pa and 40° C., there by obtaining Compound 6 (1.8 g).

Compound 6: $^{1}$H-NMR, 400 MHz, δ (CDCl$_3$) ppm: 0.85 (9H, t), 1.70 (6H, q)

<Synthesis of Compound N-1 (Compound 7 in the Above Scheme)>

Compound 3 (2.1 g) was stirred in 6 mL of dimethyl acetamide (DMAc) at room temperature, 0.99 g of Compound 6 were dropped thereto, and stirred for 3 hours at room temperature. The reaction solution was poured in 10 mL of ethyl acetate and 20 mL of water, washed with saturated sodium bicarbonate solution, water and saturated brine (15 mL each), dried over magnesium sulfate, and concentrated under reduced pressure. The concentrate was purified by column chromatography and concentrated under reduced pressure, thereby obtaining Compound 7 (2.2 g).

Compound N-1: $^{1}$H-NMR, 400 MHz, δ (CDCl$_3$) ppm: 0.82 (9H, t), 0.90 (18H, s), 1.02 (3H, d), 1.20-1.70 (19H, m), 3.47 (1H, quint), 6.02 (1H, s), 6.21 (1H, s), 10.59 (1H, s), 10.88 (1H, s)

<Synthesis of Compound O-1 (Compound 8 in the Above Scheme)>

N-methylformanilide (0.28 g) and acetonitrile (1.0 mL) were stirred at 0° C., and oxy phosphorus chloride (0.32 g) were dropped while maintaining the temperature at 5° C. or less. After stirring for one hour, Compound 7 (0.50 g) and acetonitrile (1.0 mL) were added, stirred for 30 minutes at room temperature, and stirred again for 3 hours at 40° C. The reaction solution was poured in 15 mL of water. The precipitated crystal was filtered and washed with 10 mL of water, thereby obtaining Compound 8 (0.40 g).

Compound O-1: $^{1}$H-NMR, 400 MHz, δ (CDCl$_3$) ppm: 0.84 (9H, t), 0.89 (18H, s), 1.03 (3H, d), 1.20-1.70 (7H, m), 1.43 (6H, d), 1.68 (6H, q), 4.13 (1H, quint), 6.04 (1H, s), 9.87 (1H, s), 10.95 (1H, s), 11.19 (1H, s)

<Synthesis of Compound M-148>

Compound N-1 (0.27 g), Compound O-1 (0.28 g) and acetic anhydride (5 mL) were stirred at room temperature, and trifluoroacetic acid (0.90 g) was dropped. After stirring at room temperature for 4 hours, 30 mL of water and 5 g of sodium hydrogen carbonate were stirred at room temperature, and the reaction solution was slowly poured thereto for neutralization. After stirring for 1 hour, the precipitated crystal was filtered and washed with 10 mL of water to obtain Compound M-148 (0.44 g). The maximum absorption wavelength in the absorption spectrum of M-148 in ethyl acetate was 519 nm, and the molar absorption coefficient was 46000.

Compound M-148: $^{1}$H-NMR, 400 MHz, δ (CDCl$_3$) ppm: 0.86 (18H, t), 0.87 (36H, s), 1.02 (6H, d), 1.20-1.73 (14H, m), 1.40 (12H, d), 1.69 (12H, q), 4.17 (2H, quint), 6.01 (2H, s), 7.50 (1H, s), 10.51 (2H, s)

<Synthesis of Exemplary Compound M-7>

Compound M-148 (0.42 g) and tetrahydrofuran (15 mL) were stirred at room temperature, a solution of zinc lactate trihydrate (0.122 g) dissolved in 5 mL of methanol was dropped thereto, and stirred for 2.5 hours. Thereafter, the solvent was distilled off from the reaction solution with an evaporator under reduced pressure condition of 0.013 MPa for 10 minutes at 35° C. To the resulting solution, water (10 mL) was added and the precipitated crystal was collected by filtration and dried to obtain Exemplary compound M-7 (0.21 g). The maximum absorption wavelength in the absorption spectrum of M-7 in ethyl acetate was 545 nm, and the molar absorption coefficient was 156000.

Exemplary compound M-7: $^1$H-NMR, 400 MHz, δ (CDCl$_3$) ppm: 0.83 (18H, t), 0.89 (36H, s), 1.02 (6H, d), 1.18-1.80 (41H, m), 4.01 (1H, q), 4.24 (2H, quint), 6.03 (2H, s), 7.76 (1H, s), 11.27 (2H, s)

Exemplary compound M-53 was synthesized according to the process of the following synthetic scheme.

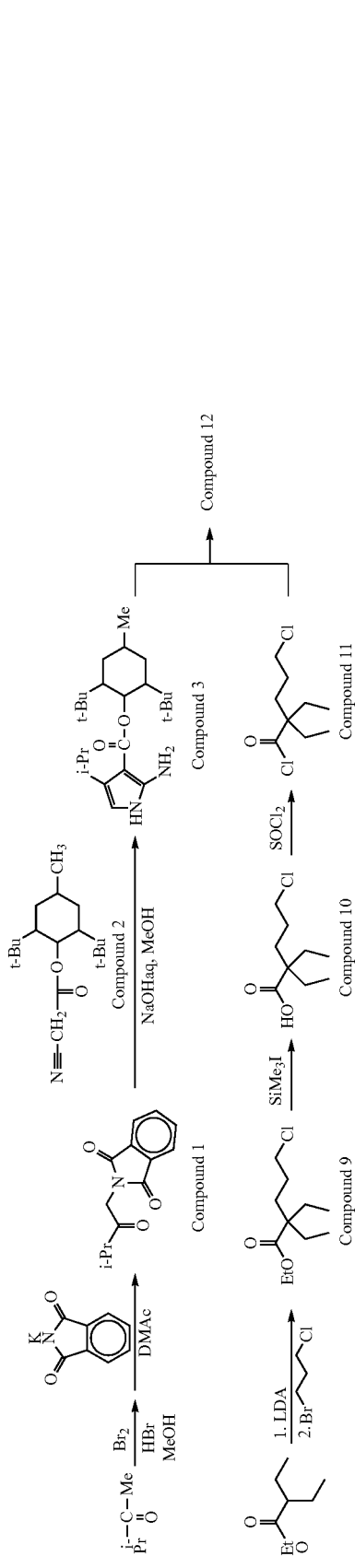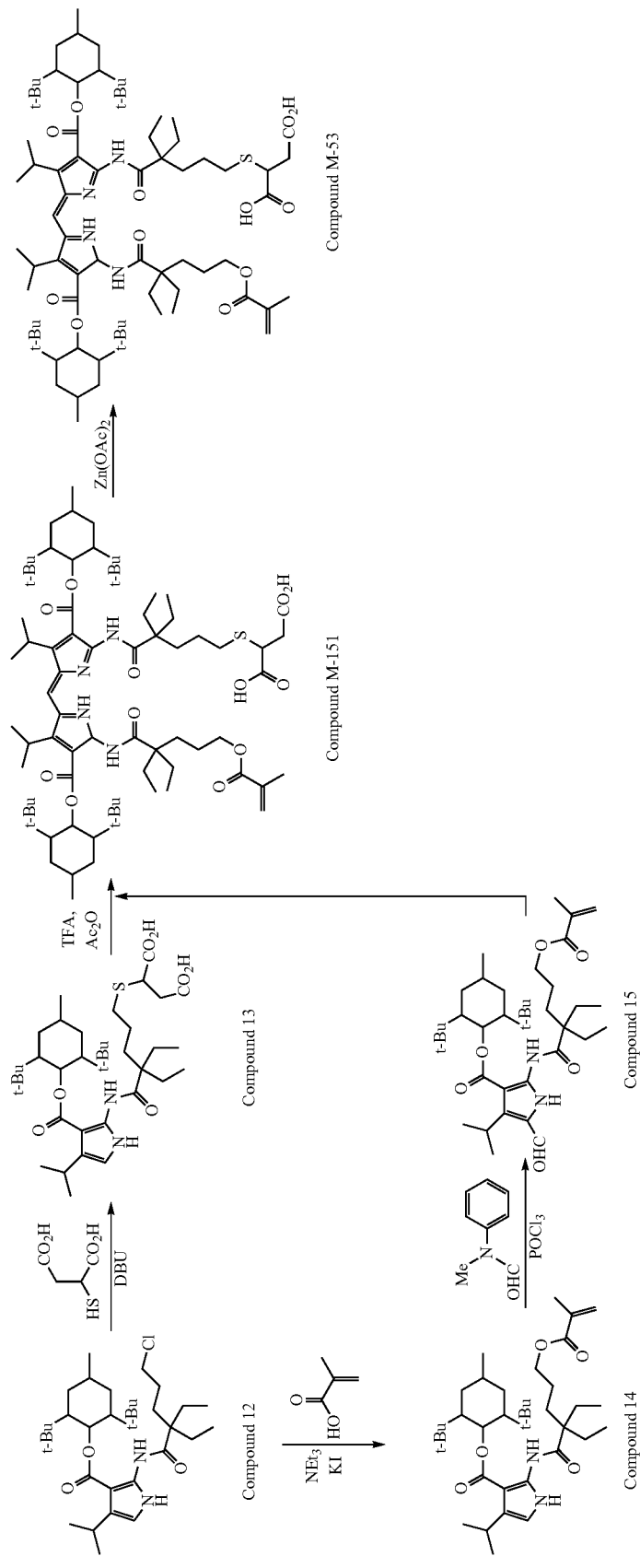

<Synthesis of Compound 9>

N,N-diisopropylamine (30 g) was stirred in dehydrated tetrahydrofuran (200 mL) under a nitrogen atmosphere, and a butyl lithium hexane solution (1.6 mol/L, 186 mL) was dropped over 20 minutes at −60° C. After stirring for 30 minutes at −40° C., ethyl 2-ethylbutyric acid (39 g) was added dropwise over 10 minutes. After stirring for 30 minutes, the temperature was lowered to −78° C. and 1-bromo-3-chloroprotane (47 g) was added dropwise over 15 minutes. The temperature was slowly raised to room temperature over 4 hours. After completion of the reaction, 1 M aqueous hydrochloric acid solution was added, extracted with ethyl acetate (400 mL), and washed with 1 M aqueous hydrochloric acid solution (200 mL), water (200 mL) and saturated brine (200 mL). The organic layer was dehydrated with 15 g of magnesium sulfate, and filtered. The filtrate was concentrated and the concentrate was purified by column chromatography and concentrated under reduced pressure to obtain Compound 9 (45 g).

Compound 9: $^1$H-NMR, 300 MHz, δ (CDCl$_3$) ppm: 0.79 (6H, t), 1.25 (3H, t), 1.57 (4H, q), 1.40-1.65 (4H, m), 3.52 (2H, t) 4.15 (2H, q)

<Synthesis of Compound 10>

To Compound 9 (17.2 g) in acetonitrile (80 mL), trimethyl silyl iodide (47 g) was added dropwise at room temperature over 10 minutes, and stirred for 60 hours at 80° C. Thereafter, the reaction solution was added dropwise to water (400 mL) over 30 minutes. The mixture was extracted with ethyl acetate (500 mL), washed with saturated sodium bicarbonate solution, water and saturated brine (300 mL each), dried over magnesium sulfate, and concentrated under reduced pressure. The concentrate was purified by column chromatography and concentrated under reduced pressure, thereby obtaining Compound 10 (8.6 g).

Compound 10: $^1$H-NMR, 300 MHz, δ (CDCl$_3$) ppm: 0.80 (6H, t), 1.57-1.82 (8H, m), 3.52 (2H, t)

<Synthesis of Compound 11>

Compound 10 (5.8 g) was dissolved in dichloromethane (10 mL), and thionyl chloride (7.1 g) was added dropwise over 10 minutes in an ice bath under a nitrogen atmosphere. After reacting for 2 hours at room temperature, the reaction solution was distilled (11 mmHg, 80° C.) to obtain Compound 11 (5.7 g).

Compound 11: $^1$H-NMR, 300 MHz, δ (CDCl$_3$) ppm: 0.87 (6H, t), 1.62-1.83 (8H, m), 3.55 (2H, t)

<Synthesis of Compound N-77 (Compound 12 in the Above Scheme)>

Compound 3 (194 g) was dissolved in acetonitrile (1900 mL) under a nitrogen atmosphere, triethylamine (63 g) was added at room temperature under stirring, and Compound 11 (120 g) was dropped over 10 minutes. Thereafter, the mixture was heated to 80° C. and stirred for 6 hours. After cooling to room temperature, water (950 mL) was added to the reaction solution, and the precipitate was collected by filtration. Then, methanol (950 mL) was added to the solid obtained, heated to 70° C., and stirred for suspension washing. After cooling to room temperature, Compound N-77 (260 g) was collected by filtration.

Compound N-77: $^1$H-NMR, 300 MHz, δ (CDCl$_3$) ppm: 0.86 (6H, t), 0.90 (18H, s), 1.02 (3H, d), 1.21 (6H, d), 1.25-1.73 (15H, m), 3.45 (1H, quint), 6.02 (1H, s), 6.20 (1H, s), 10.52 (1H, s), 10.94 (1H, s)

<Synthesis of Compound N-52 (Compound 13 in the Above Scheme)>

Compound 12 (18.0 g) and thiomalic acid (7.9 g) were added to dimethyl acetamide (70 mL) and stirred at room temperature. Diazabicyclo undecene (26.8 g) was added dropwise over 30 minutes while maintaining the temperature at 30° C. or less. After stirring for 12 hours at room temperature, the reaction solution was added dropwise to 400 mL of 0.5 N aqueous HCl in an ice bath over 30 minutes. The precipitated solid was collected by filtration, washed with water, stirred again in water (400 mL), and collected by filtration. The solid was dried under vacuum (45° C., 12 hours) to obtain Compound N-52 (18.4 g).

Compound N-52: $^1$H-NMR, 300 MHz, δ (CDCl$_3$) ppm: 0.86 (6H, t), 0.89 (18H, s), 1.02 (3H, d), 1.18-1.80 (21H, m), 2.61-2.80 (3H, m), 2.98 (1H, td), 3.46 (1H, quint), 3.64 (1H, dd), 6.01 (1H, s), 6.23 (1H, s), 10.61 (1H, s), 10.94 (1H, s)

<Synthesis of Compound N-61 (Compound 14 in the Above Scheme)>

Compound 12 (22.0 g), methacrylic acid (6.9 g), potassium iodide (6.6 g), and para methoxyphenol (11.5 mg) were added to dimethyl acetamide (50 mL), and stirred at room temperature. After adding triethylamine (10.1 g), the mixture was heated until the inside temperature was 85° C., and stirred at the same temperature for 4 hours. After completion of the reaction, ethyl acetate (75 mL) was added, washed with 1 N aqueous HCl, water and saturated sodium bicarbonate solution (50 mL each), and concentrated under reduced pressure. The resulting solid was recrystallized with acetonitrile (100 mL), thereby obtaining Compound N-61 (16.5 g).

Compound N-61: $^1$H-NMR, 300 MHz, δ (CDCl$_3$) ppm: 0.86 (6H, t), 0.89 (18H, s), 1.02 (3H, d), 1.27 (6H, d), 1.36 (4H, q), 1.73-1.93 (11H, m), 1.94 (3H, s), 3.46 (1H, quint), 4.14 (2H, t), 5.54 (1H, s), 6.02 (1H, s), 6.09 (1H, s), 6.22 (1H, s), 10.54 (1H, s), 10.94 (1H, s)

<Synthesis of Compound O-61 (Compound 15 in the Above Scheme)>

While stirring N-methylformanilide (4.3 g) in acetonitrile (25 mL) at 5° C., oxy phosphorus chloride (4.9 g) was dropped. After stirring for 1 hour, Compound 14 (16.0 g) and acetonitrile (10 mL) were added and the mixture was stirred for 30 minutes at room temperature, and stirred for 5 hours at 40° C. The reaction solution was poured in water (300 mL) and stirred for one hour. The precipitated solid was collected and recrystallized with acetone, thereby obtaining Compound O-61 (10.3 g).

Compound O-61: $^1$H-NMR, 300 MHz, δ (CDCl$_3$) ppm: 0.86 (6H, t), 0.89 (18H, s), 1.03 (3H, d), 1.26 (4H, q), 1.42 (6H, d), 1.57-1.94 (11H, m), 1.93 (3H, s), 4.11 (1H, quint), 4.14 (2H, t), 5.55 (1H, s), 6.04 (1H, s), 6.10 (1H, s), 9.87 (1H, s), 11.01 (1H, s), 11.16 (1H, s)

<Synthesis of Compound M-151>

Compound 13 (10.7 g), Compound 15 (10.1 g) and acetic anhydride (100 mL) were stirred at room temperature, and trifluoroacetic acid (8.6 g) was added dropwise. After stirring for 4 hours at room temperature, water (700 mL) and sodium hydrogen carbonate (170 g) were stirred at room temperature, and the reaction solution was slowly poured thereto for neutralization. After stirring for one hour, the precipitated crystal was collected by filtration and washed with water (300 mL). The resulting solid was dissolved again in tetrahydrofuran (50 mL) and water (50 mL) and triethylamine (10.5 g) were added to give a homogenous system, which was then stirred at room temperature for 10 minutes. The reaction solution was added with ethyl acetate (400 mL), washed twice with 1 N HCl aq and twice with water (400 mL), respectively, and concentrated under reduced pressure. The solid obtained was dried in air at 40° C. for 12 hours, thereby obtaining Compound M-151 (19.5 g). The maximum absorption wavelength in the absorption spectrum of M-151 in ethyl acetate was 519 nm, and the molar absorption coefficient was 44000.

Compound M-151: $^1$H-NMR, 300 MHz, δ (CDCl$_3$) ppm: 0.79-0.94 (48H, m), 1.02 (6H, d), 1.21-1.77 (22H, m), 1.42 (12H, d), 1.93 (3H, s), 2.59-2.78 (3H, m), 2.95 (1H, dd), 3.66 (1H, dd), 4.02-4.15 (4H, m), 5.54 (1H, s), 6.03 (2H, s), 6.11 (1H, s), 7.58 (1H, s), 10.75 (1H, s), 10.78 (1H, s)

<Synthesis of Exemplary Compound M-53>

Compound M-151 (19.0 g) was dissolved and stirred in THF (90 mL) at room temperature, and methanol (90 mL) was added thereto. Zinc acetate dihydrate (3.3 g) dissolved in methanol (90 mL) was added dropwise over 10 minutes, and stirred for 1 hour. Thereafter, the solvent (90 mL) was distilled off from the reaction solution with an evaporator under reduced pressure condition of 1000 Torr for 10 minutes at 30° C. The remaining solution was added dropwise to water (500 mL), the precipitated crystal was collected by filtration and dried to obtain Exemplary compound M-53 (19.0 g). The maximum absorption wavelength in the absorption spectrum of M-53 in ethyl acetate was 545 nm, and the molar absorption coefficient was 150000.

Exemplary compound M-53: $^1$H-NMR, 300 MHz, δ (CDCl$_3$) ppm: 0.81-0.99 (48H, m), 1.02 (6H, d), 1.15-1.90 (34H, m), 1.94 (3H, s), 2.58-2.80 (3H, m), 3.00 (1H, d), 3.46 (1H, br), 4.14-4.30 (4H, m), 5.53 (1H, s), 6.04 (1H, s), 6.06 (1H, s), 6.11 (1H, s), 7.80 (1H, s), 11.29 (1H, s), 11.45 (1H, s)

<Synthesis of Exemplary Compound I-12>

Exemplary compound I-12 was synthesized according to a process of the following synthetic scheme.

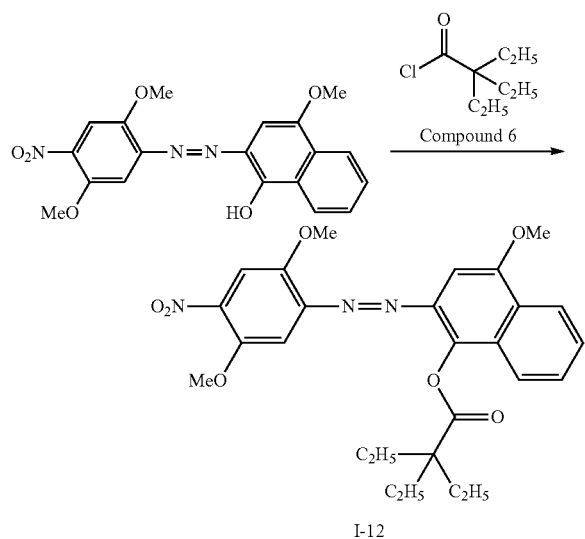

2-(2',5'-dimethoxy-4'-nitrophenylazo)-4-isopropoxy-1-naphthol (19.2 g) was synthesized according to the method described in Example 3 of U.S. Pat. No. 4,073,781, and the compound was dissolved in dimethyl acetamide. While stirring at room temperature, Compound 6 (9.0 g) was added and stirred for 3 hours at room temperature. The reaction solution was poured in ethyl acetate (100 mL) and water (200 mL), and washed with saturated sodium bicarbonate solution, water and saturated brine (150 mL each), dried over magnesium sulfate, and concentrated under reduced pressure. The concentrate was purified by column chromatography and concentrated under reduced pressure to obtain Compound I-12 (22.9 g). The maximum absorption wavelength in the absorption spectrum of I-12 in ethyl acetate was 420 nm, and the molar absorption coefficient was 45000.

Compound I-12: $^1$H-NMR, 300 MHz, δ (CDCl$_3$) ppm: 0.90 (9H, t), 1.52 (6H, q), 3.73 (6H, s), 3.86 (3H, s), 7.35-8.25 (7H, m)

<Synthesis of Exemplary Compound J-10>

Exemplary compound J-10 was synthesized according to the following process.

The synthesis was carried out by the method described in Journal of the Chemical Society, Perkin Transactions 2: Physical Organic Chemistry, 1987, p. 815-818. The maximum absorption wavelength in the absorption spectrum of J-10 in ethyl acetate was 795 nm, and the molar absorption coefficient was 39000.

Compound J-10: $^1$H-NMR, 300 MHz, δ (CDCl$_3$) ppm: 0.85 (9H, t), 1.15 (6H, t), 1.63 (6H, q), 3.45 (4H, q), 6.80-7.38 (7H, m)

The following are the compound data of Exemplary compounds M-20, M-22, M-93, M-45, M-46, M-78, M-146, N-4, N-15, N-17, N-36, N-37, N-69, O-37 and O-55. The dipyrromethene metal complexes and substituted pyrrole compounds are produced based on a reaction similar to the reaction for synthesis of M-7, M-53 and their intermediates, and may be obtained according to the same process with reference to the synthetic methods of the schemes described above.

Exemplary compound M-20: $^1$H-NMR, 400 MHz, δ (CDCl$_3$) ppm: 0.89-0.97 (48H, m), 1.02 (6H, d), 1.18-1.80 (47H, m), 2.31 (2H, m), 2.95 (4H, t), 6.09 (2H, s), 7.17 (1H, s), 11.38 (2H, s)

The maximum absorption wavelength in the absorption spectrum in ethyl acetate was 542 nm, and the molar absorption coefficient was 130000.

Exemplary compound M-22: $^1$H-NMR, 400 MHz, δ (CDCl$_3$) ppm: 0.89-0.97 (54H, m), 1.02 (6H, d), 1.18-1.80 (39H, m), 2.05 (2H, quint), 2.31 (2H, m), 2.80 (4H, d), 6.10 (2H, s), 7.18 (1H, s), 11.43 (2H, s)

The maximum absorption wavelength in the absorption spectrum in ethyl acetate was 543 nm, and the molar absorption coefficient was 130000.

Exemplary compound M-45: $^1$H-NMR, 400 MHz, δ (CDCl$_3$) ppm: 0.88-4.41 (94H, m), 5.54 (1H, s), 5.83 (1H, s), 6.03 (2H, s), 6.11 (1H, s), 6.39 (1H, s), 7.80 (1H, s), 11.40 (1H, s), 11.55 (1H, s)

The maximum absorption wavelength in the absorption spectrum in ethyl acetate was 546 nm, and the molar absorption coefficient was 140000.

Exemplary compound M-46: $^1$H-NMR, 400 MHz, δ (CDCl$_3$) ppm: 0.88-4.15 (80H, m), 6.02 (2H, s), 7.78 (1H, s), 11.33 (2H, s)

The maximum absorption wavelength in the absorption spectrum in ethyl acetate was 548 nm, and the molar absorption coefficient was 150000.

Exemplary compound M-78: $^1$H-NMR, 400 MHz, δ (CDCl$_3$) ppm: 0.81-0.99 (48H, m), 1.02 (6H, d), 1.15-1.90 (34H, m), 2.58-2.80 (3H, m), 3.00 (1H, d), 3.46 (1H, br), 3.53 (2H, t), 4.20-4.30 (2H, m), 6.04 (1H, s), 6.06 (1H, s), 7.80 (1H, s), 11.29 (1H, s), 11.45 (1H, s)

Exemplary compound M-93: $^1$H-NMR, 400 MHz, δ (DMSO-d$_6$) ppm: 0.88-4.41 (86H, m), 5.72-5.8 (2H, br), 5.82 (1H, s), 6.04 (1H, s), 6.88 (1H, s), 7.28-7.58 (10H, m), 10.41-10.49 (2H, br)

Exemplary compound M-146: $^1$H-NMR, 300 MHz, δ (CDCl$_3$) ppm: 0.79-1.02 (54H, m), 1.15-1.90 (38H, m), 1.94 (6H, s), 2.75-4.13 (10H, m), 5.58 (1H, s), 6.04 (1H, s), 6.10 (1H, s), 6.18 (1H, s), 7.76 (1H, s), 11.38 (2H, s)

The maximum absorption wavelength in the absorption spectrum in ethyl acetate was 545 nm, and the molar absorption coefficient was 130000.

Compound N-4: ¹H-NMR, 400 MHz, δ (CDCl₃) ppm: 0.82 (9H, t), 0.90 (18H, s), 0.98 (6H, d), 1.02 (3H, d), 1.20-1.70 (13H, m), 1.98 (1H, quint), 2.58 (2H, d), 6.02 (1H, s), 6.22 (1H, s), 10.43 (1H, s), 10.85 (1H, s)

Compound N-15: ¹H-NMR, 400 MHz, δ (CDCl₃) ppm: 0.90-0.98 (24H, m), 1.02 (3H, d), 1.20-1.70 (22H, m), 2.30 (1H, m), 2.71 (2H, d), 6.02 (1H, s), 6.21 (1H, s), 10.48 (1H, s), 10.89 (1H, s)

Compound N-17: ¹H-NMR, 400 MHz, δ (CDCl₃) ppm: 0.90-0.98 (27H, m), 1.02 (3H, d), 1.20-1.70 (18H, m), 1.99 (1H, quint), 2.30 (1H, m), 2.56 (2H, d), 6.02 (1H, s), 6.21 (1H, s), 10.53 (1H, s), 10.95 (1H, s)

Compound N-36: ¹H-NMR, 400 MHz, δ (CDCl₃) ppm: 0.83 (9H, t), 0.90 (18H, s), 1.21 (6H, d), 1.20-1.90 (13H, m), 2.80 (1H, dd), 3.02 (1H, dd), 3.39 (1H, quint), 3.48 (1H, d), 3.67 (1H, d), 3.90 (1H, dd), 4.08 (1H, d), 6.05 (1H, s), 6.22 (1H, s), 10.60 (1H, s), 10.95 (1H, s)

Compound N-37: ¹H-NMR, 400 MHz, δ (CDCl₃) ppm: 0.82 (9H, t), 0.90 (18H, s), 1.22 (6H, d), 1.20-1.93 (13H, m), 1.95 (3H, s), 3.40 (1H, quint), 4.03 (2H, d), 5.59 (1H, s), 6.10 (1H, s), 6.18 (1H, s), 6.21 (1H, s), 10.58 (1H, s), 10.95 (1H, s)

Compound N-69: ¹H-NMR, 400 MHz, δ (CDCl₃) ppm: 0.77-1.68 (38H, m), 1.91 (3H, s), 2.92 (2H, t), 4.56 (2H, t), 5.52 (1H, s), 5.89 (1H, s), 6.08 (1H, s), 6.33 (1H, s), 7.27-7.38 (5H, m), 10.80 (1H, br), 11.40 (1H, br)

Compound O-37: ¹H-NMR, 400 MHz, δ (CDCl₃) ppm: 0.83 (9H, t), 0.90 (18H, s), 1.21 (6H, d), 1.20-1.93 (13H, m), 1.95 (3H, s), 3.98-4.15 (3H, m), 5.59 (1H, s), 6.10 (1H, s), 6.18 (1H, s), 9.89 (1H, s), 10.95 (1H, s), 11.20 (1H, s)

Compound O-55: ¹H-NMR, 400 MHz, δ (CDCl₃) ppm: 0.75-1.69 (38H, m), 2.55-3.80 (3H, t), 5.91 (1H, s), 7.28-7.37 (5H, m), 9.06 (1H, s), 10.94 (1H, br), 11.15 (1H, br)

The following is an exemplary method for synthesis of the dye multimer represented by formula (1), but the invention is not limited to them.

<Synthesis of Exemplary Compound P51>

Propylene glycol monomethyl ether acetate (PGMEA) (5.21 g) was stirred at 80° C., and a solution in which Exemplary compound M-53 (7.0 g), methacrylic acid (0.45 g), and dodecane thiol (0.17 g), and dimethyl 2,2'-azobis(2-methylpropionate) (0.096 g) were dissolved in PGMEA (12.2 g) were added dropwise over 4 hours. Two hours after the completion of the dropwise addition, a solution of dimethyl 2,2'-azobis(2-methylpropionate) (0.029 g) and dodecane thiol (0.051 g) dissolved in PGMEA (0.35 g) was added and further stirred at 80° C. for 2 hours. To the reaction solution, PGMEA (175 mL) and methanol (200 mL) were added and, while stirring in acetonitrile (800 mL), the reaction solution was added dropwise. The precipitated crystal was collected by filtration and dried under reduced pressure, thereby obtaining Exemplary compound P51 (3.99 g). The Exemplary compound P51 had a weight average molecular weight (Mw) of 7000 and an acid value of 185 mgKOH/g.

The structure of Exemplary compound P51 was determined by ¹H-NMR. Specifically, it was confirmed by the disappearance of a peak at 5.53, 6.11, corresponding to the polymerizable groups of Compound M-53, and introduction of methacrylic acid by acid value measurement.

<Synthesis of Exemplary Compound P54>

Exemplary compound M-53 (1.67 g), methacrylic acid (0.21 g), and dodecane thiol (0.076 g) were dissolved in PGMEA (10.7 g). While stirring at 85° C., a solution of Exemplary compound M-53 (3.33 g), methacrylic acid (0.43 g), dodecane thiol (0.15 g), dimethyl-2,2'-azobis(2-methylpropionate) (0.52 g) dissolved in PGMEA (21.3 g) was added dropwise over 3 hours. Four hours after the commencement of the dropwise addition, dimethyl 2,2'-azobis(2-methylpropionate) (0.047 g) was further added and stirred at 85° C. for 2 hours. To the reaction solution, PGMEA (115 mL) and methanol (153 mL) were added and, while stirring acetonitrile (614 mL), the reaction solution was dropped thereto. The precipitated crystal was collected by filtration and dried under reduced pressure, thereby obtaining Exemplary compound P54 (1.75 g). The Exemplary compound P54 had a weight average molecular weight (Mw) of 8000 and an acid value of 112 mgKOH/g.

The structure of Exemplary compound P54 was determined by ¹H-NMR. Specifically, it was confirmed by the disappearance of a peak at 5.53, 6.11, corresponding to the polymerizable groups of Compound M-53, and introduction of methacrylic acid by acid value measurement.

<Synthesis of Exemplary Compound P101>

A solution of Exemplary compound P51 (5.0 g), glycidyl methacrylate (0.47 g), and p-methoxy phenol (5.5 mg) dissolved in PGMEA (31.0 g) was heated at 100° C. for 5 hours while stirring. Next, while stirring acetonitrile (350 mL), the reaction solution was added dropwise. The precipitated crystal was collected by filtration and dried under reduced pressure, thereby obtaining Exemplary compound P101 (3.59 g). The Exemplary compound P101 had a weight average molecular weight (Mw) of 8000 and an acid value of 110 mgKOH/g.

The structure of Exemplary compound P101 was determined by ¹H-NM. Specifically, it was confirmed by the disappearance of epoxy moiety of glycidyl methacrylate and a decrease in acid value of glycidyl methacrylate by acid value measurement. Further, the dye compound having a polymerizable group may include a dye compound before the polymerizable group is introduced thereto.

P-61

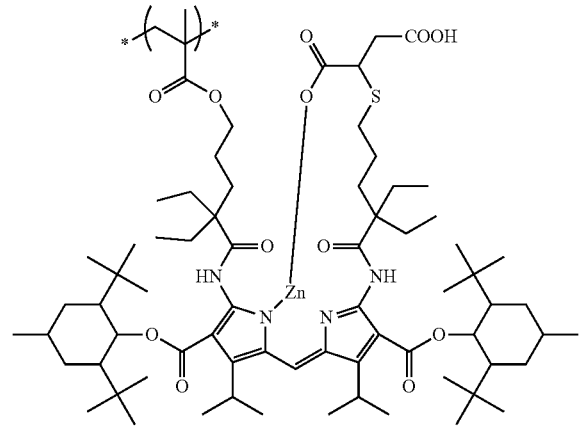

-continued

P-101

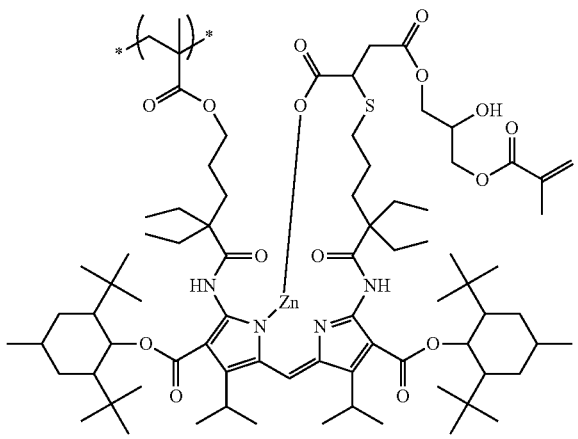

The following is an exemplary method for synthesis of the dye multimer represented by formula (B), but the invention is not limited to them.

<Synthesis of Exemplary Compound S-50>

While stirring PGMEA (5.21 g) at 80° C. for 4 hours, a solution of Exemplary compound M-78 (7.0 g), methacrylic acid (0.90 g), dodecane thiol (0.34 g), and dimethyl 2,2'-azobis(2-methylpropionate) (0.192 g) dissolved in PGMEA (12.2 g) was added dropwise. Two hours after the completion of the dropwise addition, a solution of dimethyl 2,2'-azobis (2-methylpropionate) (0.058 g) and dodecane thiol (0.102 g) dissolved in PGMEA (0.35 g) was added, and further stirred at 80° C. for 2 hours. To the reaction solution, PGMEA (175 mL) and methanol (200 mL) were added and, while stirring in acetonitrile (800 mL), the reaction solution was dropped thereto. The precipitated crystal was collected by filtration and dried under reduced pressure, thereby obtaining Exemplary compound S-50 (5.0 g). The Exemplary compound S-50 had a weight average molecular weight (Mw) of 7600 and an acid value of 190 mgKOH/g.

The structure of Exemplary compound S-50 was confirmed by $^1$H-NMR. Specifically, it was confirmed by the disappearance of a peak in the region of from 5.33 to 6.11, corresponding to the polymerizable group of Compound M-78, and introduction of methacrylic acid by the acid value measurement.

Hereinbelow, examples of the method for synthesis of the dye multimer represented by formula (C) are given, but the invention is not limited to them.

<Synthesis of Exemplary Compound S-52>

Exemplary compound M-45 (11.5 g) and commercially available diisocyanate Q-1 (2.5 g) were mixed in N-methylpyrrolidone (100 mL) and stirred at 40° C. for 4 hours. Methanol (500 mL) was added to the reaction solution. While stirring acetonitrile (800 mL), the reaction solution was added dropwise. The precipitated crystal was collected by filtration, and dried under reduced pressure to obtain Exemplary compound S-52 (7.6 g). The Exemplary compound S-52 had a weight average molecular weight (Mw) of 5400.

The structure of Exemplary compound S-52 was confirmed by $^1$H-NMR, i.e., by a shift of a methylene peak at a position of the alcohol in Compound M-45.

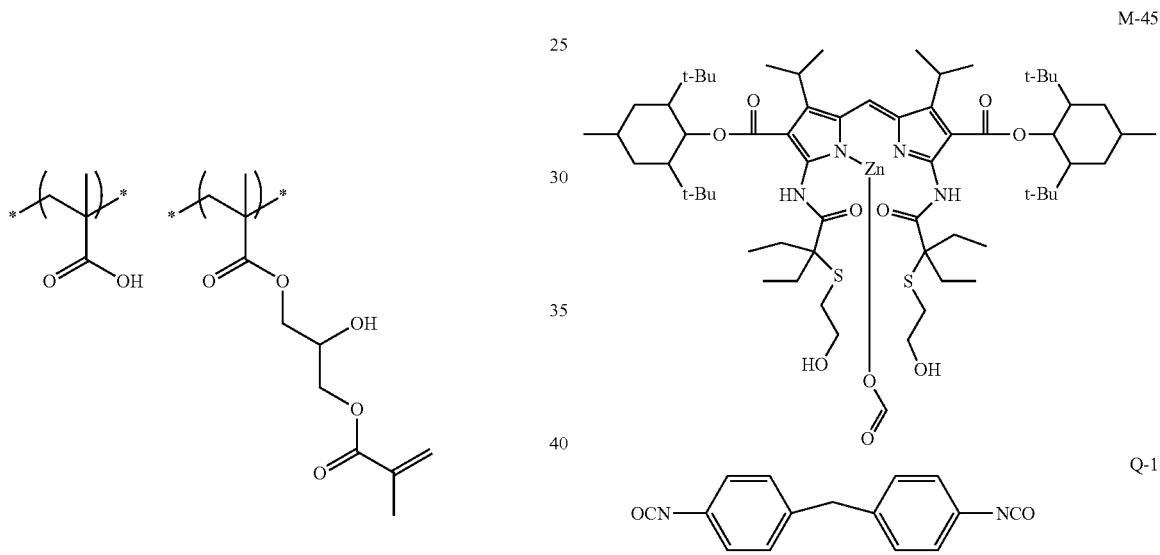

The following is an exemplary method for synthesis of the dye multimer represented by formula (D), but the invention is not limited to them.

<Synthesis of Exemplary Compound S-58>

Exemplary compound M-46 (11.7 g), commercially available tetramercapto body Q-2 (1.1 g), and diazabicyclo undecene (DBU, 7.5 g) were mixed in N-methylpyrrolidone (100 mL) and stirred at 40° C. for 4 hours. Methanol (500 mL) was added to the reaction solution. While stirring acetonitrile (800 mL), the reaction solution was added dropwise. The precipitated crystal was collected by filtration, and dried under reduced pressure to obtain Exemplary compound S-58 (4.2 g).

The structure of Exemplary compound S-58 was confirmed by $^1$H-NMR.

Exemplary compound S-58: $^1$H-NMR, 400 MHz, δ (DMSO-$d_6$) ppm: 0.88 (192H, s), 1.08-1.9 (176H, m), 2.1 (36H, s), 2.3-3.4 (36H, m), 3.17 (4H, bs), 3.4-3.65 (4H, M), 4.28 (8H, bs), 6.03 (4H, s), 7.26 (4H, s), 7.53 (4H, s), 10.59-10.63 (8H, br).

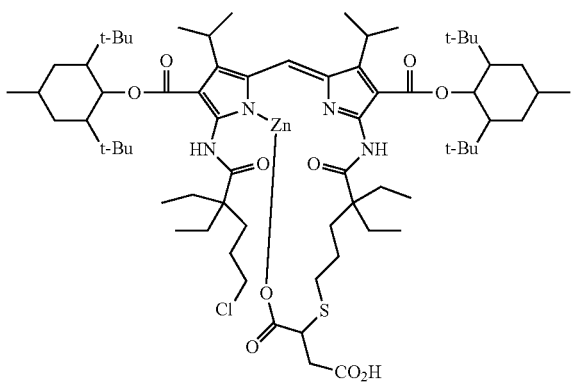

M-46

Q-2

Heat Fastness of Dye Compound

Example 1-1

Heat fastness of the dye compound obtained in the invention was evaluated in the following manner. The evaluation results are given in Table 9 below.

Exemplary compound M-7 (25.0 mg) as a dye compound was dissolved in 225 mg of tetrahydrofuran (THF), and the solution was placed in an aluminum cup. The aluminum cup was placed on a hot plate heated at 100° C. After heating for 2 minutes to evaporate the THF, the aluminum cup was placed on a hot plate heated at 260° C. for 3 minutes. Thereafter, the remaining solid was dissolved in ethyl acetate (200 mL). The change in the absorbance at a maximum absorption wavelength (i.e., residual color ratio) before and after the heating at 260° C. was measured with a spectrophotometer (CARY5, trade name, manufactured by Varian Inc.) and a color difference ($\Delta E^*ab$ value) before and after the heating was measured with a colorimeter (MCPD-1000, trade name, manufactured by Otsuka Electronics Co., Ltd.), and the results were used to evaluate the heat fastness.

The higher the residual color ratio is, and the lower the $\Delta E^*ab$ value is, the more favorable the heat fastness is. The residual color ratio is preferably 70% or more, more preferably 80% or more, further preferably 90% or more. The $\Delta E^*ab$ value is preferably 15 or less, more preferably 10 or less, further preferably 5 or less.

Examples 1-2 to 1-10, Comparative Examples 1-1 to 1-5

Evaluation was carried out in the same manner as Example 1-1, except that Exemplary compound M-7 was changed to the same amount of the dye compound described in Table 9. The evaluation results are given in Table 9. The structures of the comparative dyes 1 to 3, 7 and 8 in Table 9 are given below.

Synthesis of comparative dyes 1 to 3 employs a similar reaction to that in the synthesis of M-7 or intermediates thereof, and similar operations can be applied. Synthesis of comparative dye 7 employs a similar reaction to that in the synthesis of I-12, and similar operations can be applied. Synthesis of comparative dye 8 was carried out by a method similar to that described on pages 815 to 818 of Journal of the Chemical Society, Perkin Transactions 2: Physical Organic Chemistry, 1987.

In Table 9, the substituent group indicates a substituent group corresponding to $G^2$ in formula (5).

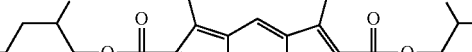

Comparative Dye 1

Comparative Dye 2

Comparative Dye 3

Comparative Dye 7

-continued
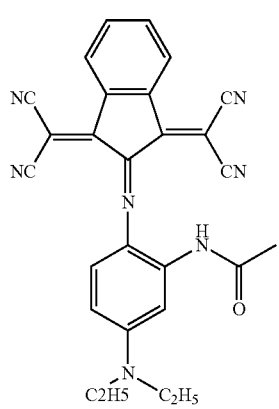
Comparative Dye 8
TABLE 9
| | Dye Compound | −Es' of Substituent | Structure of Substituent | Residual Color Ratio | ΔE*ab |
|---|---|---|---|---|---|
| Example 1-1 | M-7 | 5.29 | Et, Et, Et | 86 | 5.8 |
| Example 1-2 | M-16 | 1.63 | t-Bu | 71 | 14.8 |
| Example 1-3 | M-25 | 2.38 | (branched alkyl) | 75 | 12.2 |
| Example 1-4 | M-28 | 3.21 | t-Bu | 82 | 10.1 |
| Example 1-5 | M-31 | 5.01 | (branched alkyl) | 88 | 5.1 |
| Example 1-6 | M-1 | 5.29 | Et, Et, Et | 91 | 4.6 |
| Example 1-7 | M-32 | 6.73 | (branched alkyl) | 95 | 2.5 |
| Example 1-8 | M-148 | 5.29 | Et, Et, Et | 96 | 2.7 |

TABLE 9-continued

| | Dye Compound | −Es' of Substituent | Structure of Substituent | Residual Color Ratio | ΔE*ab |
|---|---|---|---|---|---|
| Example 1-9 | I-12 | 5.29 | 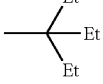 Et, Et, Et | 98 | 1.4 |
| Example 1-10 | J-10 | 5.29 | 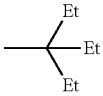 Et, Et, Et | 94 | 1.9 |
| Comp. Ex. 1-1 | Comparative dye 1 | 0.00 | —Me | 32 | 75.2 |
| Comp. Ex. 1-2 | Comparative dye 2 | 1.43 | —t-Bu | 70 | 18.5 |
| Comp. Ex. 1-3 | Comparative dye 3 | 0.00 | —Me | 75 | 15.2 |
| Comp. Ex. 1-4 | Comparative dye 7 | 0.00 | —Me | 55 | 40.5 |
| Comp. Ex. 1-5 | Comparative dye 8 | 0 | —Me | 78 | 16.8 |

<Alkali Resistance Evaluation of the Dye Compounds>

Example 2-1

The alkali resistance of the dye compound was evaluated in the following manner. The evaluation results are given in Table 10 below.

Exemplary compound M-7 (50.0 mg) was dissolved as a dye compound in 1 mL of ethyl acetate, and 1 mL of 1 M NaOH was added thereto and stirred for 5 hours at 30° C. After extracting with ethyl acetate and adjusting the total amount to be 100 mL, the resulting solution was diluted with ethyl acetate by 5 times in volume (solution 1).

Separately, exemplary compound M-7 (50 mg) was dissolved in ethyl acetate so that the total amount was 100 mL, and further diluted with ethyl acetate by 5 times in volume (solution 2).

The difference between the absorbance at a maximum absorption wavelength (i.e., residual color ratio) of solution 1 and the absorbance at a maximum absorption wavelength of solution 2 was measured with a spectrophotometer (CARY5, trade name, manufactured by Varian Inc.), and the color difference (ΔE*ab value) between solution 1 and solution 2 was measured with a colorimeter (MCPD-1000, trade name, manufactured by Otsuka Electronics Co., Ltd.), respectively. The results were used to evaluate the alkali resistance.

The higher the difference in residual color ratio is, and the lower the ΔE*ab value is, the more favorable the alkali resistance is. The residual color ratio is preferably 70% or more, more preferably 80% or more, further preferably 90% or more. Further, the ΔE*ab value is preferably 15 or less, more preferably 10 or less, further preferably 5 or less.

Examples 2-2 to 2-10, Comparative Examples 2-1 to 2-5

The evaluation was carried out in the same manner as Example 2-1, except that Exemplary compound M-7 was changed to the same amount of dye compounds described in Table 10. The evaluation results are given in Table 10. The comparative dyes 1 to 3, 7 and 8 in Table 10 are the same as above.

In Table 10, the substituent group indicates a substituent group corresponding to $G^2$ in formula (5).

TABLE 10

| | Dye Compound | −Es' of Substituent | Structure of Substituent | Residual ColorRatio | ΔE*ab |
|---|---|---|---|---|---|
| Example 2-1 | M-7 | 5.29 | 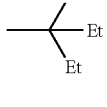 Et, Et, Et | 86 | 4.2 |
| Example 2-2 | M-16 | 1.63 | 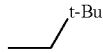 t-Bu | 70 | 14.9 |
| Example 2-3 | M-25 | 2.38 | 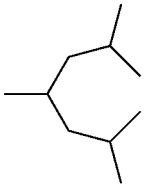 | 79 | 12.2 |
| Example 2-4 | M-28 | 3.21 | 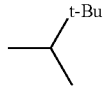 t-Bu | 82 | 10.1 |

TABLE 10-continued

| | Dye Compound | −Es' of Substituent | Structure of Substituent | Residual ColorRatio | ΔE*ab |
|---|---|---|---|---|---|
| Example 2-5 | M-31 | 5.01 | 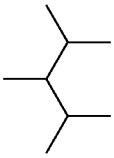 | 88 | 5.1 |
| Example 2-6 | M-1 | 5.29 | 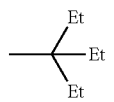 | 87 | 4.6 |
| Example 2-7 | M-32 | 6.73 | 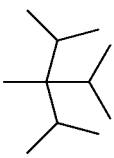 | 90 | 2.9 |
| Example 2-8 | M-148 | 5.29 | 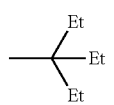 | 80 | 5.9 |
| Example 2-9 | I-12 | 5.29 | 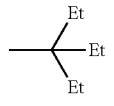 | 81 | 6.3 |
| Example 2-10 | J-10 | 5.29 | 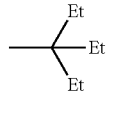 | 86 | 4.8 |
| Comp. Ex. 2-1 | Comparative dye 1 | 0.00 | —Me | 40 | 52.2 |
| Comp. Ex. 2-2 | Comparative dye 2 | 1.43 | —t-Bu | 65 | 20.5 |
| Comp. Ex. 2-3 | Comparative dye 3 | 0.00 | —Me | 55 | 46.8 |
| Comp. Ex. 2-4 | Comparative dye 7 | 0.00 | —Me | 48 | 68.4 |
| Comp. Ex. 2-5 | Comparative dye 8 | 0 | —Me | 37 | 58.1 |

As shown in Tables 9 and 10, the Examples, in which the dye compound of the invention was used, exhibit excellent heat fastness and excellent alkali resistance.

<Heat Resistance Evaluation of a Colored Curable Composition>

A colored curable composition was prepared by using the dye compound obtained in the invention, and a color filter was produced. Specific explanations are given below. Unless specifically described otherwise, "part" and "%" are based on mass.

Example 3-1

(1) Preparation of Resist Solution a (Negative Type)

The following components were mixed and dissolved to prepare Resist solution A.

Propylene glycol monomethyl ether acetate (PGMEA) 5.20 parts

Cyclohexanone (CyH): 52.60 parts

Binder: 30.50 parts (benzyl methacrylate/methacrylic acid/2-hydroxyethyl methacrylate copolymer, molar ratio=60:20:20, weight average molecular weight: 30200 (in terms of polystyrene), 41% cyclohexanone solution)

Dipentaerythritol hexaacrylate: 10.20 parts

Polymerization inhibitor (p-methoxy phenol): 0.006 parts

Fluorine-based surfactant (trade name: F-475, manufactured by DIC Corporation): 0.80 parts Photopolymerization initiator: 4-benzoxolan-2,6-bis (trichloromethyl)-s-triazine (trade name: TAZ-107, manufactured by Midori Kagaku Co., Ltd.): 0.58 parts (2) Preparation of Glass Substrate with Undercoat Layer A glass substrate (trade name: CORNING 1737, manufactured by Corning Incorporated) was subjected to ultrasonic cleaning with 0.5% aqueous NaOH, and subsequently water washing and baking (200° C./20 min) for dehydration. Next, the resist solution A obtained in process (1) was applied onto a cleaned glass substrate with a spin coater to give a film thickness of 2 µm. The coated layer obtained was heated at 220° C. for 1 hour and dried, whereby a glass substrate with an undercoat layer was prepared.

(3) Preparation of Colored Curable Composition

First, C. I. Pigment Blue 15:6 dispersion was prepared as follows.

A mixture liquid containing 11.5 parts of C. I. Pigment Blue 15:6 (average primary particle diameter: 55 nm), 3.5 parts of a dispersant (BYK-161, trade name, manufactured by BYK Japan), and 85 parts of PGMEA was mixed and dispersed for 3 hours with a bead mill (zirconia beads, diameter of 0.3 mm). Subsequently, the mixture was dispersed with a high-pressure dispersing machine (NANO-3000-10, trade name, manufactured by Beryu Co., Ltd.) equipped with a depressurization system under a pressure of 2000 kg/cm³ and at a flow rate of 500 g/min. This dispersing treatment was repeated 10 times to obtain a pigment dispersion. The average primary particle diameter of the pigment was measured by a dynamic light scattering method (trade name: NANOTRAC UPA-EX150, manufactured by Nikkiso Co., Ltd.). The result was 25 nm.

Thereafter, by mixing the following components, a colored curable composition was obtained.

CyH (cyclohexanone): 1.133 parts
Benzyl methacrylate/methacrylic acid copolymer (20% CyH solution): 1.009 parts (molar ratio=70:30, weight average molecular weight: 30000)
Fluorine-based surfactant (trade name: F-475, 1% CyH solution, manufactured by DIC Corporation): 0.125 parts
Oxime photopolymerization initiator (the following structure): 0.087 parts
Dye compound (Exemplary compound M-7): 0.183 parts
C. I. Pigment Blue 15:6 dispersion: 2.418 parts (solid content concentration: 17.70%, pigment concentration: 11.80%)
Glycerol propoxylate (1% CyH solution): 0.048 parts
Dipentaerythritol hexaacrylate: 0.225 parts

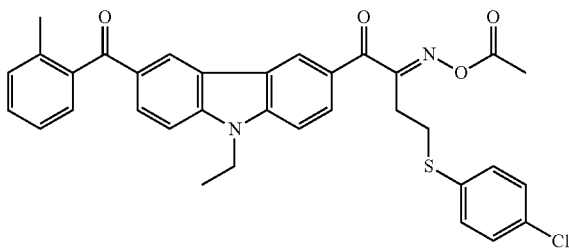 [SMILES: CCn1c2ccc(C(=O)/C(CCSc3ccc(Cl)cc3)=N/OC(C)=O)cc2c2cc(C(=O)c3ccccc3C)ccc21]

(4) Exposure and Development of Colored Curable Composition (Image Formation)

The colored curable composition obtained in process (3) was applied onto the undercoat layer of the glass substrate obtained in process (2) by a spin coater to give a film thickness of 0.6 μm. It was pre-baked at 100° C. for 120 seconds.

Thereafter, by using a developing apparatus (UX3100-SR, trade name, manufactured by Ushio Inc.), the coating layer was exposed at a wavelength of 365 nm and an exposure amount of 200 mJ/cm² through a mask with a line width of 2 μm. After the exposure, development was carried out at 25° C. for 40 seconds with a developer (CD-2000, trade name, manufactured by FUJIFILM Electronic Materials Co., Ltd.) After rinsing for 30 seconds with running water, it was subjected to spray-drying. Thereafter, post-baking was carried out for 15 minutes at 200° C.

(5) Evaluation

Heat fastness of the coating layer formed on the glass substrate was carried out in the following manner. The evaluation results are given in Table 11 below.

[Heat Fastness]

The glass substrate coated with the colored curable composition layer obtained in process (3) was placed on a hot plate heated at 200° C. such that the substrate side was in contact with the hot plate. After heating for 1 hour, the change in absorbance at a maximum absorption wavelength (i.e., residual color ratio) before and after the heating was measured with a spectrophotometer (CARY5, trade name, manufactured by Varian Inc.) and the color difference (ΔE*ab value) before and after the heating was measured with a colorimeter (MCPD-1000, trade name, manufactured by Otsuka Electronics Co., Ltd.), and the results were used to evaluate the heat fastness.

The higher the residual color ratio is, and the lower the ΔE*ab value is, the more favorable the heat fastness is. The residual color ratio of 80% or more is favorable.

The ΔE*ab value of 5 or less is favorable. The ΔE*ab value is calculated from the following color difference equation which is based on CIE1976 (L*, a*, b*) space colorimetric system (Handbook of Color Science (1985), New edition, The Color Science Association of Japan, page 266).

$$\Delta E^*ab = \{(\Delta L^*)^2 + (\Delta a^*)^2 + (\Delta b^*)^2\}^{1/2}$$

Examples 3-2 to 3-19 and Comparative Examples 3-1 to 3-3

Evaluation was carried out in the same manner as Example 3-1, except that Exemplary compound M-7 was changed to the same amount of the dye compounds described in Table 11 and Table 12 to prepare a colored curable composition. The evaluation results are given in Table 11 and Table 12. Comparative dyes 1 to 3 in Table 11 are the same as above.

In Table 11, the substituent group indicates a substituent group corresponding to $G^2$ in formula (5). In Table 12, the dye compound has a substituent group further substituted on a substituent group having an −Es' value of 1.5 or more, and the dye compound of Table 12 has an −Es' value of 1.5 or more.

Examples 3-20 to 3-24

Evaluation was carried out in the same manner to Example 3-1, except that the dispersant BYK-161 was changed to the same amount of dispersants described in Table 13 below, and that Exemplary compound M-7 was changed to the same amount of compounds described in Table 13, to prepare a colored curable composition. The evaluation results are given in Table 13. The synthesis method of dispersants 1 to 3 are described later.

TABLE 11

| | Dye Compound | −Es' of Subsituent | Structure of Substituent | Residual ColorRatio | ΔE*ab |
|---|---|---|---|---|---|
| Example 3-1 | M-7 | 5.29 | Et—C(Et)(Et)— | 89 | 2.1 |
| Example 3-2 | M-16 | 1.63 | —C(t-Bu)— | 70 | 9.8 |

TABLE 11-continued

| | Dye Compound | −Es' of Subsituent | Structure of Substituent | Residual ColorRatio | ΔE*ab |
|---|---|---|---|---|---|
| Example 3-3 | M-25 | 2.38 | 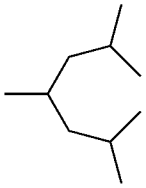 | 75 | 7.5 |
| Example 3-4 | M-28 | 3.21 |  t-Bu | 79 | 7 |
| Example 3-5 | M-31 | 5.01 |  | 85 | 2.4 |
| Example 3-6 | M-1 | 5.29 |  Et, Et, Et | 87 | 1.7 |
| Example 3-7 | M-32 | 6.73 | 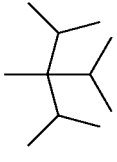 | 95 | 1.5 |
| Example 3-8 | M-148 | 5.29 |  Et, Et, Et | 97 | 1.2 |
| Comp. Ex. 3-1 | Comparative dye 1 | 0.00 | —Me | 42 | 20.3 |
| Comp. Ex. 3-2 | Comparative dye 2 | 1.43 | —t-Bu | 65 | 12.1 |
| Comp. Ex. 3-3 | Comparative dye 3 | 0.00 | —Me | 78 | 8.9 |

TABLE 12

| | Dye Compound | Residual Color Ratio | ΔE*ab |
|---|---|---|---|
| Example 3-9 | M-53 | 82 | 7.8 |
| Example 3-10 | M-82 | 81 | 6.1 |
| Example 3-11 | M-151 | 90 | 2.8 |
| Example 3-12 | P-14 | 95 | 1.6 |
| Example 3-13 | P-18 | 93 | 2.4 |
| Example 3-14 | P-22 | 96 | 1.9 |
| Example 3-15 | P-51 | 92 | 3.3 |
| Example 3-16 | P-54 | 91 | 4 |
| Example 3-17 | P-61 | 92 | 2.8 |
| Example 3-18 | S-6 | 89 | 5.1 |
| Example 3-19 | P-101 | 91 | 3.5 |

TABLE 13

| | Dye Compound | Dispersant | Residual Color Ratio | ΔE*ab |
|---|---|---|---|---|
| Example 3-20 | M-53 | Dispersant 1 | 83 | 7.1 |
| Example 3-21 | P-14 | Dispersant 2 | 95 | 1.8 |
| Example 3-22 | P-51 | Dispersant 3 | 93 | 2.9 |
| Example 3-23 | P-101 | Dispersant 2 | 92 | 3.3 |
| Example 3-24 | P-101 | Dispersant 3 | 93 | 2.8 |

From the results shown in Tables 11, 12 and 13, it was found that the colored curable composition, in which the dye compound of the invention is used, may provide a color filter with favorable heat fastness.

<Synthesis of Dispersant 1>

To a 500 mL three-neck flask, ε-caprolactone (600.0 g) and 2-ethyl-1-hexanol (22.8 g) were added and dissolved by stirring, while purging the flask with a nitrogen gas. Monobutyl tin oxide (0.1 g) was added thereto and heated to 100° C. 8 hours later, disappearance of the raw materials was confirmed by gas chromatography, and the mixture was cooled to 80° C. 2,6-di-t-butyl-4-methylphenol (0.1 g) was added, and subsequently 2-methacryloyloxyethyl isocyanate (27.2 g) was added. 5 hours later, disappearance of the raw materials was confirmed by $^1$H-NMR. After cooling to room temperature, the following precursor compound was obtained in a solid state (200 g). The structure of the precursor compound was determined by $^1$H-NMR, IR, and mass analysis.

Precursor Compound

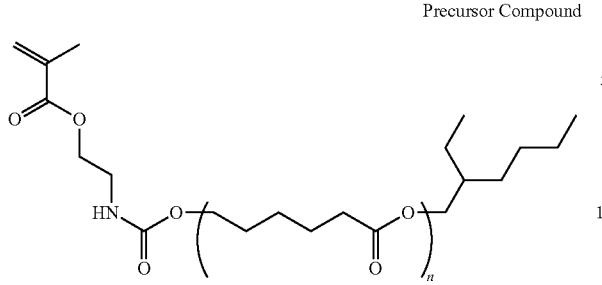

The precursor compound obtained above (80.0 g), methacrylic acid (20.0 g), dodecyl mercaptan (2.3 g), and propylene glycol monomethyl ether acetate (233.3 g) were added to a three-neck flask purged with a nitrogen gas, and stirred with a stirrer (trade name: THREE ONE MOTOR, manufactured by SHINTO Scientific Co., Ltd.). The temperature was increased to 75° C. by heating while purging the flask with nitrogen gas. To the resultant, 0.2 g of 2,2-azobis(2,4-dimethylvaleronitrile) (V-65, trade name, manufactured by Wako Pure Chemical Industries, Ltd.) were added and stirred while heating at 75° C. for 2 hours. 2 hours later, 0.2 g of V-65 were further added and heated and stirred for 3 hours. A 30% solution of dispersant 1 was obtained.

Dispersants 2 and 3 were obtained in the same manner as Dispersant 1.

(Dispersant 1)

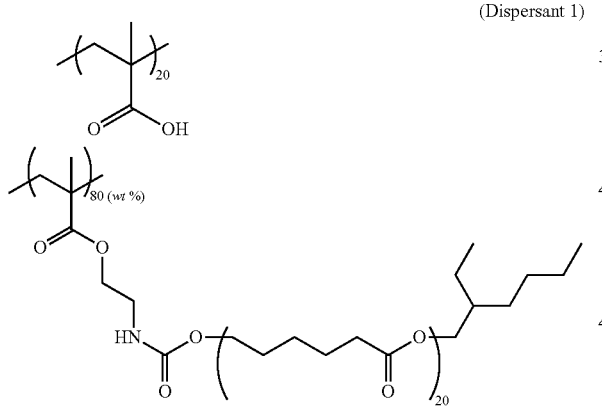

(Dispersant 2)

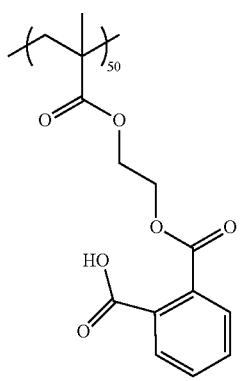

(Dispersant 3)

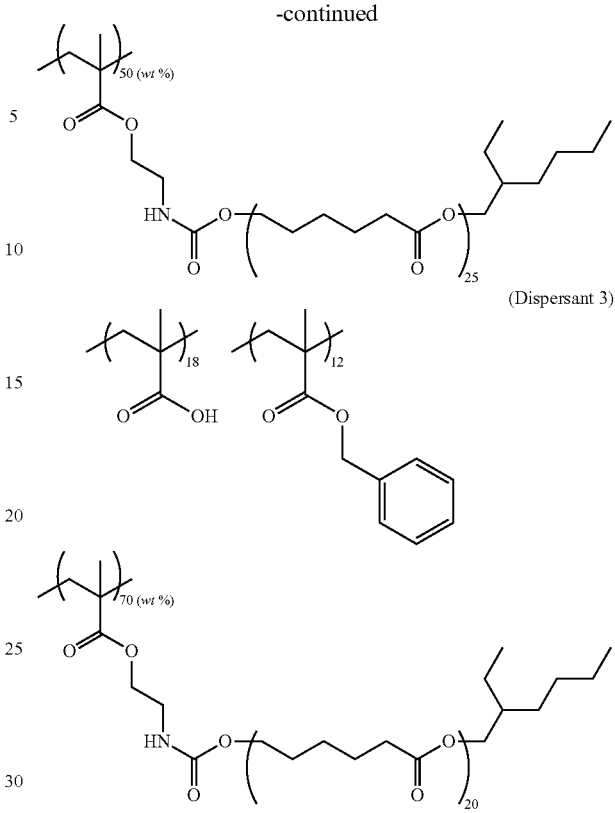

All publications, patent applications, and technical standards mentioned in this specification are herein incorporated by reference to the same extent as if each individual publication, patent application, or technical standard was specifically and individually indicated to be incorporated by reference.

What is claimed is:

1. A dye compound having a partial structure represented by the following formula (5):

$$\text{Dye} \left( \underset{G^1}{\underbrace{\hspace{1em}}} \overset{O}{\underset{\|}{C}} \underset{G^2}{\underbrace{\hspace{1em}}} \right)_p \quad (5)$$

wherein in formula (5), Dye represents a residual group of a dye compound selected from the group consisting of an azomethine dye, a dipyrromethene dye, a quinone dye, a carbonium dye, a quinoneimine dye, an azine dye, a polymethine dye, a quinophthalone dye, a phthalocyanine dye, a perinone dye, an indigo dye, a thioindigo dye, a quinoline dye, a nitro dye, a nitroso dye and a metal complex compound of these dyes; $G^1$ represents NR or an oxygen atom; $G^2$ represents a monovalent substituent group having an -Es' value as a steric parameter of 4.0 or more; p represents an integer from 1 to 8; when p is 2 or greater, the two or more structures represented by p may be the same or different from each other; and R represents a hydrogen atom or a monovalent substituent group.

2. The dye compound according to claim 1, wherein the partial structure represented by formula (5) is a partial structure represented by the following formula (6):

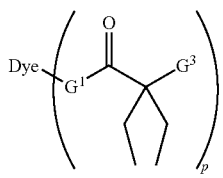

(6)

wherein in formula (6), Dye represents a dye structure; $G^1$ represents NR or an oxygen atom; $G^3$ represents a monovalent substituent that is linked to the partial structure —C(CH$_2$CH$_3$)$_2$ via a carbon atom, a sulfur atom, an oxygen atom or a nitrogen atom; p represents 1 or 2; when p is 2, the two structures represented by p may be the same or different from each other; and R represents a hydrogen atom or a monovalent substituent group.

3. The dye compound according to claim 1, wherein Dye in formula (5) is a residual group of a dipyrromethene compound or a residual group of a dipyrromethene metal complex compound obtained from the dipyrromethene compound and a metal or a metal compound.

4. The dye compound according to claim 3, wherein the dipyrromethene metal complex compound is a dipyrromethene metal complex compound obtained from a dipyrromethene compound represented by the following formula (M) and a metal or a metal compound, or a tautomer of the dipyrromethene metal complex compound:

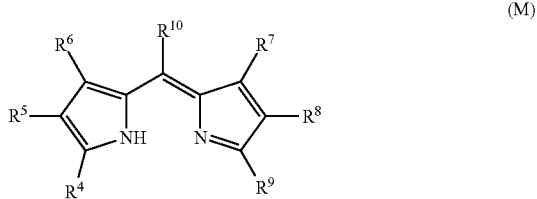

(M)

wherein in formula (M), each of $R^4$ to $R^{10}$ independently represents a hydrogen atom or a monovalent substituent group; at least one substituent group selected from $R^4$ to $R^{10}$ is linked to $G^1$ in formula (5); and $R^4$ and $R^9$ are not bonded to each other to form a ring.

5. The dye compound according to claim 3, wherein the dipyrromethene metal complex compound obtained from the dipyrromethene compound represented by formula (M) and the metal or the metal compound, or the tautomer of the dipyrromethene compound, is a dipyrromethene metal complex compound represented by the following formula (7) or the following formula (8) or a tautomer thereof:

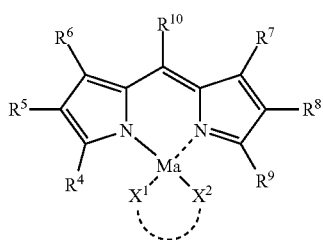

(7)

wherein in formula (7), each of $R^4$ to $R^9$ independently represents a hydrogen atom or a monovalent substituent group; $R^{10}$ represents a hydrogen atom, a halogen atom, an alkyl group, an aryl group, or a heterocyclic group; Ma represents a metal atom or a metal compound; $X^1$ represents a group capable of being bonded to Ma; $X^2$ represents a group that neutralizes a charge of Ma; $X^1$ and $X^2$ may be bonded to each other to form a 5-membered, 6-membered or 7-membered ring together with Ma; $R^4$ and $R^9$ are not bonded to each other to form a ring; and at least one of $R^4$ to $R^{10}$ is linked to $G^1$ in formula (5);

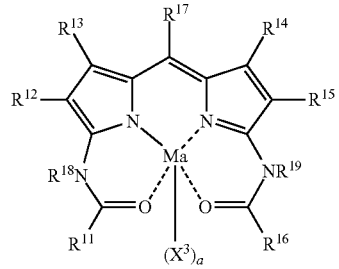

(8)

wherein in formula (8), each of $R^{11}$ and $R^{16}$ independently represent an alkyl group, an alkenyl group, an aryl group, a heterocyclic group, an alkoxy group, an aryloxy group, an alkylamino group, an arylamino group, or a heterocyclic amino group; each of $R^{12}$ to $R^{15}$ independently represents a hydrogen atom or a monovalent substituent group; $R^{17}$ represents a hydrogen atom, a halogen atom, an alkyl group, an aryl group, or a heterocyclic group; Ma represents a metal atom or a metal compound; each of $R^{18}$ and $R^{19}$ independently represents a hydrogen atom, an alkyl group, an alkenyl group, an aryl group, a heterocyclic group, an acyl group, an alkylsulfonyl group, or an arylsulfonyl group; $R^{11}$ and $R^{18}$ may be bonded to each other to form a 5-membered, 6-membered or 7-membered ring; $R^{16}$ and $R^{19}$ may be bonded to each other to form a 5-membered, 6-membered or 7-membered ring; $X^3$ represents a group capable of being bonded to Ma; a represents 0, 1 or 2; when a is 2, the two of $X^3$ may have the same structure or different structures; and at least one of the following conditions (a), (b) or (c) is satisfied;

(a) at least one of $R^{12}$ to $R^{15}$ is linked to $G^1$ in formula (5);
(b) —NR$^{18}$—(C=O) form -G$^1$-(C=O) in formula (5), and $R^{11}$ is $G^2$;
(c) —NR$^{19}$—(C=O) form -G$^1$-(C=O) in formula (5), and $R^{16}$ is $G^2$.

6. The dye compound according to claim 5, wherein each of $R^{11}$ and $R^{16}$ in formula (8) independently represents a monovalent substituent group having an -Es' value as a steric parameter of 1.5 or more, and formula (8) satisfies the conditions (b) and (c).

7. The dye compound according to claim 5, wherein Ma in formula (7) or formula (8) is any one of Zn, Co, V=O or Cu.

8. The dye compound according to claim 5, wherein Ma in formula (7) or formula (8) is Zn.

9. The dye compound according to claim 1, further comprising a polymerizable group.

10. The dye compound according to claim 1, further comprising an alkali soluble group.

11. A colored curable composition comprising the dye compound according to any one of claim 1 and a polymerizable compound.

12. A color filter formed from the colored curable composition according to claim 11.

13. A solid-state image sensor comprising the color filter according to claim 12.

14. A liquid crystal display device comprising the color filter according to claim 12.

15. A method of producing a color filter, the method comprising:
   applying the colored curable composition according to claim 11 to a substrate;
   exposing the colored curable composition to light via a mask; and
   developing the exposed colored curable composition to form a pattern image.

16. The dye compound according to claim 1, wherein G1 in formula (5) represents an oxygen atom.

17. The dye compound according to claim 1, wherein Dye in formula (5) is a residual group of a dye compound selected from the group consisting of an azomethine dye, an anthraquinone dye, a xanthene dye, a cyanine dye, and an oxonol dye.

* * * * *